US012797468B2

(12) United States Patent
Rezvani et al.

(10) Patent No.: US 12,797,468 B2
(45) Date of Patent: Nov. 17, 2026

(54) CD27-EXTRACELLULAR DOMAIN CAR TO TARGET CD70-POSITIVE TUMORS

(71) Applicant: BOARD OF REGENTS, THE UNIVERSITY OF TEXAS SYSTEM, Austin, TX (US)

(72) Inventors: Katy Rezvani, Houston, TX (US); Elizabeth Shpall, Houston, TX (US); Rafet Basar, Houston, TX (US); Sunil Acharya, Houston, TX (US); Nadima Uprety, Houston, TX (US); David Marin Costa, Houston, TX (US); Emily Ensley, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 486 days.

(21) Appl. No.: 18/261,414

(22) PCT Filed: Jan. 24, 2022

(86) PCT No.: PCT/US2022/013458
§ 371 (c)(1),
(2) Date: Jul. 13, 2023

(87) PCT Pub. No.: WO2022/159791
PCT Pub. Date: Jul. 28, 2022

(65) Prior Publication Data

US 2025/0281612 A1 Sep. 11, 2025

Related U.S. Application Data

(60) Provisional application No. 63/270,414, filed on Oct. 21, 2021, provisional application No. 63/141,016, filed on Jan. 25, 2021.

(51) Int. Cl.

| | |
|---|---|
| ***A61K 40/42*** | (2025.01) |
| ***A61K 39/00*** | (2006.01) |
| ***A61K 40/15*** | (2025.01) |
| ***A61K 40/31*** | (2025.01) |
| ***A61P 35/00*** | (2006.01) |
| ***C07K 14/705*** | (2006.01) |
| ***C12N 5/0783*** | (2010.01) |

(52) U.S. Cl.
CPC .......... *A61K 40/4232* (2025.01); *A61K 40/15* (2025.01); *A61K 40/31* (2025.01); *A61K 40/4202* (2025.01); *A61K 40/4234* (2025.01); *A61P 35/00* (2018.01); *C07K 14/7051* (2013.01); *C07K 14/70575* (2013.01); *C12N 5/0646* (2013.01); *A61K 2039/804* (2018.08); *A61K 2239/15* (2023.05); *A61K 2239/48* (2023.05); *C07K 14/70521* (2013.01); *C07K 2319/03* (2013.01); *C12N 2510/00* (2013.01)

(58) Field of Classification Search
CPC .... A61K 40/4232; A61K 40/15; A61K 40/31; A61K 40/4202; A61K 40/4234; A61K 2039/804; A61K 2239/15; A61K 2239/48; A61P 35/00; C07K 14/7051; C07K 14/70575; C07K 14/70521; C07K 2319/03; C12N 5/0646; C12N 2510/00
See application file for complete search history.

(56) References Cited

U.S. PATENT DOCUMENTS

| | | | |
|---|---|---|---|
| 6,129,914 | A | 10/2000 | Weiner et al. |
| 7,261,892 | B2 | 8/2007 | Terrett |
| 7,381,803 | B1 | 6/2008 | Weiner et al. |
| 7,550,144 | B2 | 6/2009 | Collinge et al. |
| 7,635,472 | B2 | 12/2009 | Kufer et al. |
| 7,641,903 | B2 | 1/2010 | Law et al. |
| 7,763,720 | B2 | 7/2010 | Arlen et al. |
| 7,977,093 | B2 | 7/2011 | Groux et al. |
| 8,007,796 | B2 | 8/2011 | Baeuerle et al. |
| 8,034,338 | B2 | 10/2011 | Loibner et al. |
| 8,076,459 | B2 | 12/2011 | Hofmeister et al. |
| 8,106,161 | B2 | 1/2012 | Ledbetter et al. |
| 8,221,751 | B2 | 7/2012 | Nakamura et al. |
| 8,404,233 | B2 | 3/2013 | Sunamura et al. |

(Continued)

FOREIGN PATENT DOCUMENTS

| | | |
|---|---|---|
| CA | 3138854 | 11/2020 |
| KR | 2014-0036252 | 3/2014 |

(Continued)

OTHER PUBLICATIONS

Harris and Kranz (Trends in Pharmacological Sciences (2016) 37(3): 220-230) (Year: 2016).*

(Continued)

*Primary Examiner* — Julie Wu
*Assistant Examiner* — Elizabeth A Shupe
(74) *Attorney, Agent, or Firm* — Norton Rose Fulbright US LLP

(57) ABSTRACT

Embodiments of the disclosure encompass methods and compositions that utilize an anti-CD70 chimeric antigen receptor (CAR) that lacks an antibody or antibody fragment as part of the receptor, including as part of the antigen binding region of the CAR. In particular embodiments, instead of the CAR employing an antibody to bind CD70, the CAR molecule utilizes CD27, the receptor for the ligand CD70. In specific embodiments, the CAR comprises a truncated version of CD27 rather than full length CD27. In specific cases, the CAR lacks the CD27 transmembrane domain.

19 Claims, 18 Drawing Sheets

Specification includes a Sequence Listing.

(56) References Cited

U.S. PATENT DOCUMENTS

| | | | |
|---|---|---|---|
| 8,535,667 | B2 | 9/2013 | Arlen et al. |
| 8,709,382 | B2 | 4/2014 | D'Souza et al. |
| 8,722,401 | B2 | 5/2014 | Groux et al. |
| 8,729,043 | B2 | 5/2014 | Comoglio et al. |
| 8,834,882 | B2 | 9/2014 | Silence et al. |
| 8,961,991 | B2 | 2/2015 | Zurawski et al. |
| 9,102,734 | B2 | 8/2015 | Zurawski et al. |
| 9,102,736 | B2 | 8/2015 | Hofmeister et al. |
| 9,120,854 | B2 | 9/2015 | Ryan et al. |
| 9,139,649 | B2 | 9/2015 | Chang et al. |
| 9,139,655 | B2 | 9/2015 | Nakamura et al. |
| 9,169,326 | B2 | 10/2015 | Arlen et al. |
| 9,192,665 | B2 | 11/2015 | Zugmaier et al. |
| 9,249,211 | B2 | 2/2016 | Schellenberger et al. |
| 9,272,002 | B2 | 3/2016 | Powell, Jr. et al. |
| 9,371,395 | B2 | 6/2016 | Takahashi et al. |
| 9,376,498 | B2 | 6/2016 | Di Naro |
| 9,518,108 | B2 | 12/2016 | Tissot et al. |
| 9,567,401 | B2 | 2/2017 | Banchereau et al. |
| 9,574,008 | B2 | 2/2017 | Delaney et al. |
| 9,605,077 | B2 | 3/2017 | Arlen et al. |
| 9,670,283 | B2 | 6/2017 | Su |
| 9,676,866 | B2 | 6/2017 | Albone et al. |
| 9,765,148 | B2 | 9/2017 | Silence et al. |
| 9,765,149 | B2 | 9/2017 | Silence et al. |
| 9,828,436 | B2 | 11/2017 | Chang et al. |
| 9,902,779 | B2 | 2/2018 | Yu et al. |
| 9,914,780 | B2 | 3/2018 | Su |
| 9,951,143 | B2 | 4/2018 | Chang et al. |
| 10,000,567 | B2 | 6/2018 | Ellis et al. |
| 10,022,427 | B2 | 7/2018 | Chang et al. |
| 10,040,827 | B2 | 8/2018 | Delecluse et al. |
| 10,059,767 | B2 | 8/2018 | Protzer et al. |
| 10,087,256 | B2 | 10/2018 | Banchereau et al. |
| 10,093,736 | B2 | 10/2018 | Sahin et al. |
| 10,202,452 | B2 | 2/2019 | Tan et al. |
| 10,208,126 | B2 | 2/2019 | Ni Naro |
| 10,214,587 | B2 | 2/2019 | Su |
| 10,239,952 | B2 | 3/2019 | Scheinberg et al. |
| 10,280,425 | B2 | 5/2019 | Chen et al. |
| 10,293,055 | B2 | 5/2019 | Zhao |
| 10,301,389 | B2 | 5/2019 | Ho et al. |
| 10,316,099 | B2 | 6/2019 | Collinge et al. |
| 10,364,295 | B2 | 7/2019 | Arlen et al. |
| 10,604,567 | B2 | 3/2020 | Westerman et al. |
| 10,640,576 | B2 | 5/2020 | Jang et al. |
| 10,647,768 | B2 | 5/2020 | Johnson et al. |
| 10,662,243 | B2 | 5/2020 | Nagorsen et al. |
| 10,676,537 | B2 | 6/2020 | Yu et al. |
| 10,688,182 | B2 | 6/2020 | Chen |
| 10,695,406 | B2 | 6/2020 | McGuckin et al. |
| 10,696,744 | B2 | 6/2020 | Zugmaier et al. |
| 10,730,943 | B2 | 8/2020 | Protzer et al. |
| 10,744,157 | B2 | 8/2020 | Sentman et al. |
| 10,793,628 | B2 | 10/2020 | Lee et al. |
| 10,815,307 | B2 | 10/2020 | Yu et al. |
| 10,836,796 | B2 | 11/2020 | Zhao et al. |
| 10,882,909 | B2 | 1/2021 | Ho et al. |
| 10,894,828 | B2 | 1/2021 | Boyman et al. |
| 10,919,971 | B2 | 2/2021 | Collinge et al. |
| 10,941,207 | B2 | 3/2021 | Mertens et al. |
| 11,028,175 | B2 | 6/2021 | Su |
| 11,034,766 | B2 | 6/2021 | Sentman et al. |
| 11,084,876 | B2 | 8/2021 | Kufer et al. |
| 11,124,568 | B1 | 9/2021 | Ahmed et al. |
| 11,129,910 | B2 | 9/2021 | Zhao et al. |
| 11,142,572 | B2 | 10/2021 | Westerman et al. |
| 11,202,828 | B2 | 12/2021 | Puro et al. |
| 11,242,399 | B2 | 2/2022 | Di Naro |
| 11,291,721 | B2 | 4/2022 | Loew et al. |
| 11,352,426 | B2 | 6/2022 | Tan et al. |
| 11,485,783 | B2 | 11/2022 | Li et al. |
| 11,492,409 | B2 | 11/2022 | Abujoub et al. |
| 11,534,495 | B2 | 12/2022 | Yu et al. |
| 11,535,666 | B2 | 12/2022 | Chen et al. |
| 11,566,061 | B2 | 1/2023 | Stephan |
| 11,566,063 | B2 | 1/2023 | Kruse et al. |
| 11,579,142 | B2 | 2/2023 | Nagorsen |
| 11,597,766 | B2 | 3/2023 | Zugmaier et al. |
| 11,597,914 | B2 | 3/2023 | Jang et al. |
| 11,633,408 | B2 | 4/2023 | Zugmaier et al. |
| 11,649,285 | B2 | 5/2023 | Kalabokis et al. |
| 11,702,482 | B2 | 7/2023 | Preyer et al. |
| 11,713,358 | B2 | 8/2023 | Schellenberger et al. |
| 11,939,382 | B2 | 3/2024 | Mazor et al. |
| 11,939,392 | B2 | 3/2024 | Hernandez-Hoyos et al. |
| 11,998,584 | B2 | 6/2024 | Zhao et al. |
| 12,036,256 | B2 | 7/2024 | Rottman |
| 2009/0148942 | A1 | 6/2009 | McDonagh et al. |
| 2010/0150925 | A1 | 6/2010 | Law et al. |
| 2011/0150908 | A1 | 6/2011 | Law et al. |
| 2015/0210764 | A1 | 7/2015 | Mondal et al. |
| 2016/0194402 | A1 | 7/2016 | van Eenennaam et al. |
| 2016/0361360 | A1 | 12/2016 | Chang et al. |
| 2017/0246278 | A1 | 8/2017 | Vera Valdes et al. |
| 2018/0201901 | A1 | 7/2018 | Duchateau et al. |
| 2018/0208671 | A1 | 7/2018 | Wang et al. |
| 2018/0230224 | A1 | 8/2018 | Alvarez Rodriguez et al. |
| 2019/0048085 | A1 | 2/2019 | Dotti et al. |
| 2019/0112360 | A1 | 4/2019 | Chung et al. |
| 2019/0119379 | A1 | 4/2019 | Gottschalk et al. |
| 2019/0161542 | A1 | 5/2019 | Gill et al. |
| 2019/0233528 | A1 | 8/2019 | Srivatsa Srinivasan et al. |
| 2019/0241668 | A1 | 8/2019 | Van Rompaey |
| 2020/0317807 | A1 | 10/2020 | Wang et al. |
| 2022/0411478 | A1* | 12/2022 | Maus .................... A61K 40/11 |
| 2023/0060351 | A1 | 3/2023 | Rezvani |

FOREIGN PATENT DOCUMENTS

| | | |
|---|---|---|
| WO | WO 2010/127294 | 4/2010 |
| WO | WO 2012/058460 | 5/2012 |
| WO | WO 2012/123586 | 9/2012 |
| WO | WO 2013/153391 | 10/2013 |
| WO | WO 2015/164745 | 10/2015 |
| WO | WO 2016/061574 | 4/2016 |
| WO | WO 2016/093878 | 6/2016 |
| WO | WO 2017/147383 | 8/2017 |
| WO | WO 2017/184553 | 10/2017 |
| WO | WO 2018/195339 | 10/2018 |
| WO | WO 2019/023396 | 1/2019 |
| WO | WO 2019/119036 | 6/2019 |
| WO | WO 2019/152742 | 8/2019 |
| WO | 110267677 | 9/2019 |
| WO | WO 2019/213610 | 11/2019 |
| WO | WO 2019/232503 | 12/2019 |
| WO | WO 2020/108643 | 6/2020 |
| WO | WO 2020/232292 | 11/2020 |
| WO | WO 2020/259541 | 12/2020 |
| WO | WO 2022/129216 | 6/2022 |

OTHER PUBLICATIONS

Xie (Cancers (2022) 14(13): 3230) (Year: 2022).*

U.S. Appl. No. 18/700,483. Methods for Production of Therapeutic Immune Cells Having Enhanced Metabolic Fitness and Compositions Thereof, filed 2024. Published 2025 in US 2025/0074950 A1. (Year: 2024).*

Gomez-Melero (Frontiers in Immunology (2025) 16: 1546172) (Year: 2025).*

Daher et al., "Targeting a cytokine checkpoint enhances the fitness of armored cord blood CAR-NK cells," Blood, 137(5):624-636, 2021.

English translation of Office Communication issued in Japanese Patent Application No. 2023-54489, dated Dec. 17, 2025.

Kang et al., "The Advances and Challenges of NK Cell-Based Cancer Immunotherapy," Curr. Oncol., 28(2):1077-1093, 2021.

Tokarew et al., "Teaching an old dog new tricks: next generation CAR T cells," British Journal of Cancer, 120:26-37, 2019.

English translation of Office Communication issued in Eurasian Patent Application No. 202392113, dated Aug. 15, 2024.

(56) References Cited

OTHER PUBLICATIONS

Li et al., "Human iPSC-Derived Natural Killer Cells Engineered with Chimeric Antigen Receptors Enhance Anti-tumor Activity," Cell Stem Cell, 23:181-192, 2018.
Brandt et al., "Emerging approaches for regulation and control of CAR T cells: A mini review," Front. Immunol., 11:326, pp. 1-9, 2020.
English translation of Office Communication issued in Chinese Patent Application No. 202180019200.X, dated Jul. 13, 2023.
Ge et al., "Tumor associated CD70 expression is involved in promoting tumor migration and macrophage infiltration in GBM," Int'l. J. Cancer, 141:1434-1444, 2017.
Holst et al., "Generation of T-cell receptor retrogenic mice," Nature Protocols, 1(1):406-417, 2006.
Hoyos et al., "Engineering CD19-specific T lymphocytes with interleukin-15 and a suicide gene to enhance their anti-lymphoma/leukemia effects and safety," Leukemia, 24(6):1160-1170, 2010.
Jin et al., "CD70, a novel target of CAR T-cell therapy for gliomas," Neuro-Oncology, 20(1):55-65, 2018.
National Cancer Institute, "Administering Peripheral Blood Lymphocytes Transduced with a CD70-Binding Chimeric Antigen Receptor to People with CD70 Expressing Cancers," ClinicalTrials.gov Identifier: NCT02830724, 10 pages, Apr. 26, 2019.
Office Communication issued in European Patent Application No. 21738525.1, dated Mar. 19, 2024.
Panowski et al., "Abstract 2326: Allo CAR T™ targeting CD70 for the treatment of renal cell carcinoma," Cancer Res., 79(13 Supplemental): 2326, 2 pages, 2019.
Park et al., "CD70 as a target for chimeric antigen receptor T cells in head and neck squamous cell carcinoma," Oral Oncol., 78:145-150, 2018.
PCT International Search Report and Written Opinion issued in International Application No. PCT/US2021/012510, dated Apr. 2, 2021.
Tu et al., "CD19 and CD70 dual-target chimeric antigen receptor T-Cell therapy for the treatment of relapsed and refractory primary central nervous system diffuse large B-cell lymphoma," Front. Oncol., 9:1350, pp. 1-6, 2019.
Tu et al., "Combination of CD19 and CD70 Specific Chimeric Antigen Receptor T Cells Achieves Long-Term Disease-Free Survival in Relapsed and Refractory Primary Central Nervous System Diffuse Large B Cell Lymphoma," Blood, 132(Supplement 1):5389, 2018.
Yeku et al., "Armored CAR T-cells: utilizing cytokines and pro-inflammatory ligands to enhance CAR T-cell anti-tumour efficacy," Biochem. Soc. Trans., 44(2):412-418, 2016.
Borst et al., "CD27 and CD70 in T cell and B cell activation," Curr Opin Immunol., 17(3):275-281, 2005.
Claus et al., "CD27 signaling increases the frequency of regulatory T cells and promotes tumor growth," Cancer Res., 72(14):3664-76, 2012.
Daher and Rezvani, "Next generation natural killer cells for cancer immunotherapy: the promise of genetic engineering," Curr Opin Immunol., 51:146-53, 2018.
Goodwin et al., "Molecular and biological characterization of a ligand for CD27 defines a new family of cytokines with homology to tumor necrosis factor," Cell, 73:447-456, 1993.
Grewal, "CD70 as a therapeutic target in human malignancies," Expert Opin Ther Targets, 12(3):341-51, 2008.
Jacobs et al., "CD70: An emerging target in cancer immunotherapy," Pharmacol Ther., 155:1-10, 2015.
Liu et al., "Use of CAR-Transduced Natural Killer Cells in CD19-Positive Lymphoid Tumors," N Engl J Med., 382(6):545-53, 2020.
Maude et al., "Tisagenlecleucel in Children and Young Adults with B-Cell Lymphoblastic Leukemia," N Engl J Med., 378(5): 439-48, 2018.
Neelapu et al., "Axicabtagene Ciloleucel CAR T-Cell Therapy in Refractory Large B-Cell Lymphoma," N Engl J Med., 377(26): 2531-44, 2017.
Oflazoglu et al., "Potent anticarcinoma activity of the humanized anti-CD70 antibody h1 F6 conjugated to the tubulin inhibitor auristatin via an uncleavable linker," Clin Cancer Res., 14(19):6171-6180, 2008.
O'Neill et al., "T Cell-Derived CD70 Delivers an Immune Checkpoint Function in Inflammatory T Cell Responses," J Immunol., 199(10):3700-10, 2017.
Owonikoko et al., "First-in-human multicenter phase I study of BMS-936561 (MDX-1203), an antibody-drug conjugate targeting CD70," Cancer Chemother Pharmacol., 77(1): 155-162, 2016.
RefSeq Accession No. NM_001252, "*Homo sapiens* CD70 molecule (CD70), transcript variant 1, mRNA," 1994. Available at https://www.ncbi.nlm.nih.gov/nuccore/1519313716.
RefSeq Accession No. NP_001243, "CD70 antigen isoform 1 [*Homo sapiens*]," 1994. Available at https://www.ncbi.nlm.nih.gov/protein/NP_001243.
Riether et al., "CD70/CD27 signaling promotes blast stemness and is a viable therapeutic target in acute myeloid leukemia," J Exp Med., 214(2):359-380, 2017.
Ryan et al., "Targeting pancreatic and ovarian carcinomas using the auristatin-based anti-CD70 antibody-drug conjugate SGN-75," Br J Cancer, 103(5):676-684, 2010.
Schuster et al., "Tisagenlecleucel in Adult Relapsed or Refractory Diffuse Large B-Cell Lymphoma," N Engl J Med., 380(1):45-56, 2019.
Silence et al., "ARGX-110, a highly potent antibody targeting CD70, eliminates tumors via both enhanced ADCC and immune checkpoint blockade," MAbs, 6(2):523-32, 2014.
Van Gisbergen et al., "Protective CD8 T cell memory is impaired during chronic CD70-driven costimulation," J Immunol., 182(9):5352-62, 2009.
Sauer et al., "CD70-specific CAR T cells have potent activity against acute myeloid leukemia without HSC toxicity," Blood, 138(4): 318-330, 2021.
Starzer et al., "New emerging targets in cancer immunotherapy: CD27 (TNFRSF7)," ESMO Open, 4: e000629, pp. 1-7, 2019.
Extended European Search Report for Application No. 22743308.3, mailed Nov. 18, 2024, 9 pages.
Office Communication issued in Japanese Patent Application No. 2022/541951, dated Dec. 4, 2024. (English translation provided).
PCT International Search Report and Written Opinion issued in International Application No. PCT/US2022/013458, dated May 6, 2022.
Roselli et al., "CAR-T Engineering: Optimizing Signal Transduction and Effector Mechanisms," BioDrug, 33:647-659, 2019.
Shaffer et al, "T cells redirected against CD70 for the immunotherapy of CD70-positive malignancies," Blood, 117(16):4304-4314, 2011.
Shaffer et al., "T-Cells Redirected Against CD70 for the Immunotherapy of Hematological Malignancies," Abstract No. 2757, ASH Annual Meeting Abstracts, Part 1, 110(11):810a, 2007.
Shaffer et al., "T-cells Redirected Against CD70 for the Immunotherapy of Hematological Malignancies," Biology of Blood and Marrow Transplantation, 14(2), Supplement, p. 23, 2008.
Song et al., "CD27 costimulation augments the survival and antitumor activity of redirected human T cells in vivo," Blood, 119(3):696-706, 2012.
Wajant, "Therapeutic targeting of CD70 and CD27," Expert Opinion on Therapeutic Targets, 20(8):959-973, 2016.
Wang et al., "Pre-clinical Evaluation of Chimeric Antigen Receptors Targeting CD70-Expressing Cancers," Clin. Cancer Res., 23(9):2267-2276, 2017.
Yang et al., "Tandem CAR-T cells targeting CD70 and B7-H3 exhibit potent preclinical activity against multiple solid tumors," Theranostics, 10(17):7622-7634, 2020.
Liu et al., "Cord blood NK cells engineered to express IL-15 and a CD19-targeted CAR show long-term persistence and potent antitumor activity," Leukemia, 32:520-531, 2018.
Office Communication issued in European Patent Application No. 21738525.1, dated Jul. 2, 2024.

* cited by examiner

SEQUENCE LISTING

```
<160> NUMBER OF SEQ ID NOS: 74

<210> SEQ ID NO 1
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 1

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175
```

```
His Trp Pro Pro Gln Arg Ser Leu Cys Ser Ser Asp Phe Ile Arg Phe
            180                 185                 190

Trp Val Leu Val Val Val Gly Gly Val Leu Ala Cys Tyr Ser Leu Leu
        195                 200                 205

Val Thr Val Ala Phe Ile Ile Phe Trp Val
    210                 215


<210> SEQ ID NO 2
<211> LENGTH: 191
<212> TYPE: PRT
<213> ORGANISM: Artificial Sequence
<220> FEATURE:
<223> OTHER INFORMATION: Synthetic Polypeptide

<400> SEQUENCE: 2

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg
            180                 185                 190


<210> SEQ ID NO 3
<211> LENGTH: 27
<212> TYPE: PRT
<213> ORGANISM: Artificial Sequence
<220> FEATURE:
<223> OTHER INFORMATION: Synthetic Polypeptide

<400> SEQUENCE: 3

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25


<210> SEQ ID NO 4
<211> LENGTH: 260
<212> TYPE: PRT
<213> ORGANISM: Artificial Sequence
<220> FEATURE:
<223> OTHER INFORMATION: Synthetic Polypeptide
```

<400> SEQUENCE: 4

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
        195                 200                 205

Leu Phe Leu His Gln Arg Arg Lys Tyr Arg Ser Asn Lys Gly Glu Ser
    210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260
```

<210> SEQ ID NO 5
<211> LENGTH: 172
<212> TYPE: PRT
<213> ORGANISM: Artificial Sequence
<220> FEATURE:
<223> OTHER INFORMATION: Synthetic Polypeptide

<400> SEQUENCE: 5

```
Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
```

85 90 95

Glu Cys Thr Glu Cys Asp Pro Leu Pro Asn Pro Ser Leu Thr Ala Arg
100 105 110

Ser Ser Gln Ala Leu Ser Pro His Pro Gln Pro Thr His Leu Pro Tyr
115 120 125

Val Ser Glu Met Leu Glu Ala Arg Thr Ala Gly His Met Gln Thr Leu
130 135 140

Ala Asp Phe Arg Gln Leu Pro Ala Arg Thr Leu Ser Thr His Trp Pro
145 150 155 160

Pro Gln Arg Ser Leu Cys Ser Ser Asp Phe Ile Arg
165 170

<210> SEQ ID NO 6
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 6

Met Ala Arg Pro His Pro Trp Trp Leu Cys Val Leu Gly Thr Leu Val
1 5 10 15

Gly Leu Ser

<210> SEQ ID NO 7
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 7

Ile Leu Val Ile Phe Ser Gly Met Phe Leu Val Phe Thr Leu Ala Gly
1 5 10 15

Ala Leu Phe Leu His
20

<210> SEQ ID NO 8
<211> LENGTH: 48
<212> TYPE: PRT
<213> ORGANISM: Artificial Sequence
<220> FEATURE:
<223> OTHER INFORMATION: Synthetic Polypeptide

<400> SEQUENCE: 8

Gln Arg Arg Lys Tyr Arg Ser Asn Lys Gly Glu Ser Pro Val Glu Pro
1 5 10 15

Ala Glu Pro Cys His Tyr Ser Cys Pro Arg Glu Glu Glu Gly Ser Thr
20 25 30

Ile Pro Ile Gln Glu Asp Tyr Arg Lys Pro Glu Pro Ala Cys Ser Pro
35 40 45

<210> SEQ ID NO 9
<211> LENGTH: 783
<212> TYPE: DNA
<213> ORGANISM: Artificial Sequence
<220> FEATURE:
<223> OTHER INFORMATION: Synthetic Polynucleotide

<400> SEQUENCE: 9
atggcacggc cacatccctg gtggctgtgc gttctgggga ccctggtggg gctctcagct 60

```
actccagccc ccaagagctg cccagagagg cactactggg ctcagggaaa gctgtgctgc    120

cagatgtgtg agccaggaac attcctcgtg aaggactgtg accagcatag aaaggctgct    180

cagtgtgatc cttgcatacc gggggtctcc ttctctcctg accaccacac ccggccccac    240

tgtgagagct gtcggcactg taactctggt cttctcgttc gcaactgcac catcactgcc    300

aatgctgagt gtgcctgtcg caatggctgg cagtgcaggg acaaggagtg caccgagtgt    360

gatcctcttc caaacccttc gctgaccgct cggtcgtctc aggccctgag cccacaccct    420

cagcccaccc acttacctta tgtcagtgag atgctggagg ccaggacagc tgggcacatg    480

cagactctgg ctgacttcag gcagctgcct gcccggactc tctctaccca ctggccaccc    540

caaagatccc tgtgcagctc cgattttatt cgcatccttg tgatcttctc tggaatgttc    600

cttgttttca ccctggccgg ggccctgttc ctccatcaac gaaggaaata tagatcaaac    660

aaaggagaaa gtcctgtgga gcctgcagag ccttgtcgtt acagctgccc cagggaggag    720

gagggcagca ccatccccat ccaggaggat taccgaaaac cggagcctgc ctgctccccc    780

tga                                                                  783
```

```
<210> SEQ ID NO 10
<211> LENGTH: 113
<212> TYPE: PRT
<213> ORGANISM: Artificial Sequence
<220> FEATURE:
<223> OTHER INFORMATION: Synthetic Polypeptide

<400> SEQUENCE: 10

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

Gly


<210> SEQ ID NO 11
<211> LENGTH: 41
<212> TYPE: PRT
<213> ORGANISM: Artificial Sequence
<220> FEATURE:
<223> OTHER INFORMATION: Synthetic Polypeptide

<400> SEQUENCE: 11

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40
```

<210> SEQ ID NO 12
<211> LENGTH: 42
<212> TYPE: PRT
<213> ORGANISM: Artificial Sequence
<220> FEATURE:
<223> OTHER INFORMATION: Synthetic Polypeptide

<400> SEQUENCE: 12

Lys Arg Gly Arg Lys Lys Leu Leu Tyr Ile Phe Lys Gln Pro Phe Met
1 5 10 15

Arg Pro Val Gln Thr Thr Gln Glu Glu Asp Gly Cys Ser Cys Arg Phe
20 25 30

Pro Glu Glu Glu Glu Gly Gly Cys Glu Leu
35 40

<210> SEQ ID NO 13
<211> LENGTH: 780
<212> TYPE: DNA
<213> ORGANISM: Artificial Sequence
<220> FEATURE:
<223> OTHER INFORMATION: Synthetic Polynucleotide

<400> SEQUENCE: 13
atggcgagac cacacccttg gtggctgtgc gtactcggca cacttgtagg tctgtccgct 60
acaccggctc cgaagtcctg cccggagcgg cattattggg cacagggcaa gttgtgttgt 120
caaatgtgtg agccgggaac ctttctcgtg aaggattgcg atcagcatcg gaaggccgcg 180
cagtgcgacc catgtatacc aggggtctca ttttccccag atcaccatac gaggccgcac 240
tgtgagtctt gcaggcattg taattccggc ttgttggtcc gcaactgtac tattactgcg 300
aatgcagagt gtgcttgtag aaacggatgg cagtgcaggg acaaagaatg tacggagtgt 360
gatccactgc ctaaccccag tcttacagca agatcttcac aggccctcag cccgcatcct 420
caaccaacac atcttcctta cgtgtcagaa atgttggagg cgcgaaccgc aggccatatg 480
cagaccctgg cggactttcg gcagctgcca gcacgcacac ttagtacaca ctggccacca 540
caacgcagct tgtgctcttc cgatttcatc cgcatactgg tcatcttttc tggaatgttc 600
cttgtgttca ccctggcagg agccctgttc cttcaccaga gacgcaagta caggtcaaac 660
aagggtgaga gccccgttga acccgcagag ccgtgtagat actcatgtcc tagagaagaa 720
gagggctcta ctatccctat tcaggaagat tatagaaaac ccgaacccgc gtgcagcccc 780

<210> SEQ ID NO 14
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 14

Met Leu Leu Leu Val Thr Ser Leu Leu Leu Cys Glu Leu Pro His Pro
1 5 10 15

Ala Phe Leu Leu Ile Pro
20

<210> SEQ ID NO 15
<211> LENGTH: 654
<212> TYPE: DNA
<213> ORGANISM: Artificial Sequence
<220> FEATURE:
<223> OTHER INFORMATION: Synthetic Polynucleotide

<400> SEQUENCE: 15
atggcacggc cacatccctg gtggctgtgc gttctgggga ccctggtggg gctctcagct 60
actccagccc ccaagagctg cccagagagg cactactggg ctcagggaaa gctgtgctgc 120
cagatgtgtg agccaggaac attcctcgtg aaggactgtg accagcatag aaaggctgct 180
cagtgtgatc cttgcatacc gggggtctcc ttctctcctg accaccacac ccggccccac 240
tgtgagagct gtcggcactg taactctggt cttctcgttc gcaactgcac catcactgcc 300
aatgctgagt gtgcctgtcg caatggctgg cagtgcaggg acaaggagtg caccgagtgt 360
gatcctcttc caaacccttc gctgaccgct cggtcgtctc aggccctgag cccacaccct 420
cagcccaccc acttacctta tgtcagtgag atgctggagg ccaggacagc tgggcacatg 480
cagactctgg ctgacttcag gcagctgcct gcccggactc tctctaccca ctggccaccc 540
caaagatccc tgtgcagctc cgattttatt cgcttttggg tgctggtggt ggttggtgga 600
gtcctggctt gctatagctt gctagtaaca gtggccttta ttattttctg ggtg 654

<210> SEQ ID NO 16
<211> LENGTH: 2004
<212> TYPE: DNA
<213> ORGANISM: Artificial Sequence
<220> FEATURE:
<223> OTHER INFORMATION: Synthetic Polynucleotide

<400> SEQUENCE: 16
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccaccccccac cgccctcaaa 240 gtagacggca tcgcagcttg gatacacgcc gcccacgtga aggctgccga ccccgggggt 300
ggaccatcct ctagactgcc atgctcgagg atggcacggc cacatccctg gtggctgtgc 360
gttctgggga ccctggtggg gctctcagct actccagccc ccaagagctg cccagagagg 420
cactactggg ctcagggaaa gctgtgctgc cagatgtgtg agccaggaac attcctcgtg 480
aaggactgtg accagcatag aaaggctgct cagtgtgatc cttgcatacc gggggtctcc 540
ttctctcctg accaccacac ccggccccac tgtgagagct gtcggcactg taactctggt 600
cttctcgttc gcaactgcac catcactgcc aatgctgagt gtgcctgtcg caatggctgg 660
cagtgcaggg acaaggagtg caccgagtgt gatcctcttc caaacccttc gctgaccgct 720
cggtcgtctc aggccctgag cccacaccct cagcccaccc acttacctta tgtcagtgag 780
atgctggagg ccaggacagc tgggcacatg cagactctgg ctgacttcag gcagctgcct 840
gcccggactc tctctaccca ctggccaccc caaagatccc tgtgcagctc cgattttatt 900
cgcttttggg tgctggtggt ggttggtgga gtcctggctt gctatagctt gctagtaaca 960
gtggccttta ttattttctg ggtgaaacgg ggcagaaaga aactcctgta tatattcaaa 1020
caaccattta tgagaccagt acaaactact caagaggaag atggctgtag ctgccgattt 1080
ccagaagaag aagaaggagg atgtgaactg aaacgcgtga agttcagcag gagcgcagac 1140
gcccccgcgt accagcaggg ccagaaccag ctctataacg agctcaatct aggacgaaga 1200
gaggagtacg atgttttgga caaaagacgt ggccgggacc ctgagatggg gggaaagccg 1260
agaaggaaga accctcagga aggcctgtac aatgaactgc agaaagataa gatggcggag 1320
gcctacagtg agattgggat gaaaggcgag cgccggaggg gcaaggggca cgatggcctt 1380
taccagggtc tcagtacagc caccaaggac acctacgacg cccttcacat gcaggccctg 1440
ccccctcgcg gaccgcagtg tactaattat gctctcttga aattggctgg agatgttgag 1500
agcaatcccg ggcccatgcg cattagcaag ccccacctgc ggagcatcag catccagtgc 1560
tacctgtgcc tgctgctgaa cagccacttc ctgaccgagg ccggcatcca cgtgttcatc 1620
ctgggctgct tcagcgccgg actgcccaag accgaggcca actgggtgaa cgtgatcagc 1680
gacctgaaga agatcgagga cctgatccag agcatgcaca tcgacgccac cctgtacacc 1740
gagagcgacg tgcaccccag ctgcaaggtg accgccatga agtgctttct gctggaactg 1800
caggtgatca gcctggaaag cggcgacgcc agcatccacg acaccgtgga gaacctgatc 1860
atcctggcca acaacagcct gagcagcaac ggcaacgtga ccgagagcgg ctgcaaagag 1920
tgcgaggaac tggaagagaa gaacatcaaa gagtttctgc agagcttcgt gcacatcgtg 1980
cagatgttca tcaacaccag ctga 2004

<210> SEQ ID NO 17
<211> LENGTH: 2013
<212> TYPE: DNA
<213> ORGANISM: Artificial Sequence
<220> FEATURE:
<223> OTHER INFORMATION: Synthetic Polynucleotide

<400> SEQUENCE: 17
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccaccccccac cgccctcaaa 240 gtagacggca tcgcagcttg gatacacgcc gcccacgtga aggctgccga ccccgggggt 300
ggaccatcct ctagactgcc atgctcgagg atgcttctcc tggtgacaag ccttctgctc 360
tgtgagttac cacacccagc attcctcctg atcccagcta caccggctcc gaagtcctgc 420
ccggagcggc attattgggc acagggcaag ttgtgttgtc aaatgtgtga gccgggaacc 480
tttctcgtga aggattgcga tcagcatcgg aaggccgcgc agtgcgaccc atgtatacca 540
ggggtctcat ttccccaga tcaccatacg aggccgcact gtgagtcttg caggcattgt 600
aattccggct tgttggtccg caactgtact attactgcga atgcagagtg tgcttgtaga 660
aacggatggc agtgcaggga caaagaatgt acggagtgtg atccactgcc taaccccagt 720
cttacagcaa gatcttcaca ggccctcagc ccgcatcctc aaccaacaca tcttccttac 780
gtgtcagaaa tgttggaggc gcgaaccgca ggccatatgc agaccctggc ggactttcgg 840
cagctgccag cacgcacact tagtacacac tggccaccac aacgcagctt gtgctcttcc 900
gatttcatcc gcttttgggt gctggtggtg gttggtggag tcctggcttg ctatagcttg 960
ctagtaacag tggcctttat tattttctgg gtgaaacggg gcagaaagaa actcctgtat 1020
atattcaaac aaccatttat gagaccagta caaactactc aagaggaaga tggctgtagc 1080
tgccgatttc cagaagaaga agaaggagga tgtgaactga aacgcgtgaa gttcagcagg 1140
agcgcagacg cccccgcgta ccagcagggc cagaaccagc tctataacga gctcaatcta 1200
ggacgaagag aggagtacga tgttttggac aaaagacgtg gccgggaccc tgagatgggg 1260
ggaaagccga gaaggaagaa ccctcaggaa ggcctgtaca atgaactgca gaaagataag 1320
atggcggagg cctacagtga gattgggatg aaaggcgagc gccggagggg caaggggcac 1380
gatggccttt accagggtct cagtacagcc accaaggaca cctacgacgc ccttcacatg 1440

```
caggccctgc cccctcgcgg accgcagtgt actaattatg ctctcttgaa attggctgga   1500

gatgttgaga gcaatcccgg gcccatgcgc attagcaagc cccacctgcg gagcatcagc   1560

atccagtgct acctgtgcct gctgctgaac agccacttcc tgaccgaggc cggcatccac   1620

gtgttcatcc tgggctgctt cagcgccgga ctgcccaaga ccgaggccaa ctgggtgaac   1680

gtgatcagcg acctgaagaa gatcgaggac ctgatccaga gcatgcacat cgacgccacc   1740

ctgtacaccg agagcgacgt gcaccccagc tgcaaggtga ccgccatgaa gtgctttctg   1800

ctggaactgc aggtgatcag cctggaaagc ggcgacgcca gcatccacga caccgtggag   1860

aacctgatca tcctggccaa caacagcctg agcagcaacg gcaacgtgac cgagagcggc   1920

tgcaaagagt gcgaggaact ggaagagaag aacatcaaag agtttctgca gagcttcgtg   1980

cacatcgtgc agatgttcat caacaccagc tga                                2013
```

```
<210> SEQ ID NO 18
<211> LENGTH: 1950
<212> TYPE: DNA
<213> ORGANISM: Artificial Sequence
<220> FEATURE:
<223> OTHER INFORMATION: Synthetic Polynucleotide

<400> SEQUENCE: 18

atgacaagag ttactaacag cccctctctc caagctcact tacaggctct ctacttagtc     60

cagcacgaag tctggagacc tctggcggca gcctaccaag aacaactgga ccgaccggtg    120

gtacctcacc cttaccgagt cggcgacaca gtgtgggtcc gccgacacca gactaagaac    180

ctagaacctc gctggaaagg accttacaca gtcctgctga ccacccccac cgccctcaaa    240

gtagacggca tcgcagcttg gatacacgcc gcccacgtga aggctgccga ccccgggggt    300

ggaccatcct ctagactgcc atgctcgagg atggcacggc cacatccctg gtggctgtgc    360

gttctgggga ccctggtggg gctctcagct actccagccc ccaagagctg cccagagagg    420

cactactggg ctcagggaaa gctgtgctgc cagatgtgtg agccaggaac attcctcgtg    480

aaggactgtg accagcatag aaaggctgct cagtgtgatc cttgcatacc gggggtctcc    540

ttctctcctg accaccacac ccggccccac tgtgagagct gtcggcactg taactctggt    600

cttctcgttc gcaactgcac catcactgcc aatgctgagt gtgcctgtcg caatggctgg    660

cagtgcaggg acaaggagtg caccgagtgt gatcctcttc caaacccttc gctgaccgct    720

cggtcgtctc aggccctgag cccacaccct cagcccaccc acttacctta tgtcagtgag    780

atgctggagg ccaggacagc tgggcacatg cagactctgg ctgacttcag gcagctgcct    840

gcccggactc tctctaccca ctggccaccc caaagatccc tgtgcagctc cgattttatt    900

cgcttttggg tgctggtggt ggttggtgga gtcctggctt gctatagctt gctagtaaca    960

gtggccttta ttattttctg ggtgctttgc gcacgcccac gccgcagccc cgcccaagaa   1020

gatggcaaag tctacatcaa catgccaggc aggggcaaac gcgtgaagtt cagcaggagc   1080

gcagacgccc ccgcgtacca gcagggccag aaccagctct ataacgagct caatctagga   1140

cgaagagagg agtacgatgt tttggacaaa agacgtggcc gggaccctga gatgggggga   1200

aagccgagaa ggaagaaccc tcaggaaggc ctgtacaatg aactgcagaa agataagatg   1260

gcggaggcct acagtgagat tgggatgaaa ggcgagcgcc ggaggggcaa ggggcacgat   1320

ggcctttacc agggtctcag tacagccacc aaggacacct acgacgccct tcacatgcag   1380

gccctgcccc ctcgcggacc gcagtgtact aattatgctc tcttgaaatt ggctggagat   1440
```

gttgagagca atcccgggcc catgcgcatt agcaagcccc acctgcggag catcagcatc 1500
cagtgctacc tgtgcctgct gctgaacagc cacttcctga ccgaggccgg catccacgtg 1560
ttcatcctgg gctgcttcag cgccggactg cccaagaccg aggccaactg ggtgaacgtg 1620
atcagcgacc tgaagaagat cgaggacctg atccagagca tgcacatcga cgccaccctg 1680
tacaccgaga gcgacgtgca ccccagctgc aaggtgaccg ccatgaagtg ctttctgctg 1740
gaactgcagg tgatcagcct ggaaagcggc gacgccagca tccacgacac cgtggagaac 1800
ctgatcatcc tggccaacaa cagcctgagc agcaacggca acgtgaccga gagcggctgc 1860
aaagagtgcg aggaactgga agagaagaac atcaaagagt ttctgcagag cttcgtgcac 1920
atcgtgcaga tgttcatcaa caccagctga 1950

<210> SEQ ID NO 19
<211> LENGTH: 1959
<212> TYPE: DNA
<213> ORGANISM: Artificial Sequence
<220> FEATURE:
<223> OTHER INFORMATION: Synthetic Polynucleotide

<400> SEQUENCE: 19
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccaccccac cgccctcaaa 240 gtagacggca tcgcagcttg gatacacgcc gcccacgtga aggctgccga ccccgggggt 300
ggaccatcct ctagactgcc atgctcgagg atgcttctcc tggtgacaag ccttctgctc 360
tgtgagttac cacacccagc attcctcctg atcccagcta caccggctcc gaagtcctgc 420
ccggagcggc attattgggc acagggcaag ttgtgttgtc aaatgtgtga gccgggaacc 480
tttctcgtga aggattgcga tcagcatcgg aaggccgcgc agtgcgaccc atgtatacca 540
ggggtctcat ttccccaga tcaccatacg aggccgcact gtgagtcttg caggcattgt 600
aattccggct tgttggtccg caactgtact attactgcga atgcagagtg tgcttgtaga 660
aacggatggc agtgcaggga caaagaatgt acggagtgtg atccactgcc taaccccagt 720
cttacagcaa gatcttcaca ggccctcagc ccgcatcctc aaccaacaca tcttccttac 780
gtgtcagaaa tgttggaggc gcgaaccgca ggccatatgc agaccctggc ggactttcgg 840
cagctgccag cacgcacact tagtacacac tggccaccac aacgcagctt gtgctcttcc 900
gatttcatcc gcttttgggt gctggtggtg gttggtggag tcctggcttg ctatagcttg 960
ctagtaacag tggcctttat tattttctgg gtgctttgcg cacgcccacg ccgcagcccc 1020
gcccaagaag atggcaaagt ctacatcaac atgccaggca ggggcaaacg cgtgaagttc 1080
agcaggagcg cagacgcccc cgcgtaccag cagggccaga accagctcta taacgagctc 1140
aatctaggac gaagagagga gtacgatgtt ttggacaaaa gacgtggccg ggaccctgag 1200 atgggggggaa agccgagaag gaagaaccct caggaaggcc tgtacaatga actgcagaaa 1260
gataagatgg cggaggccta cagtgagatt gggatgaaag gcgagcgccg gaggggcaag 1320
gggcacgatg gcctttacca gggtctcagt acagccacca aggacaccta cgacgccctt 1380
cacatgcagg ccctgccccc tcgcggaccg cagtgtacta attatgctct cttgaaattg 1440
gctggagatg ttgagagcaa tcccgggccc atgcgcatta gcaagcccca cctgcggagc 1500
atcagcatcc agtgctacct gtgcctgctg ctgaacagcc acttcctgac cgaggccggc 1560

```
atccacgtgt tcatcctggg ctgcttcagc gccggactgc ccaagaccga ggccaactgg   1620

gtgaacgtga tcagcgacct gaagaagatc gaggacctga tccagagcat gcacatcgac   1680

gccaccctgt acaccgagag cgacgtgcac cccagctgca aggtgaccgc catgaagtgc   1740

tttctgctgg aactgcaggt gatcagcctg gaaagcggcg acgccagcat ccacgacacc   1800

gtggagaacc tgatcatcct ggccaacaac agcctgagca gcaacggcaa cgtgaccgag   1860

agcggctgca aagagtgcga ggaactggaa gagaagaaca tcaaagagtt tctgcagagc   1920

ttcgtgcaca tcgtgcagat gttcatcaac accagctga                          1959
```

<210> SEQ ID NO 20
<211> LENGTH: 2034
<212> TYPE: DNA
<213> ORGANISM: Artificial Sequence
<220> FEATURE:
<223> OTHER INFORMATION: Synthetic Polynucleotide

<400> SEQUENCE: 20

```
atgacaagag ttactaacag cccctctctc caagctcact tacaggctct ctacttagtc     60

cagcacgaag tctggagacc tctggcggca gcctaccaag aacaactgga ccgaccggtg    120

gtacctcacc cttaccgagt cggcgacaca gtgtgggtcc gccgacacca gactaagaac    180

ctagaacctc gctggaaagg accttacaca gtcctgctga ccaccccccac cgccctcaaa    240

gtagacggca tcgcagcttg gatacacgcc gcccacgtga aggctgccga ccccgggggt    300

ggaccatcct ctagactgcc atgctcgagg atggcacggc cacatccctg gtggctgtgc    360

gttctgggga ccctggtggg gctctcagct actccagccc ccaagagctg cccagagagg    420

cactactggg ctcagggaaa gctgtgctgc cagatgtgtg agccaggaac attcctcgtg    480

aaggactgtg accagcatag aaaggctgct cagtgtgatc cttgcatacc gggggtctcc    540

ttctctcctg accaccacac ccggccccac tgtgagagct gtcggcactg taactctggt    600

cttctcgttc gcaactgcac catcactgcc aatgctgagt gtgcctgtcg caatggctgg    660

cagtgcaggg acaaggagtg caccgagtgt gatcctcttc caaacccttc gctgaccgct    720

cggtcgtctc aggccctgag cccacaccct cagcccaccc acttacctta tgtcagtgag    780

atgctggagg ccaggacagc tgggcacatg cagactctgg ctgacttcag gcagctgcct    840

gcccggactc tctctaccca ctggccaccc caaagatccc tgtgcagctc cgattttatt    900

cgcttttggg tgctggtggt ggttggtgga gtcctggctt gctatagctt gctagtaaca    960

gtggccttta ttattttctg ggtgtacttc ctgggccggc tggtccctcg gggggcgaggg   1020

gctgcggagg cagcgacccg gaaacagcgt atcactgaga ccgagtcgcc ttatcaggag   1080

ctccagggtc agaggtcgga tgtctacagc gacctcaaca cacagaggcc gtattacaaa   1140

aaacgcgtga agttcagcag gagcgcagac gcccccgcgt accagcaggg ccagaaccag   1200

ctctataacg agctcaatct aggacgaaga gaggagtacg atgttttgga caaaagacgt   1260

ggccgggacc ctgagatggg gggaaagccg agaaggaaga accctcagga aggcctgtac   1320

aatgaactgc agaaagataa gatggcggag gcctacagtg agattgggat gaaaggcgag   1380

cgccggaggg gcaaggggca cgatggcctt taccagggtc tcagtacagc caccaaggac   1440

acctacgacg cccttcacat gcaggccctg ccccctcgcg gaccgcagtg tactaattat   1500

gctctcttga aattggctgg agatgttgag agcaatcccg ggcccatgcg cattagcaag   1560

ccccacctgc ggagcatcag catccagtgc tacctgtgcc tgctgctgaa cagccacttc   1620
```

ctgaccgagg ccggcatcca cgtgttcatc ctgggctgct tcagcgccgg actgcccaag 1680
accgaggcca actgggtgaa cgtgatcagc gacctgaaga agatcgagga cctgatccag 1740
agcatgcaca tcgacgccac cctgtacacc gagagcgacg tgcaccccag ctgcaaggtg 1800
accgccatga agtgctttct gctggaactg caggtgatca gcctggaaag cggcgacgcc 1860
agcatccacg acaccgtgga gaacctgatc atcctggcca acaacagcct gagcagcaac 1920
ggcaacgtga ccgagagcgg ctgcaaagag tgcgaggaac tggaagagaa gaacatcaaa 1980
gagtttctgc agagcttcgt gcacatcgtg cagatgttca tcaacaccag ctga 2034

<210> SEQ ID NO 21
<211> LENGTH: 2043
<212> TYPE: DNA
<213> ORGANISM: Artificial Sequence
<220> FEATURE:
<223> OTHER INFORMATION: Synthetic Polynucleotide

<400> SEQUENCE: 21
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccacccccac cgccctcaaa 240
gtagacggca tcgcagcttg gatacacgcc gcccacgtga aggctgccga ccccgggggt 300
ggaccatcct ctagactgcc atgctcgagg atgcttctcc tggtgacaag ccttctgctc 360
tgtgagttac cacacccagc attcctcctg atcccagcta caccggctcc gaagtcctgc 420
ccggagcggc attattgggc acagggcaag ttgtgttgtc aaatgtgtga gccgggaacc 480
tttctcgtga aggattgcga tcagcatcgg aaggccgcgc agtgcgaccc atgtatacca 540
ggggtctcat ttccccaga tcaccatacg aggccgcact gtgagtcttg caggcattgt 600
aattccggct tgttggtccg caactgtact attactgcga atgcagagtg tgcttgtaga 660
aacggatggc agtgcaggga caaagaatgt acggagtgtg atccactgcc taaccccagt 720
cttacagcaa gatcttcaca ggccctcagc ccgcatcctc aaccaacaca tcttccttac 780
gtgtcagaaa tgttggaggc gcgaaccgca ggccatatgc agaccctggc ggactttcgg 840
cagctgccag cacgcacact tagtacacac tggccaccac aacgcagctt gtgctcttcc 900
gatttcatcc gcttttgggt gctggtggtg gttggtggag tcctggcttg ctatagcttg 960
ctagtaacag tggcctttat tattttctgg gtgtacttcc tgggccggct ggtccctcgg 1020
gggcgagggg ctgcggaggc agcgacccgg aaacagcgta tcactgagac cgagtcgcct 1080
tatcaggagc tccagggtca gaggtcggat gtctacagcg acctcaacac acagaggccg 1140
tattacaaaa aacgcgtgaa gttcagcagg agcgcagacg cccccgcgta ccagcagggc 1200
cagaaccagc tctataacga gctcaatcta ggacgaagag aggagtacga tgttttggac 1260
aaaagacgtg gccgggaccc tgagatgggg ggaaagccga gaaggaagaa ccctcaggaa 1320
ggcctgtaca atgaactgca gaaagataag atggcggagg cctacagtga gattgggatg 1380
aaaggcgagc gccggagggg caaggggcac gatggccttt accagggtct cagtacagcc 1440
accaaggaca cctacgacgc ccttcacatg caggccctgc cccctcgcgg accgcagtgt 1500
actaattatg ctctcttgaa attggctgga gatgttgaga gcaatcccgg gcccatgcgc 1560
attagcaagc cccacctgcg gagcatcagc atccagtgct acctgtgcct gctgctgaac 1620
agccacttcc tgaccgaggc cggcatccac gtgttcatcc tgggctgctt cagcgccgga 1680
ctgcccaaga ccgaggccaa ctgggtgaac gtgatcagcg acctgaagaa gatcgaggac 1740
ctgatccaga gcatgcacat cgacgccacc ctgtacaccg agagcgacgt gcaccccagc 1800
tgcaaggtga ccgccatgaa gtgctttctg ctggaactgc aggtgatcag cctggaaagc 1860
ggcgacgcca gcatccacga caccgtggag aacctgatca tcctggccaa caacagcctg 1920
agcagcaacg gcaacgtgac cgagagcggc tgcaaagagt gcgaggaact ggaagagaag 1980
aacatcaaag agtttctgca gagcttcgtg cacatcgtgc agatgttcat caacaccagc 2040
tga 2043

<210> SEQ ID NO 22
<211> LENGTH: 2031
<212> TYPE: DNA
<213> ORGANISM: Artificial Sequence
<220> FEATURE:
<223> OTHER INFORMATION: Synthetic Polynucleotide

<400> SEQUENCE: 22
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccacccccac cgccctcaaa 240
gtagacggca tcgcagcttg gatacacgcc gcccacgtga aggctgccga ccccgggggt 300
ggaccatcct ctagactgcc atgctcgagg atggcacggc cacatccctg gtggctgtgc 360
gttctgggga ccctggtggg gctctcagct actccagccc ccaagagctg cccagagagg 420
cactactggg ctcagggaaa gctgtgctgc cagatgtgtg agccaggaac attcctcgtg 480
aaggactgtg accagcatag aaaggctgct cagtgtgatc cttgcatacc ggggggtctcc 540 ttctctcctg accaccacac ccggccccac tgtgagagct gtcggcactg taactctggt 600
cttctcgttc gcaactgcac catcactgcc aatgctgagt gtgcctgtcg caatggctgg 660
cagtgcaggg acaaggagtg caccgagtgt gatcctcttc caaacccttc gctgaccgct 720
cggtcgtctc aggccctgag cccacaccct cagcccaccc acttacctta tgtcagtgag 780
atgctggagg ccaggacagc tgggcacatg cagactctgg ctgacttcag gcagctgcct 840
gcccggactc tctctaccca ctggccaccc caaagatccc tgtgcagctc cgattttatt 900
cgcttttggg tgctggtggt ggttggtgga gtcctggctt gctatagctt gctagtaaca 960
gtggccttta ttattttctg ggtgagcgcg aacgaacgct gcaaaagcaa agtggtgccg 1020
tgccgccaga aacagtggcg caccagcttt gatagcaaaa aactggatct gaactataac 1080
cattttgaaa gcatggaatg gagccatcgc agccgccgcg gccgcatttg ggcatgaaa 1140 cgcgtgaagt tcagcaggag cgcagacgcc cccgcgtacc agcagggcca gaaccagctc 1200
tataacgagc tcaatctagg acgaagagag gagtacgatg ttttggacaa aagacgtggc 1260
cgggaccctg agatgggggg aaagccgaga aggaagaacc ctcaggaagg cctgtacaat 1320
gaactgcaga aagataagat ggcggaggcc tacagtgaga ttgggatgaa aggcgagcgc 1380
cggaggggca aggggcacga tggcctttac cagggtctca gtacagccac caaggacacc 1440
tacgacgccc ttcacatgca ggccctgccc cctcgcggac cgcagtgtac taattatgct 1500
ctcttgaaat tggctggaga tgttgagagc aatcccgggc ccatgcgcat tagcaagccc 1560
cacctgcgga gcatcagcat ccagtgctac ctgtgcctgc tgctgaacag ccacttcctg 1620

```
accgaggccg gcatccacgt gttcatcctg ggctgcttca gcgccggact gcccaagacc   1680

gaggccaact gggtgaacgt gatcagcgac ctgaagaaga tcgaggacct gatccagagc   1740

atgcacatcg acgccaccct gtacaccgag agcgacgtgc accccagctg caaggtgacc   1800

gccatgaagt gctttctgct ggaactgcag gtgatcagcc tggaaagcgg cgacgccagc   1860

atccacgaca ccgtggagaa cctgatcatc ctggccaaca acagcctgag cagcaacggc   1920

aacgtgaccg agagcggctg caaagagtgc gaggaactgg aagagaagaa catcaaagag   1980

tttctgcaga gcttcgtgca catcgtgcag atgttcatca acaccagctg a            2031
```

```
<210> SEQ ID NO 23
<211> LENGTH: 2040
<212> TYPE: DNA
<213> ORGANISM: Artificial Sequence
<220> FEATURE:
<223> OTHER INFORMATION: Synthetic Polynucleotide

<400> SEQUENCE: 23

atgacaagag ttactaacag cccctctctc caagctcact tacaggctct ctacttagtc     60

cagcacgaag tctggagacc tctggcggca gcctaccaag aacaactgga ccgaccggtg    120

gtacctcacc cttaccgagt cggcgacaca gtgtgggtcc gccgacacca gactaagaac    180

ctagaacctc gctggaaagg accttacaca gtcctgctga ccaccccccac cgccctcaaa    240

gtagacggca tcgcagcttg gatacacgcc gcccacgtga aggctgccga ccccgggggt    300

ggaccatcct ctagactgcc atgctcgagg atgcttctcc tggtgacaag ccttctgctc    360

tgtgagttac cacacccagc attcctcctg atcccagcta caccggctcc gaagtcctgc    420

ccggagcggc attattgggc acagggcaag ttgtgttgtc aaatgtgtga gccgggaacc    480

tttctcgtga aggattgcga tcagcatcgg aaggccgcgc agtgcgaccc atgtatacca    540

ggggtctcat ttccccaga tcaccatacg aggccgcact gtgagtcttg caggcattgt    600

aattccggct tgttggtccg caactgtact attactgcga atgcagagtg tgcttgtaga    660

aacggatggc agtgcaggga caaagaatgt acggagtgtg atccactgcc taaccccagt    720

cttacagcaa gatcttcaca ggccctcagc ccgcatcctc aaccaacaca tcttccttac    780

gtgtcagaaa tgttggaggc gcgaaccgca ggccatatgc agaccctggc ggactttcgg    840

cagctgccag cacgcacact tagtacacac tggccaccac aacgcagctt gtgctcttcc    900

gatttcatcc gcttttgggt gctggtggtg gttggtggag tcctggcttg ctatagcttg    960

ctagtaacag tggcctttat tattttctgg gtgagcgcga acgaacgctg caaaagcaaa   1020

gtggtgccgt gccgccagaa acagtggcgc accagctttg atagcaaaaa actggatctg   1080

aactataacc attttgaaag catggaatgg agccatcgca gccgccgcgg ccgcatttgg   1140

ggcatgaaac gcgtgaagtt cagcaggagc gcagacgccc ccgcgtacca gcagggccag   1200

aaccagctct ataacgagct caatctagga cgaagagagg agtacgatgt tttggacaaa   1260

agacgtggcc gggaccctga gatgggggga aagccgagaa ggaagaaccc tcaggaaggc   1320

ctgtacaatg aactgcagaa agataagatg gcggaggcct acagtgagat tgggatgaaa   1380

ggcgagcgcc ggaggggcaa ggggcacgat ggcctttacc agggtctcag tacagccacc   1440

aaggacacct acgacgccct tcacatgcag gccctgcccc ctcgcggacc gcagtgtact   1500

aattatgctc tcttgaaatt ggctggagat gttgagagca atcccgggcc catgcgcatt   1560

agcaagcccc acctgcggag catcagcatc cagtgctacc tgtgcctgct gctgaacagc   1620

cacttcctga ccgaggccgg catccacgtg ttcatcctgg gctgcttcag cgccggactg   1680
```

cccaagaccg aggccaactg ggtgaacgtg atcagcgacc tgaagaagat cgaggacctg 1740
atccagagca tgcacatcga cgccaccctg tacaccgaga gcgacgtgca ccccagctgc 1800
aaggtgaccg ccatgaagtg ctttctgctg gaactgcagg tgatcagcct ggaaagcggc 1860
gacgccagca tccacgacac cgtggagaac ctgatcatcc tggccaacaa cagcctgagc 1920
agcaacggca acgtgaccga gagcggctgc aaagagtgcg aggaactgga agagaagaac 1980
atcaaagagt ttctgcagag cttcgtgcac atcgtgcaga tgttcatcaa caccagctga 2040

<210> SEQ ID NO 24
<211> LENGTH: 1986
<212> TYPE: DNA
<213> ORGANISM: Artificial Sequence
<220> FEATURE:
<223> OTHER INFORMATION: Synthetic Polynucleotide

<400> SEQUENCE: 24
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccacccccac cgccctcaaa 240
gtagacggca tcgcagcttg gatacacgcc gcccacgtga aggctgccga ccccgggggt 300
ggaccatcct ctagactgcc atgctcgagg atggcacggc cacatccctg gtggctgtgc 360
gttctgggga ccctggtggg gctctcagct actccagccc ccaagagctg cccagagagg 420
cactactggg ctcagggaaa gctgtgctgc cagatgtgtg agccaggaac attcctcgtg 480
aaggactgtg accagcatag aaaggctgct cagtgtgatc cttgcatacc gggggtctcc 540
ttctctcctg accaccacac ccggccccac tgtgagagct gtcggcactg taactctggt 600
cttctcgttc gcaactgcac catcactgcc aatgctgagt gtgcctgtcg caatggctgg 660
cagtgcaggg acaaggagtg caccgagtgt gatcctcttc caaacccttc gctgaccgct 720
cggtcgtctc aggccctgag cccacaccct cagcccaccc acttacctta tgtcagtgag 780
atgctggagg ccaggacagc tgggcacatg cagactctgg ctgacttcag gcagctgcct 840
gcccggactc tctctaccca ctggccaccc caaagatccc tgtgcagctc cgattttatt 900
cgcatccttg tgatcttctc tggaatgttc cttgttttca ccctggccgg ggccctgttc 960
ctccataaac ggggcagaaa gaaactcctg tatatattca aacaaccatt tatgagacca 1020
gtacaaacta ctcaagagga agatggctgt agctgccgat ttccagaaga agaagaagga 1080
ggatgtgaac tgaaacgcgt gaagttcagc aggagcgcag acgcccccgc gtaccagcag 1140
ggccagaacc agctctataa cgagctcaat ctaggacgaa gagaggagta cgatgttttg 1200
gacaaaagac gtggccggga ccctgagatg gggggaaagc cgagaaggaa gaaccctcag 1260
gaaggcctgt acaatgaact gcagaaagat aagatggcgg aggcctacag tgagattggg 1320
atgaaaggcg agcgccggag gggcaagggg cacgatggcc tttaccaggg tctcagtaca 1380
gccaccaagg acacctacga cgcccttcac atgcaggccc tgccccctcg cggaccgcag 1440
tgtactaatt atgctctctt gaaattggct ggagatgttg agagcaatcc cgggcccatg 1500
cgcattagca agcccccacct gcggagcatc agcatccagt gctacctgtg cctgctgctg 1560
aacagccact tcctgaccga ggccggcatc cacgtgttca tcctgggctg cttcagcgcc 1620
ggactgccca agaccgaggc caactgggtg aacgtgatca gcgacctgaa gaagatcgag 1680

```
gacctgatcc agagcatgca catcgacgcc accctgtaca ccgagagcga cgtgcacccc   1740

agctgcaagg tgaccgccat gaagtgcttt ctgctggaac tgcaggtgat cagcctggaa   1800

agcggcgacg ccagcatcca cgacaccgtg gagaacctga tcatcctggc caacaacagc   1860

ctgagcagca acggcaacgt gaccgagagc ggctgcaaag agtgcgagga actggaagag   1920

aagaacatca aagagtttct gcagagcttc gtgcacatcg tgcagatgtt catcaacacc   1980

agctga                                                              1986
```

<210> SEQ ID NO 25
<211> LENGTH: 1995
<212> TYPE: DNA
<213> ORGANISM: Artificial Sequence
<220> FEATURE:
<223> OTHER INFORMATION: Synthetic Polynucleotide

<400> SEQUENCE: 25

```
atgacaagag ttactaacag cccctctctc caagctcact tacaggctct ctacttagtc     60

cagcacgaag tctggagacc tctggcggca gcctaccaag aacaactgga ccgaccggtg    120

gtacctcacc cttaccgagt cggcgacaca gtgtgggtcc gccgacacca gactaagaac    180

ctagaacctc gctggaaagg accttacaca gtcctgctga ccaccccccac cgccctcaaa    240

gtagacggca tcgcagcttg gatacacgcc gcccacgtga aggctgccga ccccgggggt    300

ggaccatcct ctagactgcc atgctcgagg atgcttctcc tggtgacaag ccttctgctc    360

tgtgagttac cacacccagc attcctcctg atcccagcta caccggctcc gaagtcctgc    420

ccggagcggc attattgggc acagggcaag ttgtgttgtc aaatgtgtga gccgggaacc    480

tttctcgtga aggattgcga tcagcatcgg aaggccgcgc agtgcgaccc atgtatacca    540

ggggtctcat ttccccaga tcaccatacg aggccgcact gtgagtcttg caggcattgt    600

aattccggct tgttggtccg caactgtact attactgcga atgcagagtg tgcttgtaga    660

aacggatggc agtgcaggga caaagaatgt acggagtgtg atccactgcc taaccccagt    720

cttacagcaa gatcttcaca ggccctcagc ccgcatcctc aaccaacaca tcttccttac    780

gtgtcagaaa tgttggaggc gcgaaccgca ggccatatgc agaccctggc ggactttcgg    840

cagctgccag cacgcacact tagtacacac tggccaccac aacgcagctt gtgctcttcc    900

gatttcatcc gcatactggt catcttttct ggaatgttcc ttgtgttcac cctggcagga    960

gccctgttcc ttcacaaacg gggcagaaag aaactcctgt atatattcaa acaaccattt   1020

atgagaccag tacaaactac tcaagaggaa gatggctgta gctgccgatt tccagaagaa   1080

gaagaaggag gatgtgaact gaaacgcgtg aagttcagca ggagcgcaga cgcccccgcg   1140

taccagcagg gccagaacca gctctataac gagctcaatc taggacgaag agaggagtac   1200

gatgttttgg acaaaagacg tggccgggac cctgagatgg ggggaaagcc gagaaggaag   1260

aaccctcagg aaggcctgta caatgaactg cagaaagata agatggcgga ggcctacagt   1320

gagattggga tgaaaggcga gcgccggagg ggcaaggggc acgatggcct ttaccagggt   1380

ctcagtacag ccaccaagga cacctacgac gcccttcaca tgcaggccct gccccctcgc   1440

ggaccgcagt gtactaatta tgctctcttg aaattggctg gagatgttga gagcaatccc   1500

gggcccatgc gcattagcaa gccccacctg cggagcatca gcatccagtg ctacctgtgc   1560

ctgctgctga acagccactt cctgaccgag gccggcatcc acgtgttcat cctgggctgc   1620

ttcagcgccg gactgcccaa gaccgaggcc aactgggtga acgtgatcag cgacctgaag   1680

aagatcgagg acctgatcca gagcatgcac atcgacgcca ccctgtacac cgagagcgac   1740
```

gtgcacccca gctgcaaggt gaccgccatg aagtgctttc tgctggaact gcaggtgatc 1800
agcctggaaa gcggcgacgc cagcatccac gacaccgtgg agaacctgat catcctggcc 1860
aacaacagcc tgagcagcaa cggcaacgtg accgagagcg gctgcaaaga gtgcgaggaa 1920
ctggaagaga agaacatcaa agagtttctg cagagcttcg tgcacatcgt gcagatgttc 1980
atcaacacca gctga 1995

<210> SEQ ID NO 26
<211> LENGTH: 1860
<212> TYPE: DNA
<213> ORGANISM: Artificial Sequence
<220> FEATURE:
<223> OTHER INFORMATION: Synthetic Polynucleotide

<400> SEQUENCE: 26
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccaccccac cgccctcaaa 240 gtagacggca tcgcagcttg gatacacgcc gcccacgtga aggctgccga ccccgggggt 300
ggaccatcct ctagactgcc atgctcgagg atggcacggc cacatccctg gtggctgtgc 360
gttctgggga ccctggtggg gctctcagct actccagccc ccaagagctg cccagagagg 420
cactactggg ctcagggaaa gctgtgctgc cagatgtgtg agccaggaac attcctcgtg 480
aaggactgtg accagcatag aaaggctgct cagtgtgatc cttgcatacc ggggggtctcc 540 ttctctcctg accaccacac ccggccccac tgtgagagct gtcggcactg taactctggt 600
cttctcgttc gcaactgcac catcactgcc aatgctgagt gtgcctgtcg caatggctgg 660
cagtgcaggg acaaggagtg caccgagtgt gatcctcttc caaacccttc gctgaccgct 720
cggtcgtctc aggccctgag cccacaccct cagcccaccc acttacctta tgtcagtgag 780
atgctggagg ccaggacagc tgggcacatg cagactctgg ctgacttcag gcagctgcct 840
gcccggactc tctctaccca ctggccaccc caaagatccc tgtgcagctc cgattttatt 900
cgcatccttg tgatcttctc tggaatgttc cttgttttca ccctggccgg ggccctgttc 960
ctccataaac gcgtgaagtt cagcaggagc gcagacgccc ccgcgtacca gcagggccag 1020
aaccagctct ataacgagct caatctagga cgaagagagg agtacgatgt tttggacaaa 1080
agacgtggcc gggaccctga gatgggggga aagccgagaa ggaagaaccc tcaggaaggc 1140
ctgtacaatg aactgcagaa agataagatg gcggaggcct acagtgagat tgggatgaaa 1200
ggcgagcgcc ggaggggcaa ggggcacgat ggcctttacc agggtctcag tacagccacc 1260
aaggacacct acgacgccct tcacatgcag gccctgcccc ctcgcggacc gcagtgtact 1320
aattatgctc tcttgaaatt ggctggagat gttgagagca atcccgggcc catgcgcatt 1380
agcaagcccc acctgcggag catcagcatc cagtgctacc tgtgcctgct gctgaacagc 1440
cacttcctga ccgaggccgg catccacgtg ttcatcctgg gctgcttcag cgccggactg 1500
cccaagaccg aggccaactg ggtgaacgtg atcagcgacc tgaagaagat cgaggacctg 1560
atccagagca tgcacatcga cgccaccctg tacaccgaga gcgacgtgca ccccagctgc 1620
aaggtgaccg ccatgaagtg ctttctgctg gaactgcagg tgatcagcct ggaaagcggc 1680
gacgccagca tccacgacac cgtggagaac ctgatcatcc tggccaacaa cagcctgagc 1740
agcaacggca acgtgaccga gagcggctgc aaagagtgcg aggaactgga agagaagaac 1800
atcaaagagt ttctgcagag cttcgtgcac atcgtgcaga tgttcatcaa caccagctga 1860

<210> SEQ ID NO 27
<211> LENGTH: 1866
<212> TYPE: DNA
<213> ORGANISM: Artificial Sequence
<220> FEATURE:
<223> OTHER INFORMATION: Synthetic Polynucleotide

<400> SEQUENCE: 27
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccaccccccac cgccctcaaa 240 gtagacggca tcgcagcttg gatacacgcc gcccacgtga aggctgccga ccccgggggt 300
ggaccatcct ctagactgcc atgctcgagg atgcttctcc tggtgacaag ccttctgctc 360
tgtgagttac cacacccagc attcctcctg atcccagcta caccggctcc gaagtcctgc 420
ccggagcggc attattgggc acagggcaag ttgtgttgtc aaatgtgtga gccgggaacc 480
tttctcgtga aggattgcga tcagcatcgg aaggccgcgc agtgcgaccc atgtatacca 540
ggggtctcat tttccccaga tcaccatacg aggccgcact gtgagtcttg caggcattgt 600
aattccggct tgttggtccg caactgtact attactgcga atgcagagtg tgcttgtaga 660
aacggatggc agtgcaggga caaagaatgt acggagtgtg atccactgcc taaccccagt 720
cttacagcaa gatcttcaca ggccctcagc ccgcatcctc aaccaacaca tcttccttac 780
gtgtcagaaa tgttggaggc gcgaaccgca ggccatatgc agaccctggc ggactttcgg 840
cagctgccag cacgcacact tagtacacac tggccaccac aacgcagctt gtgctcttcc 900
gatttcatcc gcatactggt catcttttct ggaatgttcc ttgtgttcac cctggcagga 960
gccctgttcc ttcaccgcgt gaagttcagc aggagcgcag acgcccccgc gtaccagcag 1020
ggccagaacc agctctataa cgagctcaat ctaggacgaa gagaggagta cgatgttttg 1080
gacaaaagac gtggccggga ccctgagatg gggggaaagc cgagaaggaa gaaccctcag 1140
gaaggcctgt acaatgaact gcagaaagat aagatggcgg aggcctacag tgagattggg 1200
atgaaaggcg agcgccggag gggcaagggg cacgatggcc tttaccaggg tctcagtaca 1260
gccaccaagg acacctacga cgcccttcac atgcaggccc tgccccctcg cggaccgcag 1320
tgtactaatt atgctctctt gaaattggct ggagatgttg agagcaatcc cgggcccatg 1380
cgcattagca agcccccacct gcggagcatc agcatccagt gctacctgtg cctgctgctg 1440
aacagccact tcctgaccga ggccggcatc cacgtgttca tcctgggctg cttcagcgcc 1500
ggactgccca agaccgaggc caactgggtg aacgtgatca gcgacctgaa gaagatcgag 1560
gacctgatcc agagcatgca catcgacgcc accctgtaca ccgagagcga cgtgcacccc 1620
agctgcaagg tgaccgccat gaagtgcttt ctgctggaac tgcaggtgat cagcctggaa 1680
agcggcgacg ccagcatcca cgacaccgtg gagaacctga tcatcctggc caacaacagc 1740
ctgagcagca acggcaacgt gaccgagagc ggctgcaaag agtgcgagga actggaagag 1800
aagaacatca aagagtttct gcagagcttc gtgcacatcg tgcagatgtt catcaacacc 1860
agctga 1866

<210> SEQ ID NO 28
<211> LENGTH: 1980
<212> TYPE: DNA
<213> ORGANISM: Artificial Sequence
<220> FEATURE:
<223> OTHER INFORMATION: Synthetic Polynucleotide

<400> SEQUENCE: 28
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccacccccac cgccctcaaa 240
gtagacggca tcgcagcttg gatacacgcc gcccacgtga aggctgccga ccccgggggt 300
ggaccatcct ctagactgcc atgctcgagg atggcacggc cacatccctg gtggctgtgc 360
gttctgggga ccctggtggg gctctcagct actccagccc ccaagagctg cccagagagg 420
cactactggg ctcagggaaa gctgtgctgc cagatgtgtg agccaggaac attcctcgtg 480
aaggactgtg accagcatag aaaggctgct cagtgtgatc cttgcatacc gggggtctcc 540
ttctctcctg accaccacac ccggccccac tgtgagagct gtcggcactg taactctggt 600
cttctcgttc gcaactgcac catcactgcc aatgctgagt gtgcctgtcg caatggctgg 660
cagtgcaggg acaaggagtg caccgagtgt gatcctcttc caaacccttc gctgaccgct 720
cggtcgtctc aggccctgag cccacaccct cagcccaccc acttacctta tgtcagtgag 780
atgctggagg ccaggacagc tgggcacatg cagactctgg ctgacttcag gcagctgcct 840
gcccggactc tctctaccca ctggccaccc caaagatccc tgtgcagctc cgattttatt 900
cgcatccttg tgatcttctc tggaatgttc cttgttttca ccctggccgg ggccctgttc 960
ctccatagga gtaagaggag caggctcctg cacagtgact acatgaacat gactccccgc 1020
cgccccgggc ccacccgcaa gcattaccag ccctatgccc caccacgcga cttcgcagcc 1080
tatcgctcac gcgtgaagtt cagcaggagc gcagacgccc ccgcgtacca gcagggccag 1140
aaccagctct ataacgagct caatctagga cgaagagagg agtacgatgt tttggacaaa 1200
agacgtggcc gggaccctga gatgggggga aagccgagaa ggaagaaccc tcaggaaggc 1260
ctgtacaatg aactgcagaa agataagatg gcggaggcct acagtgagat tgggatgaaa 1320
ggcgagcgcc ggaggggcaa ggggcacgat ggcctttacc agggtctcag tacagccacc 1380
aaggacacct acgacgccct tcacatgcag gccctgcccc ctcgcggacc gcagtgtact 1440
aattatgctc tcttgaaatt ggctggagat gttgagagca atcccgggcc catgcgcatt 1500
agcaagcccc acctgcggag catcagcatc cagtgctacc tgtgcctgct gctgaacagc 1560
cacttcctga ccgaggccgg catccacgtg ttcatcctgg gctgcttcag cgccggactg 1620
cccaagaccg aggccaactg ggtgaacgtg atcagcgacc tgaagaagat cgaggacctg 1680
atccagagca tgcacatcga cgccaccctg tacaccgaga gcgacgtgca ccccagctgc 1740
aaggtgaccg ccatgaagtg ctttctgctg gaactgcagg tgatcagcct ggaaagcggc 1800
gacgccagca tccacgacac cgtggagaac ctgatcatcc tggccaacaa cagcctgagc 1860
agcaacggca acgtgaccga gagcggctgc aaagagtgcg aggaactgga agagaagaac 1920
atcaaagagt ttctgcagag cttcgtgcac atcgtgcaga tgttcatcaa caccagctga 1980

<210> SEQ ID NO 29
<211> LENGTH: 1989
<212> TYPE: DNA

<213> ORGANISM: Artificial Sequence
<220> FEATURE:
<223> OTHER INFORMATION: Synthetic Polynucleotide

<400> SEQUENCE: 29
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccaccccccac cgccctcaaa 240 gtagacggca tcgcagcttg gatacacgcc gcccacgtga aggctgccga ccccgggggt 300
ggaccatcct ctagactgcc atgctcgagg atgcttctcc tggtgacaag ccttctgctc 360
tgtgagttac cacacccagc attcctcctg atcccagcta caccggctcc gaagtcctgc 420
ccggagcggc attattgggc acagggcaag ttgtgttgtc aaatgtgtga gccgggaacc 480
tttctcgtga aggattgcga tcagcatcgg aaggccgcgc agtgcgaccc atgtatacca 540
ggggtctcat ttccccaga tcaccatacg aggccgcact gtgagtcttg caggcattgt 600
aattccggct tgttggtccg caactgtact attactgcga atgcagagtg tgcttgtaga 660
aacggatggc agtgcaggga caaagaatgt acggagtgtg atccactgcc taaccccagt 720
cttacagcaa gatcttcaca ggccctcagc ccgcatcctc aaccaacaca tcttccttac 780
gtgtcagaaa tgttggaggc gcgaaccgca ggccatatgc agaccctggc ggactttcgg 840
cagctgccag cacgcacact tagtacacac tggccaccac aacgcagctt gtgctcttcc 900
gatttcatcc gcatactggt catcttttct ggaatgttcc ttgtgttcac cctggcagga 960
gccctgttcc ttcacaggag taagaggagc aggctcctgc acagtgacta catgaacatg 1020
actccccgcc gccccgggcc cacccgcaag cattaccagc cctatgcccc accacgcgac 1080
ttcgcagcct atcgctcacg cgtgaagttc agcaggagcg cagacgcccc cgcgtaccag 1140
cagggccaga accagctcta taacgagctc aatctaggac gaagagagga gtacgatgtt 1200
ttggacaaaa gacgtggccg ggaccctgag atggggggaa agccgagaag gaagaaccct 1260
caggaaggcc tgtacaatga actgcagaaa gataagatgg cggaggccta cagtgagatt 1320
gggatgaaag gcgagcgccg gaggggcaag gggcacgatg gcctttacca gggtctcagt 1380
acagccacca aggacaccta cgacgccctt cacatgcagg ccctgccccc tcgcggaccg 1440
cagtgtacta attatgctct cttgaaattg gctggagatg ttgagagcaa tcccgggccc 1500
atgcgcatta gcaagcccca cctgcggagc atcagcatcc agtgctacct gtgcctgctg 1560
ctgaacagcc acttcctgac cgaggccggc atccacgtgt tcatcctggg ctgcttcagc 1620
gccggactgc ccaagaccga ggccaactgg gtgaacgtga tcagcgacct gaagaagatc 1680
gaggacctga tccagagcat gcacatcgac gccaccctgt acaccgagag cgacgtgcac 1740
cccagctgca aggtgaccgc catgaagtgc tttctgctgg aactgcaggt gatcagcctg 1800
gaaagcggcg acgccagcat ccacgacacc gtggagaacc tgatcatcct ggccaacaac 1860
agcctgagca gcaacggcaa cgtgaccgag agcggctgca aagagtgcga ggaactggaa 1920
gagaagaaca tcaaagagtt tctgcagagc ttcgtgcaca tcgtgcagat gttcatcaac 1980
accagctga 1989

<210> SEQ ID NO 30
<211> LENGTH: 1998
<212> TYPE: DNA
<213> ORGANISM: Artificial Sequence
<220> FEATURE:
<223> OTHER INFORMATION: Synthetic Polynucleotide

<400> SEQUENCE: 30

```
atgacaagag ttactaacag cccctctctc caagctcact tacaggctct ctacttagtc     60
cagcacgaag tctggagacc tctggcggca gcctaccaag aacaactgga ccgaccggtg    120
gtacctcacc cttaccgagt cggcgacaca gtgtgggtcc gccgacacca gactaagaac    180
ctagaacctc gctggaaagg accttacaca gtcctgctga ccaccccccac cgccctcaaa    240
gtagacggca tcgcagcttg gatacacgcc gcccacgtga aggctgccga ccccgggggt    300
ggaccatcct ctagactgcc atgctcgagg atggcacggc cacatccctg gtggctgtgc    360
gttctgggga ccctggtggg gctctcagct actccagccc ccaagagctg cccagagagg    420
cactactggg ctcagggaaa gctgtgctgc cagatgtgtg agccaggaac attcctcgtg    480
aaggactgtg accagcatag aaaggctgct cagtgtgatc cttgcatacc gggggtctcc    540
ttctctcctg accaccacac ccggccccac tgtgagagct gtcggcactg taactctggt    600
cttctcgttc gcaactgcac catcactgcc aatgctgagt gtgcctgtcg caatggctgg    660
cagtgcaggg acaaggagtg caccgagtgt gatcctcttc caaacccttc gctgaccgct    720
cggtcgtctc aggccctgag cccacaccct cagcccaccc acttacctta tgtcagtgag    780
atgctggagg ccaggacagc tgggcacatg cagactctgg ctgacttcag gcagctgcct    840
gcccggactc tctctaccca ctggccaccc caaagatccc tgtgcagctc cgattttatt    900
cgcttttggg tgctggtggt ggttggtgga gtcctggctt gctatagctt gctagtaaca    960
gtggccttta ttattttctg ggtgaggagt aagaggagca ggctcctgca cagtgactac   1020
atgaacatga ctccccgccg ccccgggccc acccgcaagc attaccagcc ctatgcccca   1080
ccacgcgact tcgcagccta tcgctcacgc gtgaagttca gcaggagcgc agacgccccc   1140
gcgtaccagc agggccagaa ccagctctat aacgagctca atctaggacg aagagaggag   1200
tacgatgttt tggacaaaag acgtggccgg gaccctgaga tggggggaaa gccgagaagg   1260
aagaaccctc aggaaggcct gtacaatgaa ctgcagaaag ataagatggc ggaggcctac   1320
agtgagattg ggatgaaagg cgagcgccgg aggggcaagg ggcacgatgg cctttaccag   1380
ggtctcagta cagccaccaa ggacacctac gacgcccttc acatgcaggc cctgcccccct   1440
cgcggaccgc agtgtactaa ttatgctctc ttgaaattgg ctggagatgt tgagagcaat   1500
cccgggccca tgcgcattag caagccccac ctgcggagca tcagcatcca gtgctacctg   1560
tgcctgctgc tgaacagcca cttcctgacc gaggccggca tccacgtgtt catcctgggc   1620
tgcttcagcg ccggactgcc caagaccgag gccaactggg tgaacgtgat cagcgacctg   1680
aagaagatcg aggacctgat ccagagcatg cacatcgacg ccaccctgta caccgagagc   1740
gacgtgcacc ccagctgcaa ggtgaccgcc atgaagtgct ttctgctgga actgcaggtg   1800
atcagcctgg aaagcggcga cgccagcatc cacgacaccg tggagaacct gatcatcctg   1860
gccaacaaca gcctgagcag caacggcaac gtgaccgaga gcggctgcaa agagtgcgag   1920
gaactggaag agaagaacat caaagagttt ctgcagagct tcgtgcacat cgtgcagatg   1980
ttcatcaaca ccagctga                                                  1998
```

<210> SEQ ID NO 31
<211> LENGTH: 2007
<212> TYPE: DNA
<213> ORGANISM: Artificial Sequence
<220> FEATURE:

<223> OTHER INFORMATION: Synthetic Polynucleotide

<400> SEQUENCE: 31

```
atgacaagag ttactaacag cccctctctc caagctcact tacaggctct ctacttagtc     60
cagcacgaag tctggagacc tctggcggca gcctaccaag aacaactgga ccgaccggtg    120
gtacctcacc cttaccgagt cggcgacaca gtgtgggtcc gccgacacca gactaagaac    180
ctagaacctc gctggaaagg accttacaca gtcctgctga ccacccccac cgccctcaaa    240
gtagacggca tcgcagcttg gatacacgcc gcccacgtga aggctgccga ccccgggggt    300
ggaccatcct ctagactgcc atgctcgagg atgcttctcc tggtgacaag ccttctgctc    360
tgtgagttac cacacccagc attcctcctg atcccagcta caccggctcc gaagtcctgc    420
ccggagcggc attattgggc acagggcaag ttgtgttgtc aaatgtgtga gccgggaacc    480
tttctcgtga aggattgcga tcagcatcgg aaggccgcgc agtgcgaccc atgtatacca    540
ggggtctcat tttccccaga tcaccatacg aggccgcact gtgagtcttg caggcattgt    600
aattccggct tgttggtccg caactgtact attactgcga atgcagagtg tgcttgtaga    660
aacggatggc agtgcaggga caaagaatgt acggagtgtg atccactgcc taaccccagt    720
cttacagcaa gatcttcaca ggccctcagc ccgcatcctc aaccaacaca tcttccttac    780
gtgtcagaaa tgttggaggc gcgaaccgca ggccatatgc agaccctggc ggactttcgg    840
cagctgccag cacgcacact tagtacacac tggccaccac aacgcagctt gtgctcttcc    900
gatttcatcc gcttttgggt gctggtggtg gttggtggag tcctggcttg ctatagcttg    960
ctagtaacag tggcctttat tattttctgg gtgaggagta agaggagcag gctcctgcac   1020
agtgactaca tgaacatgac tccccgccgc cccgggccca cccgcaagca ttaccagccc   1080
tatgccccac cacgcgactt cgcagcctat cgctcacgcg tgaagttcag caggagcgca   1140
gacgcccccg cgtaccagca gggccagaac cagctctata acgagctcaa tctaggacga   1200
agagaggagt acgatgtttt ggacaaaaga cgtggccggg accctgagat ggggggaaag   1260
ccgagaagga agaaccctca ggaaggcctg tacaatgaac tgcagaaaga taagatggcg   1320
gaggcctaca gtgagattgg gatgaaaggc gagcgccgga ggggcaaggg gcacgatggc   1380
ctttaccagg gtctcagtac agccaccaag gacacctacg acgcccttca catgcaggcc   1440
ctgccccctc gcggaccgca gtgtactaat tatgctctct tgaaattggc tggagatgtt   1500
gagagcaatc ccgggcccat gcgcattagc aagccccacc tgcggagcat cagcatccag   1560
tgctacctgt gcctgctgct gaacagccac ttcctgaccg aggccggcat ccacgtgttc   1620
atcctgggct gcttcagcgc cggactgccc aagaccgagg ccaactgggt gaacgtgatc   1680
agcgacctga agaagatcga ggacctgatc cagagcatgc acatcgacgc caccctgtac   1740
accgagagcg acgtgcaccc cagctgcaag gtgaccgcca tgaagtgctt tctgctggaa   1800
ctgcaggtga tcagcctgga aagcggcgac gccagcatcc acgacaccgt ggagaacctg   1860
atcatcctgg ccaacaacag cctgagcagc aacggcaacg tgaccgagag cggctgcaaa   1920
gagtgcgagg aactggaaga gaagaacatc aaagagtttc tgcagagctt cgtgcacatc   1980
gtgcagatgt tcatcaacac cagctga                                        2007
```

<210> SEQ ID NO 32
<211> LENGTH: 1932
<212> TYPE: DNA
<213> ORGANISM: Artificial Sequence
<220> FEATURE:
<223> OTHER INFORMATION: Synthetic Polynucleotide

<400> SEQUENCE: 32

```
atgacaagag ttactaacag cccctctctc caagctcact tacaggctct ctacttagtc     60
cagcacgaag tctggagacc tctggcggca gcctaccaag aacaactgga ccgaccggtg    120
gtacctcacc cttaccgagt cggcgacaca gtgtgggtcc gccgacacca gactaagaac    180
ctagaacctc gctggaaagg accttacaca gtcctgctga ccaccccccac cgccctcaaa    240
gtagacggca tcgcagcttg gatacacgcc gcccacgtga aggctgccga ccccgggggt    300
ggaccatcct ctagactgcc atgctcgagg atggcacggc cacatccctg gtggctgtgc    360
gttctgggga ccctggtggg gctctcagct actccagccc ccaagagctg cccagagagg    420
cactactggg ctcagggaaa gctgtgctgc cagatgtgtg agccaggaac attcctcgtg    480
aaggactgtg accagcatag aaaggctgct cagtgtgatc cttgcatacc gggggtctcc    540
ttctctcctg accaccacac ccggccccac tgtgagagct gtcggcactg taactctggt    600
cttctcgttc gcaactgcac catcactgcc aatgctgagt gtgcctgtcg caatggctgg    660
cagtgcaggg acaaggagtg caccgagtgt gatcctcttc caaacccttc gctgaccgct    720
cggtcgtctc aggccctgag cccacaccct cagcccaccc acttacctta tgtcagtgag    780
atgctggagg ccaggacagc tgggcacatg cagactctgg ctgacttcag gcagctgcct    840
gcccggactc tctctaccca ctggccaccc caaagatccc tgtgcagctc cgattttatt    900
cgcatactgg tcatcttttc tggaatgttc cttgtgttca ccctggcagg agccctgttc    960
cttcaccttt gcgcacgccc acgccgcagc cccgcccaag aagatggcaa agtctacatc   1020
aacatgccag gcaggggcaa acgcgtgaag ttcagcagga gcgcagacgc cccgcgtac   1080
cagcagggcc agaaccagct ctataacgag ctcaatctag gacgaagaga ggagtacgat   1140
gttttggaca aaagacgtgg ccgggaccct gagatggggg gaaagccgag aaggaagaac   1200
cctcaggaag gcctgtacaa tgaactgcag aaagataaga tggcggaggc ctacagtgag   1260
attgggatga aaggcgagcg ccggaggggc aaggggcacg atggccttta ccagggtctc   1320
agtacagcca ccaaggacac ctacgacgcc cttcacatgc aggccctgcc ccctcgcgga   1380
ccgcagtgta ctaattatgc tctcttgaaa ttggctggag atgttgagag caatcccggg   1440
cccatgcgca ttagcaagcc ccacctgcgg agcatcagca tccagtgcta cctgtgcctg   1500
ctgctgaaca gccacttcct gaccgaggcc ggcatccacg tgttcatcct gggctgcttc   1560
agcgccggac tgcccaagac cgaggccaac tgggtgaacg tgatcagcga cctgaagaag   1620
atcgaggacc tgatccagag catgcacatc gacgccaccc tgtacaccga gagcgacgtg   1680
caccccagct gcaaggtgac cgccatgaag tgctttctgc tggaactgca ggtgatcagc   1740
ctggaaagcg gcgacgccag catccacgac accgtggaga acctgatcat cctggccaac   1800
aacagcctga gcagcaacgg caacgtgacc gagagcggct gcaaagagtg cgaggaactg   1860
gaagagaaga acatcaaaga gtttctgcag agcttcgtgc acatcgtgca gatgttcatc   1920
aacaccagct ga                                                       1932
```

<210> SEQ ID NO 33
<211> LENGTH: 1941
<212> TYPE: DNA
<213> ORGANISM: Artificial Sequence
<220> FEATURE:
<223> OTHER INFORMATION: Synthetic Polynucleotide

<400> SEQUENCE: 33

```
atgacaagag ttactaacag cccctctctc caagctcact tacaggctct ctacttagtc     60

cagcacgaag tctggagacc tctggcggca gcctaccaag aacaactgga ccgaccggtg    120

gtacctcacc cttaccgagt cggcgacaca gtgtgggtcc gccgacacca gactaagaac    180

ctagaacctc gctggaaagg accttacaca gtcctgctga ccaccccccac cgccctcaaa    240

gtagacggca tcgcagcttg gatacacgcc gcccacgtga aggctgccga ccccgggggt    300

ggaccatcct ctagactgcc atgctcgagg atgcttctcc tggtgacaag ccttctgctc    360

tgtgagttac cacacccagc attcctcctg atcccagcta caccggctcc gaagtcctgc    420

ccggagcggc attattgggc acagggcaag ttgtgttgtc aaatgtgtga gccgggaacc    480

tttctcgtga aggattgcga tcagcatcgg aaggccgcgc agtgcgaccc atgtatacca    540

ggggtctcat ttccccaga tcaccatacg aggccgcact gtgagtcttg caggcattgt    600

aattccggct tgttggtccg caactgtact attactgcga atgcagagtg tgcttgtaga    660

aacggatggc agtgcaggga caaagaatgt acggagtgtg atccactgcc taaccccagt    720

cttacagcaa gatcttcaca ggccctcagc ccgcatcctc aaccaacaca tcttccttac    780

gtgtcagaaa tgttggaggc gcgaaccgca ggccatatgc agaccctggc ggactttcgg    840

cagctgccag cacgcacact tagtacacac tggccaccac aacgcagctt gtgctcttcc    900

gatttcatcc gcatactggt catcttttct ggaatgttcc ttgtgttcac cctggcagga    960

gccctgttcc ttcacctttg cgcacgccca cgccgcagcc ccgcccaaga agatggcaaa   1020

gtctacatca acatgccagg caggggcaaa cgcgtgaagt tcagcaggag cgcagacgcc   1080

cccgcgtacc agcagggcca gaaccagctc tataacgagc tcaatctagg acgaagagag   1140

gagtacgatg ttttggacaa aagacgtggc cgggaccctg agatgggggg aaagccgaga   1200

aggaagaacc ctcaggaagg cctgtacaat gaactgcaga aagataagat ggcggaggcc   1260

tacagtgaga ttgggatgaa aggcgagcgc cggaggggca aggggcacga tggcctttac   1320

cagggtctca gtacagccac caaggacacc tacgacgccc ttcacatgca ggccctgccc   1380

cctcgcggac cgcagtgtac taattatgct ctcttgaaat tggctggaga tgttgagagc   1440

aatcccgggc ccatgcgcat tagcaagccc cacctgcgga gcatcagcat ccagtgctac   1500

ctgtgcctgc tgctgaacag ccacttcctg accgaggccg gcatccacgt gttcatcctg   1560

ggctgcttca gcgccggact gcccaagacc gaggccaact gggtgaacgt gatcagcgac   1620

ctgaagaaga tcgaggacct gatccagagc atgcacatcg acgccaccct gtacaccgag   1680

agcgacgtgc accccagctg caaggtgacc gccatgaagt gctttctgct ggaactgcag   1740

gtgatcagcc tggaaagcgg cgacgccagc atccacgaca ccgtggagaa cctgatcatc   1800

ctggccaaca acagcctgag cagcaacggc aacgtgaccg agagcggctg caaagagtgc   1860

gaggaactgg aagagaagaa catcaaagag tttctgcaga gcttcgtgca catcgtgcag   1920

atgttcatca acaccagctg a                                              1941
```

<210> SEQ ID NO 34
<211> LENGTH: 2016
<212> TYPE: DNA
<213> ORGANISM: Artificial Sequence
<220> FEATURE:
<223> OTHER INFORMATION: Synthetic Polynucleotide

<400> SEQUENCE: 34

```
atgacaagag ttactaacag cccctctctc caagctcact tacaggctct ctacttagtc     60

cagcacgaag tctggagacc tctggcggca gcctaccaag aacaactgga ccgaccggtg    120
```

gtacctcacc cttaccgagt cggcgacaca gtgtgggtcc gccgacacca gactaagaac 180
ctagaacctc gctggaaagg accttacaca gtcctgctga ccacccccac cgccctcaaa 240
gtagacggca tcgcagcttg gatacacgcc gcccacgtga aggctgccga ccccgggggt 300
ggaccatcct ctagactgcc atgctcgagg atggcacggc cacatccctg gtggctgtgc 360
gttctgggga ccctggtggg gctctcagct actccagccc ccaagagctg cccagagagg 420
cactactggg ctcagggaaa gctgtgctgc cagatgtgtg agccaggaac attcctcgtg 480
aaggactgtg accagcatag aaaggctgct cagtgtgatc cttgcatacc gggggtctcc 540
ttctctcctg accaccacac ccggccccac tgtgagagct gtcggcactg taactctggt 600
cttctcgttc gcaactgcac catcactgcc aatgctgagt gtgcctgtcg caatggctgg 660
cagtgcaggg acaaggagtg caccgagtgt gatcctcttc caaacccttc gctgaccgct 720
cggtcgtctc aggccctgag cccacaccct cagcccaccc acttacctta tgtcagtgag 780
atgctggagg ccaggacagc tgggcacatg cagactctgg ctgacttcag gcagctgcct 840
gcccggactc tctctaccca ctggccaccc caaagatccc tgtgcagctc cgattttatt 900
cgcatccttg tgatcttctc tggaatgttc cttgttttca ccctggccgg ggccctgttc 960
ctccattact tcctgggccg gctggtccct cgggggcgag ggctgcggga ggcagcgacc 1020
cggaaacagc gtatcactga gaccgagtcg ccttatcagg agctccaggg tcagaggtcg 1080
gatgtctaca gcgacctcaa cacacagagg ccgtattaca aaaaacgcgt gaagttcagc 1140
aggagcgcag acgcccccgc gtaccagcag ggccagaacc agctctataa cgagctcaat 1200
ctaggacgaa gagaggagta cgatgttttg gacaaaagac gtggccggga ccctgagatg 1260
gggggaaagc cgagaaggaa gaaccctcag gaaggcctgt acaatgaact gcagaaagat 1320
aagatggcgg aggcctacag tgagattggg atgaaaggcg agcgccggag gggcaagggg 1380
cacgatggcc tttaccaggg tctcagtaca gccaccaagg acacctacga cgcccttcac 1440
atgcaggccc tgccccctcg cggaccgcag tgtactaatt atgctctctt gaaattggct 1500
ggagatgttg agagcaatcc cgggcccatg cgcattagca agccccacct gcggagcatc 1560
agcatccagt gctacctgtg cctgctgctg aacagccact tcctgaccga ggccggcatc 1620
cacgtgttca tcctgggctg cttcagcgcc ggactgccca agaccgaggc caactgggtg 1680
aacgtgatca gcgacctgaa gaagatcgag gacctgatcc agagcatgca catcgacgcc 1740
accctgtaca ccgagagcga cgtgcacccc agctgcaagg tgaccgccat gaagtgcttt 1800
ctgctggaac tgcaggtgat cagcctggaa agcggcgacg ccagcatcca cgacaccgtg 1860
gagaacctga tcatcctggc caacaacagc ctgagcagca acggcaacgt gaccgagagc 1920
ggctgcaaag agtgcgagga actggaagag aagaacatca aagagtttct gcagagcttc 1980
gtgcacatcg tgcagatgtt catcaacacc agctga 2016

<210> SEQ ID NO 35
<211> LENGTH: 2025
<212> TYPE: DNA
<213> ORGANISM: Artificial Sequence
<220> FEATURE:
<223> OTHER INFORMATION: Synthetic Polynucleotide

<400> SEQUENCE: 35
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180
ctagaacctc gctggaaagg accttacaca gtcctgctga ccacccccac cgccctcaaa 240
gtagacggca tcgcagcttg gatacacgcc gcccacgtga aggctgccga ccccgggggt 300
ggaccatcct ctagactgcc atgctcgagg atgcttctcc tggtgacaag ccttctgctc 360
tgtgagttac cacacccagc attcctcctg atcccagcta caccggctcc gaagtcctgc 420
ccggagcggc attattgggc acagggcaag ttgtgttgtc aaatgtgtga gccgggaacc 480
tttctcgtga aggattgcga tcagcatcgg aaggccgcgc agtgcgaccc atgtatacca 540
ggggtctcat tttccccaga tcaccatacg aggccgcact gtgagtcttg caggcattgt 600
aattccggct tgttggtccg caactgtact attactgcga atgcagagtg tgcttgtaga 660
aacggatggc agtgcaggga caaagaatgt acggagtgtg atccactgcc taaccccagt 720
cttacagcaa gatcttcaca ggccctcagc ccgcatcctc aaccaacaca tcttccttac 780
gtgtcagaaa tgttggaggc gcgaaccgca ggccatatgc agaccctggc ggactttcgg 840
cagctgccag cacgcacact tagtacacac tggccaccac aacgcagctt gtgctcttcc 900
gatttcatcc gcatactggt catcttttct ggaatgttcc ttgtgttcac cctggcagga 960
gccctgttcc ttcactactt cctgggccgg ctggtccctc gggggcgagg ggctgcggag 1020
gcagcgaccc ggaaacagcg tatcactgag accgagtcgc cttatcagga gctccagggt 1080
cagaggtcgg atgtctacag cgacctcaac acacagaggc cgtattacaa aaaacgcgtg 1140
aagttcagca ggagcgcaga cgcccccgcg taccagcagg gccagaacca gctctataac 1200
gagctcaatc taggacgaag agaggagtac gatgttttgg acaaaagacg tggccgggac 1260
cctgagatgg ggggaaagcc gagaaggaag aaccctcagg aaggcctgta caatgaactg 1320
cagaaagata agatggcgga ggcctacagt gagattggga tgaaaggcga gcgccggagg 1380
ggcaaggggc acgatggcct ttaccagggt ctcagtacag ccaccaagga cacctacgac 1440
gcccttcaca tgcaggccct gccccctcgc ggaccgcagt gtactaatta tgctctcttg 1500
aaattggctg gagatgttga gagcaatccc gggcccatgc gcattagcaa gccccacctg 1560
cggagcatca gcatccagtg ctacctgtgc ctgctgctga acagccactt cctgaccgag 1620
gccggcatcc acgtgttcat cctgggctgc ttcagcgccg gactgcccaa gaccgaggcc 1680
aactgggtga acgtgatcag cgacctgaag aagatcgagg acctgatcca gagcatgcac 1740
atcgacgcca ccctgtacac cgagagcgac gtgcacccca gctgcaaggt gaccgccatg 1800
aagtgctttc tgctggaact gcaggtgatc agcctggaaa gcggcgacgc cagcatccac 1860
gacaccgtgg agaacctgat catcctggcc aacaacagcc tgagcagcaa cggcaacgtg 1920
accgagagcg gctgcaaaga gtgcgaggaa ctggaagaga agaacatcaa agagtttctg 1980
cagagcttcg tgcacatcgt gcagatgttc atcaacacca gctga 2025

<210> SEQ ID NO 36
<211> LENGTH: 2013
<212> TYPE: DNA
<213> ORGANISM: Artificial Sequence
<220> FEATURE:
<223> OTHER INFORMATION: Synthetic Polynucleotide

<400> SEQUENCE: 36
atgacaagag ttactaacag cccctctctc caagctcact tacaggctct ctacttagtc 60
cagcacgaag tctggagacc tctggcggca gcctaccaag aacaactgga ccgaccggtg 120
gtacctcacc cttaccgagt cggcgacaca gtgtgggtcc gccgacacca gactaagaac 180

```
ctagaacctc gctggaaagg accttacaca gtcctgctga ccacccccac cgccctcaaa    240

gtagacggca tcgcagcttg gatacacgcc gcccacgtga aggctgccga ccccgggggt    300

ggaccatcct ctagactgcc atgctcgagg atggcacggc cacatccctg gtggctgtgc    360

gttctgggga ccctggtggg gctctcagct actccagccc ccaagagctg cccagagagg    420

cactactggg ctcagggaaa gctgtgctgc cagatgtgtg agccaggaac attcctcgtg    480

aaggactgtg accagcatag aaaggctgct cagtgtgatc cttgcatacc gggggtctcc    540

ttctctcctg accaccacac ccggccccac tgtgagagct gtcggcactg taactctggt    600

cttctcgttc gcaactgcac catcactgcc aatgctgagt gtgcctgtcg caatggctgg    660

cagtgcaggg acaaggagtg caccgagtgt gatcctcttc caaacccttc gctgaccgct    720

cggtcgtctc aggccctgag cccacaccct cagcccaccc acttacctta tgtcagtgag    780

atgctggagg ccaggacagc tgggcacatg cagactctgg ctgacttcag gcagctgcct    840

gcccggactc tctctaccca ctggccaccc caaagatccc tgtgcagctc cgattttatt    900

cgcatccttg tgatcttctc tggaatgttc cttgttttca ccctggccgg ggccctgttc    960

ctccatagcg cgaacgaacg ctgcaaaagc aaagtggtgc cgtgccgcca gaaacagtgg   1020

cgcaccagct ttgatagcaa aaaactggat ctgaactata accattttga aagcatggaa   1080

tggagccatc gcagccgccg cggccgcatt tggggcatga aacgcgtgaa gttcagcagg   1140

agcgcagacg cccccgcgta ccagcagggc cagaaccagc tctataacga gctcaatcta   1200

ggacgaagag aggagtacga tgttttggac aaaagacgtg gccgggaccc tgagatgggg   1260

ggaaagccga gaaggaagaa ccctcaggaa ggcctgtaca atgaactgca gaaagataag   1320

atggcggagg cctacagtga gattgggatg aaaggcgagc gccggagggg caaggggcac   1380

gatggccttt accagggtct cagtacagcc accaaggaca cctacgacgc ccttcacatg   1440

caggccctgc cccctcgcgg accgcagtgt actaattatg ctctcttgaa attggctgga   1500

gatgttgaga gcaatcccgg gcccatgcgc attagcaagc cccacctgcg gagcatcagc   1560

atccagtgct acctgtgcct gctgctgaac agccacttcc tgaccgaggc cggcatccac   1620

gtgttcatcc tgggctgctt cagcgccgga ctgcccaaga ccgaggccaa ctgggtgaac   1680

gtgatcagcg acctgaagaa gatcgaggac ctgatccaga gcatgcacat cgacgccacc   1740

ctgtacaccg agagcgacgt gcaccccagc tgcaaggtga ccgccatgaa gtgctttctg   1800

ctggaactgc aggtgatcag cctggaaagc ggcgacgcca gcatccacga caccgtggag   1860

aacctgatca tcctggccaa caacagcctg agcagcaacg gcaacgtgac cgagagcggc   1920

tgcaaagagt gcgaggaact ggaagagaag aacatcaaag agtttctgca gagcttcgtg   1980

cacatcgtgc agatgttcat caacaccagc tga                                2013
```

<210> SEQ ID NO 37
<211> LENGTH: 2022
<212> TYPE: DNA
<213> ORGANISM: Artificial Sequence
<220> FEATURE:
<223> OTHER INFORMATION: Synthetic Polynucleotide

<400> SEQUENCE: 37

```
atgacaagag ttactaacag cccctctctc caagctcact tacaggctct ctacttagtc     60

cagcacgaag tctggagacc tctggcggca gcctaccaag aacaactgga ccgaccggtg    120

gtacctcacc cttaccgagt cggcgacaca gtgtgggtcc gccgacacca gactaagaac    180
```

```
ctagaacctc gctggaaagg accttacaca gtcctgctga ccacccccac cgccctcaaa    240

gtagacggca tcgcagcttg gatacacgcc gcccacgtga aggctgccga ccccgggggt    300

ggaccatcct ctagactgcc atgctcgagg atgcttctcc tggtgacaag ccttctgctc    360

tgtgagttac cacacccagc attcctcctg atcccagcta caccggctcc gaagtcctgc    420

ccggagcggc attattgggc acagggcaag ttgtgttgtc aaatgtgtga gccgggaacc    480

tttctcgtga aggattgcga tcagcatcgg aaggccgcgc agtgcgaccc atgtatacca    540

ggggtctcat ttccccaga  tcaccatacg aggccgcact gtgagtcttg caggcattgt    600

aattccggct tgttggtccg caactgtact attactgcga atgcagagtg tgcttgtaga    660

aacggatggc agtgcaggga caaagaatgt acggagtgtg atccactgcc taaccccagt    720

cttacagcaa gatcttcaca ggccctcagc ccgcatcctc aaccaacaca tcttccttac    780

gtgtcagaaa tgttggaggc gcgaaccgca ggccatatgc agaccctggc ggactttcgg    840

cagctgccag cacgcacact tagtacacac tggccaccac aacgcagctt gtgctcttcc    900

gatttcatcc gcatactggt catcttttct ggaatgttcc ttgtgttcac cctggcagga    960

gccctgttcc ttcacagcgc gaacgaacgc tgcaaaagca aagtggtgcc gtgccgccag   1020

aaacagtggc gcaccagctt tgatagcaaa aaactggatc tgaactataa ccattttgaa   1080

agcatggaat ggagccatcg cagccgccgc ggccgcattt ggggcatgaa acgcgtgaag   1140

ttcagcagga gcgcagacgc ccccgcgtac cagcagggcc agaaccagct ctataacgag   1200

ctcaatctag gacgaagaga ggagtacgat gttttggaca aaagacgtgg ccgggaccct   1260

gagatggggg gaaagccgag aaggaagaac cctcaggaag gcctgtacaa tgaactgcag   1320

aaagataaga tggcggaggc ctacagtgag attgggatga aaggcgagcg ccggaggggc   1380

aaggggcacg atggccttta ccagggtctc agtacagcca ccaaggacac ctacgacgcc   1440

cttcacatgc aggccctgcc ccctcgcgga ccgcagtgta ctaattatgc tctcttgaaa   1500

ttggctggag atgttgagag caatcccggg cccatgcgca ttagcaagcc ccacctgcgg   1560

agcatcagca tccagtgcta cctgtgcctg ctgctgaaca gccacttcct gaccgaggcc   1620

ggcatccacg tgttcatcct gggctgcttc agcgccggac tgcccaagac cgaggccaac   1680

tgggtgaacg tgatcagcga cctgaagaag atcgaggacc tgatccagag catgcacatc   1740

gacgccaccc tgtacaccga gagcgacgtg caccccagct gcaaggtgac cgccatgaag   1800

tgctttctgc tggaactgca ggtgatcagc ctggaaagcg gcgacgccag catccacgac   1860

accgtggaga acctgatcat cctggccaac aacagcctga gcagcaacgg caacgtgacc   1920

gagagcggct gcaaagagtg cgaggaactg gaagagaaga acatcaaaga gtttctgcag   1980

agcttcgtgc acatcgtgca gatgttcatc aacaccagct ga                      2022
```

<210> SEQ ID NO 38
<211> LENGTH: 218
<212> TYPE: PRT
<213> ORGANISM: Artificial Sequence
<220> FEATURE:
<223> OTHER INFORMATION: Synthetic Polypeptide

<400> SEQUENCE: 38

```
Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
```

```
        35                  40                  45

Leu Val Lys Asp Cys Asp Gln His Arg Lys Ala Ala Gln Cys Asp Pro
    50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
                85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
        115                 120                 125

Thr Ala Arg Ser Ser Gln Ala Leu Ser Pro His Pro Gln Pro Thr His
    130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
                165                 170                 175

His Trp Pro Pro Gln Arg Ser Leu Cys Ser Ser Asp Phe Ile Arg Phe
            180                 185                 190

Trp Val Leu Val Val Val Gly Gly Val Leu Ala Cys Tyr Ser Leu Leu
        195                 200                 205

Val Thr Val Ala Phe Ile Ile Phe Trp Val
    210                 215


<210> SEQ ID NO 39
<211> LENGTH: 667
<212> TYPE: PRT
<213> ORGANISM: Artificial Sequence
<220> FEATURE:
<223> OTHER INFORMATION: Synthetic Polypeptide

<400> SEQUENCE: 39

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
```

```
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Lys Arg Gly Arg Lys Lys Leu Leu
                325                 330                 335

Tyr Ile Phe Lys Gln Pro Phe Met Arg Pro Val Gln Thr Thr Gln Glu
            340                 345                 350

Glu Asp Gly Cys Ser Cys Arg Phe Pro Glu Glu Glu Glu Gly Gly Cys
        355                 360                 365

Glu Leu Lys Arg Val Lys Phe Ser Arg Ser Ala Asp Ala Pro Ala Tyr
    370                 375                 380

Gln Gln Gly Gln Asn Gln Leu Tyr Asn Glu Leu Asn Leu Gly Arg Arg
385                 390                 395                 400

Glu Glu Tyr Asp Val Leu Asp Lys Arg Arg Gly Arg Asp Pro Glu Met
                405                 410                 415

Gly Gly Lys Pro Arg Arg Lys Asn Pro Gln Glu Gly Leu Tyr Asn Glu
            420                 425                 430

Leu Gln Lys Asp Lys Met Ala Glu Ala Tyr Ser Glu Ile Gly Met Lys
        435                 440                 445

Gly Glu Arg Arg Arg Gly Lys Gly His Asp Gly Leu Tyr Gln Gly Leu
    450                 455                 460

Ser Thr Ala Thr Lys Asp Thr Tyr Asp Ala Leu His Met Gln Ala Leu
465                 470                 475                 480

Pro Pro Arg Gly Pro Gln Cys Thr Asn Tyr Ala Leu Leu Lys Leu Ala
                485                 490                 495

Gly Asp Val Glu Ser Asn Pro Gly Pro Met Arg Ile Ser Lys Pro His
            500                 505                 510

Leu Arg Ser Ile Ser Ile Gln Cys Tyr Leu Cys Leu Leu Leu Asn Ser
        515                 520                 525

His Phe Leu Thr Glu Ala Gly Ile His Val Phe Ile Leu Gly Cys Phe
    530                 535                 540

Ser Ala Gly Leu Pro Lys Thr Glu Ala Asn Trp Val Asn Val Ile Ser
545                 550                 555                 560

Asp Leu Lys Lys Ile Glu Asp Leu Ile Gln Ser Met His Ile Asp Ala
                565                 570                 575

Thr Leu Tyr Thr Glu Ser Asp Val His Pro Ser Cys Lys Val Thr Ala
            580                 585                 590

Met Lys Cys Phe Leu Leu Glu Leu Gln Val Ile Ser Leu Glu Ser Gly
        595                 600                 605
```

```
Asp Ala Ser Ile His Asp Thr Val Glu Asn Leu Ile Ile Leu Ala Asn
    610                 615                 620

Asn Ser Leu Ser Ser Asn Gly Asn Val Thr Glu Ser Gly Cys Lys Glu
625                 630                 635                 640

Cys Glu Glu Leu Glu Glu Lys Asn Ile Lys Glu Phe Leu Gln Ser Phe
                645                 650                 655

Val His Ile Val Gln Met Phe Ile Asn Thr Ser
            660                 665


<210> SEQ ID NO 40
<211> LENGTH: 670
<212> TYPE: PRT
<213> ORGANISM: Artificial Sequence
<220> FEATURE:
<223> OTHER INFORMATION: Synthetic Polypeptide

<400> SEQUENCE: 40

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125

Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300
```

```
Phe Trp Val Leu Val Val Val Gly Gly Val Leu Ala Cys Tyr Ser Leu
305                 310                 315                 320

Leu Val Thr Val Ala Phe Ile Ile Phe Trp Val Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Lys Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Pro Gln Cys Thr Asn Tyr Ala Leu Leu
                485                 490                 495

Lys Leu Ala Gly Asp Val Glu Ser Asn Pro Gly Pro Met Arg Ile Ser
            500                 505                 510

Lys Pro His Leu Arg Ser Ile Ser Ile Gln Cys Tyr Leu Cys Leu Leu
        515                 520                 525

Leu Asn Ser His Phe Leu Thr Glu Ala Gly Ile His Val Phe Ile Leu
    530                 535                 540

Gly Cys Phe Ser Ala Gly Leu Pro Lys Thr Glu Ala Asn Trp Val Asn
545                 550                 555                 560

Val Ile Ser Asp Leu Lys Lys Ile Glu Asp Leu Ile Gln Ser Met His
                565                 570                 575

Ile Asp Ala Thr Leu Tyr Thr Glu Ser Asp Val His Pro Ser Cys Lys
            580                 585                 590

Val Thr Ala Met Lys Cys Phe Leu Leu Glu Leu Gln Val Ile Ser Leu
        595                 600                 605

Glu Ser Gly Asp Ala Ser Ile His Asp Thr Val Glu Asn Leu Ile Ile
    610                 615                 620

Leu Ala Asn Asn Ser Leu Ser Ser Asn Gly Asn Val Thr Glu Ser Gly
625                 630                 635                 640

Cys Lys Glu Cys Glu Glu Leu Glu Glu Lys Asn Ile Lys Glu Phe Leu
                645                 650                 655

Gln Ser Phe Val His Ile Val Gln Met Phe Ile Asn Thr Ser
            660                 665                 670
```

<210> SEQ ID NO 41
<211> LENGTH: 649
<212> TYPE: PRT
<213> ORGANISM: Artificial Sequence
<220> FEATURE:
<223> OTHER INFORMATION: Synthetic Polypeptide

<400> SEQUENCE: 41

```
Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Leu Cys Ala Arg Pro Arg Arg Ser
                325                 330                 335

Pro Ala Gln Glu Asp Gly Lys Val Tyr Ile Asn Met Pro Gly Arg Gly
            340                 345                 350

Lys Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
                405                 410                 415
```

```
Lys Asp Lys Met Ala Glu Ala Tyr Ser Glu Ile Gly Met Lys Gly Glu
            420                 425                 430

Arg Arg Arg Gly Lys Gly His Asp Gly Leu Tyr Gln Gly Leu Ser Thr
        435                 440                 445

Ala Thr Lys Asp Thr Tyr Asp Ala Leu His Met Gln Ala Leu Pro Pro
    450                 455                 460

Arg Gly Pro Gln Cys Thr Asn Tyr Ala Leu Leu Lys Leu Ala Gly Asp
465                 470                 475                 480

Val Glu Ser Asn Pro Gly Pro Met Arg Ile Ser Lys Pro His Leu Arg
                485                 490                 495

Ser Ile Ser Ile Gln Cys Tyr Leu Cys Leu Leu Leu Asn Ser His Phe
            500                 505                 510

Leu Thr Glu Ala Gly Ile His Val Phe Ile Leu Gly Cys Phe Ser Ala
        515                 520                 525

Gly Leu Pro Lys Thr Glu Ala Asn Trp Val Asn Val Ile Ser Asp Leu
    530                 535                 540

Lys Lys Ile Glu Asp Leu Ile Gln Ser Met His Ile Asp Ala Thr Leu
545                 550                 555                 560

Tyr Thr Glu Ser Asp Val His Pro Ser Cys Lys Val Thr Ala Met Lys
                565                 570                 575

Cys Phe Leu Leu Glu Leu Gln Val Ile Ser Leu Glu Ser Gly Asp Ala
            580                 585                 590

Ser Ile His Asp Thr Val Glu Asn Leu Ile Ile Leu Ala Asn Asn Ser
        595                 600                 605

Leu Ser Ser Asn Gly Asn Val Thr Glu Ser Gly Cys Lys Glu Cys Glu
    610                 615                 620

Glu Leu Glu Glu Lys Asn Ile Lys Glu Phe Leu Gln Ser Phe Val His
625                 630                 635                 640

Ile Val Gln Met Phe Ile Asn Thr Ser
                645


<210> SEQ ID NO 42
<211> LENGTH: 652
<212> TYPE: PRT
<213> ORGANISM: Artificial Sequence
<220> FEATURE:
<223> OTHER INFORMATION: Synthetic Polypeptide

<400> SEQUENCE: 42

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125
```

```
Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Phe Trp Val Leu Val Val Val Gly Gly Val Leu Ala Cys Tyr Ser Leu
305                 310                 315                 320

Leu Val Thr Val Ala Phe Ile Ile Phe Trp Val Leu Cys Ala Arg Pro
                325                 330                 335

Arg Arg Ser Pro Ala Gln Glu Asp Gly Lys Val Tyr Ile Asn Met Pro
            340                 345                 350

Gly Arg Gly Lys Arg Val Lys Phe Ser Arg Ser Ala Asp Ala Pro Ala
        355                 360                 365

Tyr Gln Gln Gly Gln Asn Gln Leu Tyr Asn Glu Leu Asn Leu Gly Arg
    370                 375                 380

Arg Glu Glu Tyr Asp Val Leu Asp Lys Arg Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
        435                 440                 445

Leu Ser Thr Ala Thr Lys Asp Thr Tyr Asp Ala Leu His Met Gln Ala
    450                 455                 460

Leu Pro Pro Arg Gly Pro Gln Cys Thr Asn Tyr Ala Leu Leu Lys Leu
465                 470                 475                 480

Ala Gly Asp Val Glu Ser Asn Pro Gly Pro Met Arg Ile Ser Lys Pro
                485                 490                 495

His Leu Arg Ser Ile Ser Ile Gln Cys Tyr Leu Cys Leu Leu Leu Asn
            500                 505                 510

Ser His Phe Leu Thr Glu Ala Gly Ile His Val Phe Ile Leu Gly Cys
        515                 520                 525

Phe Ser Ala Gly Leu Pro Lys Thr Glu Ala Asn Trp Val Asn Val Ile
    530                 535                 540

Ser Asp Leu Lys Lys Ile Glu Asp Leu Ile Gln Ser Met His Ile Asp
```

```
545                 550                 555                 560

Ala Thr Leu Tyr Thr Glu Ser Asp Val His Pro Ser Cys Lys Val Thr
                565                 570                 575

Ala Met Lys Cys Phe Leu Leu Glu Leu Gln Val Ile Ser Leu Glu Ser
            580                 585                 590

Gly Asp Ala Ser Ile His Asp Thr Val Glu Asn Leu Ile Ile Leu Ala
        595                 600                 605

Asn Asn Ser Leu Ser Ser Asn Gly Asn Val Thr Glu Ser Gly Cys Lys
    610                 615                 620

Glu Cys Glu Glu Leu Glu Glu Lys Asn Ile Lys Glu Phe Leu Gln Ser
625                 630                 635                 640

Phe Val His Ile Val Gln Met Phe Ile Asn Thr Ser
                645                 650


<210> SEQ ID NO 43
<211> LENGTH: 677
<212> TYPE: PRT
<213> ORGANISM: Artificial Sequence
<220> FEATURE:
<223> OTHER INFORMATION: Synthetic Polypeptide

<400> SEQUENCE: 43

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
```

```
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Tyr Phe Leu Gly Arg Leu Val Pro
                325                 330                 335

Arg Gly Arg Gly Ala Ala Glu Ala Ala Thr Arg Lys Gln Arg Ile Thr
            340                 345                 350

Glu Thr Glu Ser Pro Tyr Gln Glu Leu Gln Gly Gln Arg Ser Asp Val
        355                 360                 365

Tyr Ser Asp Leu Asn Thr Gln Arg Pro Tyr Tyr Lys Lys Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg Gly Pro Gln
                485                 490                 495

Cys Thr Asn Tyr Ala Leu Leu Lys Leu Ala Gly Asp Val Glu Ser Asn
            500                 505                 510

Pro Gly Pro Met Arg Ile Ser Lys Pro His Leu Arg Ser Ile Ser Ile
        515                 520                 525

Gln Cys Tyr Leu Cys Leu Leu Leu Asn Ser His Phe Leu Thr Glu Ala
    530                 535                 540

Gly Ile His Val Phe Ile Leu Gly Cys Phe Ser Ala Gly Leu Pro Lys
545                 550                 555                 560

Thr Glu Ala Asn Trp Val Asn Val Ile Ser Asp Leu Lys Lys Ile Glu
                565                 570                 575

Asp Leu Ile Gln Ser Met His Ile Asp Ala Thr Leu Tyr Thr Glu Ser
            580                 585                 590

Asp Val His Pro Ser Cys Lys Val Thr Ala Met Lys Cys Phe Leu Leu
        595                 600                 605

Glu Leu Gln Val Ile Ser Leu Glu Ser Gly Asp Ala Ser Ile His Asp
    610                 615                 620

Thr Val Glu Asn Leu Ile Ile Leu Ala Asn Asn Ser Leu Ser Ser Asn
625                 630                 635                 640

Gly Asn Val Thr Glu Ser Gly Cys Lys Glu Cys Glu Glu Leu Glu Glu
                645                 650                 655

Lys Asn Ile Lys Glu Phe Leu Gln Ser Phe Val His Ile Val Gln Met
            660                 665                 670

Phe Ile Asn Thr Ser
        675
```

<210> SEQ ID NO 44
<211> LENGTH: 680
<212> TYPE: PRT
<213> ORGANISM: Artificial Sequence
<220> FEATURE:
<223> OTHER INFORMATION: Synthetic Polypeptide

<400> SEQUENCE: 44

```
Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125

Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Phe Trp Val Leu Val Val Val Gly Gly Val Leu Ala Cys Tyr Ser Leu
305                 310                 315                 320

Leu Val Thr Val Ala Phe Ile Ile Phe Trp Val Tyr Phe Leu Gly Arg
                325                 330                 335

Leu Val Pro Arg Gly Arg Gly Ala Ala Glu Ala Ala Thr Arg Lys Gln
            340                 345                 350

Arg Ile Thr Glu Thr Glu Ser Pro Tyr Gln Glu Leu Gln Gly Gln Arg
        355                 360                 365
```

Ser Asp Val Tyr Ser Asp Leu Asn Thr Gln Arg Pro Tyr Tyr Lys Lys
370 375 380

Arg Val Lys Phe Ser Arg Ser Ala Asp Ala Pro Ala Tyr Gln Gln Gly
385 390 395 400

Gln Asn Gln Leu Tyr Asn Glu Leu Asn Leu Gly Arg Arg Glu Glu Tyr
405 410 415

Asp Val Leu Asp Lys Arg Arg Gly Arg Asp Pro Glu Met Gly Gly Lys
420 425 430

Pro Arg Arg Lys Asn Pro Gln Glu Gly Leu Tyr Asn Glu Leu Gln Lys
435 440 445

Asp Lys Met Ala Glu Ala Tyr Ser Glu Ile Gly Met Lys Gly Glu Arg
450 455 460

Arg Arg Gly Lys Gly His Asp Gly Leu Tyr Gln Gly Leu Ser Thr Ala
465 470 475 480

Thr Lys Asp Thr Tyr Asp Ala Leu His Met Gln Ala Leu Pro Pro Arg
485 490 495

Gly Pro Gln Cys Thr Asn Tyr Ala Leu Leu Lys Leu Ala Gly Asp Val
500 505 510

Glu Ser Asn Pro Gly Pro Met Arg Ile Ser Lys Pro His Leu Arg Ser
515 520 525

Ile Ser Ile Gln Cys Tyr Leu Cys Leu Leu Leu Asn Ser His Phe Leu
530 535 540

Thr Glu Ala Gly Ile His Val Phe Ile Leu Gly Cys Phe Ser Ala Gly
545 550 555 560

Leu Pro Lys Thr Glu Ala Asn Trp Val Asn Val Ile Ser Asp Leu Lys
565 570 575

Lys Ile Glu Asp Leu Ile Gln Ser Met His Ile Asp Ala Thr Leu Tyr
580 585 590

Thr Glu Ser Asp Val His Pro Ser Cys Lys Val Thr Ala Met Lys Cys
595 600 605

Phe Leu Leu Glu Leu Gln Val Ile Ser Leu Glu Ser Gly Asp Ala Ser
610 615 620

Ile His Asp Thr Val Glu Asn Leu Ile Ile Leu Ala Asn Asn Ser Leu
625 630 635 640

Ser Ser Asn Gly Asn Val Thr Glu Ser Gly Cys Lys Glu Cys Glu Glu
645 650 655

Leu Glu Glu Lys Asn Ile Lys Glu Phe Leu Gln Ser Phe Val His Ile
660 665 670

Val Gln Met Phe Ile Asn Thr Ser
675 680

<210> SEQ ID NO 45
<211> LENGTH: 676
<212> TYPE: PRT
<213> ORGANISM: Artificial Sequence
<220> FEATURE:
<223> OTHER INFORMATION: Synthetic Polypeptide

<400> SEQUENCE: 45

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

```
Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Ser Ala Asn Glu Arg Cys Lys Ser
                325                 330                 335

Lys Val Val Pro Cys Arg Gln Lys Gln Trp Arg Thr Ser Phe Asp Ser
            340                 345                 350

Lys Lys Leu Asp Leu Asn Tyr Asn His Phe Glu Ser Met Glu Trp Ser
        355                 360                 365

His Arg Ser Arg Arg Gly Arg Ile Trp Gly Met Lys Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460
```

Gly His Asp Gly Leu Tyr Gln Gly Leu Ser Thr Ala Thr Lys Asp Thr
465 470 475 480

Tyr Asp Ala Leu His Met Gln Ala Leu Pro Pro Arg Gly Pro Gln Cys
485 490 495

Thr Asn Tyr Ala Leu Leu Lys Leu Ala Gly Asp Val Glu Ser Asn Pro
500 505 510

Gly Pro Met Arg Ile Ser Lys Pro His Leu Arg Ser Ile Ser Ile Gln
515 520 525

Cys Tyr Leu Cys Leu Leu Leu Asn Ser His Phe Leu Thr Glu Ala Gly
530 535 540

Ile His Val Phe Ile Leu Gly Cys Phe Ser Ala Gly Leu Pro Lys Thr
545 550 555 560

Glu Ala Asn Trp Val Asn Val Ile Ser Asp Leu Lys Lys Ile Glu Asp
565 570 575

Leu Ile Gln Ser Met His Ile Asp Ala Thr Leu Tyr Thr Glu Ser Asp
580 585 590

Val His Pro Ser Cys Lys Val Thr Ala Met Lys Cys Phe Leu Leu Glu
595 600 605

Leu Gln Val Ile Ser Leu Glu Ser Gly Asp Ala Ser Ile His Asp Thr
610 615 620

Val Glu Asn Leu Ile Ile Leu Ala Asn Asn Ser Leu Ser Ser Asn Gly
625 630 635 640

Asn Val Thr Glu Ser Gly Cys Lys Glu Cys Glu Glu Leu Glu Glu Lys
645 650 655

Asn Ile Lys Glu Phe Leu Gln Ser Phe Val His Ile Val Gln Met Phe
660 665 670

Ile Asn Thr Ser
675

<210> SEQ ID NO 46
<211> LENGTH: 679
<212> TYPE: PRT
<213> ORGANISM: Artificial Sequence
<220> FEATURE:
<223> OTHER INFORMATION: Synthetic Polypeptide

<400> SEQUENCE: 46

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

Trp Lys Gly Pro Tyr Thr Val Leu Leu Thr Thr Pro Thr Ala Leu Lys
65 70 75 80

Val Asp Gly Ile Ala Ala Trp Ile His Ala Ala His Val Lys Ala Ala
85 90 95

Asp Pro Gly Gly Gly Pro Ser Ser Arg Leu Pro Cys Ser Arg Met Leu
100 105 110

Leu Leu Val Thr Ser Leu Leu Leu Cys Glu Leu Pro His Pro Ala Phe
115 120 125

Leu Leu Ile Pro Ala Thr Pro Ala Pro Lys Ser Cys Pro Glu Arg His
130 135 140

-continued

```
Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Phe Trp Val Leu Val Val Val Gly Gly Val Leu Ala Cys Tyr Ser Leu
305                 310                 315                 320

Leu Val Thr Val Ala Phe Ile Ile Phe Trp Val Ser Ala Asn Glu Arg
                325                 330                 335

Cys Lys Ser Lys Val Val Pro Cys Arg Gln Lys Gln Trp Arg Thr Ser
            340                 345                 350

Phe Asp Ser Lys Lys Leu Asp Leu Asn Tyr Asn His Phe Glu Ser Met
        355                 360                 365

Glu Trp Ser His Arg Ser Arg Arg Gly Arg Ile Trp Gly Met Lys Arg
    370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
    450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Gly
                485                 490                 495

Pro Gln Cys Thr Asn Tyr Ala Leu Leu Lys Leu Ala Gly Asp Val Glu
            500                 505                 510

Ser Asn Pro Gly Pro Met Arg Ile Ser Lys Pro His Leu Arg Ser Ile
        515                 520                 525

Ser Ile Gln Cys Tyr Leu Cys Leu Leu Leu Asn Ser His Phe Leu Thr
    530                 535                 540

Glu Ala Gly Ile His Val Phe Ile Leu Gly Cys Phe Ser Ala Gly Leu
545                 550                 555                 560

Pro Lys Thr Glu Ala Asn Trp Val Asn Val Ile Ser Asp Leu Lys Lys
```

565 570 575

Ile Glu Asp Leu Ile Gln Ser Met His Ile Asp Ala Thr Leu Tyr Thr
580 585 590

Glu Ser Asp Val His Pro Ser Cys Lys Val Thr Ala Met Lys Cys Phe
595 600 605

Leu Leu Glu Leu Gln Val Ile Ser Leu Glu Ser Gly Asp Ala Ser Ile
610 615 620

His Asp Thr Val Glu Asn Leu Ile Ile Leu Ala Asn Asn Ser Leu Ser
625 630 635 640

Ser Asn Gly Asn Val Thr Glu Ser Gly Cys Lys Glu Cys Glu Glu Leu
645 650 655

Glu Glu Lys Asn Ile Lys Glu Phe Leu Gln Ser Phe Val His Ile Val
660 665 670

Gln Met Phe Ile Asn Thr Ser
675

<210> SEQ ID NO 47
<211> LENGTH: 661
<212> TYPE: PRT
<213> ORGANISM: Artificial Sequence
<220> FEATURE:
<223> OTHER INFORMATION: Synthetic Polypeptide

<400> SEQUENCE: 47

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

Trp Lys Gly Pro Tyr Thr Val Leu Leu Thr Thr Pro Thr Ala Leu Lys
65 70 75 80

Val Asp Gly Ile Ala Ala Trp Ile His Ala Ala His Val Lys Ala Ala
85 90 95

Asp Pro Gly Gly Gly Pro Ser Ser Arg Leu Pro Cys Ser Arg Met Ala
100 105 110

Arg Pro His Pro Trp Trp Leu Cys Val Leu Gly Thr Leu Val Gly Leu
115 120 125

Ser Ala Thr Pro Ala Pro Lys Ser Cys Pro Glu Arg His Tyr Trp Ala
130 135 140

Gln Gly Lys Leu Cys Cys Gln Met Cys Glu Pro Gly Thr Phe Leu Val
145 150 155 160

Lys Asp Cys Asp Gln His Arg Lys Ala Ala Gln Cys Asp Pro Cys Ile
165 170 175

Pro Gly Val Ser Phe Ser Pro Asp His His Thr Arg Pro His Cys Glu
180 185 190

Ser Cys Arg His Cys Asn Ser Gly Leu Leu Val Arg Asn Cys Thr Ile
195 200 205

Thr Ala Asn Ala Glu Cys Ala Cys Arg Asn Gly Trp Gln Cys Arg Asp
210 215 220

Lys Glu Cys Thr Glu Cys Asp Pro Leu Pro Asn Pro Ser Leu Thr Ala
225 230 235 240

Arg Ser Ser Gln Ala Leu Ser Pro His Pro Gln Pro Thr His Leu Pro

```
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Ile Leu Val
    290                 295                 300

Ile Phe Ser Gly Met Phe Leu Val Phe Thr Leu Ala Gly Ala Leu Phe
305                 310                 315                 320

Leu His Lys Arg Gly Arg Lys Lys Leu Leu Tyr Ile Phe Lys Gln Pro
                325                 330                 335

Phe Met Arg Pro Val Gln Thr Thr Gln Glu Glu Asp Gly Cys Ser Cys
            340                 345                 350

Arg Phe Pro Glu Glu Glu Glu Gly Gly Cys Glu Leu Lys Arg Val Lys
        355                 360                 365

Phe Ser Arg Ser Ala Asp Ala Pro Ala Tyr Gln Gln Gly Gln Asn Gln
    370                 375                 380

Leu Tyr Asn Glu Leu Asn Leu Gly Arg Arg Glu Glu Tyr Asp Val Leu
385                 390                 395                 400

Asp Lys Arg Arg Gly Arg Asp Pro Glu Met Gly Gly Lys Pro Arg Arg
                405                 410                 415

Lys Asn Pro Gln Glu Gly Leu Tyr Asn Glu Leu Gln Lys Asp Lys Met
            420                 425                 430

Ala Glu Ala Tyr Ser Glu Ile Gly Met Lys Gly Glu Arg Arg Arg Gly
        435                 440                 445

Lys Gly His Asp Gly Leu Tyr Gln Gly Leu Ser Thr Ala Thr Lys Asp
    450                 455                 460

Thr Tyr Asp Ala Leu His Met Gln Ala Leu Pro Pro Arg Gly Pro Gln
465                 470                 475                 480

Cys Thr Asn Tyr Ala Leu Leu Lys Leu Ala Gly Asp Val Glu Ser Asn
                485                 490                 495

Pro Gly Pro Met Arg Ile Ser Lys Pro His Leu Arg Ser Ile Ser Ile
            500                 505                 510

Gln Cys Tyr Leu Cys Leu Leu Leu Asn Ser His Phe Leu Thr Glu Ala
        515                 520                 525

Gly Ile His Val Phe Ile Leu Gly Cys Phe Ser Ala Gly Leu Pro Lys
    530                 535                 540

Thr Glu Ala Asn Trp Val Asn Val Ile Ser Asp Leu Lys Lys Ile Glu
545                 550                 555                 560

Asp Leu Ile Gln Ser Met His Ile Asp Ala Thr Leu Tyr Thr Glu Ser
                565                 570                 575

Asp Val His Pro Ser Cys Lys Val Thr Ala Met Lys Cys Phe Leu Leu
            580                 585                 590

Glu Leu Gln Val Ile Ser Leu Glu Ser Gly Asp Ala Ser Ile His Asp
        595                 600                 605

Thr Val Glu Asn Leu Ile Ile Leu Ala Asn Asn Ser Leu Ser Ser Asn
    610                 615                 620

Gly Asn Val Thr Glu Ser Gly Cys Lys Glu Cys Glu Glu Leu Glu Glu
625                 630                 635                 640

Lys Asn Ile Lys Glu Phe Leu Gln Ser Phe Val His Ile Val Gln Met
                645                 650                 655

Phe Ile Asn Thr Ser
            660
```

<210> SEQ ID NO 48
<211> LENGTH: 664
<212> TYPE: PRT
<213> ORGANISM: Artificial Sequence
<220> FEATURE:
<223> OTHER INFORMATION: Synthetic Polypeptide

<400> SEQUENCE: 48

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

Trp Lys Gly Pro Tyr Thr Val Leu Leu Thr Thr Pro Thr Ala Leu Lys
65 70 75 80

Val Asp Gly Ile Ala Ala Trp Ile His Ala Ala His Val Lys Ala Ala
85 90 95

Asp Pro Gly Gly Gly Pro Ser Ser Arg Leu Pro Cys Ser Arg Met Leu
100 105 110

Leu Leu Val Thr Ser Leu Leu Leu Cys Glu Leu Pro His Pro Ala Phe
115 120 125

Leu Leu Ile Pro Ala Thr Pro Ala Pro Lys Ser Cys Pro Glu Arg His
130 135 140

Tyr Trp Ala Gln Gly Lys Leu Cys Cys Gln Met Cys Glu Pro Gly Thr
145 150 155 160

Phe Leu Val Lys Asp Cys Asp Gln His Arg Lys Ala Ala Gln Cys Asp
165 170 175

Pro Cys Ile Pro Gly Val Ser Phe Ser Pro Asp His His Thr Arg Pro
180 185 190

His Cys Glu Ser Cys Arg His Cys Asn Ser Gly Leu Leu Val Arg Asn
195 200 205

Cys Thr Ile Thr Ala Asn Ala Glu Cys Ala Cys Arg Asn Gly Trp Gln
210 215 220

Cys Arg Asp Lys Glu Cys Thr Glu Cys Asp Pro Leu Pro Asn Pro Ser
225 230 235 240

Leu Thr Ala Arg Ser Ser Gln Ala Leu Ser Pro His Pro Gln Pro Thr
245 250 255

His Leu Pro Tyr Val Ser Glu Met Leu Glu Ala Arg Thr Ala Gly His
260 265 270

Met Gln Thr Leu Ala Asp Phe Arg Gln Leu Pro Ala Arg Thr Leu Ser
275 280 285

Thr His Trp Pro Pro Gln Arg Ser Leu Cys Ser Ser Asp Phe Ile Arg
290 295 300

Ile Leu Val Ile Phe Ser Gly Met Phe Leu Val Phe Thr Leu Ala Gly
305 310 315 320

Ala Leu Phe Leu His Lys Arg Gly Arg Lys Lys Leu Leu Tyr Ile Phe
325 330 335

Lys Gln Pro Phe Met Arg Pro Val Gln Thr Thr Gln Glu Glu Asp Gly
340 345 350

Cys Ser Cys Arg Phe Pro Glu Glu Glu Glu Gly Gly Cys Glu Leu Lys
355 360 365

Arg Val Lys Phe Ser Arg Ser Ala Asp Ala Pro Ala Tyr Gln Gln Gly
370 375 380

Gln Asn Gln Leu Tyr Asn Glu Leu Asn Leu Gly Arg Arg Glu Glu Tyr
385 390 395 400

Asp Val Leu Asp Lys Arg Arg Gly Arg Asp Pro Glu Met Gly Gly Lys
405 410 415

Pro Arg Arg Lys Asn Pro Gln Glu Gly Leu Tyr Asn Glu Leu Gln Lys
420 425 430

Asp Lys Met Ala Glu Ala Tyr Ser Glu Ile Gly Met Lys Gly Glu Arg
435 440 445

Arg Arg Gly Lys Gly His Asp Gly Leu Tyr Gln Gly Leu Ser Thr Ala
450 455 460

Thr Lys Asp Thr Tyr Asp Ala Leu His Met Gln Ala Leu Pro Pro Arg
465 470 475 480

Gly Pro Gln Cys Thr Asn Tyr Ala Leu Leu Lys Leu Ala Gly Asp Val
485 490 495

Glu Ser Asn Pro Gly Pro Met Arg Ile Ser Lys Pro His Leu Arg Ser
500 505 510

Ile Ser Ile Gln Cys Tyr Leu Cys Leu Leu Leu Asn Ser His Phe Leu
515 520 525

Thr Glu Ala Gly Ile His Val Phe Ile Leu Gly Cys Phe Ser Ala Gly
530 535 540

Leu Pro Lys Thr Glu Ala Asn Trp Val Asn Val Ile Ser Asp Leu Lys
545 550 555 560

Lys Ile Glu Asp Leu Ile Gln Ser Met His Ile Asp Ala Thr Leu Tyr
565 570 575

Thr Glu Ser Asp Val His Pro Ser Cys Lys Val Thr Ala Met Lys Cys
580 585 590

Phe Leu Leu Glu Leu Gln Val Ile Ser Leu Glu Ser Gly Asp Ala Ser
595 600 605

Ile His Asp Thr Val Glu Asn Leu Ile Ile Leu Ala Asn Asn Ser Leu
610 615 620

Ser Ser Asn Gly Asn Val Thr Glu Ser Gly Cys Lys Glu Cys Glu Glu
625 630 635 640

Leu Glu Glu Lys Asn Ile Lys Glu Phe Leu Gln Ser Phe Val His Ile
645 650 655

Val Gln Met Phe Ile Asn Thr Ser
660

<210> SEQ ID NO 49
<211> LENGTH: 619
<212> TYPE: PRT
<213> ORGANISM: Artificial Sequence
<220> FEATURE:
<223> OTHER INFORMATION: Synthetic Polypeptide

<400> SEQUENCE: 49

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

```
Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Ile Leu Val
    290                 295                 300

Ile Phe Ser Gly Met Phe Leu Val Phe Thr Leu Ala Gly Ala Leu Phe
305                 310                 315                 320

Leu His Lys Arg Val Lys Phe Ser Arg Ser Ala Asp Ala Pro Ala Tyr
                325                 330                 335

Gln Gln Gly Gln Asn Gln Leu Tyr Asn Glu Leu Asn Leu Gly Arg Arg
            340                 345                 350

Glu Glu Tyr Asp Val Leu Asp Lys Arg Arg Gly Arg Asp Pro Glu Met
        355                 360                 365

Gly Gly Lys Pro Arg Arg Lys Asn Pro Gln Glu Gly Leu Tyr Asn Glu
    370                 375                 380

Leu Gln Lys Asp Lys Met Ala Glu Ala Tyr Ser Glu Ile Gly Met Lys
385                 390                 395                 400

Gly Glu Arg Arg Arg Gly Lys Gly His Asp Gly Leu Tyr Gln Gly Leu
                405                 410                 415

Ser Thr Ala Thr Lys Asp Thr Tyr Asp Ala Leu His Met Gln Ala Leu
            420                 425                 430

Pro Pro Arg Gly Pro Gln Cys Thr Asn Tyr Ala Leu Leu Lys Leu Ala
        435                 440                 445

Gly Asp Val Glu Ser Asn Pro Gly Pro Met Arg Ile Ser Lys Pro His
    450                 455                 460

Leu Arg Ser Ile Ser Ile Gln Cys Tyr Leu Cys Leu Leu Leu Asn Ser
465                 470                 475                 480
```

His Phe Leu Thr Glu Ala Gly Ile His Val Phe Ile Leu Gly Cys Phe
485 490 495

Ser Ala Gly Leu Pro Lys Thr Glu Ala Asn Trp Val Asn Val Ile Ser
500 505 510

Asp Leu Lys Lys Ile Glu Asp Leu Ile Gln Ser Met His Ile Asp Ala
515 520 525

Thr Leu Tyr Thr Glu Ser Asp Val His Pro Ser Cys Lys Val Thr Ala
530 535 540

Met Lys Cys Phe Leu Leu Glu Leu Gln Val Ile Ser Leu Glu Ser Gly
545 550 555 560

Asp Ala Ser Ile His Asp Thr Val Glu Asn Leu Ile Ile Leu Ala Asn
565 570 575

Asn Ser Leu Ser Ser Asn Gly Asn Val Thr Glu Ser Gly Cys Lys Glu
580 585 590

Cys Glu Glu Leu Glu Glu Lys Asn Ile Lys Glu Phe Leu Gln Ser Phe
595 600 605

Val His Ile Val Gln Met Phe Ile Asn Thr Ser
610 615

<210> SEQ ID NO 50
<211> LENGTH: 622
<212> TYPE: PRT
<213> ORGANISM: Artificial Sequence
<220> FEATURE:
<223> OTHER INFORMATION: Synthetic Polypeptide

<400> SEQUENCE: 50

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

Trp Lys Gly Pro Tyr Thr Val Leu Leu Thr Thr Pro Thr Ala Leu Lys
65 70 75 80

Val Asp Gly Ile Ala Ala Trp Ile His Ala Ala His Val Lys Ala Ala
85 90 95

Asp Pro Gly Gly Gly Pro Ser Ser Arg Leu Pro Cys Ser Arg Met Leu
100 105 110

Leu Leu Val Thr Ser Leu Leu Leu Cys Glu Leu Pro His Pro Ala Phe
115 120 125

Leu Leu Ile Pro Ala Thr Pro Ala Pro Lys Ser Cys Pro Glu Arg His
130 135 140

Tyr Trp Ala Gln Gly Lys Leu Cys Cys Gln Met Cys Glu Pro Gly Thr
145 150 155 160

Phe Leu Val Lys Asp Cys Asp Gln His Arg Lys Ala Ala Gln Cys Asp
165 170 175

Pro Cys Ile Pro Gly Val Ser Phe Ser Pro Asp His His Thr Arg Pro
180 185 190

His Cys Glu Ser Cys Arg His Cys Asn Ser Gly Leu Leu Val Arg Asn
195 200 205

Cys Thr Ile Thr Ala Asn Ala Glu Cys Ala Cys Arg Asn Gly Trp Gln
210 215 220

```
Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Ile Leu Val Ile Phe Ser Gly Met Phe Leu Val Phe Thr Leu Ala Gly
305                 310                 315                 320

Ala Leu Phe Leu His Lys Arg Val Lys Phe Ser Arg Ser Ala Asp Ala
                325                 330                 335

Pro Ala Tyr Gln Gln Gly Gln Asn Gln Leu Tyr Asn Glu Leu Asn Leu
            340                 345                 350

Gly Arg Arg Glu Glu Tyr Asp Val Leu Asp Lys Arg Arg Gly Arg Asp
        355                 360                 365

Pro Glu Met Gly Gly Lys Pro Arg Arg Lys Asn Pro Gln Glu Gly Leu
    370                 375                 380

Tyr Asn Glu Leu Gln Lys Asp Lys Met Ala Glu Ala Tyr Ser Glu Ile
385                 390                 395                 400

Gly Met Lys Gly Glu Arg Arg Arg Gly Lys Gly His Asp Gly Leu Tyr
                405                 410                 415

Gln Gly Leu Ser Thr Ala Thr Lys Asp Thr Tyr Asp Ala Leu His Met
            420                 425                 430

Gln Ala Leu Pro Pro Arg Gly Pro Gln Cys Thr Asn Tyr Ala Leu Leu
        435                 440                 445

Lys Leu Ala Gly Asp Val Glu Ser Asn Pro Gly Pro Met Arg Ile Ser
    450                 455                 460

Lys Pro His Leu Arg Ser Ile Ser Ile Gln Cys Tyr Leu Cys Leu Leu
465                 470                 475                 480

Leu Asn Ser His Phe Leu Thr Glu Ala Gly Ile His Val Phe Ile Leu
                485                 490                 495

Gly Cys Phe Ser Ala Gly Leu Pro Lys Thr Glu Ala Asn Trp Val Asn
            500                 505                 510

Val Ile Ser Asp Leu Lys Lys Ile Glu Asp Leu Ile Gln Ser Met His
        515                 520                 525

Ile Asp Ala Thr Leu Tyr Thr Glu Ser Asp Val His Pro Ser Cys Lys
    530                 535                 540

Val Thr Ala Met Lys Cys Phe Leu Leu Glu Leu Gln Val Ile Ser Leu
545                 550                 555                 560

Glu Ser Gly Asp Ala Ser Ile His Asp Thr Val Glu Asn Leu Ile Ile
                565                 570                 575

Leu Ala Asn Asn Ser Leu Ser Ser Asn Gly Asn Val Thr Glu Ser Gly
            580                 585                 590

Cys Lys Glu Cys Glu Glu Leu Glu Glu Lys Asn Ile Lys Glu Phe Leu
        595                 600                 605

Gln Ser Phe Val His Ile Val Gln Met Phe Ile Asn Thr Ser
    610                 615                 620
```

<210> SEQ ID NO 51
<211> LENGTH: 659
<212> TYPE: PRT

<213> ORGANISM: Artificial Sequence
<220> FEATURE:
<223> OTHER INFORMATION: Synthetic Polypeptide

<400> SEQUENCE: 51

```
Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Ile Leu Val
    290                 295                 300

Ile Phe Ser Gly Met Phe Leu Val Phe Thr Leu Ala Gly Ala Leu Phe
305                 310                 315                 320

Leu His Arg Ser Lys Arg Ser Arg Leu Leu His Ser Asp Tyr Met Asn
                325                 330                 335

Met Thr Pro Arg Arg Pro Gly Pro Thr Arg Lys His Tyr Gln Pro Tyr
            340                 345                 350

Ala Pro Pro Arg Asp Phe Ala Ala Tyr Arg Ser Arg Val Lys Phe Ser
        355                 360                 365

Arg Ser Ala Asp Ala Pro Ala Tyr Gln Gln Gly Gln Asn Gln Leu Tyr
    370                 375                 380

Asn Glu Leu Asn Leu Gly Arg Arg Glu Glu Tyr Asp Val Leu Asp Lys
```

```
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg Gly Pro Gln Cys Thr
465                 470                 475                 480

Asn Tyr Ala Leu Leu Lys Leu Ala Gly Asp Val Glu Ser Asn Pro Gly
                485                 490                 495

Pro Met Arg Ile Ser Lys Pro His Leu Arg Ser Ile Ser Ile Gln Cys
            500                 505                 510

Tyr Leu Cys Leu Leu Leu Asn Ser His Phe Leu Thr Glu Ala Gly Ile
        515                 520                 525

His Val Phe Ile Leu Gly Cys Phe Ser Ala Gly Leu Pro Lys Thr Glu
    530                 535                 540

Ala Asn Trp Val Asn Val Ile Ser Asp Leu Lys Lys Ile Glu Asp Leu
545                 550                 555                 560

Ile Gln Ser Met His Ile Asp Ala Thr Leu Tyr Thr Glu Ser Asp Val
                565                 570                 575

His Pro Ser Cys Lys Val Thr Ala Met Lys Cys Phe Leu Leu Glu Leu
            580                 585                 590

Gln Val Ile Ser Leu Glu Ser Gly Asp Ala Ser Ile His Asp Thr Val
        595                 600                 605

Glu Asn Leu Ile Ile Leu Ala Asn Asn Ser Leu Ser Ser Asn Gly Asn
    610                 615                 620

Val Thr Glu Ser Gly Cys Lys Glu Cys Glu Glu Leu Glu Glu Lys Asn
625                 630                 635                 640

Ile Lys Glu Phe Leu Gln Ser Phe Val His Ile Val Gln Met Phe Ile
                645                 650                 655

Asn Thr Ser


<210> SEQ ID NO 52
<211> LENGTH: 662
<212> TYPE: PRT
<213> ORGANISM: Artificial Sequence
<220> FEATURE:
<223> OTHER INFORMATION: Synthetic Polypeptide

<400> SEQUENCE: 52

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95
```

```
Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125

Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Ile Leu Val Ile Phe Ser Gly Met Phe Leu Val Phe Thr Leu Ala Gly
305                 310                 315                 320

Ala Leu Phe Leu His Arg Ser Lys Arg Ser Arg Leu Leu His Ser Asp
                325                 330                 335

Tyr Met Asn Met Thr Pro Arg Arg Pro Gly Pro Thr Arg Lys His Tyr
            340                 345                 350

Gln Pro Tyr Ala Pro Pro Arg Asp Phe Ala Ala Tyr Arg Ser Arg Val
        355                 360                 365

Lys Phe Ser Arg Ser Ala Asp Ala Pro Ala Tyr Gln Gln Gly Gln Asn
    370                 375                 380

Gln Leu Tyr Asn Glu Leu Asn Leu Gly Arg Arg Glu Glu Tyr Asp Val
385                 390                 395                 400

Leu Asp Lys Arg Arg Gly Arg Asp Pro Glu Met Gly Gly Lys Pro Arg
                405                 410                 415

Arg Lys Asn Pro Gln Glu Gly Leu Tyr Asn Glu Leu Gln Lys Asp Lys
            420                 425                 430

Met Ala Glu Ala Tyr Ser Glu Ile Gly Met Lys Gly Glu Arg Arg Arg
        435                 440                 445

Gly Lys Gly His Asp Gly Leu Tyr Gln Gly Leu Ser Thr Ala Thr Lys
    450                 455                 460

Asp Thr Tyr Asp Ala Leu His Met Gln Ala Leu Pro Pro Arg Gly Pro
465                 470                 475                 480

Gln Cys Thr Asn Tyr Ala Leu Leu Lys Leu Ala Gly Asp Val Glu Ser
                485                 490                 495

Asn Pro Gly Pro Met Arg Ile Ser Lys Pro His Leu Arg Ser Ile Ser
            500                 505                 510
```

```
Ile Gln Cys Tyr Leu Cys Leu Leu Leu Asn Ser His Phe Leu Thr Glu
        515                 520                 525

Ala Gly Ile His Val Phe Ile Leu Gly Cys Phe Ser Ala Gly Leu Pro
    530                 535                 540

Lys Thr Glu Ala Asn Trp Val Asn Val Ile Ser Asp Leu Lys Lys Ile
545                 550                 555                 560

Glu Asp Leu Ile Gln Ser Met His Ile Asp Ala Thr Leu Tyr Thr Glu
                565                 570                 575

Ser Asp Val His Pro Ser Cys Lys Val Thr Ala Met Lys Cys Phe Leu
            580                 585                 590

Leu Glu Leu Gln Val Ile Ser Leu Glu Ser Gly Asp Ala Ser Ile His
        595                 600                 605

Asp Thr Val Glu Asn Leu Ile Ile Leu Ala Asn Asn Ser Leu Ser Ser
    610                 615                 620

Asn Gly Asn Val Thr Glu Ser Gly Cys Lys Glu Cys Glu Glu Leu Glu
625                 630                 635                 640

Glu Lys Asn Ile Lys Glu Phe Leu Gln Ser Phe Val His Ile Val Gln
                645                 650                 655

Met Phe Ile Asn Thr Ser
            660
```

<210> SEQ ID NO 53
<211> LENGTH: 665
<212> TYPE: PRT
<213> ORGANISM: Artificial Sequence
<220> FEATURE:
<223> OTHER INFORMATION: Synthetic Polypeptide

<400> SEQUENCE: 53

```
Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205
```

```
Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Phe Trp Val
    290                 295                 300

Leu Val Val Val Gly Gly Val Leu Ala Cys Tyr Ser Leu Leu Val Thr
305                 310                 315                 320

Val Ala Phe Ile Ile Phe Trp Val Arg Ser Lys Arg Ser Arg Leu Leu
                325                 330                 335

His Ser Asp Tyr Met Asn Met Thr Pro Arg Arg Pro Gly Pro Thr Arg
            340                 345                 350

Lys His Tyr Gln Pro Tyr Ala Pro Pro Arg Asp Phe Ala Ala Tyr Arg
        355                 360                 365

Ser Arg Val Lys Phe Ser Arg Ser Ala Asp Ala Pro Ala Tyr Gln Gln
    370                 375                 380

Gly Gln Asn Gln Leu Tyr Asn Glu Leu Asn Leu Gly Arg Arg Glu Glu
385                 390                 395                 400

Tyr Asp Val Leu Asp Lys Arg Arg Gly Arg Asp Pro Glu Met Gly Gly
                405                 410                 415

Lys Pro Arg Arg Lys Asn Pro Gln Glu Gly Leu Tyr Asn Glu Leu Gln
            420                 425                 430

Lys Asp Lys Met Ala Glu Ala Tyr Ser Glu Ile Gly Met Lys Gly Glu
        435                 440                 445

Arg Arg Arg Gly Lys Gly His Asp Gly Leu Tyr Gln Gly Leu Ser Thr
    450                 455                 460

Ala Thr Lys Asp Thr Tyr Asp Ala Leu His Met Gln Ala Leu Pro Pro
465                 470                 475                 480

Arg Gly Pro Gln Cys Thr Asn Tyr Ala Leu Leu Lys Leu Ala Gly Asp
                485                 490                 495

Val Glu Ser Asn Pro Gly Pro Met Arg Ile Ser Lys Pro His Leu Arg
            500                 505                 510

Ser Ile Ser Ile Gln Cys Tyr Leu Cys Leu Leu Leu Asn Ser His Phe
        515                 520                 525

Leu Thr Glu Ala Gly Ile His Val Phe Ile Leu Gly Cys Phe Ser Ala
    530                 535                 540

Gly Leu Pro Lys Thr Glu Ala Asn Trp Val Asn Val Ile Ser Asp Leu
545                 550                 555                 560

Lys Lys Ile Glu Asp Leu Ile Gln Ser Met His Ile Asp Ala Thr Leu
                565                 570                 575

Tyr Thr Glu Ser Asp Val His Pro Ser Cys Lys Val Thr Ala Met Lys
            580                 585                 590

Cys Phe Leu Leu Glu Leu Gln Val Ile Ser Leu Glu Ser Gly Asp Ala
        595                 600                 605

Ser Ile His Asp Thr Val Glu Asn Leu Ile Ile Leu Ala Asn Asn Ser
    610                 615                 620

Leu Ser Ser Asn Gly Asn Val Thr Glu Ser Gly Cys Lys Glu Cys Glu
```

625 630 635 640

Glu Leu Glu Glu Lys Asn Ile Lys Glu Phe Leu Gln Ser Phe Val His
645 650 655

Ile Val Gln Met Phe Ile Asn Thr Ser
660 665

<210> SEQ ID NO 54
<211> LENGTH: 668
<212> TYPE: PRT
<213> ORGANISM: Artificial Sequence
<220> FEATURE:
<223> OTHER INFORMATION: Synthetic Polypeptide

<400> SEQUENCE: 54

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

Trp Lys Gly Pro Tyr Thr Val Leu Leu Thr Thr Pro Thr Ala Leu Lys
65 70 75 80

Val Asp Gly Ile Ala Ala Trp Ile His Ala Ala His Val Lys Ala Ala
85 90 95

Asp Pro Gly Gly Gly Pro Ser Ser Arg Leu Pro Cys Ser Arg Met Leu
100 105 110

Leu Leu Val Thr Ser Leu Leu Leu Cys Glu Leu Pro His Pro Ala Phe
115 120 125

Leu Leu Ile Pro Ala Thr Pro Ala Pro Lys Ser Cys Pro Glu Arg His
130 135 140

Tyr Trp Ala Gln Gly Lys Leu Cys Cys Gln Met Cys Glu Pro Gly Thr
145 150 155 160

Phe Leu Val Lys Asp Cys Asp Gln His Arg Lys Ala Ala Gln Cys Asp
165 170 175

Pro Cys Ile Pro Gly Val Ser Phe Ser Pro Asp His His Thr Arg Pro
180 185 190

His Cys Glu Ser Cys Arg His Cys Asn Ser Gly Leu Leu Val Arg Asn
195 200 205

Cys Thr Ile Thr Ala Asn Ala Glu Cys Ala Cys Arg Asn Gly Trp Gln
210 215 220

Cys Arg Asp Lys Glu Cys Thr Glu Cys Asp Pro Leu Pro Asn Pro Ser
225 230 235 240

Leu Thr Ala Arg Ser Ser Gln Ala Leu Ser Pro His Pro Gln Pro Thr
245 250 255

His Leu Pro Tyr Val Ser Glu Met Leu Glu Ala Arg Thr Ala Gly His
260 265 270

Met Gln Thr Leu Ala Asp Phe Arg Gln Leu Pro Ala Arg Thr Leu Ser
275 280 285

Thr His Trp Pro Pro Gln Arg Ser Leu Cys Ser Ser Asp Phe Ile Arg
290 295 300

Phe Trp Val Leu Val Val Val Gly Gly Val Leu Ala Cys Tyr Ser Leu
305 310 315 320

Leu Val Thr Val Ala Phe Ile Ile Phe Trp Val Arg Ser Lys Arg Ser

```
                325                 330                 335

Arg Leu Leu His Ser Asp Tyr Met Asn Met Thr Pro Arg Arg Pro Gly
            340                 345                 350

Pro Thr Arg Lys His Tyr Gln Pro Tyr Ala Pro Pro Arg Asp Phe Ala
        355                 360                 365

Ala Tyr Arg Ser Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg Gly Pro Gln Cys Thr Asn Tyr Ala Leu Leu Lys Leu
                485                 490                 495

Ala Gly Asp Val Glu Ser Asn Pro Gly Pro Met Arg Ile Ser Lys Pro
            500                 505                 510

His Leu Arg Ser Ile Ser Ile Gln Cys Tyr Leu Cys Leu Leu Leu Asn
        515                 520                 525

Ser His Phe Leu Thr Glu Ala Gly Ile His Val Phe Ile Leu Gly Cys
    530                 535                 540

Phe Ser Ala Gly Leu Pro Lys Thr Glu Ala Asn Trp Val Asn Val Ile
545                 550                 555                 560

Ser Asp Leu Lys Lys Ile Glu Asp Leu Ile Gln Ser Met His Ile Asp
                565                 570                 575

Ala Thr Leu Tyr Thr Glu Ser Asp Val His Pro Ser Cys Lys Val Thr
            580                 585                 590

Ala Met Lys Cys Phe Leu Leu Glu Leu Gln Val Ile Ser Leu Glu Ser
        595                 600                 605

Gly Asp Ala Ser Ile His Asp Thr Val Glu Asn Leu Ile Ile Leu Ala
    610                 615                 620

Asn Asn Ser Leu Ser Ser Asn Gly Asn Val Thr Glu Ser Gly Cys Lys
625                 630                 635                 640

Glu Cys Glu Glu Leu Glu Glu Lys Asn Ile Lys Glu Phe Leu Gln Ser
                645                 650                 655

Phe Val His Ile Val Gln Met Phe Ile Asn Thr Ser
            660                 665


<210> SEQ ID NO 55
<211> LENGTH: 643
<212> TYPE: PRT
<213> ORGANISM: Artificial Sequence
<220> FEATURE:
<223> OTHER INFORMATION: Synthetic Polypeptide

<400> SEQUENCE: 55

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
```

```
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Ile Leu Val
    290                 295                 300

Ile Phe Ser Gly Met Phe Leu Val Phe Thr Leu Ala Gly Ala Leu Phe
305                 310                 315                 320

Leu His Leu Cys Ala Arg Pro Arg Arg Ser Pro Ala Gln Glu Asp Gly
                325                 330                 335

Lys Val Tyr Ile Asn Met Pro Gly Arg Gly Lys Arg Val Lys Phe Ser
            340                 345                 350

Arg Ser Ala Asp Ala Pro Ala Tyr Gln Gln Gly Gln Asn Gln Leu Tyr
        355                 360                 365

Asn Glu Leu Asn Leu Gly Arg Arg Glu Glu Tyr Asp Val Leu Asp Lys
    370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
        435                 440                 445
```

```
Asp Ala Leu His Met Gln Ala Leu Pro Pro Arg Gly Pro Gln Cys Thr
    450                 455                 460

Asn Tyr Ala Leu Leu Lys Leu Ala Gly Asp Val Glu Ser Asn Pro Gly
465                 470                 475                 480

Pro Met Arg Ile Ser Lys Pro His Leu Arg Ser Ile Ser Ile Gln Cys
                485                 490                 495

Tyr Leu Cys Leu Leu Leu Asn Ser His Phe Leu Thr Glu Ala Gly Ile
            500                 505                 510

His Val Phe Ile Leu Gly Cys Phe Ser Ala Gly Leu Pro Lys Thr Glu
        515                 520                 525

Ala Asn Trp Val Asn Val Ile Ser Asp Leu Lys Lys Ile Glu Asp Leu
    530                 535                 540

Ile Gln Ser Met His Ile Asp Ala Thr Leu Tyr Thr Glu Ser Asp Val
545                 550                 555                 560

His Pro Ser Cys Lys Val Thr Ala Met Lys Cys Phe Leu Leu Glu Leu
                565                 570                 575

Gln Val Ile Ser Leu Glu Ser Gly Asp Ala Ser Ile His Asp Thr Val
            580                 585                 590

Glu Asn Leu Ile Ile Leu Ala Asn Asn Ser Leu Ser Ser Asn Gly Asn
        595                 600                 605

Val Thr Glu Ser Gly Cys Lys Glu Cys Glu Glu Leu Glu Glu Lys Asn
    610                 615                 620

Ile Lys Glu Phe Leu Gln Ser Phe Val His Ile Val Gln Met Phe Ile
625                 630                 635                 640

Asn Thr Ser


<210> SEQ ID NO 56
<211> LENGTH: 646
<212> TYPE: PRT
<213> ORGANISM: Artificial Sequence
<220> FEATURE:
<223> OTHER INFORMATION: Synthetic Polypeptide

<400> SEQUENCE: 56

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125

Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160
```

```
Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Ile Leu Val Ile Phe Ser Gly Met Phe Leu Val Phe Thr Leu Ala Gly
305                 310                 315                 320

Ala Leu Phe Leu His Leu Cys Ala Arg Pro Arg Arg Ser Pro Ala Gln
                325                 330                 335

Glu Asp Gly Lys Val Tyr Ile Asn Met Pro Gly Arg Gly Lys Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445

Asp Thr Tyr Asp Ala Leu His Met Gln Ala Leu Pro Pro Arg Gly Pro
    450                 455                 460

Gln Cys Thr Asn Tyr Ala Leu Leu Lys Leu Ala Gly Asp Val Glu Ser
465                 470                 475                 480

Asn Pro Gly Pro Met Arg Ile Ser Lys Pro His Leu Arg Ser Ile Ser
                485                 490                 495

Ile Gln Cys Tyr Leu Cys Leu Leu Leu Asn Ser His Phe Leu Thr Glu
            500                 505                 510

Ala Gly Ile His Val Phe Ile Leu Gly Cys Phe Ser Ala Gly Leu Pro
        515                 520                 525

Lys Thr Glu Ala Asn Trp Val Asn Val Ile Ser Asp Leu Lys Lys Ile
    530                 535                 540

Glu Asp Leu Ile Gln Ser Met His Ile Asp Ala Thr Leu Tyr Thr Glu
545                 550                 555                 560

Ser Asp Val His Pro Ser Cys Lys Val Thr Ala Met Lys Cys Phe Leu
                565                 570                 575

Leu Glu Leu Gln Val Ile Ser Leu Glu Ser Gly Asp Ala Ser Ile His
```

```
            580                 585                 590

Asp Thr Val Glu Asn Leu Ile Ile Leu Ala Asn Asn Ser Leu Ser Ser
        595                 600                 605

Asn Gly Asn Val Thr Glu Ser Gly Cys Lys Glu Cys Glu Glu Leu Glu
    610                 615                 620

Glu Lys Asn Ile Lys Glu Phe Leu Gln Ser Phe Val His Ile Val Gln
625                 630                 635                 640

Met Phe Ile Asn Thr Ser
                645


<210> SEQ ID NO 57
<211> LENGTH: 671
<212> TYPE: PRT
<213> ORGANISM: Artificial Sequence
<220> FEATURE:
<223> OTHER INFORMATION: Synthetic Polypeptide

<400> SEQUENCE: 57

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Ile Leu Val
```

```
    290                 295                 300

Ile Phe Ser Gly Met Phe Leu Val Phe Thr Leu Ala Gly Ala Leu Phe
305                 310                 315                 320

Leu His Tyr Phe Leu Gly Arg Leu Val Pro Arg Gly Arg Gly Ala Ala
                325                 330                 335

Glu Ala Ala Thr Arg Lys Gln Arg Ile Thr Glu Thr Glu Ser Pro Tyr
            340                 345                 350

Gln Glu Leu Gln Gly Gln Arg Ser Asp Val Tyr Ser Asp Leu Asn Thr
        355                 360                 365

Gln Arg Pro Tyr Tyr Lys Lys Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg Gly Pro Gln Cys Thr Asn Tyr Ala Leu
                485                 490                 495

Leu Lys Leu Ala Gly Asp Val Glu Ser Asn Pro Gly Pro Met Arg Ile
            500                 505                 510

Ser Lys Pro His Leu Arg Ser Ile Ser Ile Gln Cys Tyr Leu Cys Leu
        515                 520                 525

Leu Leu Asn Ser His Phe Leu Thr Glu Ala Gly Ile His Val Phe Ile
    530                 535                 540

Leu Gly Cys Phe Ser Ala Gly Leu Pro Lys Thr Glu Ala Asn Trp Val
545                 550                 555                 560

Asn Val Ile Ser Asp Leu Lys Lys Ile Glu Asp Leu Ile Gln Ser Met
                565                 570                 575

His Ile Asp Ala Thr Leu Tyr Thr Glu Ser Asp Val His Pro Ser Cys
            580                 585                 590

Lys Val Thr Ala Met Lys Cys Phe Leu Leu Glu Leu Gln Val Ile Ser
        595                 600                 605

Leu Glu Ser Gly Asp Ala Ser Ile His Asp Thr Val Glu Asn Leu Ile
    610                 615                 620

Ile Leu Ala Asn Asn Ser Leu Ser Ser Asn Gly Asn Val Thr Glu Ser
625                 630                 635                 640

Gly Cys Lys Glu Cys Glu Glu Leu Glu Glu Lys Asn Ile Lys Glu Phe
                645                 650                 655

Leu Gln Ser Phe Val His Ile Val Gln Met Phe Ile Asn Thr Ser
            660                 665                 670
```

<210> SEQ ID NO 58
<211> LENGTH: 674
<212> TYPE: PRT
<213> ORGANISM: Artificial Sequence
<220> FEATURE:
<223> OTHER INFORMATION: Synthetic Polypeptide

<400> SEQUENCE: 58

```
Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125

Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Ile Leu Val Ile Phe Ser Gly Met Phe Leu Val Phe Thr Leu Ala Gly
305                 310                 315                 320

Ala Leu Phe Leu His Tyr Phe Leu Gly Arg Leu Val Pro Arg Gly Arg
                325                 330                 335

Gly Ala Ala Glu Ala Ala Thr Arg Lys Gln Arg Ile Thr Glu Thr Glu
            340                 345                 350

Ser Pro Tyr Gln Glu Leu Gln Gly Gln Arg Ser Asp Val Tyr Ser Asp
        355                 360                 365

Leu Asn Thr Gln Arg Pro Tyr Tyr Lys Lys Arg Val Lys Phe Ser Arg
    370                 375                 380

Ser Ala Asp Ala Pro Ala Tyr Gln Gln Gly Gln Asn Gln Leu Tyr Asn
385                 390                 395                 400

Glu Leu Asn Leu Gly Arg Arg Glu Glu Tyr Asp Val Leu Asp Lys Arg
                405                 410                 415
```

Arg Gly Arg Asp Pro Glu Met Gly Gly Lys Pro Arg Arg Lys Asn Pro
420 425 430

Gln Glu Gly Leu Tyr Asn Glu Leu Gln Lys Asp Lys Met Ala Glu Ala
435 440 445

Tyr Ser Glu Ile Gly Met Lys Gly Glu Arg Arg Arg Gly Lys Gly His
450 455 460

Asp Gly Leu Tyr Gln Gly Leu Ser Thr Ala Thr Lys Asp Thr Tyr Asp
465 470 475 480

Ala Leu His Met Gln Ala Leu Pro Pro Arg Gly Pro Gln Cys Thr Asn
485 490 495

Tyr Ala Leu Leu Lys Leu Ala Gly Asp Val Glu Ser Asn Pro Gly Pro
500 505 510

Met Arg Ile Ser Lys Pro His Leu Arg Ser Ile Ser Ile Gln Cys Tyr
515 520 525

Leu Cys Leu Leu Leu Asn Ser His Phe Leu Thr Glu Ala Gly Ile His
530 535 540

Val Phe Ile Leu Gly Cys Phe Ser Ala Gly Leu Pro Lys Thr Glu Ala
545 550 555 560

Asn Trp Val Asn Val Ile Ser Asp Leu Lys Lys Ile Glu Asp Leu Ile
565 570 575

Gln Ser Met His Ile Asp Ala Thr Leu Tyr Thr Glu Ser Asp Val His
580 585 590

Pro Ser Cys Lys Val Thr Ala Met Lys Cys Phe Leu Leu Glu Leu Gln
595 600 605

Val Ile Ser Leu Glu Ser Gly Asp Ala Ser Ile His Asp Thr Val Glu
610 615 620

Asn Leu Ile Ile Leu Ala Asn Asn Ser Leu Ser Ser Asn Gly Asn Val
625 630 635 640

Thr Glu Ser Gly Cys Lys Glu Cys Glu Glu Leu Glu Glu Lys Asn Ile
645 650 655

Lys Glu Phe Leu Gln Ser Phe Val His Ile Val Gln Met Phe Ile Asn
660 665 670

Thr Ser

<210> SEQ ID NO 59
<211> LENGTH: 670
<212> TYPE: PRT
<213> ORGANISM: Artificial Sequence
<220> FEATURE:
<223> OTHER INFORMATION: Synthetic Polypeptide

<400> SEQUENCE: 59

Met Thr Arg Val Thr Asn Ser Pro Ser Leu Gln Ala His Leu Gln Ala
1 5 10 15

Leu Tyr Leu Val Gln His Glu Val Trp Arg Pro Leu Ala Ala Ala Tyr
20 25 30

Gln Glu Gln Leu Asp Arg Pro Val Val Pro His Pro Tyr Arg Val Gly
35 40 45

Asp Thr Val Trp Val Arg Arg His Gln Thr Lys Asn Leu Glu Pro Arg
50 55 60

Trp Lys Gly Pro Tyr Thr Val Leu Leu Thr Thr Pro Thr Ala Leu Lys
65 70 75 80

Val Asp Gly Ile Ala Ala Trp Ile His Ala Ala His Val Lys Ala Ala
85 90 95

```
Asp Pro Gly Gly Gly Pro Ser Ser Arg Leu Pro Cys Ser Arg Met Ala
            100                 105                 110

Arg Pro His Pro Trp Trp Leu Cys Val Leu Gly Thr Leu Val Gly Leu
        115                 120                 125

Ser Ala Thr Pro Ala Pro Lys Ser Cys Pro Glu Arg His Tyr Trp Ala
    130                 135                 140

Gln Gly Lys Leu Cys Cys Gln Met Cys Glu Pro Gly Thr Phe Leu Val
145                 150                 155                 160

Lys Asp Cys Asp Gln His Arg Lys Ala Ala Gln Cys Asp Pro Cys Ile
                165                 170                 175

Pro Gly Val Ser Phe Ser Pro Asp His His Thr Arg Pro His Cys Glu
            180                 185                 190

Ser Cys Arg His Cys Asn Ser Gly Leu Leu Val Arg Asn Cys Thr Ile
        195                 200                 205

Thr Ala Asn Ala Glu Cys Ala Cys Arg Asn Gly Trp Gln Cys Arg Asp
    210                 215                 220

Lys Glu Cys Thr Glu Cys Asp Pro Leu Pro Asn Pro Ser Leu Thr Ala
225                 230                 235                 240

Arg Ser Ser Gln Ala Leu Ser Pro His Pro Gln Pro Thr His Leu Pro
                245                 250                 255

Tyr Val Ser Glu Met Leu Glu Ala Arg Thr Ala Gly His Met Gln Thr
            260                 265                 270

Leu Ala Asp Phe Arg Gln Leu Pro Ala Arg Thr Leu Ser Thr His Trp
        275                 280                 285

Pro Pro Gln Arg Ser Leu Cys Ser Ser Asp Phe Ile Arg Ile Leu Val
    290                 295                 300

Ile Phe Ser Gly Met Phe Leu Val Phe Thr Leu Ala Gly Ala Leu Phe
305                 310                 315                 320

Leu His Ser Ala Asn Glu Arg Cys Lys Ser Lys Val Val Pro Cys Arg
                325                 330                 335

Gln Lys Gln Trp Arg Thr Ser Phe Asp Ser Lys Lys Leu Asp Leu Asn
            340                 345                 350

Tyr Asn His Phe Glu Ser Met Glu Trp Ser His Arg Ser Arg Arg Gly
        355                 360                 365

Arg Ile Trp Gly Met Lys Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg Gly Pro Gln Cys Thr Asn Tyr Ala Leu Leu
                485                 490                 495

Lys Leu Ala Gly Asp Val Glu Ser Asn Pro Gly Pro Met Arg Ile Ser
            500                 505                 510

Lys Pro His Leu Arg Ser Ile Ser Ile Gln Cys Tyr Leu Cys Leu Leu
```

```
        515                 520                 525

Leu Asn Ser His Phe Leu Thr Glu Ala Gly Ile His Val Phe Ile Leu
    530                 535                 540

Gly Cys Phe Ser Ala Gly Leu Pro Lys Thr Glu Ala Asn Trp Val Asn
545                 550                 555                 560

Val Ile Ser Asp Leu Lys Lys Ile Glu Asp Leu Ile Gln Ser Met His
                565                 570                 575

Ile Asp Ala Thr Leu Tyr Thr Glu Ser Asp Val His Pro Ser Cys Lys
            580                 585                 590

Val Thr Ala Met Lys Cys Phe Leu Leu Glu Leu Gln Val Ile Ser Leu
        595                 600                 605

Glu Ser Gly Asp Ala Ser Ile His Asp Thr Val Glu Asn Leu Ile Ile
    610                 615                 620

Leu Ala Asn Asn Ser Leu Ser Ser Asn Gly Asn Val Thr Glu Ser Gly
625                 630                 635                 640

Cys Lys Glu Cys Glu Glu Leu Glu Glu Lys Asn Ile Lys Glu Phe Leu
                645                 650                 655

Gln Ser Phe Val His Ile Val Gln Met Phe Ile Asn Thr Ser
            660                 665                 670


<210> SEQ ID NO 60
<211> LENGTH: 673
<212> TYPE: PRT
<213> ORGANISM: Artificial Sequence
<220> FEATURE:
<223> OTHER INFORMATION: Synthetic Polypeptide

<400> SEQUENCE: 60

Met Thr Arg Val Thr Asn Ser Pro Ser Leu Gln Ala His Leu Gln Ala
1               5                   10                  15

Leu Tyr Leu Val Gln His Glu Val Trp Arg Pro Leu Ala Ala Ala Tyr
            20                  25                  30

Gln Glu Gln Leu Asp Arg Pro Val Val Pro His Pro Tyr Arg Val Gly
        35                  40                  45

Asp Thr Val Trp Val Arg Arg His Gln Thr Lys Asn Leu Glu Pro Arg
    50                  55                  60

Trp Lys Gly Pro Tyr Thr Val Leu Leu Thr Thr Pro Thr Ala Leu Lys
65                  70                  75                  80

Val Asp Gly Ile Ala Ala Trp Ile His Ala Ala His Val Lys Ala Ala
                85                  90                  95

Asp Pro Gly Gly Gly Pro Ser Ser Arg Leu Pro Cys Ser Arg Met Leu
            100                 105                 110

Leu Leu Val Thr Ser Leu Leu Leu Cys Glu Leu Pro His Pro Ala Phe
        115                 120                 125

Leu Leu Ile Pro Ala Thr Pro Ala Pro Lys Ser Cys Pro Glu Arg His
    130                 135                 140

Tyr Trp Ala Gln Gly Lys Leu Cys Cys Gln Met Cys Glu Pro Gly Thr
145                 150                 155                 160

Phe Leu Val Lys Asp Cys Asp Gln His Arg Lys Ala Ala Gln Cys Asp
                165                 170                 175

Pro Cys Ile Pro Gly Val Ser Phe Ser Pro Asp His His Thr Arg Pro
            180                 185                 190

His Cys Glu Ser Cys Arg His Cys Asn Ser Gly Leu Leu Val Arg Asn
        195                 200                 205

Cys Thr Ile Thr Ala Asn Ala Glu Cys Ala Cys Arg Asn Gly Trp Gln
```

```
    210                 215                 220

Cys Arg Asp Lys Glu Cys Thr Glu Cys Asp Pro Leu Pro Asn Pro Ser
225                 230                 235                 240

Leu Thr Ala Arg Ser Ser Gln Ala Leu Ser Pro His Pro Gln Pro Thr
                245                 250                 255

His Leu Pro Tyr Val Ser Glu Met Leu Glu Ala Arg Thr Ala Gly His
            260                 265                 270

Met Gln Thr Leu Ala Asp Phe Arg Gln Leu Pro Ala Arg Thr Leu Ser
        275                 280                 285

Thr His Trp Pro Pro Gln Arg Ser Leu Cys Ser Ser Asp Phe Ile Arg
    290                 295                 300

Ile Leu Val Ile Phe Ser Gly Met Phe Leu Val Phe Thr Leu Ala Gly
305                 310                 315                 320

Ala Leu Phe Leu His Ser Ala Asn Glu Arg Cys Lys Ser Lys Val Val
                325                 330                 335

Pro Cys Arg Gln Lys Gln Trp Arg Thr Ser Phe Asp Ser Lys Lys Leu
            340                 345                 350

Asp Leu Asn Tyr Asn His Phe Glu Ser Met Glu Trp Ser His Arg Ser
        355                 360                 365

Arg Arg Gly Arg Ile Trp Gly Met Lys Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg Gly Pro Gln Cys Thr Asn Tyr
                485                 490                 495

Ala Leu Leu Lys Leu Ala Gly Asp Val Glu Ser Asn Pro Gly Pro Met
            500                 505                 510

Arg Ile Ser Lys Pro His Leu Arg Ser Ile Ser Ile Gln Cys Tyr Leu
        515                 520                 525

Cys Leu Leu Leu Asn Ser His Phe Leu Thr Glu Ala Gly Ile His Val
    530                 535                 540

Phe Ile Leu Gly Cys Phe Ser Ala Gly Leu Pro Lys Thr Glu Ala Asn
545                 550                 555                 560

Trp Val Asn Val Ile Ser Asp Leu Lys Lys Ile Glu Asp Leu Ile Gln
                565                 570                 575

Ser Met His Ile Asp Ala Thr Leu Tyr Thr Glu Ser Asp Val His Pro
            580                 585                 590

Ser Cys Lys Val Thr Ala Met Lys Cys Phe Leu Leu Glu Leu Gln Val
        595                 600                 605

Ile Ser Leu Glu Ser Gly Asp Ala Ser Ile His Asp Thr Val Glu Asn
    610                 615                 620

Leu Ile Ile Leu Ala Asn Asn Ser Leu Ser Ser Asn Gly Asn Val Thr
625                 630                 635                 640
```

Glu Ser Gly Cys Lys Glu Cys Glu Glu Leu Glu Glu Lys Asn Ile Lys
645 650 655

Glu Phe Leu Gln Ser Phe Val His Ile Val Gln Met Phe Ile Asn Thr
660 665 670

Ser

<210> SEQ ID NO 61
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 61
atggcacggc cacatccctg gtggctgtgc gttctgggga ccctggtggg gctctca 57

<210> SEQ ID NO 62
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 62
atgcttctcc tggtgacaag ccttctgctc tgtgagttac cacacccagc attcctcctg 60
atccca 66

<210> SEQ ID NO 63
<211> LENGTH: 516
<212> TYPE: DNA
<213> ORGANISM: Artificial Sequence
<220> FEATURE:
<223> OTHER INFORMATION: Synthetic Polynucleotide

<400> SEQUENCE: 63
gctactccag cccccaagag ctgcccagag aggcactact gggctcaggg aaagctgtgc 60
tgccagatgt gtgagccagg aacattcctc gtgaaggact gtgaccagca tagaaaggct 120
gctcagtgtg atccttgcat accgggggtc tccttctctc ctgaccacca cacccggccc 180
cactgtgaga gctgtcggca ctgtaactct ggtcttctcg ttcgcaactg caccatcact 240
gccaatgctg agtgtgcctg tcgcaatggc tggcagtgca gggacaagga gtgcaccgag 300
tgtgatcctc ttccaaaccc ttcgctgacc gctcggtcgt ctcaggccct gagcccacac 360
cctcagccca cccacttacc ttatgtcagt gagatgctgg aggccaggac agctgggcac 420
atgcagactc tggctgactt caggcagctg cctgcccgga ctctctctac ccactggcca 480
ccccaaagat ccctgtgcag ctccgatttt attcgc 516

<210> SEQ ID NO 64
<211> LENGTH: 516
<212> TYPE: DNA
<213> ORGANISM: Artificial Sequence
<220> FEATURE:
<223> OTHER INFORMATION: Synthetic Polynucleotide

<400> SEQUENCE: 64
gctacaccgg ctccgaagtc ctgcccggag cggcattatt gggcacaggg caagttgtgt 60
tgtcaaatgt gtgagccggg aacctttctc gtgaaggatt gcgatcagca tcggaaggcc 120
gcgcagtgcg acccatgtat accaggggtc tcattttccc cagatcacca tacgaggccg 180
cactgtgagt cttgcaggca ttgtaattcc ggcttgttgg tccgcaactg tactattact 240
gcgaatgcag agtgtgcttg tagaaacgga tggcagtgca gggacaaaga atgtacggag 300
tgtgatccac tgcctaaccc cagtcttaca gcaagatctt cacaggccct cagcccgcat 360
cctcaaccaa cacatcttcc ttacgtgtca gaaatgttgg aggcgcgaac cgcaggccat 420
atgcagaccc tggcggactt tcggcagctg ccagcacgca cacttagtac acactggcca 480
ccacaacgca gcttgtgctc ttccgatttc atccgc 516

<210> SEQ ID NO 65
<211> LENGTH: 81
<212> TYPE: DNA
<213> ORGANISM: Artificial Sequence
<220> FEATURE:
<223> OTHER INFORMATION: Synthetic Polynucleotide

<400> SEQUENCE: 65
ttttgggtgc tggtggtggt tggtggagtc ctggcttgct atagcttgct agtaacagtg 60
gcctttatta ttttctgggt g 81

<210> SEQ ID NO 66
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 66
atccttgtga tcttctctgg aatgttcctt gttttcaccc tggccggggc cctgttcctc 60
cat 63

<210> SEQ ID NO 67
<211> LENGTH: 340
<212> TYPE: DNA
<213> ORGANISM: Artificial Sequence
<220> FEATURE:
<223> OTHER INFORMATION: Synthetic Polynucleotide

<400> SEQUENCE: 67
cgcgtgaagt tcagcaggag cgcagacgcc cccgcgtacc agcagggcca gaaccagctc 60
tataacgagc tcaatctagg acgaagagag gagtacgatg ttttggacaa aagacgtggc 120
cgggaccctg agatgggggg aaagccgaga aggaagaacc ctcaggaagg cctgtacaat 180
gaactgcaga aagataagat ggcggaggcc tacagtgaga ttgggatgaa aggcgagcgc 240
cggaggggca aggggcacga tggcctttac cagggtctca gtacagccac caaggacacc 300
tacgacgccc ttcacatgca ggccctgccc cctcgcggac 340

<210> SEQ ID NO 68
<211> LENGTH: 126
<212> TYPE: DNA
<213> ORGANISM: Artificial Sequence
<220> FEATURE:
<223> OTHER INFORMATION: Synthetic Polynucleotide

<400> SEQUENCE: 68
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 69
<211> LENGTH: 72
<212> TYPE: DNA
<213> ORGANISM: Artificial Sequence
<220> FEATURE:
<223> OTHER INFORMATION: Synthetic Polynucleotide

<400> SEQUENCE: 69
ctttgcgcac gcccacgccg cagccccgcc caagaagatg gcaaagtcta catcaacatg 60
ccaggcaggg gc 72

<210> SEQ ID NO 70
<211> LENGTH: 153
<212> TYPE: DNA
<213> ORGANISM: Artificial Sequence
<220> FEATURE:
<223> OTHER INFORMATION: Synthetic Polynucleotide

<400> SEQUENCE: 70
agcgcgaacg aacgctgcaa aagcaaagtg gtgccgtgcc gccagaaaca gtggcgcacc 60
agctttgata gcaaaaaact ggatctgaac tataaccatt ttgaaagcat ggaatggagc 120
catcgcagcc gccgcggccg catttggggc atg 153

<210> SEQ ID NO 71
<211> LENGTH: 156
<212> TYPE: DNA
<213> ORGANISM: Artificial Sequence
<220> FEATURE:
<223> OTHER INFORMATION: Synthetic Polynucleotide

<400> SEQUENCE: 71
tacttcctgg gccggctggt ccctcggggg cgaggggctg cggaggcagc gacccggaaa 60
cagcgtatca ctgagaccga gtcgccttat caggagctcc agggtcagag gtcggatgtc 120
tacagcgacc tcaacacaca gaggccgtat tacaaa 156

<210> SEQ ID NO 72
<211> LENGTH: 24
<212> TYPE: PRT
<213> ORGANISM: Artificial Sequence
<220> FEATURE:
<223> OTHER INFORMATION: Synthetic Polypeptide

<400> SEQUENCE: 72

Leu Cys Ala Arg Pro Arg Arg Ser Pro Ala Gln Glu Asp Gly Lys Val
1 5 10 15

Tyr Ile Asn Met Pro Gly Arg Gly
20

<210> SEQ ID NO 73
<211> LENGTH: 51
<212> TYPE: PRT
<213> ORGANISM: Artificial Sequence
<220> FEATURE:
<223> OTHER INFORMATION: Synthetic Polypeptide

<400> SEQUENCE: 73

Ser Ala Asn Glu Arg Cys Lys Ser Lys Val Val Pro Cys Arg Gln Lys
1 5 10 15

Gln Trp Arg Thr Ser Phe Asp Ser Lys Lys Leu Asp Leu Asn Tyr Asn
20 25 30

His Phe Glu Ser Met Glu Trp Ser His Arg Ser Arg Arg Gly Arg Ile
35 40 45

-continued

```
Trp Gly Met
    50


<210> SEQ ID NO 74
<211> LENGTH: 52
<212> TYPE: PRT
<213> ORGANISM: Artificial Sequence
<220> FEATURE:
<223> OTHER INFORMATION: Synthetic Polypeptide

<400> SEQUENCE: 74

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys
    50
```

CD27-EXTRACELLULAR DOMAIN CAR TO TARGET CD70-POSITIVE TUMORS

This application is a national phase application under 35 U.S.C. § 371 of International Application No. PCT/US2022/013458, filed Jan. 24, 2022, which claims benefit of priority of U.S. Provisional Application No. 63/141,016, filed Jan. 25, 2021, and U.S. Provisional Application No. 63/270,414, filed Oct. 21, 2021, each of which are hereby incorporated by reference in their entirety.

SEQUENCE LISTING

The instant application contains a Sequence Listing which has been submitted in ASCII format and is hereby incorporated by reference in its entirety. Said ASCII copy, created on Jan. 18, 2022, is named "MDACP1261US_ST25.txt" and is 209,797 bytes in size.

TECHNICAL FIELD

Embodiments of the disclosure include at least the fields of cell biology, molecular biology, immunology, and medicine, including cancer medicine.

BACKGROUND

Genetic reprogramming of Natural Killer (NK) cells for adoptive cancer immunotherapy has clinically relevant applications and benefits such as 1) innate anti-tumor surveillance without prior need for sensitization 2) allogeneic efficacy without graft versus host reactivity and 3) direct cell-mediated cytotoxicity and cytolysis of target tumors. Human NK cell development and acquisition of self-tolerance, alloreactivity, and effector functions is an adaptive process of licensing, calibration, and arming. At the molecular level, specific activating and inhibitory receptors direct NK cellular functions by aggregating, balancing, and integrating extracellular signals into distinct effector functions. The functional activity of NK cells and responsiveness to extrinsic stimuli follow the 'rheostat' model of continuous education and thus are amenable to reprogramming. Genetic modification of NK cells to redirect their effector functions is an effective method to harness their cytotoxic capability to kill tumor cells.

CD70, the ligand for the cytokine receptor CD27, is an attractive 'pan-cancer antigen' since in addition to being expressed on hematologic malignancies such as acute myeloid leukemia (AML) and lymphoma, it also expressed on many solid tumors, including renal, bladder, lung, triple negative breast cancer, renal cell carcinoma, pancreatic cancer and melanoma, and it is only transiently found on activated T and B lymphocytes and dendritic cells. CD70 is especially advantageous as a target for the immunotherapy of AML as, unlike other AML targets, it is not expressed on normal hematopoietic stem cells and, therefore, as opposed to most of the CAR-T therapies for AML in clinic today, it is unlikely to result in prolonged cytopenias and the need for a hematopoietic stem cell transplant for the recipient after CAR therapy. The present disclosure provides a solution to long-felt needs in the art of cancer therapies for CD70-positive cancers.

BRIEF SUMMARY

The present disclosure is directed to method and compositions for the treatment or prevention of cancers having CD70-expressing cells. The disclosure concerns particular anti-CD70 chimeric antigen receptors (CAR) and their use to target CD70-positive cancers of any kind. In particular embodiments, the antigen binding domain that targets CD70, including upon specific binding of CD70, is not an antibody. In particular embodiments, the anti-CD70 CAR lacks an antibody of any kind, including a scFv that binds CD70. In particular embodiments, the extracellular domain of the anti-CD70 CAR does not comprise an scFv or any other type of antibody.

In particular embodiments, the antigen binding domain that targets CD70 is a natural receptor of CD70, such as the receptor CD27. In specific cases, part or all of CD27 is employed in the CAR molecule. In aspects of the disclosure, the antigen binding domain present in the anti-CD70 CAR molecule comprises part or all of the extracellular domain of CD27, and in specific cases the CAR molecule does or does not utilize the transmembrane domain of CD27. In some cases, the CD28 transmembrane domain is employed instead of the CD27 transmembrane domain, despite the use of the CD27 extracellular domain in the CAR. Particular intracellular domains may be utilized for the CAR, such as CD3zeta alone or combinations of CD3zeta with either DAP10 or DAP12, and in some cases the intracellular domain does not comprise that of 4-1BB.

Embodiments of the disclosure include any polynucleotide that encodes part or all of the anti-CD70 CAR. Specific embodiments encompass polynucleotides that encode anti-CD70 CARs comprising an antigen binding domain, transmembrane domain, and at least one intracellular domain (including one or more costimulatory domains), wherein the CAR comprises an antigen binding domain that does not comprise an antibody. Vectors that harbor expression constructs that encode the anti-CD70 CARs, and optionally other genes, are contemplated. The vectors may or may not be viral. Cells harboring the vectors are also contemplated, including immune cells of any kind, such as at least NK cells or T cells. In some cases the cells are off-the-shelf cells, including NK cells, and these cells may or may not already be manipulated to express one or more heterologous genes, such as one or more exogenous cytokines.

Methods of treating or preventing cancer of any kind are encompassed herein, including by administering cells expressing particular anti-CD70 CARs at a therapeutically effective amount to ameliorate or prevent the cancer, or reduce the risk of the cancer, reduce the severity of the cancer, prevent metastasis or risk thereof, or delay the onset of the cancer.

Embodiments of the disclosure include methods of targeting CD70-expressing cells and, in specific embodiments, the cells are cancerous, whereas in other methods the CD70-expressing cells are immunoregulatory cells such as Tregs.

The present disclosure includes methods to genetically engineer human NK cells (including from cord blood (CB)) to target CD70+ve tumors using a CD27-ectodomain CAR. Encompassed herein are a variety of novel CAR constructs that fuse the extracellular binding portion of CD27 (CD27eCAR, or CD27 EC) with activating signaling endodomains that incorporate either CD3ζ alone or in combination with costimulatory or adaptor signaling domains, such as 4-1BB, CD28, DAP10 or DAP12, and a cytokine gene such as IL-15, IL-12, IL-18, or IL-21, to support NK cell survival and proliferation. In a series of in vitro studies, the activity of CD27eCAR/IL-15 transduced CB-NK cells against AML and lymphoma targets is confirmed.

Embodiments of the disclosure include polynucleotides that encode an anti-CD70 chimeric antigen receptor (CAR) comprising a signal peptide, an anti-CD70 antigen binding domain, transmembrane domain, and at least one intracellular domain, wherein the anti-CD70 antigen binding domain does not comprise an antibody, and optionally wherein a transmembrane domain of the CAR is not a CD27 transmembrane domain. In specific embodiments, the anti-CD70 antigen binding domain is comprised in an extracellular domain of CD27 and/or may be codon optimized. In specific aspects, the antigen binding domain comprises, consists of, or consists essentially of SEQ ID NO:2. In some cases, the antigen binding domain and transmembrane domain comprise, consist of, or consist essentially of SEQ ID NO:1. The sequence that encodes the transmembrane domain may be codon optimized, and/or the transmembrane domain may be from CD28, the alpha chain of the T- cell receptor, beta chain of the T- cell receptor, zeta chain of the T- cell receptor, CD3 zeta, CD3 epsilon, CD3 gamma, CD3 delta, CD45, CD4, CD5, CD8, CD9, CD16, CD22, CD33, CD37, CD64, CD80, CD86, CD134, CD137, CD154, ICOS/CD278, GITR/CD357, NKG2D, DAP10, or DAP12. In a specific case, the CD28 transmembrane domain comprises, consists of, or consists essentially of SEQ ID NO:3. The CAR may comprises two or more, or three or more, intracellular domains. An intracellular domain may comprise any ITAM-containing signaling domain. An intracellular domain may comprise CD3zeta. The intracellular domain may be an intracellular costimulatory domain, such as one selected from the group consisting of CD27, CD28, 4-1BB, DAP12, NKG2D, OX-40 (CD134), DAP10, CD40L, 2B4, DNAM, CS1, CD48, NKp30, NKp44, NKp46, NKp80, and a combination thereof.

In some embodiments, the signal peptide is from CD27 or granulocyte-macrophage colony-stimulating factor receptor (GMSCF-R), and the sequence of the CD27 signal peptide may comprise, consist of, or consist essentially of SEQ ID NO:6. The signal peptide may be from CD27, the anti-CD70 antigen binding domain may be from CD27, the transmembrane domain may be from CD27, and an intracellular domain is from CD27. The signal peptide may comprise, consist of, or consist essentially of SEQ ID NO:6. The CAR may comprise, consist of, or consist essentially of SEQ ID NO:4. In some cases, the transmembrane domain comprises, consists of, or consists essentially of SEQ ID NO:3 or SEQ ID NO:7. In certain aspects, the intracellular domain comprises one or more of SEQ ID NO:8, SEQ ID NO:10, SEQ ID NO:11, or SEQ ID NO:12. The CAR may comprise, consist of, or consist essentially of SEQ ID NO:5. The CAR may comprise, consist of, or consist essentially of SEQ ID NO:1.

In specific embodiments, the polynucleotide encodes a CAR, and the CAR comprises one or more of the following:

(a) CD27 signal peptide (SP), CD27 extracellular domain (EC), CD27 transmembrane domain (TMD), DAP12 intracellular domain (ICD), and CD3zeta;
(b) GMSCF-R SP, codon optimized CD27 EC, codon optimized CD27 TMD, DAP12 ICD;
(c) CD27 SP, CD27 EC, CD28 TMD, DAP12 ICD, and CD3zeta;
(d) GMSCF-R SP, codon optimized CD27 EC, CD28 TMD, DAP12 ICD, and CD3zeta;
(e) CD27 SP, CD27 EC, CD27 TMD, Natural killer group 2 member D (NKG2D) ICD, and CD3zeta;
(f) GMSCF-R SP, codon optimized CD27 EC, codon optimized CD27 TMD, NKG2D ICD, and CD3zeta;
(g) CD27 SP, CD27 EC, CD28 TMD, Natural killer group 2 member D (NKG2D) ICD, and CD3zeta;
(h) GMSCF-R SP, codon optimized CD27 EC, CD28 TMD, NKG2D ICD, and CD3zeta;
(i) CD27 SP, CD27 EC, CD27 TMD, 4-1BB ICD, and CD3zeta;
(j) GMSCF-R SP, codon optimized CD27 EC, codon optimized CD27 TMD, 4-1BB ICD, and CD3zeta;
(k) CD27 SP, CD27 EC, CD28 TMD, 4-1BB ICD, and CD3zeta;
(l) GMSCF-R SP, codon optimized CD27 EC, CD28 TMD, 4-1BB ICD, and CD3zeta;
(m) CD27 SP, CD27 EC, CD27 TMD, DAP10 ICD, and CD3zeta;
(n) GMSCF-R SP, codon optimized CD27 EC, codon optimized CD27 TMD, DAP10 ICD, and CD3zeta;
(o) CD27 SP, CD27 EC, CD28 TMD, DAP10 ICD, and CD3zeta;
(p) GMSCF-R SP, codon optimized CD27 EC, CD28 TMD, DAP10 ICD, and CD3zeta;
(q) CD27 SP, CD27 full length (FL), CD27 TMD, CD27 ICD, and CD3zeta;
(r) GMSCF-R SP, codon optimized CD27 FL, codon optimized CD27 TMD, codon optimized CD27 ICD, and CD3zeta;
(s) CD27 SP, CD27 FL, CD27 TMD, CD27 ICD, CD28 ICD, and CD3zeta;
(t) GMSCF-R SP, codon optimized CD27 FL, codon optimized CD27 TMD, codon optimized CD27 ICD, CD28 ICD, and CD3zeta;
(u) CD27 SP, CD27 FL, CD27 TMD, CD27 ICD, 4-1BB ICD, and CD3zeta;
(v) GMSCF-R SP, codon optimized CD27 FL, codon optimized CD27 TMD, codon optimized CD27 ICD, 4-1BB ICD, and CD3zeta;
(w) CD27 SP, CD27 FL, CD27 TMD, CD27 ICD, DAP10 ICD, and CD3zeta;
(x) GMSCF-R SP, CD27 FL, CD27 TMD, CD27 ICD, DAP10 ICD, and CD3zeta;
(y) CD27 SP, CD27 FL, CD27 TMD, CD27 ICD, DAP12 ICD, and CD3zeta;
(z) GMSCF-R SP, codon optimized CD27 FL, codon optimized CD27 TMD, codon optimized CD27 ICD, DAP12 ICD, and CD3zeta;
(aa) CD27 SP, CD27 FL, CD27 TMD, CD27 ICD, NKG2D ICD, and CD3zeta;
(bb) GMSCF-R SP, codon optimized CD27 FL, codon optimized CD27 TMD, codon optimized CD27 ICD, NKG2D ICD, and CD3zeta;
(cc) CD27 SP, CD27 EC, CD27 TMD, and CD3zeta;
(dd) GMSCF-R SP, codon optimized CD27 EC, codon optimized CD27 TMD, and CD3zeta;
(ee) CD27 SP, CD27 EC, CD28 TMD, and CD3zeta;
(ff) GMSCF-R SP, codon optimized CD27 EC, codon optimized CD28 TMD, and CD3zeta;
(gg) CD27 SP, CD27 EC, CD27 TMD, CD28 ICD, and CD3zeta;
(hh) GMSCF-R SP, codon optimized CD27 EC, codon optimized CD27 TMD, CD28 ICD, and CD3zeta;
(ii) CD27 SP, CD27 EC, CD28 TMD, CD28 ICD, and CD3zeta; or
(jj) GMSCF-R SP, codon optimized CD27 EC, CD28 TMD, and CD3zeta.

Embodiments of the disclosure include cells that comprise any polynucleotides encompassed herein. The cells may or may not be immune cells. Examples of immune cells include Natural Killer (NK) cells, T cell, gamma delta T cells, invariant NKT (iNKT) cells, B cells, macrophages, mesenchymal stem cells (MSCs), or dendritic cells. When the cells are NK cells, they may be derived from cord blood, peripheral blood, induced pluripotent stem cells, bone marrow, hematopoietic stem cells (HSCs), from a cell line, or a mixture thereof. The NK cell line may be a NK-92 cell line or another NK cell line derived from a tumor or from a healthy NK cell, or is a progenitor cell. In specific embodiments, the NK cell is derived from a cord blood mononuclear cell. The NK cell may be a CD56+ NK cell. In some cases, the NK cells express one or more exogenously provided cytokines, such as IL-15, IL-2, IL-12, IL-18, IL-21, IL-7, or a combination thereof.

Embodiments of the disclosure include populations of immune cells of the disclosure, said cells present in a suitable medium. In specific cases, the immune cells are NK cells. The immune cells may or may not be obtained from cryopreserved storage.

In particular embodiments, there are methods of killing CD70-positive cells in an individual, comprising the step of administering to the individual a therapeutically effective amount of cells harboring any polynucleotide encompassed herein. The cells may be NK cells, T cells, gamma delta T cells, invariant NKT (iNKT) cells, B cells, macrophages, gamma delta T cells, or dendritic cells. The NK cells may be derived from cord blood, peripheral blood, induced pluripotent stem cells, bone marrow, HSCs, or from a cell line. The NK cells may be derived from cord blood mononuclear cells. In some cases, the CD70-positive cells are not cancer cells and may be T regulatory cells. The individual may have or be suspected of having any CD70-expressing cancer. The individual may have or be suspected of having, for example, acute myeloid leukemia, lymphoma, lung cancer, renal cancer, bladder cancer, melanoma, glioblastoma, breast cancer, head and neck cancer, mesothelioma, multiple myeloma, pancreatic cancer or a combination thereof. The cells may be allogeneic or autologous with respect to the individual. The individual may be a human. In some embodiments, the cells are administered to the individual once or more than once. The duration of time between administrations of the cells to the individual may be 1-24 hours, 1-7 days, 1-4 weeks, 1-12 months, or one or more years.

In certain embodiments of methods encompassed herein, the method further comprises the step of providing to the individual an effective amount of an additional therapy, such as surgery, radiation, gene therapy, immunotherapy, and/or hormone therapy. In certain cases, the additional therapy comprises one or more antibodies.

In particular embodiments, the cells are administered to the individual by injection, intravenously, intraarterially, intraperitoneally, intratracheally, intratumorally, intramuscularly, endoscopically, intralesionally, intracranially, percutaneously, subcutaneously, regionally, by perfusion, in a tumor microenvironment, or a combination thereof. In specific embodiments, the method further comprises the step of identifying CD70-positive cells in the individual.

The foregoing has outlined rather broadly the features and technical advantages of the present disclosure in order that the detailed description that follows may be better understood. Additional features and advantages will be described hereinafter which form the subject of the claims herein. It should be appreciated by those skilled in the art that the conception and specific embodiments disclosed may be readily utilized as a basis for modifying or designing other structures for carrying out the same purposes of the present designs. It should also be realized by those skilled in the art that such equivalent constructions do not depart from the spirit and scope as set forth in the appended claims. The novel features which are believed to be characteristic of the designs disclosed herein, both as to the organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

For a more complete understanding of the present disclosure, reference is now made to the following descriptions taken in conjunction with the accompanying drawings.

The following table provides information regarding the truncated (tr) and full length (fl) CD27 constructs and their respective reference numbers used in data encompassed herein. S. No refers to serial number.

| S. No | Construct Name | ID |
|---|---|---|
| 1 | CD27TrCD28icdCD3ZIL1 | trCD27 #1 |
| 2 | GSPco27Tr28CD3z15 | trCD27 #2 |
| 3 | CD27tr28tdmCD3zIL15 | trCD27 #3 |
| 4 | GSPco27Tr28tmd3z15 | trCD27 #4 |
| 5 | CD27TrCD3ZIL15 | trCD27 #5 |
| 6 | GSPco27Tr3z15 | trCD27 #6 |
| 7 | CD27TrNKG2Dic3z15 | trCD27 #7 |
| 8 | GSPco27TrNKG2Dicd3z1 | trCD27 #8 |
| 9 | CD27Tr28tmd NKG2Dic 3z | trCD27 #9 |
| 10 | GSPco27Tr28tmdNKG2Di | trCD27 #10 |
| 11 | CD27Tr28tmdDAP12icd3 | trCD27 #11 |
| 12 | GSPco27Tr28tmddap12i | trCD27 #12 |
| 13 | CD27TrDAP12icd3z15 | trCD27 #12 |
| 14 | GSPco27Trda p12icd3z1 | trCD27 #14 |
| 15 | CD27Tr28tmdDAP10icd3 | trCD27 #15 |
| 16 | GSPco27Tr28tmdDAP10i | trCD27 #16 |
| 17 | CD27TrDAP10icd3z15 | trCD27 #17 |
| 18 | GSPco27FLdap10icd3z1 | trCD27 #18 |
| 19 | CD27Tr28tmd41BBicd3z | trCD27 #19 |
| 20 | GSPco27Tr28tmd41BBic | trCD27 #20 |
| 21 | CD27Tr41BBicd3z15 | trCD27 #21 |
| 22 | GSPco27Tr41BBicd3z15 | trCD27 #22 |
| 23 | CD27TrCD28tmdicd3z15 | trCD27 #24 |
| 24 | GSPco27Tr28tmdicCD3z | trCD27 #25 |
| 25 | CD27FLDAP10icd3z15 | flCD27 #1 |
| 26 | SPco27FLdap10icd3z15 | flCD27 #2 |
| 27 | CD27FLDAP12icd3z15 | flCD27 #3 |
| 28 | SPco27FLdap12icd3z15 | flCD27 #4 |
| 29 | CD27FLNKG2Dic3z15 | flCD27 #5 |
| 30 | SPco27FLNKG2Dicd3z15 | flCD27 #6 |
| 31 | CD27FLCD3zIL15 | flCD27 #7 |
| 32 | GSPco27FLcd3z15 | flCD27 #8 |
| 33 | CD27FLCD28icd3z15 | flCD27 #9 |
| 34 | GSPco27FL28CD3z15 | flCD27 #10 |
| 35 | CD27FL41BBicd3z15 | flCD27 #11 |
| 36 | GSPco27FL41BBicd3z15 | flCD27 #12 |

With respect to this table, information regarding the truncated (tr) and full length (fl) CD27 constructs and their respective identification numbers used in the figures are as follows:

GSP: GMCSF receptor signal peptide co: codon optimized

CD28 tmd: CD28 transmembrane domain

CD27 tmd: CD27 transmembrane domain

3z: CD3 zeta signal

CD28 ic: CD28 intracellular domain

Natural killer group 2 member D (NKG2D) ic: NKG2D intracellular domain

Dap12 icd: DAP12 intracellular domain

Dap10 icd: DAP12 intracellular domain

41bb icd: 41bb intracellular domain

Figure 3:
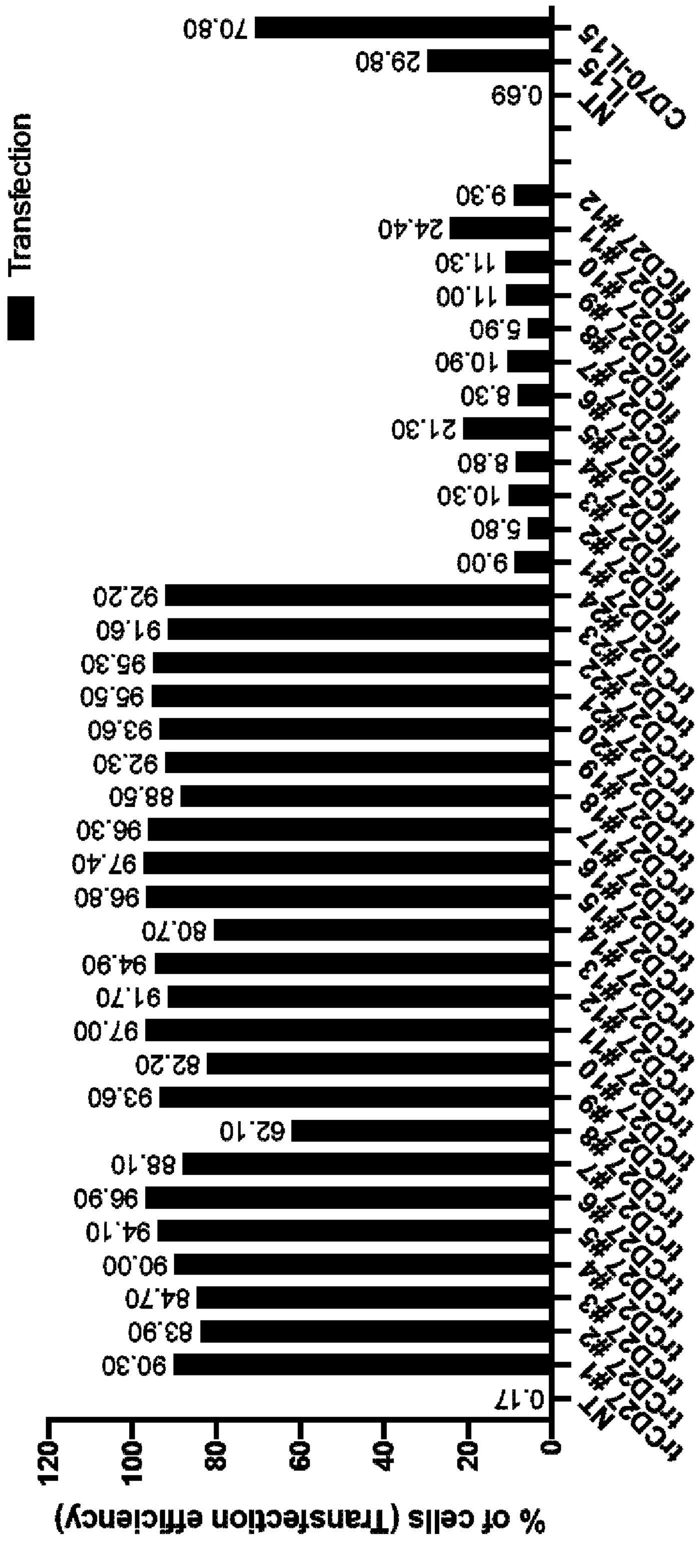

FIG. 3 demonstrates transfection efficiency of truncated (tr) and full length (fl) CD27 constructs in 293T cells.

Figure 4:
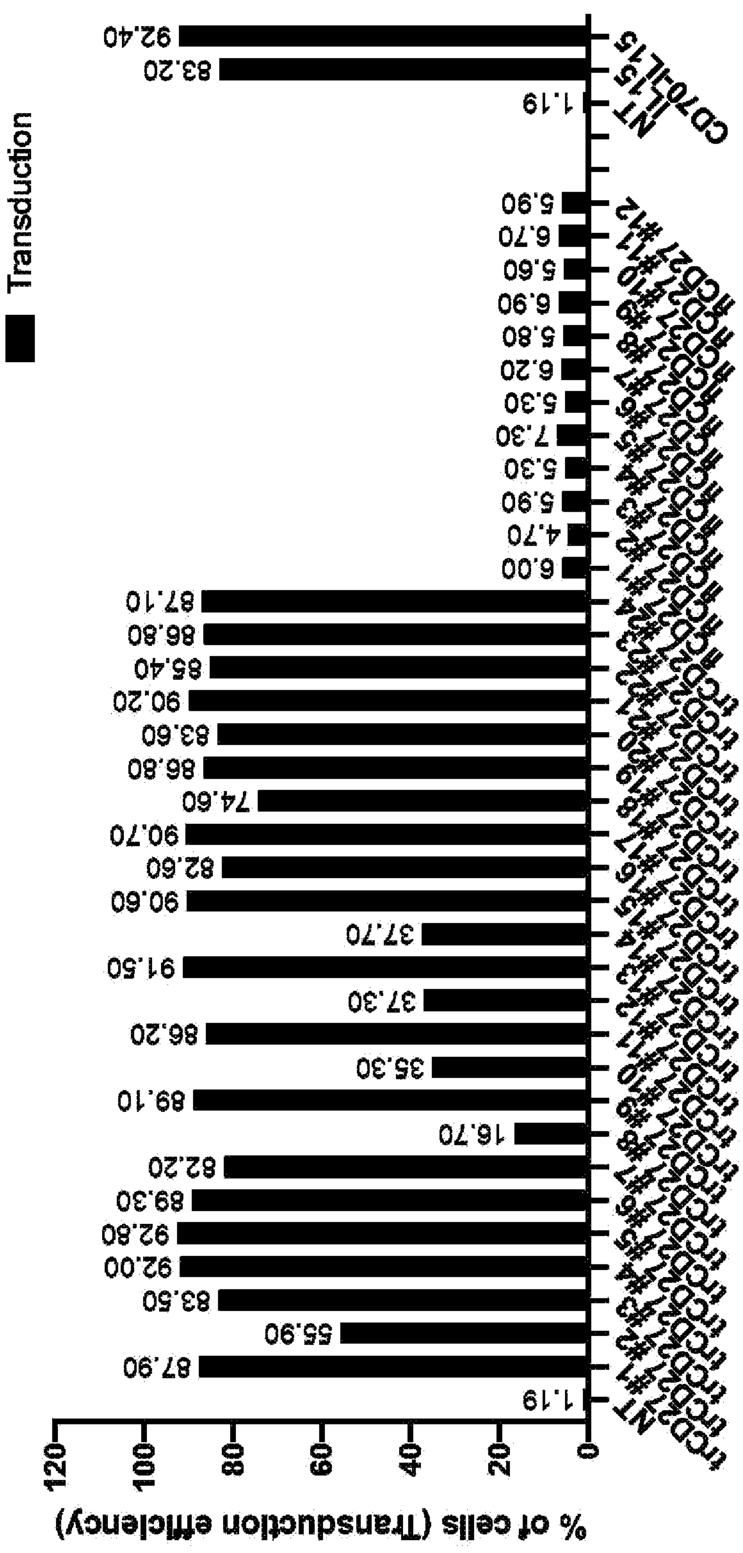

FIG. 4 demonstrates transduction efficiency of truncated (tr) and full length (fl) CD27 constructs in cord blood derived NK cells.

Figure 5A:
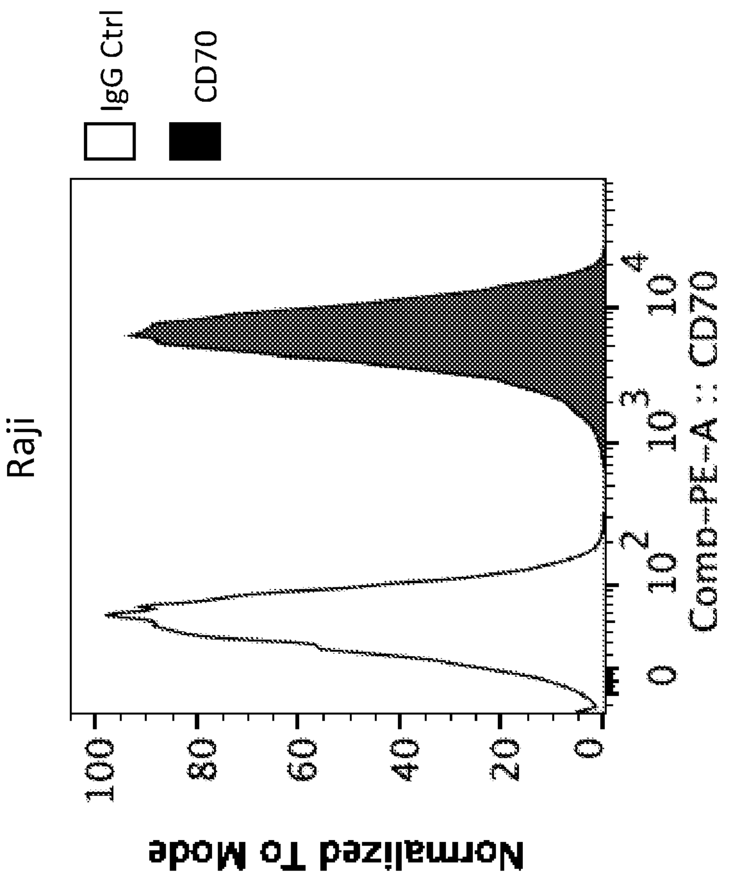
Figure 5B:
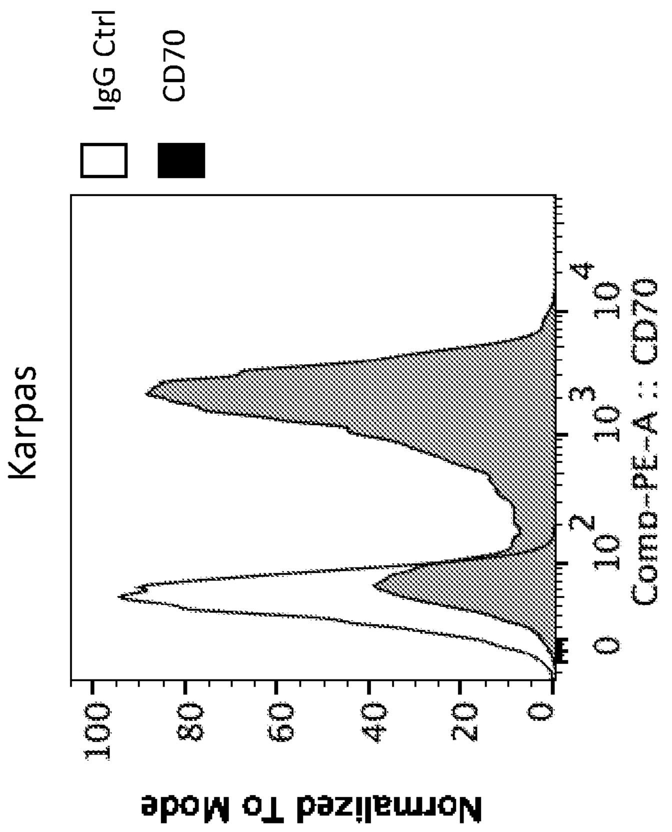
Figure 5C:
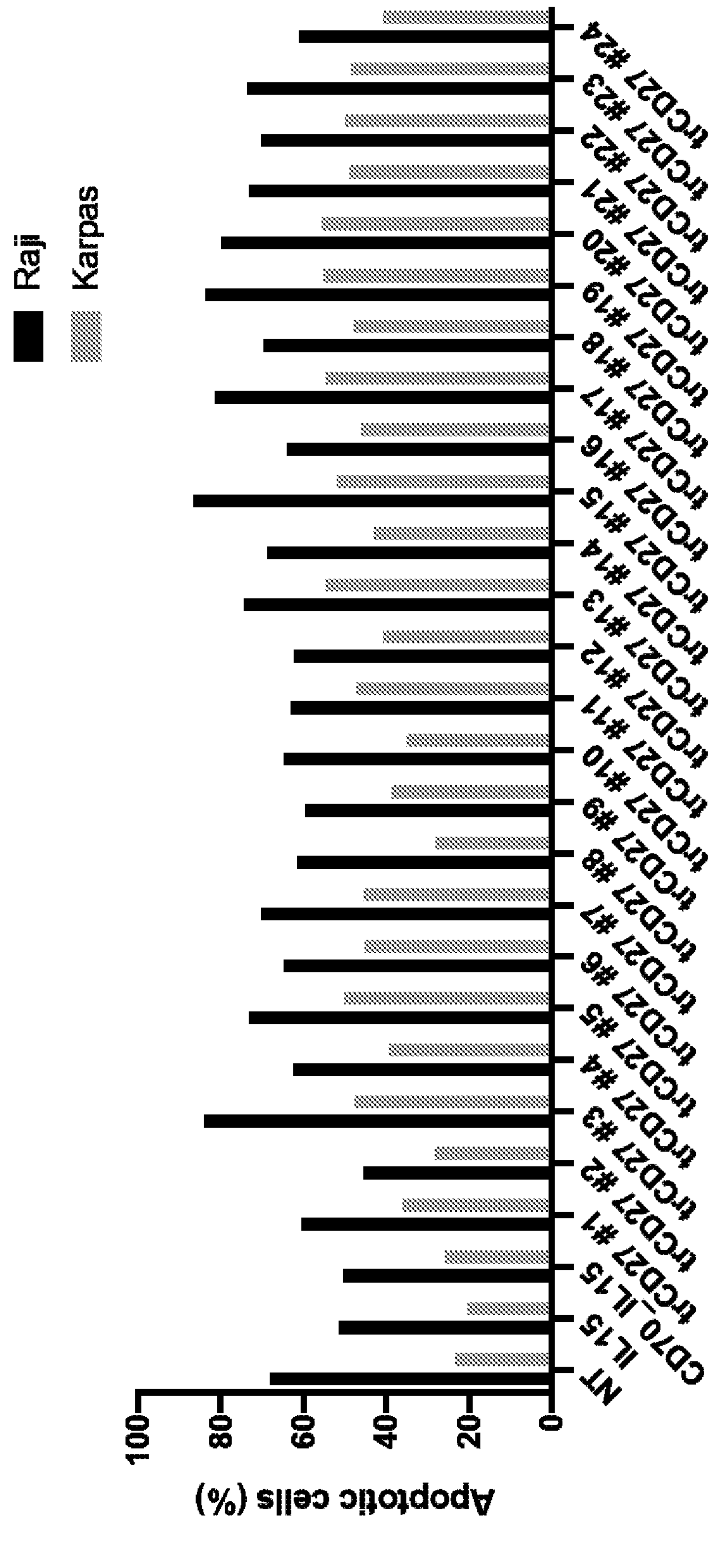

FIGS. 5A-5C demonstrate CD70 expression on tumor targets and killing activity of cord blood natural killer (CB-NK) cells transduced with various trCD27 constructs against CD70-positive Raji (FIG. 5A) and Karpas cells (FIG. 5B) using a 4 hr Annexin-V assay (FIG. 5C). FIG. 5C shows better killing for various trCD70 transduced CB-NK cells of both Raji (black bar) and Karpas (grey bar) cells, when compared to NT (non-transduced), IL15 (construct with only IL15 cytokine gene) or CD70-IL15 (construct with CD70 scFv together with IL15) CAR-transduced CBNK cells.

Figure 6:
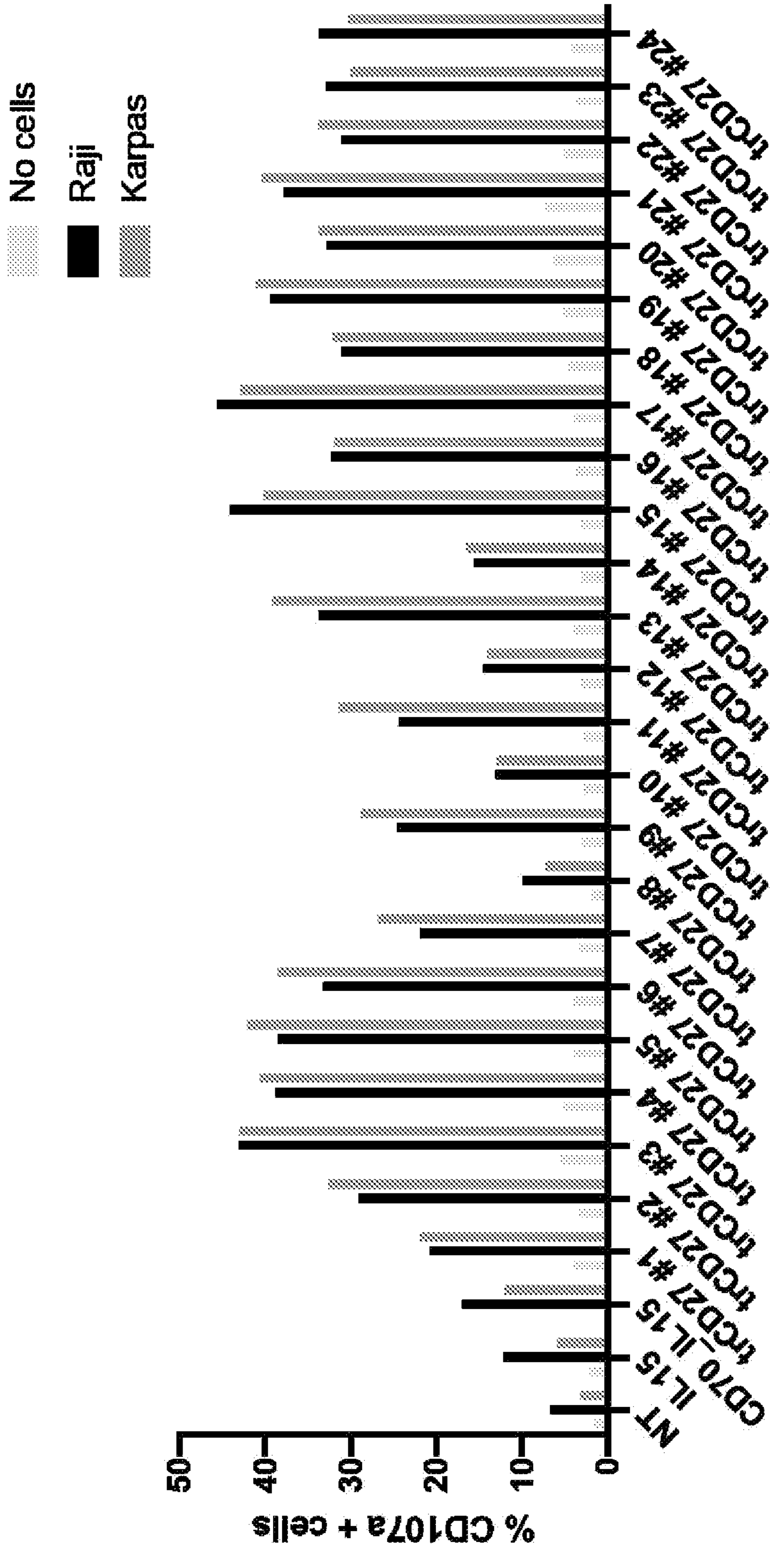

FIG. 6 demonstrates CD107a degranulation (a marker for the cytotoxic activity of NK cells) by CB-NK cells transduced with various trCD27 constructs against Raji and Karpas cells. TrCD27 CAR transduced CBNK cells and cancer cells (Raji and Karpas) were co-cultured at a 1:1 ratio in the presence of CD107a antibody for 6 hrs. After incubation, CD107a expression is assessed by flow cytometry. In the bars grouped in three, the left (green) bar is the control with CB-NK cells in the absence of co-culture with cancer cells, the middle (black) bar is trCD70-transduced CB-NK cells co-cultured with Raji cells, and the right (gray) bar is trCD70-transduced CB-NK cells co-cultured with Karpas cells. Most of the trCD27 transduced CB-NK cells showed enhanced cytotoxic activity against Raji and Karpas cells, when compared to NT, IL15 or CD70-IL15 CAR-transduced CB-NK cells.

Figure 7A:
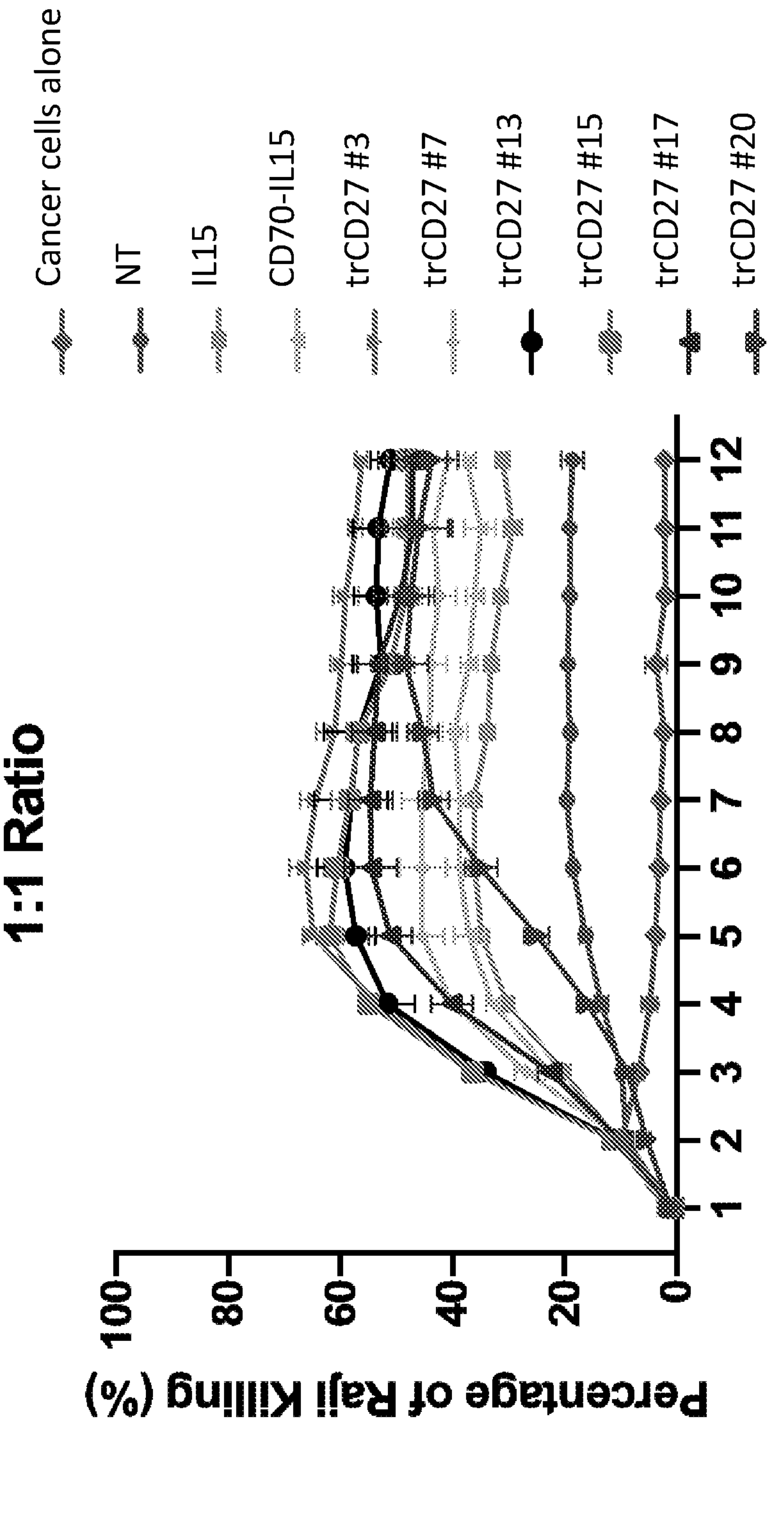
Figure 7B:
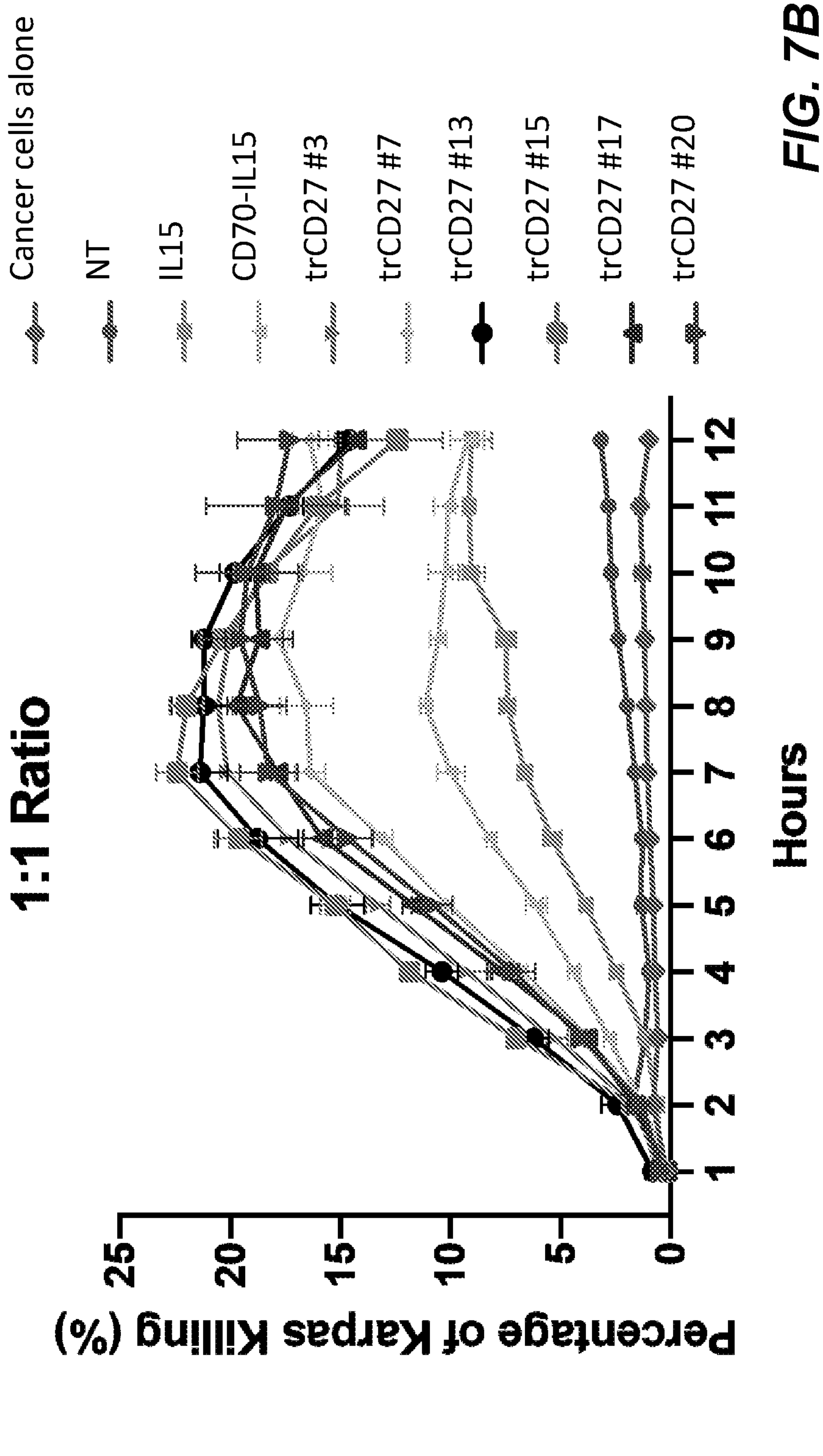

FIGS. 7A-7B show killing activity of CB-NK cells transduced with various trCD27 constructs against Raji cells (FIG. 7A) and Karpas cells (FIG. 7B) using Incucyte live imaging. TrCD27 CAR transduced CBNK cells and Raji or Karpas cells were co-cultured at 1:1 ratio, and real-time cytotoxicity of NK cells against Raji and Karpas cells was measured every hour over a 12 hour period. TrCD27 transduced CB-NK cells showed enhanced cytotoxic activity against Raji and Karpas cells, when compared to NT, IL15 or CD70-IL15 CAR-transduced CB-NK cells. Cancer cells cultured in the absence of CBNK cells (cancer cells alone) was used as control.

Figure 8A:
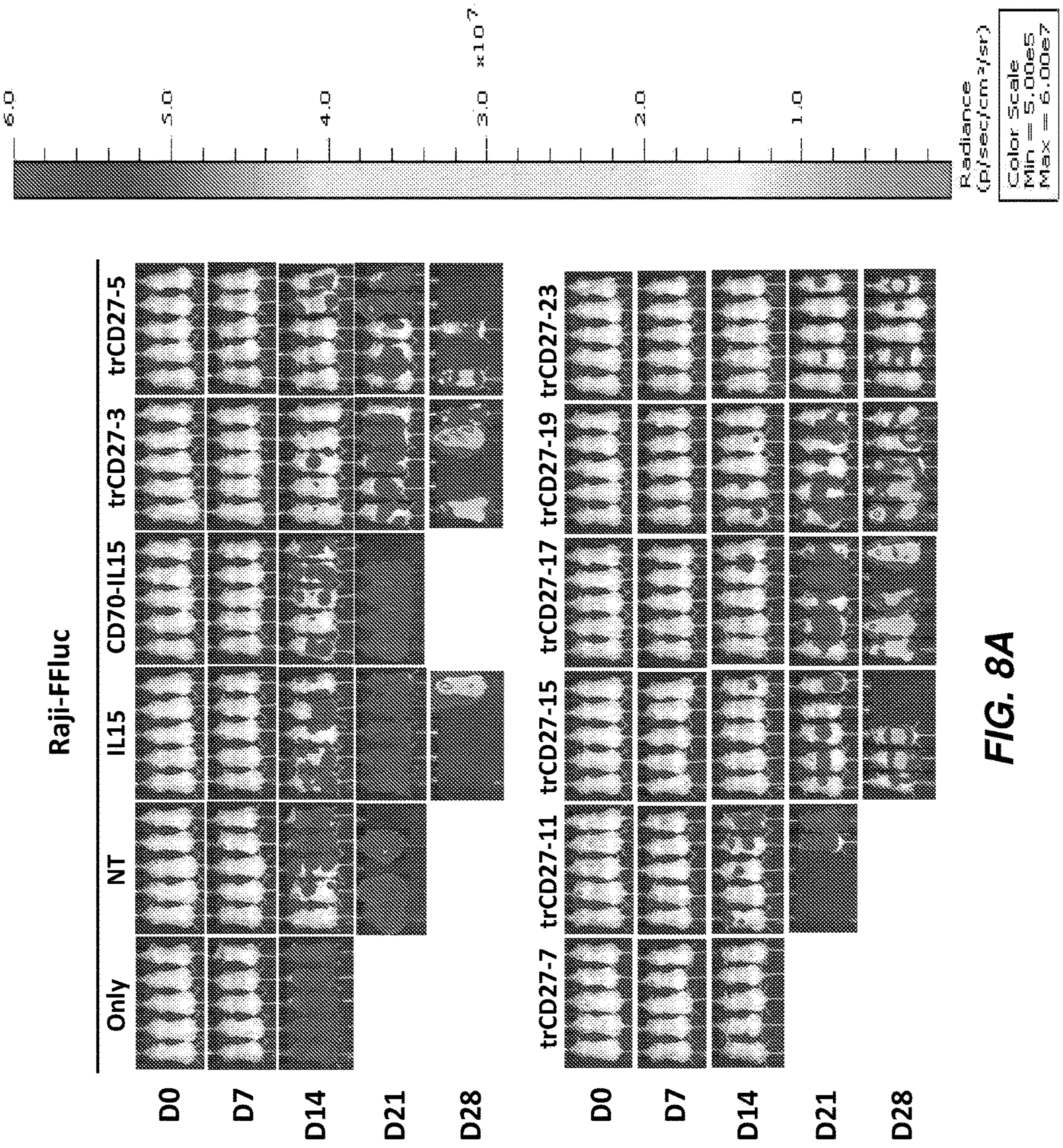
Figure 8B:
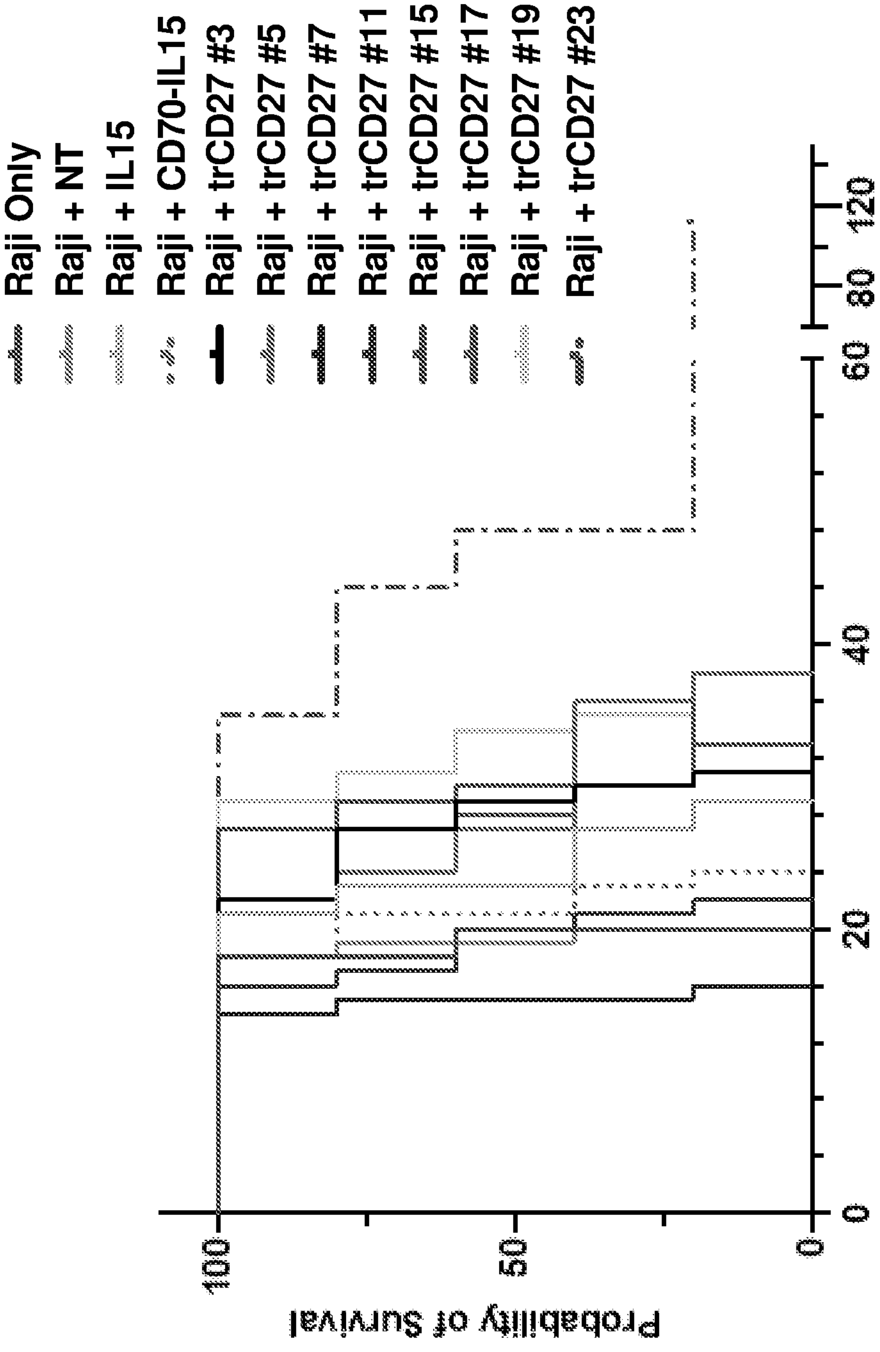

FIGS. 8A-8B show in vivo anti-tumor activity of CB-NK cells transduced with various trCD27 constructs against Raji cells having high CD70 expression. FIG. 8A shows bioluminescence imaging of Raji tumors after infusion with CB-NK cells transduced with various trCD27 CARs. FIG. 8B shows survival curves after infusion with CB-NK cells transduced with various trCD27 CARs.

Figure 9A:
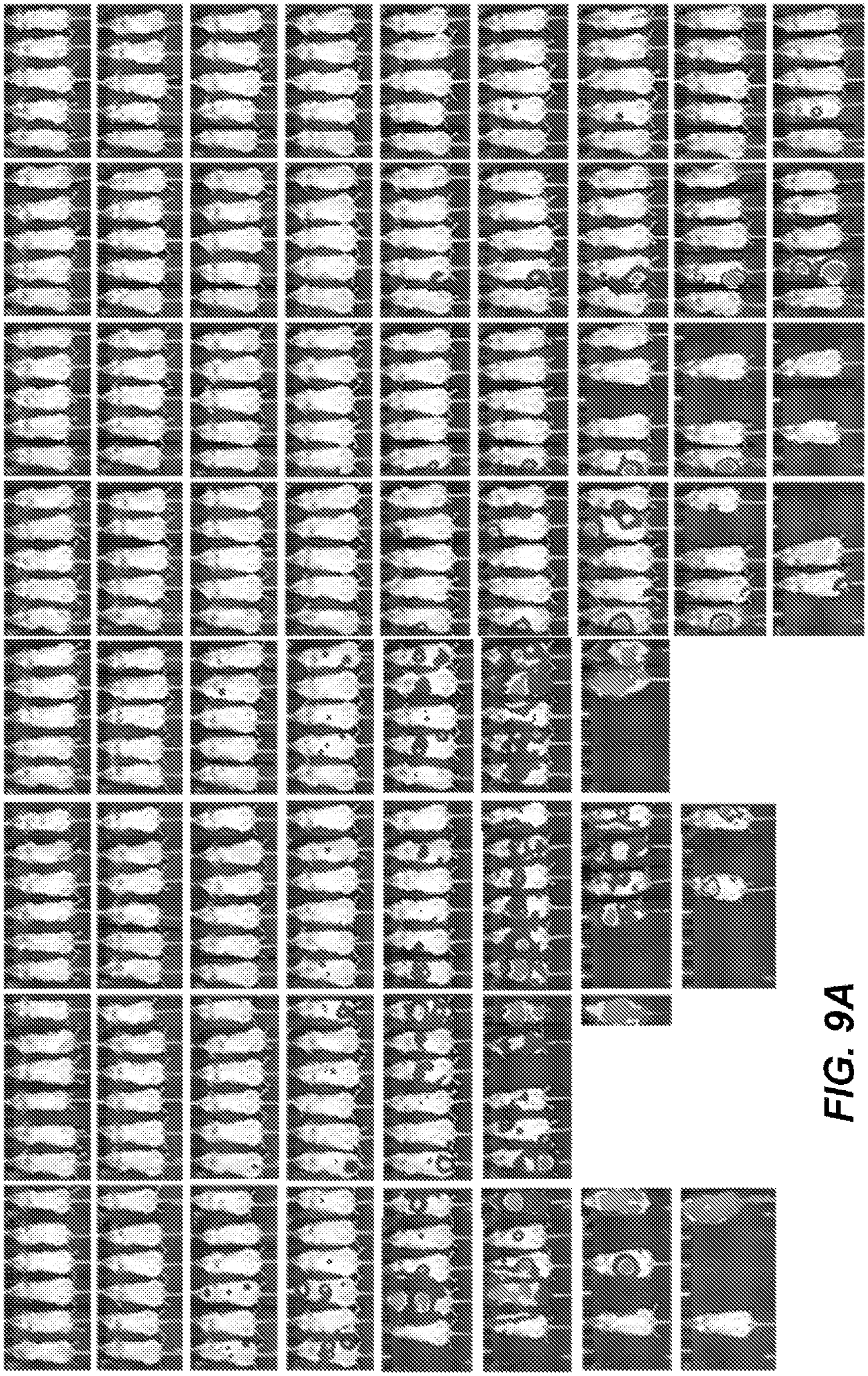
Figure 9B:
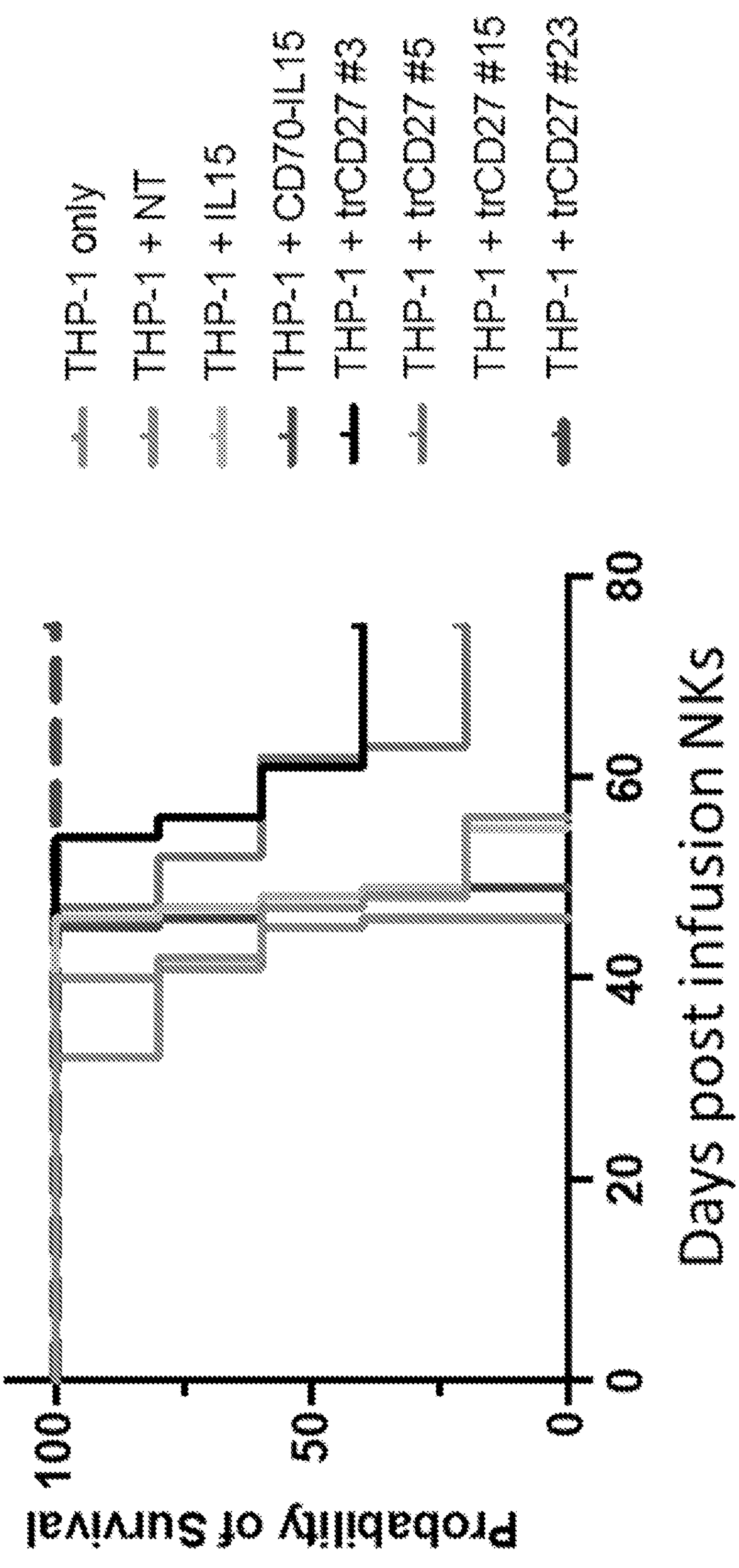

FIGS. 9A-9B show in vivo anti-tumor activity of CB-NK cells transduced with various trCD27 constructs against THP-1 cells having high CD70 expression. FIG. 9A shows bioluminescence imaging of THP-1 tumors after infusion with CB-NK cells transduced with various trCD27 CARs. FIG. 9B shows survival curves after infusion with CB-NK cells transduced with various trCD27 CARs.

DETAILED DESCRIPTION

In keeping with long-standing patent law convention, the words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein and that different embodiments may be combined.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment of the present invention. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

Throughout this application, the term "about" is used according to its plain and ordinary meaning in the area of cell and molecular biology to indicate that a value includes the standard deviation of error for the device or method being employed to determine the value.

The term "engineered" as used herein refers to an entity that is generated by the hand of man, including a cell, nucleic acid, polypeptide, vector, and so forth. In at least some cases, an engineered entity is synthetic and comprises elements that are not naturally present or configured in the manner in which it is utilized in the disclosure. In specific embodiments, a vector is engineered through recombinant nucleic acid technologies, and a cell is engineered through transfection or transduction of an engineered vector.

As used herein, "prevent," and similar words such as "prevented," "preventing" etc., indicate an approach for preventing, inhibiting, or reducing the likelihood of the occurrence or recurrence of, a disease or condition, e.g., cancer. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

The term "sample," as used herein, generally refers to a biological sample. The sample may be taken from tissue or cells from an individual. In some examples, the sample may comprise, or be derived from, a tissue biopsy, blood (e.g., whole blood), blood plasma, extracellular fluid, dried blood spots, cultured cells, discarded tissue. The sample may have been isolated from the source prior to collection. Non-limiting examples include blood (including but not limited to cord blood), serum, plasma, cerebral spinal fluid, pleural fluid, amniotic fluid, lymph fluid, saliva, urine, stool, tears, sweat, bone marrow, or mucosal excretions, and other bodily fluids isolated from the primary source prior to collection. In some examples, the sample is isolated from its primary source (cells, tissue, bodily fluids such as blood, environmental samples, etc.) during sample preparation. The sample may or may not be purified or otherwise enriched from its primary source. In some cases the primary source is homogenized prior to further processing. The sample may be filtered or centrifuged to remove buffy coat, lipids, or particulate matter. The sample may also be purified or enriched for nucleic acids, or may be treated with RNases. The sample may contain tissues or cells that are intact, fragmented, or partially degraded.

The term "subject," as used herein, generally refers to an individual having a biological sample that is undergoing processing or analysis and, in specific cases, has or is suspected of having cancer. The subject can be any organism or animal subject that is an object of a method or material, including mammals, e.g., humans, laboratory animals (e.g., primates, rats, mice, rabbits), livestock (e.g., cows, sheep, goats, pigs, turkeys, and chickens), household pets (e.g., dogs, cats, and rodents), horses, and transgenic non-human animals. The subject can be a patient, e.g., have or be suspected of having a disease (that may be referred to as a medical condition), such as benign or malignant neoplasias, or cancer. The subject may being undergoing or having undergone treatment. The subject may be asymptomatic. The subject may be healthy individuals but that are desirous of prevention of cancer. The term "individual" may be used interchangeably, in at least some cases. The "subject" or "individual", as used herein, may or may not be housed in a medical facility and may be treated as an outpatient of a medical facility. The individual may be receiving one or more medical compositions via the internet. An individual may comprise any age of a human or non-human animal and therefore includes both adult and juveniles (i.e., children) and infants and includes in utero individuals. It is not intended that the term connote a need for medical treatment, therefore, an individual may voluntarily or involuntarily be part of experimentation whether clinical or in support of basic science studies.

As used herein "treatment" or "treating," includes any beneficial or desirable effect on the symptoms or pathology of a disease or pathological condition, and may include even minimal reductions in one or more measurable markers of the disease or condition being treated, e.g., cancer. Treatment can involve optionally either the reduction or amelioration of symptoms of the disease or condition, or the delaying of the progression of the disease or condition. "Treatment" does not necessarily indicate complete eradication or cure of the disease or condition, or associated symptoms thereof.

The disclosure includes the targeting of cancers expressing CD70 using an anti-CD70 CAR, and in some cases the CAR is expressed on NK cells derived from cord blood. A number of novel CAR molecules are described herein that were produced by fusing the extracellular binding portion of CD27 (CD27eCAR) with an activating signaling endodomain that incorporates either CD3ζ alone or in combination with costimulatory or adaptor signaling domains such as 4-1BB, CD28, DAP10 or DAP12, and, at least in some cases, a cytokine gene such as IL-15, IL-12, IL-18 or IL-21. In some embodiments, the CAR is a fusion of the extracellular domain of CD27 (the natural ligand for CD70) with specificity for human CD70 antigen. In addition, in some cases codon optimization was utilized to improve the surface expression of CD27 on the surface of the transduced cells. In some case, the vector comprising the expression construct that encodes the anti-CD70 CAR also carries a cytokine gene, such as to produce human interleukin 15 (IL-15), IL-12, IL-18 or IL-21, to aid in the survival and maintenance of the cells harboring the vector, including NK cells as examples.

I. Chimeric Antigen Receptors (CARs)

Immune cells of the present disclosure can be genetically engineered to express one or more antigen-binding receptors that target one or more antigens, e.g., CD70, such as engineered CARs. For example, the immune cells may be immune cells that are modified to express a CAR having antigenic specificity for CD70. Other CARs may be expressed by the same cells as the CD70 antigen receptor-expressing cells, and they may be directed to different antigens. In some aspects, the immune cells are engineered to express the CD70-specific CAR by knock-in of the CAR using, for example, CRISPR/Cas technology.

Suitable methods of modification of cells are known in the art. See, for instance, Sambrook and Ausubel, supra. For example, the cells may be transduced to express a CAR having antigenic specificity for a cancer antigen using transduction techniques described in Heemskerk et al., 2008 and Johnson et al., 2009.

In some embodiments, the cells comprise one or more nucleic acids introduced via genetic engineering that encode one or more antigen-targeting receptors (at least one of which may be directed against CD70), and genetically engineered products of such nucleic acids. In some embodiments, the nucleic acids are heterologous, i.e., normally not present in a cell or sample obtained from the cell, such as one obtained from another organism or cell, which for example, is not ordinarily found in the cell being engineered and/or an organism from which such cell is derived. In some embodiments, the nucleic acids are not naturally occurring, such as a nucleic acid not found in nature (e.g., chimeric).

The present disclosure encompasses CD70-specific CARs that comprise: a) an extracellular domain comprising an antigen binding region that targets, including specifically binds to, CD70; b) a transmembrane domain; and c) one or more intracellular domains, including intracellular signaling domains. In some aspects, the antigen-specific binding or recognition component is linked to a transmembrane domain and one or more intracellular signaling domains. In some embodiments, the CAR includes a transmembrane domain fused to the extracellular domain of the CAR that comprises the antigen binding region or domain. In one embodiment, the transmembrane domain that naturally is associated with one of the domains in the CAR is used, although in other cases it is not used. In some instances, the transmembrane domain is selected or modified by amino acid substitution to avoid binding of such domains to the transmembrane domains of the same or different surface membrane proteins to minimize interactions with other members of the receptor complex.

The present disclosure regards anti-CD70 CARs that comprise an antigen binding domain that does not employ an antibody or antibody fragment. In particular embodiments, instead of the anti-CD70 CARs utilizing an antibody or antibody fragment as an antigen binding domain, the CAR instead utilizes part or all of CD27 in the CAR, including using the extracellular domain of CD27 as the antigen binding domain of the CAR, in some cases.

As a matter of reference, the *Homo sapiens* CD27 molecule (CD27) on chromosome 12 is provided at National Center for Biotechnology Information (NCBI) GenBank® Accession No. NG_031995.1, which is incorporated by reference herein in its entirety. A nucleotide sequence that encodes the entire CD27 protein includes the following:

(SEQ ID NO: 9)
```
ATGGCACGGCCACATCCCTGGTGGCTGTGCGTTCTGGGGACCCTGG

TGGGGCTCTCAGCTACTCCAGCCCCCAAGAGCTGCCCAGAGAGGCACTA

CTGGGCTCAGGGAAAGCTGTGCTGCCAGATGTGTGAGCCAGGAACATTC

CTCGTGAAGGACTGTGACCAGCATAGAAAGGCTGCTCAGTGTGATCCTT

GCATACCGGGGGTCTCCTTCTCTCCTGACCACCACACCCGGCCCCACTG

TGAGAGCTGTCGGCACTGTAACTCTGGTCTTCTCGTTCGCAACTGCACC

ATCACTGCCAATGCTGAGTGTGCCTGTCGCAATGGCTGGCAGTGCAGGG

ACAAGGAGTGCACCGAGTGTGATCCTCTTCCAAACCCTTCGCTGACCGC

TCGGTCGTCTCAGGCCCTGAGCCCACACCCTCAGCCCACCCACTTACCT

TATGTCAGTGAGATGCTGGAGGCCAGGACAGCTGGGCACATGCAGACTC

TGGCTGACTTCAGGCAGCTGCCTGCCCGGACTCTCTCTACCCACTGGCC

ACCCCAAAGATCCCTGTGCAGCTCCGATTTTATTCGCATCCTTGTGATC

TTCTCTGGAATGTTCCTTGTTTTCACCCTGGCCGGGGCCCTGTTCCTCC

ATCAACGAAGGAAATATAGATCAAACAAAGGAGAAAGTCCTGTGGAGCC

TGCAGAGCCTTGTCGTTACAGCTGCCCCAGGGAGGAGGAGGGCAGCACC

ATCCCCATCCAGGAGGATTACCGAAAACCGGAGCCTGCCTGCTCCCCCT

GA
```

Any polynucleotide encompassed by the present disclosure may utilized SEQ ID NO:9 or a sequence that is at least 70, 75, 80, 85, 90, 95, 96, 97, 98, 99, or more % identical to SEQ ID NO:9.

One example of a full wild-type CD27 protein sequence is at NCBI GenBank® Accession No. P26842 (and is also identical to the amino acid sequence in Accession No. NG_031995.1):

In particular embodiments, part or all of SEQ ID NO:4 is utilized in the CAR. Although in certain embodiments the full length wild-type (or codon optimized) CD27 protein is utilized in the CAR, in other embodiments a truncated version of the wild-type CD27 protein is utilized as the antigen binding domain in the CAR. In specific examples, part or all of the extracellular domain of CD27 is employed, such that the truncated CD27 that is used as the antigen binding domain is a truncated version of CD27 that is truncated at the C-terminus of the natural protein.

A nucleotide sequence that encodes a truncated version of the wild-type CD27 protein includes the following:

(SEQ ID NO: 63)
```
GCTACTCCAGCCCCCAAGAGCTGCCCAGAGAGGCACTACTGGGCTC

AGGGAAAGCTGTGCTGCCAGATGTGTGAGCCAGGAACATTCCTCGTGAA

GGACTGTGACCAGCATAGAAAGGCTGCTCAGTGTGATCCTTGCATACCG

GGGGTCTCCTTCTCTCCTGACCACCACACCCGGCCCCACTGTGAGAGCT

GTCGGCACTGTAACTCTGGTCTTCTCGTTCGCAACTGCACCATCACTGC

CAATGCTGAGTGTGCCTGTCGCAATGGCTGGCAGTGCAGGGACAAGGAG

TGCACCGAGTGTGATCCTCTTCCAAACCCTTCGCTGACCGCTCGGTCGT

CTCAGGCCCTGAGCCCACACCCTCAGCCCACCCACTTACCTTATGTCAG

TGAGATGCTGGAGGCCAGGACAGCTGGGCACATGCAGACTCTGGCTGAC

TTCAGGCAGCTGCCTGCCCGGACTCTCTCTACCCACTGGCCACCCCAAA

GATCCCTGTGCAGCTCCGATTTTATTCGC
```

Any polynucleotide encompassed by the present disclosure may utilized SEQ ID NO:63 or a sequence that is at least 70, 75, 80, 85, 90, 95, 96, 97, 98, 99, or more % identical to SEQ ID NO:63.

A polypeptide sequence that encodes a truncated version of the wild-type CD27 protein includes the following:

(SEQ ID NO: 5)
```
ATPAPKSCPERHYWAQGKLCCQMCEPGTFLVKDCDQHRKAAQCDPCI

PGVSFSPDHHTRPHCESCRHCNSGLLVRNCTITANAECACRNGWQCRDK

ECTECDPLPNPSLTARSSQALSPHPQPTHLPYVSEMLEARTAGHMQTLA

DFRQLPARTLSTHWPPQRSLCSSDFIR
```

Any polypeptide encompassed by the present disclosure may utilized SEQ ID NO:5 or a sequence that is at least 70, 75, 80, 85, 90, 95, 96, 97, 98, 99, or more % identical to SEQ ID NO:5.

In specific cases wherein the full length CD27 protein is used in the CAR molecule, an additional transmembrane domain is not utilized. In specific cases wherein the full length CD27 protein is used in the CAR molecule, which (SEQ ID NO: 4)
```
  1  MARPHPWWLC VLGTLVGLSA TPAPKSCPER HYWAQGKLCC QMCEPGTFLV KDCDQHRKAA

 61  QCDPCIPGVS FSPDHHTRPH CESCRHCNSG LLVRNCTITA NAECACRNGW QCRDKECTEC

121  DPLPNPSLTA RSSQALSPHP QPTHLPYVSE MLEARTAGHM QTLADFRQLP ARTLSTHWPP

181  QRSLCSSDFI RILVIFSGMF LVFTLAGALF LHQRRKYRSN KGESPVEPAE PCHYSCPREE

241  EGSTIPIQED YRKPEPACSP
```

comprises its own intracellular signaling domain, an additional intracellular signaling domain may or may not be used in the CAR. In specific cases wherein the full length CD27 protein is used in the CAR molecule, although it comprises its own signal peptide, an additional signal peptide may or may not be utilized. In particular embodiments, CD3zeta (and/or DAP10, DAP12, 2B4, CD28, NKG2D, 41BB, or any ITAM-containing signaling domain) is utilized in the CAR.

In one example, the region of CD27 that is utilized as the antigen binding domain in the CAR molecule comprises, consists of, or consists essentially of amino acids 1-211 (includes CD27 TMD) of SEQ ID NO:4. In another example, the region of CD27 that is utilized in the CAR molecule as the antigen binding domain comprises, consists of, or consists essentially of amino acids 1-191 (lacks CD27 TMD) of SEQ ID NO:4. In specific examples, the region of CD27 that is utilized in the CAR molecule comprises, consists of, or consists essentially of amino acids 1-50, 1-51, 1-52, 1-53, 1-54, 1-55, 1-56, 1-57, 1-58, 1-59, 1-60, 1-61, 1-62, 1-63, 1-64, 1-65, 1-66, 1-67, 1-68, 1-69, 1-70, 1-71, 1-72, 1-73, 1-74, 1-75, 1-76, 1-77, 1-78, 1-79, 1-80, 1-81, 1-82, 1-83, 1-84, 1-85, 1-86, 1-87, 1-88, 1-89, 1-90, 1-91, 1-92, 1-93, 1-94, 1-95, 1-96, 1-97, 1-98, 1-99, 1-100, 1-101, 1-102, 1-103, 1-104, 1-105, 1-106, 1-107, 1-108, 1-109, 1-110, 1-111, 1-112, 1-113, 1-114, 1-115, 1-116, 1-117, 1-118, 1-119, 1-120, 1-121, 1-122, 1-123, 1-124, 1-125, 1-126, 1-127, 1-128, 1-129, 1-130, 1-131, 1-132, 1-133, 1-134, 1-135, 1-136, 1-137, 1-138, 1-139, 1-140, 1-141, 1-142, 1-143, 1-144, 1-145, 1-146, 1-147, 1-148, 1-149, 1-150, 1-151, 1-152, 1-153, 1-154, 1-155, 1-156, 1-157, 1-158, 1-159, 1-160, 1-161, 1-162, 1-163, 1-164, 1-165, 1-166, 1-167, 1-168, 1-169, 1-170, 1-171, 1-172, 1-173, 1-174, 1-175, 1-176, 1-177, 1-178, 1-179, 1-180, 1-181, 1-182, 1-183, 1-184, 1-185, 1-186, 1-187, 1-188, 1-189, 1-190, 1-191, 1-192, 1-193, 1-194, 1-195, 1-196, 1-197, 1-198, 1-199, 1-200, 1-201, 1-202, 1-203, 1-204, 1-205, 1-206, 1-207, 1-208, 1-209, 1-210, 1-211, 1-212, 1-213, 1-214, 1-215, 1-216, 1-217, 1-218, 1-219, 1-220, 1-221, 1-222, 1-223, 1-224, 1-225, 1-226, 1-227, 1-228, 1-229, 1-230, 1-231, 1-232, 1-233, 1-234, 1-235, 1-236, 1-237, 1-238, 1-239, 1-240, 1-241, 1-242, 1-243, 1-244, 1-245, 1-246, 1-247, 1-248, 1-249, 1-250, 1-251, 1-252, 1-253, 1-254, 1-255, 1-256, 1-57, 1-258, 1-259 or all (1-260) of SEQ ID NO:4; in specific embodiments, such amino acids in these ranges are contiguous. In some embodiments, a region of SEQ ID NO:4 is utilized that has truncation at the N-terminus, such as 1, 2, 3, 4, 5, 6, 7, 8, 9, 10, 11, 12, 13, 14, 15, 16, 17, 18, 19, 20, or more amino acids from the N-terminus. In certain cases, there is truncation at that N-terminus of 1, 2, 3, 4, 5, 6, 7, 8, 9, 10, 11, 12, 13, 14, 15, 16, 17, 18, 19, 20, or more amino acids and there is truncation at the C-terminus, such as the truncation endpoints as noted in the list above.

In certain embodiments, any region of the CAR molecule is codon optimized. In some embodiments, the antigen binding domain comprises any of the examples of CD27 sequences encompassed herein but is codon optimized. In specific cases, the antigen binding domain comprises a C-terminal truncated CD27 (e.g., the extracellular domain) and is also codon optimized. In certain aspects, the antigen binding domain comprises, consists of, or consists essentially of amino acids 1-191 of CD27 and is also codon optimized. In other aspects, the antigen binding domain and transmembrane domain comprises, consists of, or consists essentially of amino acids 1-211 of CD27 and is also codon optimized.

In some cases, a specific component of the CAR molecule is utilized. In particular embodiments, the CAR comprises a particular transmembrane domain. Examples include the transmembrane domains from CD28 or from CD27. In some embodiments, the CD27 transmembrane domain or the CD28 transmembrane domain are not utilized in the CAR, whereas in alternative embodiments the CD27 transmembrane domain is utilized in the CAR. In particular embodiments, signal peptides are employed for the CAR, and examples include the CD27 or GMCSF-R signal peptides, or both may be used. Examples of intracellular signaling domains for the CAR include at least CD27, CD28, DAP10, DAP12, NKG2D, 4-1BB, or a combination thereof.

In some cases, the CD27 signal peptide is utilized (MARPHPWWLCVLGTLVGLS (SEQ ID NO:6); ATGGCACGGCCA-CATCCCTGGTGGCTGTGCGTTCTGGGGACCC-TGGTGGGGCTCT CA (SEQ ID NO:61)) in the CAR, or a sequence that is at least 70, 75, 80, 85, 90, 95, 96, 97, 98, 99, or more % identical to SEQ ID NO:6 or 61. In some cases, the GMCSF-R signal peptide (MLLLVTSLLLCEL-PHPAFLLIP (SEQ ID NO:14); ATGCTTCTCCTGGTGACAAGCCTTCTGCTCTGT-GAGTTACCACACCCAGCATTCCT CCTGATCCCA (SEQ ID NO:62)) is used in the CAR, or a sequence that is at least 70, 75, 80, 85, 90, 95, 96, 97, 98, 99, or more % identical to SEQ ID NO:14 or 62.

The CAR may or may not comprise CD27 TM (IL-VIFSGMFLVFTLAGALFLH (SEQ ID NO:7); ATCCTTGTGATCTTCTCTGGAATGTTCCTTGTTTT-CACCCTGGCCGGGGCCCTGTT CCTCCAT (SEQ ID NO:66)), or a sequence that is at least 70, 75, 80, 85, 90, 95, 96, 97, 98, 99, or more % identical to SEQ ID NO:7 or 66.

The CAR may or may not comprise the ICD of CD27, which is QRRKYRSNKGESPVEPAEPCHYSCPREEEG-STIPIQEDYRKPEPACSP (SEQ ID NO:8), or a sequence that is at least 70, 75, 80, 85, 90, 95, 96, 97, 98, 99, or more % identical to SEQ ID NO:8.

In some embodiments, the CD3zeta ICD is RVKFSRSAD APAYQQGQNQ LYNELNLGRR EEYDVLDKRR GRDPEMGGKPRRKNPQEGL YNELQKDKMA EAY-SEIGMKG ERRRGKGHDG LYQGLSTATKDTY-DALHMQA LPPRG (SEQ ID NO:10), CGCGT-GAAGTTCAGCAGGAGCGCAGACGCCCCCGCG-TACCAGCAGGGCCAGAAC CAGCTC-TATAACGAGCTCAATCTAGGACGAAGAGAG-GAGTACGATGTTTTGGAC AAAA-GACGTGGCCGGGACCCTGAGATGGGGGGAA-AGCCGAGAAGGAAGAACCC TCAG-GAAGGCCTGTACAATGAACTGCAGAAAGATAA-GATGGCGGAGGCCTACAG TGAGATTGGGAT-GAAAGGCGAGCGCCGGAGGGGCAAGGGGCACG-ATGGCCTTTA CCAGGGTCTCAGTACAGCCAC-CAAGGACACCTACGACGCCCTTCACATGCAGGC CCTGCCCCCTCGCGGAC (SEQ ID NO:67), and the sequence may be used in the CAR, or a sequence that is at least 70, 75, 80, 85, 90, 95, 96, 97, 98, 99, or more % identical to SEQ ID NO:10 or 67.

In some embodiments, the CD28 ICD (RSKRSRLLHSD YMNMTPRRPGPTRKHYQPYA PPRDFAAYRS; SEQ ID NO:11) is utilized in the CAR molecule, or a sequence that is at least 70, 75, 80, 85, 90, 95, 96, 97, 98, 99, or more % identical to SEQ ID NO:11.

In some embodiments, the 4-1BB ICD (KRGRKKL LYIFKQPFMR PVQTTQEEDG CSCRFPEEEEGGCEL (SEQ ID NO:12); AAACGGGGCAGAAAGAAACTCCTGTATATATT- CAAACAACCATTTATGAGACCA GTACAAACTACT-CAAGAGGAAGATGGCTGTAGCTGCCGAT-TTCCAGAAGAAGAA GAAGGAGGATGTGAACTG (SEQ ID NO:68)) is used in the CAR molecule, or a sequence that is at least 70, 75, 80, 85, 90, 95, 96, 97, 98, 99, or more % identical to SEQ ID NO:12 or 68.

In some embodiments, the DAP10 ICD (LCARPRR-SPAQEDGKVYINMPGRG (SEQ ID NO:72); CTTTGCGCACGCCCACGCCGCAGCCCCGCC-CAAGAAGATGGCAAAGTCTACATC AACATGCCAGGCAGGGGC (SEQ ID NO:69)) is used in the CAR molecule, or a sequence that is at least 70, 75, 80, 85, 90, 95, 96, 97, 98, 99, or more % identical to SEQ ID NO:69 or 72.

In some embodiments, the DAP12 ICD (YFLGRLVPR-GRGAAEAATRKQRITETESPYQELQGQRSDVYSD-LNTQRPYYK (SEQ ID NO:74); TACTTCCTGGGCCGGCTGGTCCCTCGGGGGCGA-GGGGCTGCGGAGGCAGCGACC CGGAAACAGCGTATCACTGAGACCGAGTCGCCT-TATCAGGAGCTCCAGGGTCAG AGGTCGGATGTC-TACAGCGACCTCAACACACAGAGGCCGTATTA-CAAA (SEQ ID NO:71)) is used in the CAR molecule, or a sequence that is at least 70, 75, 80, 85, 90, 95, 96, 97, 98, 99, or more % identical to SEQ ID NO:71 or 74.

In some embodiments, the NKG2D ICD (SANERCK-SKVVPCRQKQWRTSFDSKKLDLNYNHFESMEWS-HRSRRGRIWGM (SEQ ID NO:73); AGCGCGAACGAACGCTGCAAAAGCAAAGTGGT-GCCGTGCCGCCAGAAACAGTG GCGCACCAGCTTT-GATAGCAAAAAACTGGATCTGAACTATAACCAT-TTTGAAAGC ATGGAATGGAGC-CATCGCAGCCGCCGCGGCCGCATTTGGGGCATG (SEQ ID NO:70)) is used in the CAR molecule, or a sequence that is at least 70, 75, 80, 85, 90, 95, 96, 97, 98, 99, or more % identical to SEQ ID NO:70 or 73.

In particular embodiments, codon optimized CD27 is utilized, and one example is as follows:

```
                                                  (SEQ ID NO: 13)
ATG GCG AGA CCA CAC CCT TGG TGG CTG TGC GTA CTC GGC ACA

CTT GTA GGT CTG TCC GCT ACA CCG GCT CCG AAG TCC TGC CCG GAG CGG

CAT TAT TGG GCA CAG GGC AAG TTG TGT TGT CAA ATG TGT GAG CCG GGA

ACC TTT CTC GTG AAG GAT TGC GAT CAG CAT CGG AAG GCC GCG CAG TGC

GAC CCA TGT ATA CCA GGG GTC TCA TTT TCC CCA GAT CAC CAT ACG AGG

CCG CAC TGT GAG TCT TGC AGG CAT TGT AAT TCC GGC TTG TTG GTC CGC AAC

TGT ACT ATT ACT GCG AAT GCA GAG TGT GCT TGT AGA AAC GGA TGG CAG

TGC AGG GAC AAA GAA TGT ACG GAG TGT GAT CCA CTG CCT AAC CCC AGT

CTT ACA GCA AGA TCT TCA CAG GCC CTC AGC CCG CAT CCT CAA CCA ACA

CAT CTT CCT TAC GTG TCA GAA ATG TTG GAG GCG CGA ACC GCA GGC CAT

ATG CAG ACC CTG GCG GAC TTT CGG CAG CTG CCA GCA CGC ACA CTT AGT

ACA CAC TGG CCA CCA CAA CGC AGC TTG TGC TCT TCC GAT TTC ATC CGC

ATA CTG GTC ATC TTT TCT GGA ATG TTC CTT GTG TTC ACC CTG GCA GGA GCC

CTG TTC CTT CAC CAG AGA CGC AAG TAC AGG TCA AAC AAG GGT GAG AGC

CCC GTT GAA CCC GCA GAG CCG TGT AGA TAC TCA TGT CCT AGA GAA GAA

GAG GGC TCT ACT ATC CCT ATT CAG GAA GAT TAT AGA AAA CCC GAA CCC

GCG TGC AGC CCC.
```

Any polynucleotide encompassed by the present disclosure may utilized SEQ ID NO:13 or a sequence that is at least 70, 75, 80, 85, 90, 95, 96, 97, 98, 99, or more % identical to SEQ ID NO:13.

In particular embodiments, the codon optimized extracellular domain of CD27 is utilized, and one example is as follows:

```
                                              (SEQ ID NO: 64)
GCTACACCGGCTCCGAAGTCCTGCCCGGAGCGGCATTATTGGGCAC

AGGGCAAGTTGTGTTGTCAAATGTGTGAGCCGGGAACCTTTCTCGTGAA

GGATTGCGATCAGCATCGGAAGGCCGCGCAGTGCGACCCATGTATACCA

GGGGTCTCATTTTCCCCAGATCACCATACGAGGCCGCACTGTGAGTCTT

GCAGGCATTGTAATTCCGGCTTGTTGGTCCGCAACTGTACTATTACTGC

GAATGCAGAGTGTGCTTGTAGAAACGGATGGCAGTGCAGGGACAAAGAA

TGTACGGAGTGTGATCCACTGCCTAACCCCAGTCTTACAGCAAGATCTT

CACAGGCCCTCAGCCCGCATCCTCAACCAACACATCTTCCTTACGTGTC

AGAAATGTTGGAGGCGCGAACCGCAGGCCATATGCAGACCCTGGCGGAC

TTTCGGCAGCTGCCAGCACGCACACTTAGTACACACTGGCCACCACAAC

GCAGCTTGTGCTCTTCCGATTTCATCCGC
```

Any polynucleotide encompassed by the present disclosure may utilized SEQ ID NO:64 or a sequence that is at least 70, 75, 80, 85, 90, 95, 96, 97, 98, 99, or more % identical to SEQ ID NO:64.

FIGS. 2A-2E provide specific examples of CAR constructs comprising particular components. These are specific examples in which the CAR construct may comprise full length CD27 (FL; all 260 amino acids). In alternative cases, when the full length CD27 is not utilized, the extracellular domain of CD27 (CD27 EC) may be utilized, which is residues 20-191 of CD27. In particular embodiments, when a truncated CD27 is utilized in the CAR, the CD27 intracellular costimulatory domain (ICD) may not be utilized in the CAR and/or the CD27 transmembrane domain (TMD) may not be utilized in the CAR.

Figure 2A:
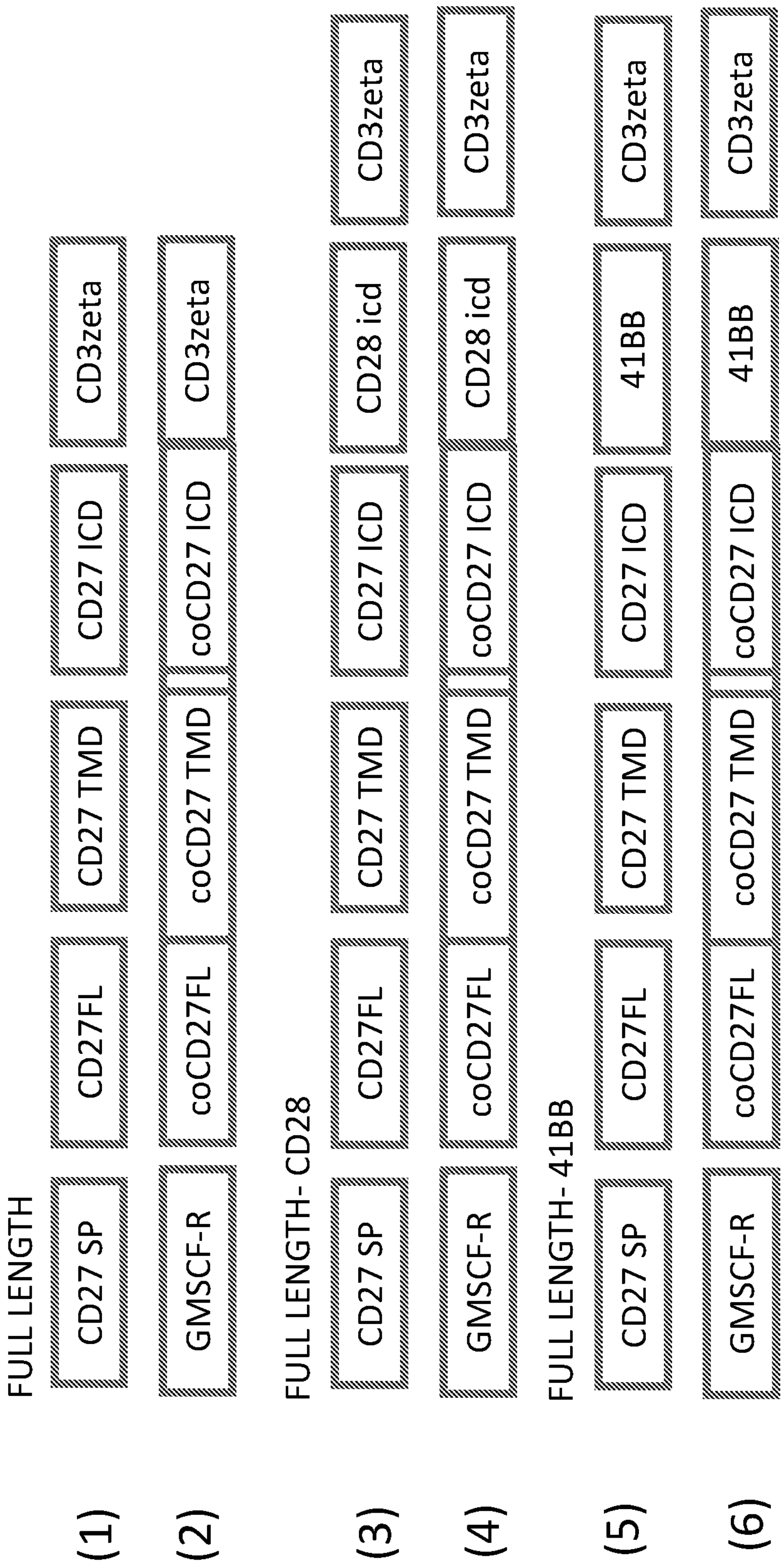
FIGS. 2A-2E illustrate a variety of anti-CD70 CAR constructs.

In FIG. 2A, example (1) of an anti-CD70 CAR comprises the CD27 signal peptide (SP), the full length CD27 (FL), the CD27 TMD, the CD27 ICD, and CD3zeta. Example (2) of FIG. 2A includes the granulocyte-macrophage colony-stimulating factor receptor (GMSCF-R) signal peptide, a codon optimized (co) full length CD27, a codon optimized CD27 transmembrane domain, a codon optimized CD27 ICD, and CD3zeta. Example (3) of FIG. 2A includes the CD27 SP, full length CD27, the CD27 TMD, the CD27 ICD, the CD28 ICD, and CD3 zeta. Example (4) of FIG. 2A includes the GMSCF-R SP, the codon optimized full length CD27, the codon optimized full length CD27 TMD, a codon optimized CD27 ICD, CD28 ICD, and CD3zeta. Example (5) of FIG. 2A includes the CD27 SP, full length CD27, CD27 TMD, CD27 ICD, 4-1BB ICD, and CD3zeta. Example (6) includes the GMSCF-R SP, codon optimized full length CD27, codon optimize CD27 TMD, codon optimized CD27 ICD, 4-1BB ICD, and CD3zeta.

Figure 2B:
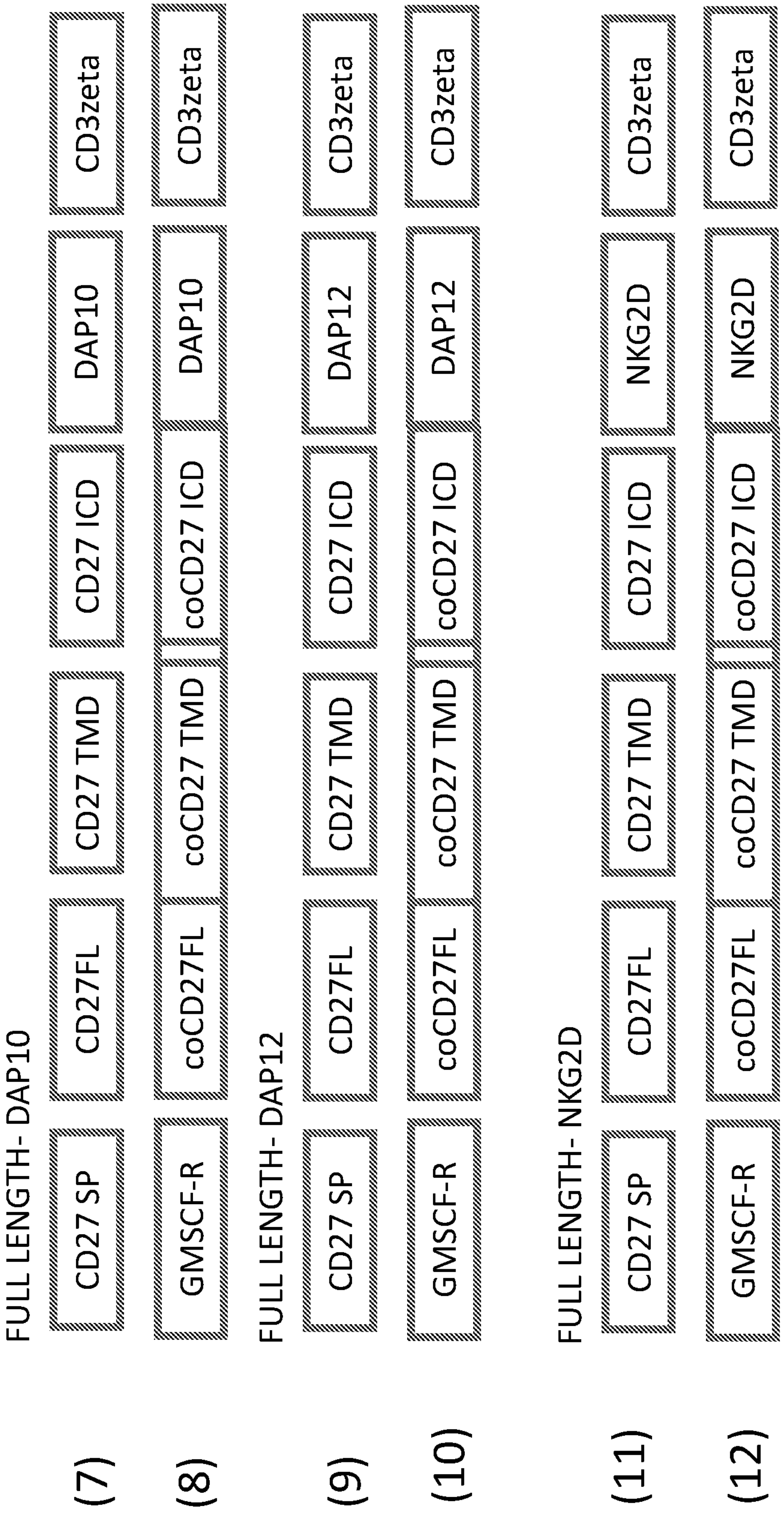

Example (7) in FIG. 2B includes the CD27 SP, full length CD27, CD27 TMD, CD27 ICD, DAP10 ICD, and CD3zeta. Example (8) of FIG. 2B includes the GMSCF-R SP, codon optimized full length CD27, codon optimized CD27 TMD, codon optimized CD27 ICD, DAP10 ICD, and CD3zeta. Example (9) in FIG. 2B includes the CD27 SP, full length CD27, CD27 TMD, CD27 ICD, DAP12 ICD, and CD3zeta. Example (10) of FIG. 2B includes the GMSCF-R SP, codon optimized full length CD27, codon optimized CD27 TMD, codon optimized CD27 ICD, DAP12 ICD, and CD3zeta. Example (11) of FIG. 2B includes the CD27 SP, full length CD27, CD27 TMD, CD27 ICD, NKG2D ICD, and CD3zeta. Example (12) of FIG. 2B includes the GMSCF-R SP, codon optimized full length CD27, codon optimized CD27 TMD, codon optimized CD27 ICD, NKG2D ICD, and CD3zeta.

Figure 2C:
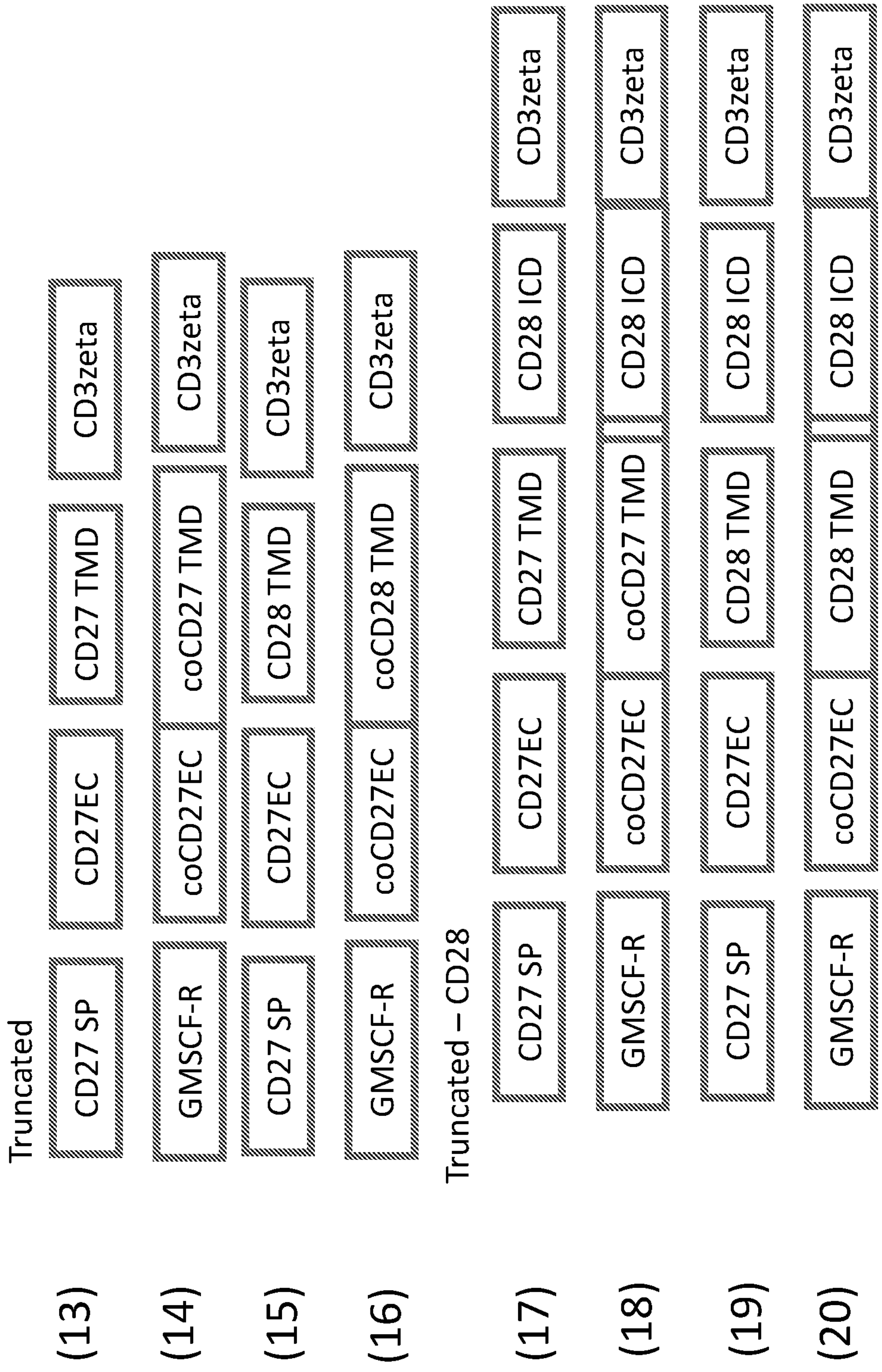

Example (13) in FIG. 2C includes the CD27 SP, CD27 extracellular domain (EC), the CD27 TMD, and CD3zeta. Example (14) in FIG. 2C includes the GMSCF-R SP, codon optimized CD27 EC, codon optimized TMD, and CD3zeta. Example (15) in FIG. 2C includes the CD27 SP, CD27 EC, CD28 TMD, and CD3zeta. Example (16) in FIG. 2C includes GMSCF-R SP, codon optimized CD27 EC, codon optimized CD28 TMD, and CD3zeta. Example (17) in FIG. 2C includes CD27 SP, CD27 EC, CD27 TMD, CD28 ICD, and CD3zeta. Example (18) of FIG. 2C includes GMSCF-R SP, codon optimized CD27 EC, codon optimized CD27 TMD, CD28 ICD, and CD3zeta. Example (19) of FIG. 2C includes CD27SP, CD27 EC, CD28 TMD, CD28 ICD, and CD3zeta. Example (20) of FIG. 2C includes GMSCF-R SP, codon optimized CD27 EC, CD28 TMD, CD28 ICD, and CD3zeta.

Figure 2D:
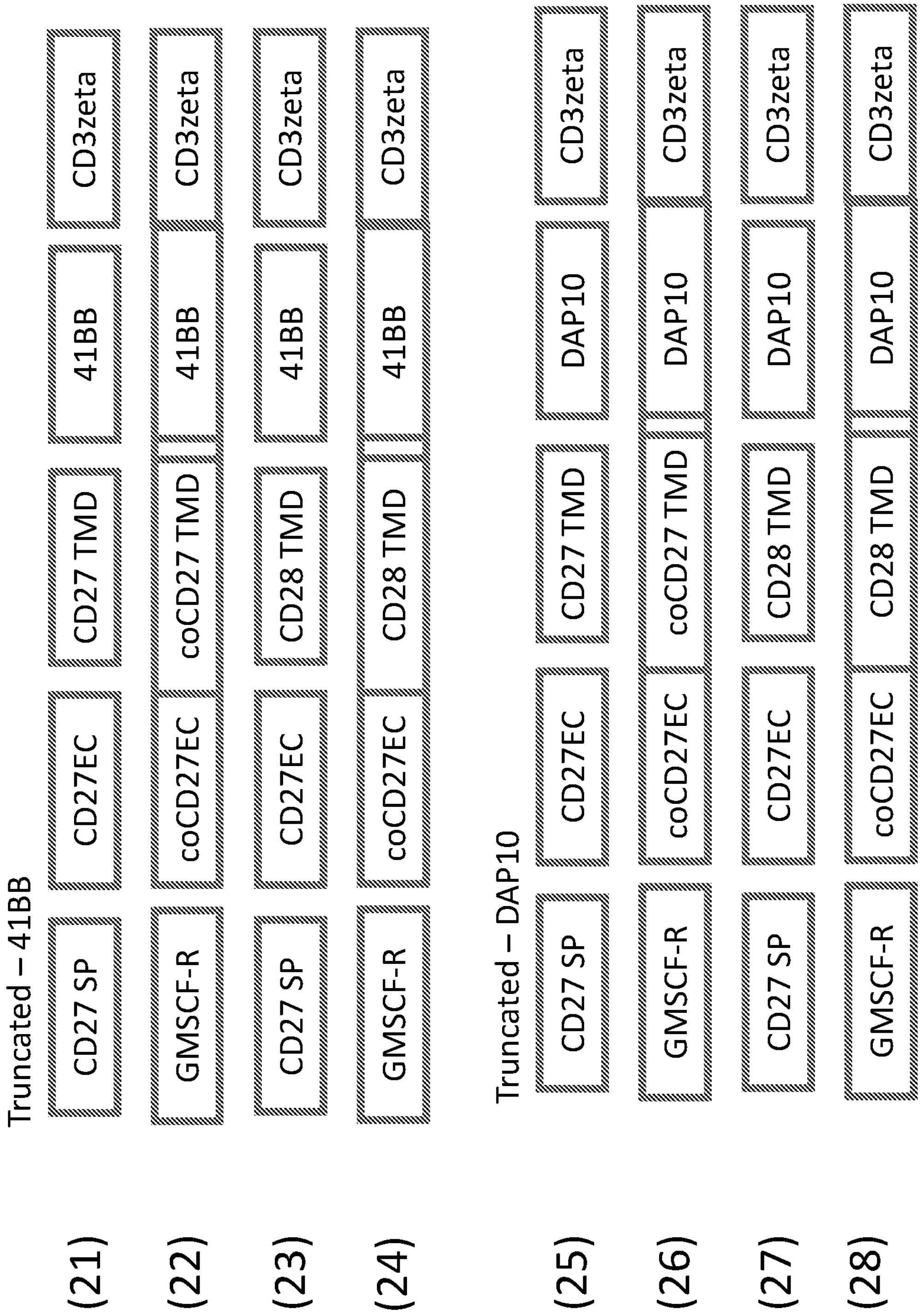

Example (21) of FIG. 2D includes CD27 SP, CD27 EC, CD27 TMD, 4-1BB ICD, and CD3zeta. Example (22) of FIG. 2D includes GMSCF-R SP, codon optimized CD27 EC, codon optimized CD27 TMD, 4-1BB ICD, and CD3zeta. Example (23) of FIG. 2D includes CD27 SP, CD27 EC, CD28 TMD, 4-1BB ICD, and CD3zeta. Example (24) of FIG. 2D includes GMSCF-R SP, codon optimized CD27 EC, CD28 TMD, 4-1BB ICD, and CD3zeta. Example (25) of FIG. 2D includes CD27 SP, CD27 EC, CD27 TMD, DAP10 ICD, and CD3zeta. Example (26) of FIG. 2D includes GMSCF-R SP, codon optimized CD27 EC, codon optimized CD27 TMD, DAP10 ICD, and CD3zeta. Example (27) of FIG. 2D includes CD27 SP, CD27 EC, CD28 costimulatory domain, DAP10 ICD, and CD3zeta. Example (28) of FIG. 2D includes GMSCF-R SP, codon optimized CD27 EC, CD28 TMD, DAP10 ICD, and CD3zeta.

Figure 2E:
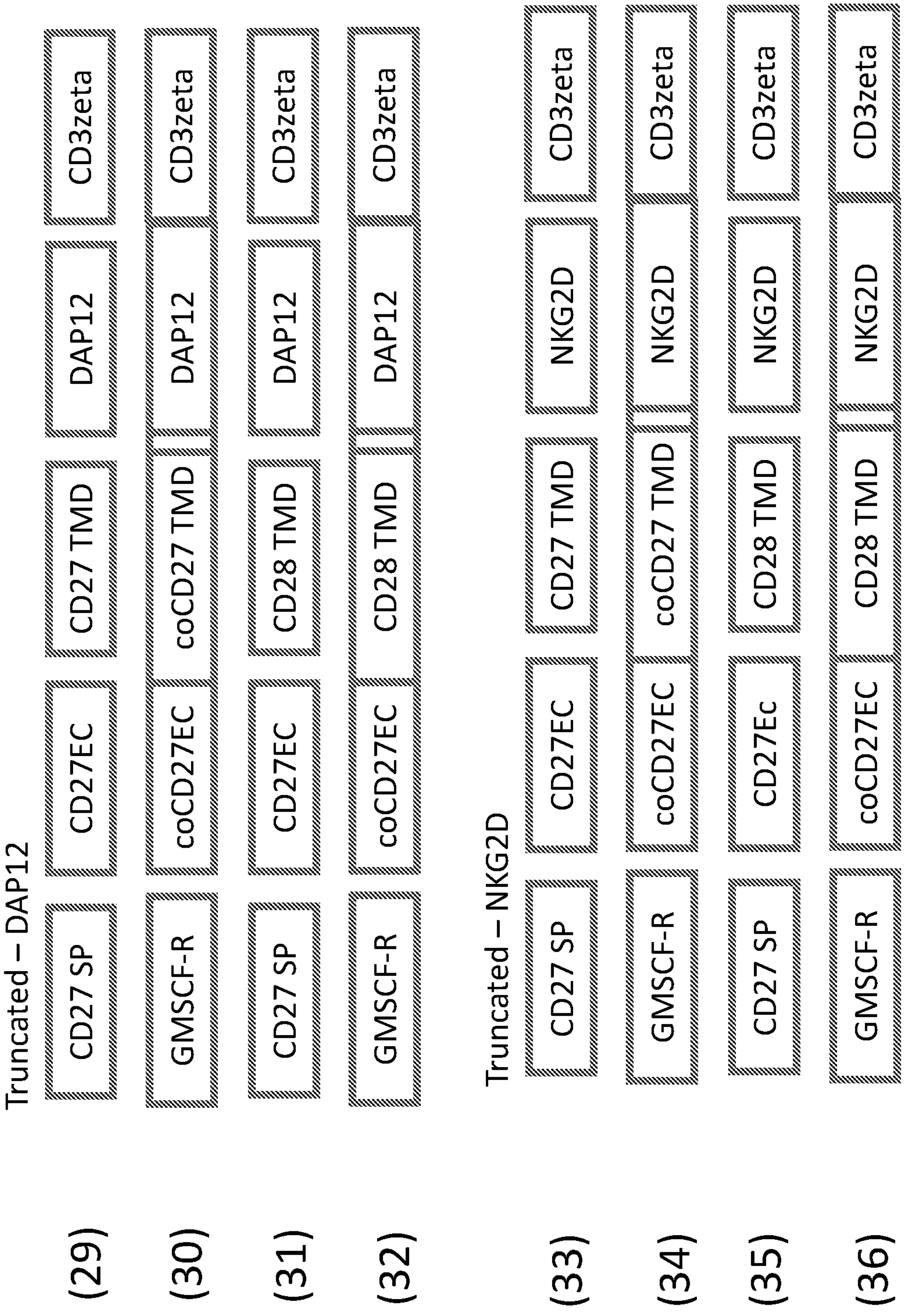

Example (29) of FIG. 2E includes CD27 SP, CD27 EC, CD27 TMD, DAP12 ICD, and CD3zeta. Example (30) of FIG. 2E includes GMSCF-R SP, codon optimized CD27 EC, codon optimized CD27 TMD, DAP12 ICD, and CD3zeta. Example (31) of FIG. 2E includes CD27 SP, CD27 EC, CD28 TMD, DAP12 ICD, and CD3zeta. Example (32) of FIG. 2E includes GMSCF-R SP, codon optimized CD27 EC, CD28 TMD, DAP12 ICD, and CD3zeta. Example (33) of FIG. 2E includes CD27 SP, CD27 EC, CD27 TMD, NKG2D ICD, and CD3zeta. Example (34) of FIG. 2E includes GMSCF-R SP, codon optimized CD27 EC, CD28 TMD, NKG2D ICD, and CD3zeta. Example (35) of FIG. 2E includes CD27 SP, CD27 EC, CD28 TMD, NKG2D ICD, and CD3zeta. Example (36) of FIG. 2E includes GMSCF-R SP, codon optimized CD27 EC, CD28 TMD, NKG2D ICD, and CD3zeta.

One example of an anti-CD70 CAR of the disclosure comprises SEQ ID NO:1 that comprises a CD27 extracellular domain (not underlined in SEQ ID NO:1 below) operably linked to a CD28 transmembrane domain (underlined in SEQ ID NO:1 below) and a CD27 signal peptide (bolded in SEQ ID NO:1 below):

(SEQ ID NO: 1)

MARPHPWWLCVLGTLVGLSATPAPKSCPERHYWAQGKLCCQMCEP

GTFLVKDCDQHRKAAQCDPCIPGVSFSPDHHTRPHCESCRHCNSGLLVR

NCTITANAECACRNGWQCRDKECTECDPLPNPSLTARSSQALSPHPQPT

HLPYVSEMLEARTAGHMQTLADFRQLPARTLSTHWPPQRSLCSSDFIR<u>F</u>

<u>WVLVVVGGVLACYSLLVTVAFIIFWV</u>

The CD27 extracellular domain of SEQ ID NO:1 comprises the following as SEQ ID NO:2: MARPHPWWLCVLGTLVGLSATPAPKSCPERHY-WAQGKLCCQMCEPGTFLVKDCDQ HRKAAQCDPCIPGVSFSPDHHTRPHC-ESCRHCNSGLLVRNCTITANAECACRNGWQC RDKE-CTECDPLPNPSLTARSSQALSPHPQPTHLPYVSEM-LEARTAGHMQTLADFRQL PARTLSTHWPPQRSLCSSDFIR.

The CD28 transmembrane domain of SEQ ID NO:1 comprises the following as SEQ ID NO:3: FWVLVVVGGVLACYSLLVTVAFIIFWV (TTTTGGGTGCTGGTGGTGGTTGGTG-GAGTCCTGGCTTGCTATAGCTTGCTAGTAA CAGTGGCCTTTATTATTTTCTGGGTG (SEQ ID NO:65)).

The CD27 signal peptide of SEQ ID NO:1 comprises the following as SEQ ID NO:6: MARPHPWWLCVLGTLVGLS (ATGGCACGGCCA-CATCCCTGGTGGCTGTGCGTTCTGGGGACCCT-GGTGGGGCTC TCA (SEQ ID NO:61)).

The present disclosure provides for cells (including immune cells, such as NK cells) that harbor a vector that encodes at least one CAR, and the CAR may be first generation, second generation, or third or a subsequent generation, for example. The CAR may or may not be bispecific for two or more different antigens, one of which is CD70. In particular embodiments, the CAR is not a bivalent tandem CAR. The CAR may comprise one or more costimulatory domains. Each costimulatory domain may comprise the costimulatory domain of any one or more of, for example, members of the TNFR superfamily, CD28, CD137 (4-1BB), CD134 (OX40), DAP10, DAP12, CD27, CD2, CD5, ICAM-1, LFA-1 (CD11a/CD18), Lck, TNFR-I, TNFR-II, Fas, CD30, CD40, any ITAM-containing signaling domain, or combinations thereof, for example. In specific embodiments, the CAR comprises CD3zeta. In certain embodiments, the CAR lacks one or more specific costimulatory domains; for example, the CAR may lack 4-1BB and/or lack CD28.

In particular embodiments, the CAR polypeptide in the cells comprises an extracellular spacer domain that links the antigen binding domain and the transmembrane domain. Extracellular spacer domains may include, but are not limited to, Fc fragments of antibodies or fragments or derivatives thereof, hinge regions of antibodies or fragments or derivatives thereof, CH2 regions of antibodies, CH3 regions antibodies, artificial spacer sequences or combinations thereof. Examples of extracellular spacer domains include but are not limited to CD8-alpha hinge, CD28, artificial spacers made of polypeptides such as Gly3, or CH1, CH3 domains of IgGs (such as human IgG1 or IgG4). In specific cases, the extracellular spacer domain may comprise (i) a hinge, CH2 and CH3 regions of IgG4, (ii) a hinge region of IgG4, (iii) a hinge and CH2 of IgG4, (iv) a hinge region of CD8-alpha, (v) a hinge, CH2 and CH3 regions of IgG1, (vi) a hinge region of IgG1 or (vii) a hinge and CH2 of IgG1, (viii) a hinge region of CD28, or a combination thereof.

In specific embodiments, the hinge is from IgG1 and in certain aspects the CAR polypeptide comprises a particular IgG1 hinge amino acid sequence or is encoded by a particular IgG1 hinge nucleic acid sequence.

In specific embodiments, the hinge is from CD28 and in certain aspects the CAR polypeptide comprises a particular CD28 hinge amino acid sequence or is encoded by a particular CD28 hinge nucleic acid sequence.

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T- cell receptor, CD28, CD3 zeta, CD3 epsilon, CD3 gamma, CD3 delta, CD45, CD4, CD5, CD8, CD9, CD16, CD22, CD33, CD37, CD64, CD80, CD86, CD134, CD137, CD154, ICOS/CD278, GITR/CD357, NKG2D, and DAP molecules, such as DAP10 or DAP12. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine may be found at each end of a synthetic transmembrane domain.

In certain embodiments, the CD70-specific CAR may be co-expressed with one or more cytokines to improve persistence when there is a low amount of tumor-associated antigen. For example, the CAR may be co-expressed with one or more cytokines, such as IL-7, IL-2, IL-15, IL-12, IL-18, IL-21, IL-7, GMCSF, or a combination thereof.

In specific examples, an anti-CD70 CAR may have the following nucleotide sequence:

CD27tr28tdmCD3zIL15:

```
                                    (SEQ ID NO: 15)
ATGGCACGGCCACATCCCTGGTGGCTGTGCGTTCTGGGGACCCTGG
TGGGGCTCTCAGCTACTCCAGCCCCCAAGAGCTGCCCAGAGAGGCACTA
CTGGGCTCAGGGAAAGCTGTGCTGCCAGATGTGTGAGCCAGGAACATTC
CTCGTGAAGGACTGTGACCAGCATAGAAAGGCTGCTCAGTGTGATCCTT
GCATACCGGGGGTCTCCTTCTCTCCTGACCACCACACCCGGCCCCACTG
TGAGAGCTGTCGGCACTGTAACTCTGGTCTTCTCGTTCGCAACTGCACC
ATCACTGCCAATGCTGAGTGTGCCTGTCGCAATGGCTGGCAGTGCAGGG
ACAAGGAGTGCACCGAGTGTGATCCTCTTCCAAACCCTTCGCTGACCGC
TCGGTCGTCTCAGGCCCTGAGCCCACACCCTCAGCCCACCCACTTACCT
TATGTCAGTGAGATGCTGGAGGCCAGGACAGCTGGGCACATGCAGACTC
TGGCTGACTTCAGGCAGCTGCCTGCCCGGACTCTCTCTACCCACTGGCC
ACCCCAAAGATCCCTGTGCAGCTCCGATTTTATTCGCTTTTGGGTGCTG
GTGGTGGTTGGTGGAGTCCTGGCTTGCTATAGCTTGCTAGTAACAGTGG
CCTTTATTATTTTCTGGGTG
```

A corresponding amino acid sequence for CD27tr28tdmCD3zIL15 is as follows:

```
                                    (SEQ ID NO: 38)
MARPHPWWLCVLGTLVGLSATPAPKSCPERHYWAQGKLCCQMCEPG
TFLVKDCDQHRKAAQCDPCIPGVSFSPDHHTRPHCESCRHCNSGLLVRN
CTITANAECACRNGWQCRDKECTECDPLPNPSLTARSSQALSPHPQPTH
LPYVSEMLEARTAGHMQTLADFRQLPARTLSTHWPPQRSLCSSDFIRFW
VLVVVGGVLACYSLLVTVAFIIFWV
```

CD27Tr28tmd41BBicd3zIL15:

```
                                    (SEQ ID NO: 16)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGGCACGGC
CACATCCCTGGTGGCTGTGCGTTCTGGGGACCCTGGTGGGGCTCTCAGC
TACTCCAGCCCCCAAGAGCTGCCCAGAGAGGCACTACTGGGCTCAGGGA
AAGCTGTGCTGCCAGATGTGTGAGCCAGGAACATTCCTCGTGAAGGACT
GTGACCAGCATAGAAAGGCTGCTCAGTGTGATCCTTGCATACCGGGGGT
CTCCTTCTCTCCTGACCACCACACCCGGCCCCACTGTGAGAGCTGTCGG
CACTGTAACTCTGGTCTTCTCGTTCGCAACTGCACCATCACTGCCAATG
CTGAGTGTGCCTGTCGCAATGGCTGGCAGTGCAGGGACAAGGAGTGCAC
```

-continued

CGAGTGTGATCCTCTTCCAAACCCTTCGCTGACCGCTCGGTCGTCTCAG
GCCCTGAGCCCACACCCTCAGCCCACCCACTTACCTTATGTCAGTGAGA
TGCTGGAGGCCAGGACAGCTGGGCACATGCAGACTCTGGCTGACTTCAG
GCAGCTGCCTGCCCGGACTCTCTCTACCCACTGGCCACCCCAAAGATCC
CTGTGCAGCTCCGATTTTATTCGCTTTTGGGTGCTGGTGGTGGTTGGTG
GAGTCCTGGCTTGCTATAGCTTGCTAGTAACAGTGGCCTTTATTATTTT
CTGGGTGAAACGGGGCAGAAAGAAACTCCTGTATATATTCAAACAACCA
TTTATGAGACCAGTACAAACTACTCAAGAGGAAGATGGCTGTAGCTGCC
GATTTCCAGAAGAAGAAGAAGGAGGATGTGAACTGAAACGCGTGAAGTT
CAGCAGGAGCGCAGACGCCCCCGCGTACCAGCAGGGCCAGAACCAGCTC
TATAACGAGCTCAATCTAGGACGAAGAGAGGAGTACGATGTTTTGGACA
AAAGACGTGGCCGGGACCCTGAGATGGGGGGAAAGCCGAGAAGGAAGAA
CCCTCAGGAAGGCCTGTACAATGAACTGCAGAAAGATAAGATGGCGGAG
GCCTACAGTGAGATTGGGATGAAAGGCGAGCGCCGGAGGGGCAAGGGGC
ACGATGGCCTTTACCAGGGTCTCAGTACAGCCACCAAGGACACCTACGA
CGCCCTTCACATGCAGGCCCTGCCCCCTCGCGGACCGCAGTGTACTAAT
TATGCTCTCTTGAAATTGGCTGGAGATGTTGAGAGCAATCCCGGGCCCA
TGCGCATTAGCAAGCCCCACCTGCGGAGCATCAGCATCCAGTGCTACCT
GTGCCTGCTGCTGAACAGCCACTTCCTGACCGAGGCCGGCATCCACGTG
TTCATCCTGGGCTGCTTCAGCGCCGGACTGCCCAAGACCGAGGCCAACT
GGGTGAACGTGATCAGCGACCTGAAGAAGATCGAGGACCTGATCCAGAG
CATGCACATCGACGCCACCCTGTACACCGAGAGCGACGTGCACCCCAGC
TGCAAGGTGACCGCCATGAAGTGCTTTCTGCTGGAACTGCAGGTGATCA
GCCTGGAAAGCGGCGACGCCAGCATCCACGACACCGTGGAGAACCTGAT
CATCCTGGCCAACAACAGCCTGAGCAGCAACGGCAACGTGACCGAGAGC
GGCTGCAAAGAGTGCGAGGAACTGGAAGAGAAGAACATCAAAGAGTTTC
TGCAGAGCTTCGTGCACATCGTGCAGATGTTCATCAACACCAGCTGA

A corresponding amino acid sequence for CD27Tr28tmd41BBicd3zIL15 is as follows:

(SEQ ID NO: 39)
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMARPHPWWLCVLGTLVGLSATPAPKSCPERHYWA
QGKLCCQMCEPGTFLVKDCDQHRKAAQCDPCIPGVSFSPDHHTRPHCES
CRHCNSGLLVRNCTITANAECACRNGWQCRDKECTECDPLPNPSLTARS
SQALSPHPQPTHLPYVSEMLEARTAGHMQTLADFRQLPARTLSTHWPPQ
RSLCSSDFIRFWVLVVVGGVLACYSLLVTVAFIIFWVKRGRKKLLYIFK
QPFMRPVQTTQEEDGCSCRFPEEEEGGCELKRVKFSRSADAPAYQQGQN
QLYNELNLGRREEYDVLDKRRGRDPEMGGKPRRKNPQEGLYNELQKDKM
AEAYSEIGMKGERRRGKGHDGLYQGLSTATKDTYDALHMQALPPRGPQC

-continued

TNYALLKLAGDVESNPGPMRISKPHLRSISIQCYLCLLLNSHFLTEAGI
HVFILGCFSAGLPKTEANWVNVISDLKKIEDLIQSMHIDATLYTESDVH
PSCKVTAMKCFLLELQVISLESGDASIHDTVENLIILANNSLSSNGNVT
ESGCKECEELEEKNIKEFLQSFVHIVQMFINTS

GSPco27Tr28tmd41BBicCD3zIL15:

(SEQ ID NO: 17)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGCTTCTCC
TGGTGACAAGCCTTCTGCTCTGTGAGTTACCACACCCAGCATTCCTCCT
GATCCCAGCTACACCGGCTCCGAAGTCCTGCCCGGAGCGGCATTATTGG
GCACAGGGCAAGTTGTGTTGTCAAATGTGTGAGCCGGGAACCTTTCTCG
TGAAGGATTGCGATCAGCATCGGAAGGCCGCGCAGTGCGACCCATGTAT
ACCAGGGGTCTCATTTTCCCCAGATCACCATACGAGGCCGCACTGTGAG
TCTTGCAGGCATTGTAATTCCGGCTTGTTGGTCCGCAACTGTACTATTA
CTGCGAATGCAGAGTGTGCTTGTAGAAACGGATGGCAGTGCAGGGACAA
AGAATGTACGGAGTGTGATCCACTGCCTAACCCCAGTCTTACAGCAAGA
TCTTCACAGGCCCTCAGCCCGCATCCTCAACCAACACATCTTCCTTACG
TGTCAGAAATGTTGGAGGCGCGAACCGCAGGCCATATGCAGACCCTGGC
GGACTTTCGGCAGCTGCCAGCACGCACACTTAGTACACACTGGCCACCA
CAACGCAGCTTGTGCTCTTCCGATTTCATCCGCTTTTGGGTGCTGGTGG
TGGTTGGTGGAGTCCTGGCTTGCTATAGCTTGCTAGTAACAGTGGCCTT
TATTATTTTCTGGGTGAAACGGGGCAGAAAGAAACTCCTGTATATATTC
AAACAACCATTTATGAGACCAGTACAAACTACTCAAGAGGAAGATGGCT
GTAGCTGCCGATTTCCAGAAGAAGAAGAAGGAGGATGTGAACTGAAACG
CGTGAAGTTCAGCAGGAGCGCAGACGCCCCCGCGTACCAGCAGGGCCAG
AACCAGCTCTATAACGAGCTCAATCTAGGACGAAGAGAGGAGTACGATG
TTTTGGACAAAAGACGTGGCCGGGACCCTGAGATGGGGGGAAAGCCGAG
AAGGAAGAACCCTCAGGAAGGCCTGTACAATGAACTGCAGAAAGATAAG
ATGGCGGAGGCCTACAGTGAGATTGGGATGAAAGGCGAGCGCCGGAGGG
GCAAGGGGCACGATGGCCTTTACCAGGGTCTCAGTACAGCCACCAAGGA
CACCTACGACGCCCTTCACATGCAGGCCCTGCCCCCTCGCGGACCGCAG
TGTACTAATTATGCTCTCTTGAAATTGGCTGGAGATGTTGAGAGCAATC
CCGGGCCCATGCGCATTAGCAAGCCCCACCTGCGGAGCATCAGCATCCA
GTGCTACCTGTGCCTGCTGCTGAACAGCCACTTCCTGACCGAGGCCGGC
ATCCACGTGTTCATCCTGGGCTGCTTCAGCGCCGGACTGCCCAAGACCG

-continued

AGGCCAACTGGGTGAACGTGATCAGCGACCTGAAGAAGATCGAGGACCT

GATCCAGAGCATGCACATCGACGCCACCCTGTACACCGAGAGCGACGTG

CACCCCAGCTGCAAGGTGACCGCCATGAAGTGCTTTCTGCTGGAACTGC

AGGTGATCAGCCTGGAAAGCGGCGACGCCAGCATCCACGACACCGTGGA

GAACCTGATCATCCTGGCCAACAACAGCCTGAGCAGCAACGGCAACGTG

ACCGAGAGCGGCTGCAAAGAGTGCGAGGAACTGGAAGAGAAGAACATCA

AAGAGTTTCTGCAGAGCTTCGTGCACATCGTGCAGATGTTCATCAACAC

CAGCTGA

A corresponding amino acid sequence for GSPco27Tr28tmd41BBicCD3zIL15 is as follows:

(SEQ ID NO: 40)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMLLLVTSLLLCELPHPAFLLIPATPAPKSCPERH

YWAQGKLCCQMCEPGTFLVKDCDQHRKAAQCDPCIPGVSFSPDHHTRPH

CESCRHCNSGLLVRNCTITANAECACRNGWQCRDKECTECDPLPNPSLT

ARSSQALSPHPQPTHLPYVSEMLEARTAGHMQTLADFRQLPARTLSTHW

PPQRSLCSSDFIRFWVLVVVGGVLACYSLLVTVAFIIFWVKRGRKKLLY

IFKQPFMRPVQTTQEEDGCSCRFPEEEEGGCELKRVKFSRSADAPAYQQ

GQNQLYNELNLGRREEYDVLDKRRGRDPEMGGKPRRKNPQEGLYNELQK

DKMAEAYSEIGMKGERRRGKGHDGLYQGLSTATKDTYDALHMQALPPRG

PQCTNYALLKLAGDVESNPGPMRISKPHLRSISIQCYLCLLLNSHFLTE

AGIHVFILGCFSAGLPKTEANWVNVISDLKKIEDLIQSMHIDATLYTES

DVHPSCKVTAMKCFLLELQVISLESGDASIHDTVENLIILANNSLSSNG

NVTESGCKECEELEEKNIKEFLQSFVHIVQMFINTS

CD27Tr28tmdDAP10icd3z15:

(SEQ ID NO: 18)

ATGACAAGAGTTACTAACAGCCCCTCTCTCCAAGCTCACTTACAGG

CTCTCTACTTAGTCCAGCACGAAGTCTGGAGACCTCTGGCGGCAGCCTA

CCAAGAACAACTGGACCGACCGGTGGTACCTCACCCTTACCGAGTCGGC

GACACAGTGTGGGTCCGCCGACACCAGACTAAGAACCTAGAACCTCGCT

GGAAAGGACCTTACACAGTCCTGCTGACCACCCCCACCGCCCTCAAAGT

AGACGGCATCGCAGCTTGGATACACGCCGCCCACGTGAAGGCTGCCGAC

CCCGGGGGTGGACCATCCTCTAGACTGCCATGCTCGAGGATGGCACGGC

CACATCCCTGGTGGCTGTGCGTTCTGGGGACCCTGGTGGGGCTCTCAGC

TACTCCAGCCCCCAAGAGCTGCCCAGAGAGGCACTACTGGGCTCAGGGA

AAGCTGTGCTGCCAGATGTGTGAGCCAGGAACATTCCTCGTGAAGGACT

GTGACCAGCATAGAAAGGCTGCTCAGTGTGATCCTTGCATACCGGGGGT

CTCCTTCTCTCCTGACCACCACACCCGGCCCCACTGTGAGAGCTGTCGG

CACTGTAACTCTGGTCTTCTCGTTCGCAACTGCACCATCACTGCCAATG

CTGAGTGTGCCTGTCGCAATGGCTGGCAGTGCAGGGACAAGGAGTGCAC

-continued

CGAGTGTGATCCTCTTCCAAACCCTTCGCTGACCGCTCGGTCGTCTCAG

GCCCTGAGCCCACACCCTCAGCCCACCCACTTACCTTATGTCAGTGAGA

TGCTGGAGGCCAGGACAGCTGGGCACATGCAGACTCTGGCTGACTTCAG

GCAGCTGCCTGCCCGGACTCTCTCTACCCACTGGCCACCCCAAAGATCC

CTGTGCAGCTCCGATTTTATTCGCTTTTGGGTGCTGGTGGTGGTTGGTG

GAGTCCTGGCTTGCTATAGCTTGCTAGTAACAGTGGCCTTTATTATTTT

CTGGGTGCTTTGCGCACGCCCACGCCGCAGCCCCGCCCAAGAAGATGGC

AAAGTCTACATCAACATGCCAGGCAGGGGCAAACGCGTGAAGTTCAGCA

GGAGCGCAGACGCCCCCGCGTACCAGCAGGGCCAGAACCAGCTCTATAA

CGAGCTCAATCTAGGACGAAGAGAGGAGTACGATGTTTTGGACAAAAGA

CGTGGCCGGGACCCTGAGATGGGGGGAAAGCCGAGAAGGAAGAACCCTC

AGGAAGGCCTGTACAATGAACTGCAGAAAGATAAGATGGCGGAGGCCTA

CAGTGAGATTGGGATGAAAGGCGAGCGCCGGAGGGGCAAGGGGCACGAT

GGCCTTTACCAGGGTCTCAGTACAGCCACCAAGGACACCTACGACGCCC

TTCACATGCAGGCCCTGCCCCCTCGCGGACCGCAGTGTACTAATTATGC

TCTCTTGAAATTGGCTGGAGATGTTGAGAGCAATCCCGGGCCCATGCGC

ATTAGCAAGCCCCACCTGCGGAGCATCAGCATCCAGTGCTACCTGTGCC

TGCTGCTGAACAGCCACTTCCTGACCGAGGCCGGCATCCACGTGTTCAT

CCTGGGCTGCTTCAGCGCCGGACTGCCCAAGACCGAGGCCAACTGGGTG

AACGTGATCAGCGACCTGAAGAAGATCGAGGACCTGATCCAGAGCATGC

ACATCGACGCCACCCTGTACACCGAGAGCGACGTGCACCCCAGCTGCAA

GGTGACCGCCATGAAGTGCTTTCTGCTGGAACTGCAGGTGATCAGCCTG

GAAAGCGGCGACGCCAGCATCCACGACACCGTGGAGAACCTGATCATCC

TGGCCAACAACAGCCTGAGCAGCAACGGCAACGTGACCGAGAGCGGCTG

CAAAGAGTGCGAGGAACTGGAAGAGAAGAACATCAAAGAGTTTCTGCAG

AGCTTCGTGCACATCGTGCAGATGTTCATCAACACCAGCTGA

A corresponding amino acid sequence for CD27Tr28tmdDAP10icd3z15 is as follows:

(SEQ ID NO: 41)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMARPHPWWLCVLGTLVGLSATPAPKSCPERHYWA

QGKLCCQMCEPGTFLVKDCDQHRKAAQCDPCIPGVSFSPDHHTRPHCES

CRHCNSGLLVRNCTITANAECACRNGWQCRDKECTECDPLPNPSLTARS

SQALSPHPQPTHLPYVSEMLEARTAGHMQTLADFRQLPARTLSTHWPPQ

RSLCSSDFIRFWVLVVVGGVLACYSLLVTVAFIIFWVLCARPRRSPAQE

DGKVYINMPGRGKRVKFSRSADAPAYQQGQNQLYNELNLGRREEYDVLD

KRRGRDPEMGGKPRRKNPQEGLYNELQKDKMAEAYSEIGMKGERRRGKG

HDGLYQGLSTATKDTYDALHMQALPPRGPQCTNYALLKLAGDVESNPGP

MRISKPHLRSISIQCYLCLLLNSHFLTEAGIHVFILGCFSAGLPKTEAN

-continued

WVNVISDLKKIEDLIQSMHIDATLYTESDVHPSCKVTAMKCFLLELQVI
SLESGDASIHDTVENLIILANNSLSSNGNVTESGCKECEELEEKNIKEF
LQSFVHIVQMFINTS

GSPco27Tr28tmdDAP10IL15:

(SEQ ID NO: 19)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGCTTCTCC
TGGTGACAAGCCTTCTGCTCTGTGAGTTACCACACCCAGCATTCCTCCT
GATCCCAGCTACACCGGCTCCGAAGTCCTGCCCGGAGCGGCATTATTGG
GCACAGGGCAAGTTGTGTTGTCAAATGTGTGAGCCGGGAACCTTTCTCG
TGAAGGATTGCGATCAGCATCGGAAGGCCGCGCAGTGCGACCCATGTAT
ACCAGGGGTCTCATTTTCCCCAGATCACCATACGAGGCCGCACTGTGAG
TCTTGCAGGCATTGTAATTCCGGCTTGTTGGTCCGCAACTGTACTATTA
CTGCGAATGCAGAGTGTGCTTGTAGAAACGGATGGCAGTGCAGGGACAA
AGAATGTACGGAGTGTGATCCACTGCCTAACCCCAGTCTTACAGCAAGA
TCTTCACAGGCCCTCAGCCCGCATCCTCAACCAACACATCTTCCTTACG
TGTCAGAAATGTTGGAGGCGCGAACCGCAGGCCATATGCAGACCCTGGC
GGACTTTCGGCAGCTGCCAGCACGCACACTTAGTACACACTGGCCACCA
CAACGCAGCTTGTGCTCTTCCGATTTCATCCGCTTTTGGGTGCTGGTGG
TGGTTGGTGGAGTCCTGGCTTGCTATAGCTTGCTAGTAACAGTGGCCTT
TATTATTTTCTGGGTGCTTTGCGCACGCCCACGCCGCAGCCCCGCCCAA
GAAGATGGCAAAGTCTACATCAACATGCCAGGCAGGGGCAAACGCGTGA
AGTTCAGCAGGAGCGCAGACGCCCCCGCGTACCAGCAGGGCCAGAACCA
GCTCTATAACGAGCTCAATCTAGGACGAAGAGAGGAGTACGATGTTTTG
GACAAAAGACGTGGCCGGGACCCTGAGATGGGGGGAAAGCCGAGAAGGA
AGAACCCTCAGGAAGGCCTGTACAATGAACTGCAGAAAGATAAGATGGC
GGAGGCCTACAGTGAGATTGGGATGAAAGGCGAGCGCCGGAGGGGCAAG
GGGCACGATGGCCTTTACCAGGGTCTCAGTACAGCCACCAAGGACACCT
ACGACGCCCTTCACATGCAGGCCCTGCCCCCTCGCGGACCGCAGTGTAC
TAATTATGCTCTCTTGAAATTGGCTGGAGATGTTGAGAGCAATCCCGGG
CCCATGCGCATTAGCAAGCCCCACCTGCGGAGCATCAGCATCCAGTGCT
ACCTGTGCCTGCTGCTGAACAGCCACTTCCTGACCGAGGCCGGCATCCA
CGTGTTCATCCTGGGCTGCTTCAGCGCCGGACTGCCCAAGACCGAGGCC
AACTGGGTGAACGTGATCAGCGACCTGAAGAAGATCGAGGACCTGATCC
AGAGCATGCACATCGACGCCACCCTGTACACCGAGAGCGACGTGCACCC
CAGCTGCAAGGTGACCGCCATGAAGTGCTTTCTGCTGGAACTGCAGGTG
ATCAGCCTGGAAAGCGGCGACGCCAGCATCCACGACACCGTGGAGAACC
TGATCATCCTGGCCAACAACAGCCTGAGCAGCAACGGCAACGTGACCGA
GAGCGGCTGCAAAGAGTGCGAGGAACTGGAAGAGAAGAACATCAAAGAG
TTTCTGCAGAGCTTCGTGCACATCGTGCAGATGTTCATCAACACCAGCT
GA

A corresponding amino acid sequence for GSPco27Tr28tmdDAP10IL15 is as follows:

(SEQ ID NO: 42)
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMLLLVTSLLLCELPHPAFLLIPATPAPKSCPERH
YWAQGKLCCQMCEPGTFLVKDCDQHRKAAQCDPCIPGVSFSPDHHTRPH
CESCRHCNSGLLVRNCTITANAECACRNGWQCRDKECTECDPLPNPSLT
ARSSQALSPHPQPTHLPYVSEMLEARTAGHMQTLADFRQLPARTLSTHW
PPQRSLCSSDFIRFWVLVVVGGVLACYSLLVTVAFIIFWVLCARPRRSP
AQEDGKVYINMPGRGRKRVKFSRSADAPAYQQGQNQLYNELNLGRREEYD
VLDKRRGRDPEMGGKPRRKNPQEGLYNELQKDKMAEAYSEIGMKGERRR
GKGHDGLYQGLSTATKDTYDALHMQALPPRGPQCTNYALLKLAGDVESN
PGPMRISKPHLRSISIQCYLCLLLNSHFLTEAGIHVFILGCFSAGLPKT
EANWVNVISDLKKIEDLIQSMHIDATLYTESDVHPSCKVTAMKCFLLEL
QVISLESGDASIHDTVENLIILANNSLSSNGNVTESGCKECEELEEKNI
KEFLQSFVHIVQMFINTS

CD27Tr28tmdDAP12icd3z15:

(SEQ ID NO: 20)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGGCACGGC
CACATCCCTGGTGGCTGTGCGTTCTGGGGACCCTGGTGGGGCTCTCAGC
TACTCCAGCCCCCAAGAGCTGCCCAGAGAGGCACTACTGGGCTCAGGGA
AAGCTGTGCTGCCAGATGTGTGAGCCAGGAACATTCCTCGTGAAGGACT
GTGACCAGCATAGAAAGGCTGCTCAGTGTGATCCTTGCATACCGGGGGT
CTCCTTCTCTCCTGACCACCACACCCGGCCCCACTGTGAGAGCTGTCGG
CACTGTAACTCTGGTCTTCTCGTTCGCAACTGCACCATCACTGCCAATG
CTGAGTGTGCCTGTCGCAATGGCTGGCAGTGCAGGGACAAGGAGTGCAC
CGAGTGTGATCCTCTTCCAAACCCTTCGCTGACCGCTCGGTCGTCTCAG
GCCCTGAGCCCACACCCTCAGCCCACCCACTTACCTTATGTCAGTGAGA

-continued

TGCTGGAGGCCAGGACAGCTGGGCACATGCAGACTCTGGCTGACTTCAG
GCAGCTGCCTGCCCGGACTCTCTCTACCCACTGGCCACCCCAAAGATCC
CTGTGCAGCTCCGATTTTATTCGCTTTTGGGTGCTGGTGGTGGTTGGTG
GAGTCCTGGCTTGCTATAGCTTGCTAGTAACAGTGGCCTTTATTATTTT
CTGGGTGTACTTCCTGGGCCGGCTGGTCCCTCGGGGGCGAGGGGCTGCG
GAGGCAGCGACCCGGAAACAGCGTATCACTGAGACCGAGTCGCCTTATC
AGGAGCTCCAGGGTCAGAGGTCGGATGTCTACAGCGACCTCAACACACA
GAGGCCGTATTACAAAAAACGCGTGAAGTTCAGCAGGAGCGCAGACGCC
CCCGCGTACCAGCAGGGCCAGAACCAGCTCTATAACGAGCTCAATCTAG
GACGAAGAGAGGAGTACGATGTTTTGGACAAAAGACGTGGCCGGGACCC
TGAGATGGGGGGAAAGCCGAGAAGGAAGAACCCTCAGGAAGGCCTGTAC
AATGAACTGCAGAAAGATAAGATGGCGGAGGCCTACAGTGAGATTGGGA
TGAAAGGCGAGCGCCGGAGGGGCAAGGGGCACGATGGCCTTTACCAGGG
TCTCAGTACAGCCACCAAGGACACCTACGACGCCCTTCACATGCAGGCC
CTGCCCCCTCGCGGACCGCAGTGTACTAATTATGCTCTCTTGAAATTGG
CTGGAGATGTTGAGAGCAATCCCGGGCCCATGCGCATTAGCAAGCCCCA
CCTGCGGAGCATCAGCATCCAGTGCTACCTGTGCCTGCTGCTGAACAGC
CACTTCCTGACCGAGGCCGGCATCCACGTGTTCATCCTGGGCTGCTTCA
GCGCCGGACTGCCCAAGACCGAGGCCAACTGGGTGAACGTGATCAGCGA
CCTGAAGAAGATCGAGGACCTGATCCAGAGCATGCACATCGACGCCACC
CTGTACACCGAGAGCGACGTGCACCCCAGCTGCAAGGTGACCGCCATGA
AGTGCTTTCTGCTGGAACTGCAGGTGATCAGCCTGGAAAGCGGCGACGC
CAGCATCCACGACACCGTGGAGAACCTGATCATCCTGGCCAACAACAGC
CTGAGCAGCAACGGCAACGTGACCGAGAGCGGCTGCAAAGAGTGCGAGG
AACTGGAAGAGAAGAACATCAAAGAGTTTCTGCAGAGCTTCGTGCACAT
CGTGCAGATGTTCATCAACACCAGCTGA

A corresponding amino acid sequence for CD27Tr28tmdDAP12icd3z15 is as follows:

(SEQ ID NO: 43)
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMARPHPWWLCVLGTLVGLSATPAPKSCPERHYWA
QGKLCCQMCEPGTFLVKDCDQHRKAAQCDPCIPGVSFSPDHHTRPHCES
CRHCNSGLLVRNCTITANAECACRNGWQCRDKECTECDPLPNPSLTARS
SQALSPHPQPTHLPYVSEMLEARTAGHMQTLADFRQLPARTLSTHWPPQ
RSLCSSDFIRFWVLVVVGGVLACYSLLVTVAFIIFWVYFLGRLVPRGRG
AAEAATRKQRITETESPYQELQGQRSDVYSDLNTQRPYYKKRVKFSRSA
DAPAYQQGQNQLYNELNLGRREEYDVLDKRRGRDPEMGGKPRRKNPQEG
LYNELQKDKMAEAYSEIGMKGERRRGKGHDGLYQGLSTATKDTYDALHM
QALPPRGPQCTNYALLKLAGDVESNPGPMRISKPHLRSISIQCYLCLLL

-continued

NSHFLTEAGIHVFILGCFSAGLPKTEANWVNVISDLKKIEDLIQSMHID
ATLYTESDVHPSCKVTAMKCFLLELQVISLESGDASIHDTVENLIILAN
NSLSSNGNVTESGCKECEELEEKNIKEFLQSFVHIVQMFINTS

GSPco27Tr28tmddap12icd15:

(SEQ ID NO: 21)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGCTTCTCC
TGGTGACAAGCCTTCTGCTCTGTGAGTTACCACACCCAGCATTCCTCCT
GATCCCAGCTACACCGGCTCCGAAGTCCTGCCCGGAGCGGCATTATTGG
GCACAGGGCAAGTTGTGTTGTCAAATGTGTGAGCCGGGAACCTTTCTCG
TGAAGGATTGCGATCAGCATCGGAAGGCCGCGCAGTGCGACCCATGTAT
ACCAGGGGTCTCATTTTCCCCAGATCACCATACGAGGCCGCACTGTGAG
TCTTGCAGGCATTGTAATTCCGGCTTGTTGGTCCGCAACTGTACTATTA
CTGCGAATGCAGAGTGTGCTTGTAGAAACGGATGGCAGTGCAGGGACAA
AGAATGTACGGAGTGTGATCCACTGCCTAACCCCAGTCTTACAGCAAGA
TCTTCACAGGCCCTCAGCCCGCATCCTCAACCAACACATCTTCCTTACG
TGTCAGAAATGTTGGAGGCGCGAACCGCAGGCCATATGCAGACCCTGGC
GGACTTTCGGCAGCTGCCAGCACGCACACTTAGTACACACTGGCCACCA
CAACGCAGCTTGTGCTCTTCCGATTTCATCCGCTTTTGGGTGCTGGTGG
TGGTTGGTGGAGTCCTGGCTTGCTATAGCTTGCTAGTAACAGTGGCCTT
TATTATTTTCTGGGTGTACTTCCTGGGCCGGCTGGTCCCTCGGGGGCGA
GGGGCTGCGGAGGCAGCGACCCGGAAACAGCGTATCACTGAGACCGAGT
CGCCTTATCAGGAGCTCCAGGGTCAGAGGTCGGATGTCTACAGCGACCT
CAACACACAGAGGCCGTATTACAAAAAACGCGTGAAGTTCAGCAGGAGC
GCAGACGCCCCCGCGTACCAGCAGGGCCAGAACCAGCTCTATAACGAGC
TCAATCTAGGACGAAGAGAGGAGTACGATGTTTTGGACAAAAGACGTGG
CCGGGACCCTGAGATGGGGGGAAAGCCGAGAAGGAAGAACCCTCAGGAA
GGCCTGTACAATGAACTGCAGAAAGATAAGATGGCGGAGGCCTACAGTG
AGATTGGGATGAAAGGCGAGCGCCGGAGGGGCAAGGGGCACGATGGCCT
TTACCAGGGTCTCAGTACAGCCACCAAGGACACCTACGACGCCCTTCAC
ATGCAGGCCCTGCCCCCTCGCGGACCGCAGTGTACTAATTATGCTCTCT
TGAAATTGGCTGGAGATGTTGAGAGCAATCCCGGGCCCATGCGCATTAG
CAAGCCCCACCTGCGGAGCATCAGCATCCAGTGCTACCTGTGCCTGCTG
CTGAACAGCCACTTCCTGACCGAGGCCGGCATCCACGTGTTCATCCTGG
GCTGCTTCAGCGCCGGACTGCCCAAGACCGAGGCCAACTGGGTGAACGT

-continued

GATCAGCGACCTGAAGAAGATCGAGGACCTGATCCAGAGCATGCACATC

GACGCCACCCTGTACACCGAGAGCGACGTGCACCCCAGCTGCAAGGTGA

CCGCCATGAAGTGCTTTCTGCTGGAACTGCAGGTGATCAGCCTGGAAAG

CGGCGACGCCAGCATCCACGACACCGTGGAGAACCTGATCATCCTGGCC

AACAACAGCCTGAGCAGCAACGGCAACGTGACCGAGAGCGGCTGCAAAG

AGTGCGAGGAACTGGAAGAGAAGAACATCAAAGAGTTTCTGCAGAGCTT

CGTGCACATCGTGCAGATGTTCATCAACACCAGCTGA

A corresponding amino acid sequence for GSPco27Tr28tmddap12icd15 is as follows:

(SEQ ID NO: 44)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMLLLVTSLLLCELPHPAFLLIPATPAPKSCPERH

YWAQGKLCCQMCEPGTFLVKDCDQHRKAAQCDPCIPGVSFSPDHHTRPH

CESCRHCNSGLLVRNCTITANAECACRNGWQCRDKECTECDPLPNPSLT

ARSSQALSPHPQPTHLPYVSEMLEARTAGHMQTLADFRQLPARTLSTHW

PPQRSLCSSDFIRFWVLVVVGGVLACYSLLVTVAFIIFWVYFLGRLVPR

GRGAAEAATRKQRITETESPYQELQGQRSDVYSDLNTQRPYYKKRVKFS

RSADAPAYQQGQNQLYNELNLGRREEYDVLDKRRGRDPEMGGKPRRKNP

QEGLYNELQKDKMAEAYSEIGMKGERRRGKGHDGLYQGLSTATKDTYDA

LHMQALPPRGPQCTNYALLKLAGDVESNPGPMRISKPHLRSISIQCYLC

LLLNSHFLTEAGIHVFILGCFSAGLPKTEANWVNVISDLKKIEDLIQSM

HIDATLYTESDVHPSCKVTAMKCFLLELQVISLESGDASIHDTVENLII

LANNSLSSNGNVTESGCKECEELEEKNIKEFLQSFVHIVQMFINTS

CD27Tr28tmdNKG2Dic3z15:

(SEQ ID NO: 22)

ATGACAAGAGTTACTAACAGCCCCTCTCTCCAAGCTCACTTACAGG

CTCTCTACTTAGTCCAGCACGAAGTCTGGAGACCTCTGGCGGCAGCCTA

CCAAGAACAACTGGACCGACCGGTGGTACCTCACCCTTACCGAGTCGGC

GACACAGTGTGGGTCCGCCGACACCAGACTAAGAACCTAGAACCTCGCT

GGAAAGGACCTTACACAGTCCTGCTGACCACCCCCACCGCCCTCAAAGT

AGACGGCATCGCAGCTTGGATACACGCCGCCCACGTGAAGGCTGCCGAC

CCCGGGGGTGGACCATCCTCTAGACTGCCATGCTCGAGGATGGCACGGC

CACATCCCTGGTGGCTGTGCGTTCTGGGGACCCTGGTGGGGCTCTCAGC

TACTCCAGCCCCCAAGAGCTGCCCAGAGAGGCACTACTGGGCTCAGGGA

AAGCTGTGCTGCCAGATGTGTGAGCCAGGAACATTCCTCGTGAAGGACT

GTGACCAGCATAGAAAGGCTGCTCAGTGTGATCCTTGCATACCGGGGGT

CTCCTTCTCTCCTGACCACCACACCCGGCCCCACTGTGAGAGCTGTCGG

CACTGTAACTCTGGTCTTCTCGTTCGCAACTGCACCATCACTGCCAATG

CTGAGTGTGCCTGTCGCAATGGCTGGCAGTGCAGGGACAAGGAGTGCAC

CGAGTGTGATCCTCTTCCAAACCCTTCGCTGACCGCTCGGTCGTCTCAG

GCCCTGAGCCCACACCCTCAGCCCACCCACTTACCTTATGTCAGTGAGA

TGCTGGAGGCCAGGACAGCTGGGCACATGCAGACTCTGGCTGACTTCAG

GCAGCTGCCTGCCCGGACTCTCTCTACCCACTGGCCACCCCAAAGATCC

CTGTGCAGCTCCGATTTTATTCGCTTTTGGGTGCTGGTGGTGGTTGGTG

GAGTCCTGGCTTGCTATAGCTTGCTAGTAACAGTGGCCTTTATTATTTT

CTGGGTGAGCGCGAACGAACGCTGCAAAAGCAAAGTGGTGCCGTGCCGC

CAGAAACAGTGGCGCACCAGCTTTGATAGCAAAAAACTGGATCTGAACT

ATAACCATTTTGAAAGCATGGAATGGAGCCATCGCAGCCGCCGCGGCCG

CATTTGGGGCATGAAACGCGTGAAGTTCAGCAGGAGCGCAGACGCCCCC

GCGTACCAGCAGGGCCAGAACCAGCTCTATAACGAGCTCAATCTAGGAC

GAAGAGAGGAGTACGATGTTTTGGACAAAAGACGTGGCCGGGACCCTGA

GATGGGGGGAAAGCCGAGAAGGAAGAACCCTCAGGAAGGCCTGTACAAT

GAACTGCAGAAAGATAAGATGGCGGAGGCCTACAGTGAGATTGGGATGA

AAGGCGAGCGCCGGAGGGGCAAGGGGCACGATGGCCTTTACCAGGGTCT

CAGTACAGCCACCAAGGACACCTACGACGCCCTTCACATGCAGGCCCTG

CCCCCTCGCGGACCGCAGTGTACTAATTATGCTCTCTTGAAATTGGCTG

GAGATGTTGAGAGCAATCCCGGGCCCATGCGCATTAGCAAGCCCCACCT

GCGGAGCATCAGCATCCAGTGCTACCTGTGCCTGCTGCTGAACAGCCAC

TTCCTGACCGAGGCCGGCATCCACGTGTTCATCCTGGGCTGCTTCAGCG

CCGGACTGCCCAAGACCGAGGCCAACTGGGTGAACGTGATCAGCGACCT

GAAGAAGATCGAGGACCTGATCCAGAGCATGCACATCGACGCCACCCTG

TACACCGAGAGCGACGTGCACCCCAGCTGCAAGGTGACCGCCATGAAGT

GCTTTCTGCTGGAACTGCAGGTGATCAGCCTGGAAAGCGGCGACGCCAG

CATCCACGACACCGTGGAGAACCTGATCATCCTGGCCAACAACAGCCTG

AGCAGCAACGGCAACGTGACCGAGAGCGGCTGCAAAGAGTGCGAGGAAC

TGGAAGAGAAGAACATCAAAGAGTTTCTGCAGAGCTTCGTGCACATCGT

GCAGATGTTCATCAACACCAGCTGA

A corresponding amino acid sequence for CD27Tr28tmdNKG2Dic3z15 is as follows:

(SEQ ID NO: 45)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMARPHPWWLCVLGTLVGLSATPAPKSCPERHYWA

QGKLCCQMCEPGTFLVKDCDQHRKAAQCDPCIPGVSFSPDHHTRPHCES

CRHCNSGLLVRNCTITANAECACRNGWQCRDKECTECDPLPNPSLTARS

SQALSPHPQPTHLPYVSEMLEARTAGHMQTLADFRQLPARTLSTHWPPQ

RSLCSSDFIRFWVLVVVGGVLACYSLLVTVAFIIFWVSANERCKSKVVP

CRQKQWRTSFDSKKLDLNYNHFESMEWSHRSRRGRIWGMKRVKFSRSAD

APAYQQGQNQLYNELNLGRREEYDVLDKRRGRDPEMGGKPRRKNPQEGL

YNELQKDKMAEAYSEIGMKGERRRGKGHDGLYQGLSTATKDTYDALHMQ

-continued

ALPPRGPQCTNYALLKLAGDVESNPGPMRISKPHLRSISIQCYLCLLLN

SHFLTEAGIHVFILGCFSAGLPKTEANWVNVISDLKKIEDLIQSMHIDA

-continued

TLYTESDVHPSCKVTAMKCFLLELQVISLESGDASIHDTVENLIILANN

SLSSNGNVTESGCKECEELEEKNIKEFLQSFVHIVQMFINTS

GSPco27Tr28tmdNKG2Dicd3z15:

(SEQ ID NO: 23)

ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG

GGGGTGGACCATCCTCTAGACTGCCATGCTCGAGGATGCTTCTCCTGGTGACAAGCCTT

CTGCTCTGTGAGTTACCACACCCAGCATTCCTCCTGATCCCAGCTACACCGGCTCCGAA

GTCCTGCCCGGAGCGGCATTATTGGGCACAGGGCAAGTTGTGTTGTCAAATGTGTGAGC

CGGGAACCTTTCTCGTGAAGGATTGCGATCAGCATCGGAAGGCCGCGCAGTGCGACCCA

TGTATACCAGGGGTCTCATTTTCCCCAGATCACCATACGAGGCCGCACTGTGAGTCTTG

CAGGCATTGTAATTCCGGCTTGTTGGTCCGCAACTGTACTATTACTGCGAATGCAGAGT

GTGCTTGTAGAAACGGATGGCAGTGCAGGGACAAAGAATGTACGGAGTGTGATCCACTG

CCTAACCCCAGTCTTACAGCAAGATCTTCACAGGCCCTCAGCCCGCATCCTCAACCAAC

ACATCTTCCTTACGTGTCAGAAATGTTGGAGGCGCGAACCGCAGGCCATATGCAGACCC

TGGCGGACTTTCGGCAGCTGCCAGCACGCACACTTAGTACACACTGGCCACCACAACGC

AGCTTGTGCTCTTCCGATTTCATCCGCTTTTGGGTGCTGGTGGTGGTTGGTGGAGTCCT

GGCTTGCTATAGCTTGCTAGTAACAGTGGCCTTTATTATTTTCTGGGTGAGCGCGAACG

AACGCTGCAAAAGCAAAGTGGTGCCGTGCCGCCAGAAACAGTGGCGCACCAGCTTTGAT

AGCAAAAAACTGGATCTGAACTATAACCATTTTGAAAGCATGGAATGGAGCCATCGCAG

CCGCCGCGGCCGCATTTGGGGCATGAAACGCGTGAAGTTCAGCAGGAGCGCAGACGCCC

CCGCGTACCAGCAGGGCCAGAACCAGCTCTATAACGAGCTCAATCTAGGACGAAGAGAG

GAGTACGATGTTTTGGACAAAAGACGTGGCCGGGACCCTGAGATGGGGGGAAAGCCGAG

AAGGAAGAACCCTCAGGAAGGCCTGTACAATGAACTGCAGAAAGATAAGATGGCGGAGG

CCTACAGTGAGATTGGGATGAAAGGCGAGCGCCGGAGGGGCAAGGGGCACGATGGCCTT

TACCAGGGTCTCAGTACAGCCACCAAGGACACCTACGACGCCCTTCACATGCAGGCCCT

GCCCCCTCGCGGACCGCAGTGTACTAATTATGCTCTCTTGAAATTGGCTGGAGATGTTG

AGAGCAATCCCGGGCCCATGCGCATTAGCAAGCCCCACCTGCGGAGCATCAGCATCCAG

TGCTACCTGTGCCTGCTGCTGAACAGCCACTTCCTGACCGAGGCCGGCATCCACGTGTT

CATCCTGGGCTGCTTCAGCGCCGGACTGCCCAAGACCGAGGCCAACTGGGTGAACGTGA

TCAGCGACCTGAAGAAGATCGAGGACCTGATCCAGAGCATGCACATCGACGCCACCCTG

TACACCGAGAGCGACGTGCACCCCAGCTGCAAGGTGACCGCCATGAAGTGCTTTCTGCT

GGAACTGCAGGTGATCAGCCTGGAAAGCGGCGACGCCAGCATCCACGACACCGTGGAGA

ACCTGATCATCCTGGCCAACAACAGCCTGAGCAGCAACGGCAACGTGACCGAGAGCGGC

TGCAAAGAGTGCGAGGAACTGGAAGAGAAGAACATCAAAGAGTTTCTGCAGAGCTTCGT

GCACATCGTGCAGATGTTCATCAACACCAGCTGA

A corresponding amino acid sequence for GSPco27Tr28tmdNKG2Dicd3z15 is as follows:

(SEQ ID NO: 46)

MTRVTNSPSLQAHLQALYLVQHEVWRPLAAAYQEQLDRPVVPHPYRVGDT

VWVRRHQTKNLEPRWKGPYTVLLTTPTALKVDGIAAWIHAAHVKAADPGG

GPSSRLPCSRMLLLVTSLLLCELPHPAFLLIPATPAPKSCPERHYWAQGK

LCCQMCEPGTFLVKDCDQHRKAAQCDPCIPGVSFSPDHHTRPHCESCRHC

NSGLLVRNCTITANAECACRNGWQCRDKECTECDPLPNPSLTARSSQALS

PHPQPTHLPYVSEMLEARTAGHMQTLADFRQLPARTLSTHWPPQRSLCSS

-continued

DFIRFWVLVVVGGVLACYSLLVTVAFIIFWVSANERCKSKVVPCRQKQWR

TSFDSKKLDLNYNHFESMEWSHRSRRGRIWGMKRVKFSRSADAPAYQQGQ

NQLYNELNLGRREEYDVLDKRRGRDPEMGGKPRRKNPQEGLYNELQKDKM

AEAYSEIGMKGERRRGKGHDGLYQGLSTATKDTYDALHMQALPPRGPQCT

NYALLKLAGDVESNPGPMRISKPHLRSISIQCYLCLLLNSHFLTEAGIHV

FILGCFSAGLPKTEANWVNVISDLKKIEDLIQSMHIDATLYTESDVHPSC

KVTAMKCFLLELQVISLESGDASIHDTVENLIILANNSLSSNGNVTESGC

KECEELEEKNIKEFLQSFVHIVQMFINTS

CD27Tr41BBicd3z15:

(SEQ ID NO: 24)

ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG

GGGGTGGACCATCCTCTAGACTGCCATGCTCGAGGATGGCACGGCCACATCCCTGGTGG

CTGTGCGTTCTGGGGACCCTGGTGGGGCTCTCAGCTACTCCAGCCCCCAAGAGCTGCCC

AGAGAGGCACTACTGGGCTCAGGGAAAGCTGTGCTGCCAGATGTGTGAGCCAGGAACAT

TCCTCGTGAAGGACTGTGACCAGCATAGAAAGGCTGCTCAGTGTGATCCTTGCATACCG

GGGGTCTCCTTCTCTCCTGACCACCACACCCGGCCCCACTGTGAGAGCTGTCGGCACTG

TAACTCTGGTCTTCTCGTTCGCAACTGCACCATCACTGCCAATGCTGAGTGTGCCTGTC

GCAATGGCTGGCAGTGCAGGGACAAGGAGTGCACCGAGTGTGATCCTCTTCCAAACCCT

TCGCTGACCGCTCGGTCGTCTCAGGCCCTGAGCCCACACCCTCAGCCCACCCACTTACC

TTATGTCAGTGAGATGCTGGAGGCCAGGACAGCTGGGCACATGCAGACTCTGGCTGACT

TCAGGCAGCTGCCTGCCCGGACTCTCTCTACCCACTGGCCACCCCAAAGATCCCTGTGC

AGCTCCGATTTTATTCGCATCCTTGTGATCTTCTCTGGAATGTTCCTTGTTTTCACCCT

GGCCGGGGCCCTGTTCCTCCATAAACGGGGCAGAAAGAAACTCCTGTATATATTCAAAC

AACCATTTATGAGACCAGTACAAACTACTCAAGAGGAAGATGGCTGTAGCTGCCGATTT

CCAGAAGAAGAAGAAGGAGGATGTGAACTGAAACGCGTGAAGTTCAGCAGGAGCGCAGA

CGCCCCCGCGTACCAGCAGGGCCAGAACCAGCTCTATAACGAGCTCAATCTAGGACGAA

GAGAGGAGTACGATGTTTTGGACAAAAGACGTGGCCGGGACCCTGAGATGGGGGGAAAG

CCGAGAAGGAAGAACCCTCAGGAAGGCCTGTACAATGAACTGCAGAAAGATAAGATGGC

GGAGGCCTACAGTGAGATTGGGATGAAAGGCGAGCGCCGGAGGGGCAAGGGGCACGATG

GCCTTTACCAGGGTCTCAGTACAGCCACCAAGGACACCTACGACGCCCTTCACATGCAG

GCCCTGCCCCCTCGCGGACCGCAGTGTACTAATTATGCTCTCTTGAAATTGGCTGGAGA

TGTTGAGAGCAATCCCGGGCCCATGCGCATTAGCAAGCCCCACCTGCGGAGCATCAGCA

TCCAGTGCTACCTGTGCCTGCTGCTGAACAGCCACTTCCTGACCGAGGCCGGCATCCAC

GTGTTCATCCTGGGCTGCTTCAGCGCCGGACTGCCCAAGACCGAGGCCAACTGGGTGAA

CGTGATCAGCGACCTGAAGAAGATCGAGGACCTGATCCAGAGCATGCACATCGACGCCA

CCCTGTACACCGAGAGCGACGTGCACCCCAGCTGCAAGGTGACCGCCATGAAGTGCTTT

-continued

CTGCTGGAACTGCAGGTGATCAGCCTGGAAAGCGGCGACGCCAGCATCCACGACACCGT

GGAGAACCTGATCATCCTGGCCAACAACAGCCTGAGCAGCAACGGCAACGTGACCGAGA

GCGGCTGCAAAGAGTGCGAGGAACTGGAAGAGAAGAACATCAAAGAGTTTCTGCAGAGC

TTCGTGCACATCGTGCAGATGTTCATCAACACCAGCTGA

A corresponding amino acid sequence for CD27Tr41BBicd3z15 is as follows:

(SEQ ID NO: 47)

MTRVTNSPSLQAHLQALYLVQHEVWRPLAAAYQEQLDRPVVPHPYRVGDT

VWVRRHQTKNLEPRWKGPYTVLLTTPTALKVDGIAAWIHAAHVKAADPGG

GPSSRLPCSRMARPHPWWLCVLGTLVGLSATPAPKSCPERHYWAQGKLCC

QMCEPGTFLVKDCDQHRKAAQCDPCIPGVSFSPDHHTRPHCESCRHCNSG

LLVRNCTITANAECACRNGWQCRDKECTECDPLPNPSLTARSSQALSPHP

QPTHLPYVSEMLEARTAGHMQTLADFRQLPARTLSTHWPPQRSLCSSDFI

-continued

RILVIFSGMFLVFTLAGALFLHKRGRKKLLYIFKQPFMRPVQTTQEEDGC

SCRFPEEEEGGCELKRVKFSRSADAPAYQQGQNQLYNELNLGRREEYDVL

DKRRGRDPEMGGKPRRKNPQEGLYNELQKDKMAEAYSEIGMKGERRRGKG

HDGLYQGLSTATKDTYDALHMQALPPRGPQCTNYALLKLAGDVESNPGPM

RISKPHLRSISIQCYLCLLLNSHFLTEAGIHVFILGCFSAGLPKTEANWV

NVISDLKKIEDLIQSMHIDATLYTESDVHPSCKVTAMKCFLLELQVISLE

SGDASIHDTVENLIILANNSLSSNGNVTESGCKECEELEEKNIKEFLQSF

VHIVQMFINTS

GSPco27Tr41BBicd3z15:

(SEQ ID NO: 25)

ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG

GGGGTGGACCATCCTCTAGACTGCCATGCTCGAGGATGCTTCTCCTGGTGACAAGCCTT

CTGCTCTGTGAGTTACCACACCCAGCATTCCTCCTGATCCCAGCTACACCGGCTCCGAA

GTCCTGCCCGGAGCGGCATTATTGGGCACAGGGCAAGTTGTGTTGTCAAATGTGTGAGC

CGGGAACCTTTCTCGTGAAGGATTGCGATCAGCATCGGAAGGCCGCGCAGTGCGACCCA

TGTATACCAGGGGTCTCATTTTCCCCAGATCACCATACGAGGCCGCACTGTGAGTCTTG

CAGGCATTGTAATTCCGGCTTGTTGGTCCGCAACTGTACTATTACTGCGAATGCAGAGT

GTGCTTGTAGAAACGGATGGCAGTGCAGGGACAAAGAATGTACGGAGTGTGATCCACTG

CCTAACCCCAGTCTTACAGCAAGATCTTCACAGGCCCTCAGCCCGCATCCTCAACCAAC

ACATCTTCCTTACGTGTCAGAAATGTTGGAGGCGCGAACCGCAGGCCATATGCAGACCC

TGGCGGACTTTCGGCAGCTGCCAGCACGCACACTTAGTACACACTGGCCACCACAACGC

AGCTTGTGCTCTTCCGATTTCATCCGCATACTGGTCATCTTTTCTGGAATGTTCCTTGT

GTTCACCCTGGCAGGAGCCCTGTTCCTTCACAAACGGGGCAGAAAGAAACTCCTGTATA

TATTCAAACAACCATTTATGAGACCAGTACAAACTACTCAAGAGGAAGATGGCTGTAGC

TGCCGATTTCCAGAAGAAGAAGAAGGAGGATGTGAACTGAAACGCGTGAAGTTCAGCAG

GAGCGCAGACGCCCCCGCGTACCAGCAGGGCCAGAACCAGCTCTATAACGAGCTCAATC

TAGGACGAAGAGAGGAGTACGATGTTTTGGACAAAAGACGTGGCCGGGACCCTGAGATG

GGGGGAAAGCCGAGAAGGAAGAACCCTCAGGAAGGCCTGTACAATGAACTGCAGAAAGA

TAAGATGGCGGAGGCCTACAGTGAGATTGGGATGAAAGGCGAGCGCCGGAGGGGCAAGG

GGCACGATGGCCTTTACCAGGGTCTCAGTACAGCCACCAAGGACACCTACGACGCCCTT

CACATGCAGGCCCTGCCCCCTCGCGGACCGCAGTGTACTAATTATGCTCTCTTGAAATT

-continued

GGCTGGAGATGTTGAGAGCAATCCCGGGCCCATGCGCATTAGCAAGCCCCACCTGCGGA

GCATCAGCATCCAGTGCTACCTGTGCCTGCTGCTGAACAGCCACTTCCTGACCGAGGCC

GGCATCCACGTGTTCATCCTGGGCTGCTTCAGCGCCGGACTGCCCAAGACCGAGGCCAA

CTGGGTGAACGTGATCAGCGACCTGAAGAAGATCGAGGACCTGATCCAGAGCATGCACA

TCGACGCCACCCTGTACACCGAGAGCGACGTGCACCCCAGCTGCAAGGTGACCGCCATG

AAGTGCTTTCTGCTGGAACTGCAGGTGATCAGCCTGGAAAGCGGCGACGCCAGCATCCA

CGACACCGTGGAGAACCTGATCATCCTGGCCAACAACAGCCTGAGCAGCAACGGCAACG

TGACCGAGAGCGGCTGCAAAGAGTGCGAGGAACTGGAAGAGAAGAACATCAAAGAGTTT

CTGCAGAGCTTCGTGCACATCGTGCAGATGTTCATCAACACCAGCTGA

A corresponding amino acid sequence for GSPco27Tr41BBicd3z15 is as follows:

(SEQ ID NO: 48)

MTRVTNSPSLQAHLQALYLVQHEVWRPLAAAYQEQLDRPVVPHPYRVGDT

VWVRRHQTKNLEPRWKGPYTVLLTTPTALKVDGIAAWIHAAHVKAADPGG

GPSSRLPCSRMLLLVTSLLLCELPHPAFLLIPATPAPKSCPERHYWAQGK

LCCQMCEPGTFLVKDCDQHRKAAQCDPCIPGVSFSPDHHTRPHCESCRHC

NSGLLVRNCTITANAECACRNGWQCRDKECTECDPLPNPSLTARSSQALS

PHPQPTHLPYVSEMLEARTAGHMQTLADFRQLPARTLSTHWPPQRSLCSS

-continued

DFIRILVIFSGMFLVFTLAGALFLHKRGRKKLLYIFKQPFMRPVQTTQEE

DGCSCRFPEEEEGGCELKRVKFSRSADAPAYQQGQNQLYNELNLGRREEY

DVLDKRRGRDPEMGGKPRRKNPQEGLYNELQKDKMAEAYSEIGMKGERRR

GKGHDGLYQGLSTATKDTYDALHMQALPPRGPQCTNYALLKLAGDVESNP

GPMRISKPHLRSISIQCYLCLLLNSHFLTEAGIHVFILGCFSAGLPKTEA

NWVNVISDLKKIEDLIQSMHIDATLYTESDVHPSCKVTAMKCFLLELQVI

SLESGDASIHDTVENLIILANNSLSSNGNVTESGCKECEELEEKNIKEFL

QSFVHIVQMFINTS

CD27TrCD3ZIL15:

(SEQ ID NO: 26)

ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG

GGGGTGGACCATCCTCTAGACTGCCATGCTCGAGGATGGCACGGCCACATCCCTGGTGG

CTGTGCGTTCTGGGGACCCTGGTGGGGCTCTCAGCTACTCCAGCCCCCAAGAGCTGCCC

AGAGAGGCACTACTGGGCTCAGGGAAAGCTGTGCTGCCAGATGTGTGAGCCAGGAACAT

TCCTCGTGAAGGACTGTGACCAGCATAGAAAGGCTGCTCAGTGTGATCCTTGCATACCG

GGGGTCTCCTTCTCTCCTGACCACCACACCCGGCCCCACTGTGAGAGCTGTCGGCACTG

TAACTCTGGTCTTCTCGTTCGCAACTGCACCATCACTGCCAATGCTGAGTGTGCCTGTC

GCAATGGCTGGCAGTGCAGGGACAAGGAGTGCACCGAGTGTGATCCTCTTCCAAACCCT

TCGCTGACCGCTCGGTCGTCTCAGGCCCTGAGCCCACACCCTCAGCCCACCCACTTACC

TTATGTCAGTGAGATGCTGGAGGCCAGGACAGCTGGGCACATGCAGACTCTGGCTGACT

TCAGGCAGCTGCCTGCCCGGACTCTCTCTACCCACTGGCCACCCCAAAGATCCCTGTGC

AGCTCCGATTTTATTCGCATCCTTGTGATCTTCTCTGGAATGTTCCTTGTTTTCACCCT

GGCCGGGGCCCTGTTCCTCCATAAACGCGTGAAGTTCAGCAGGAGCGCAGACGCCCCCG

CGTACCAGCAGGGCCAGAACCAGCTCTATAACGAGCTCAATCTAGGACGAAGAGAGGAG

TACGATGTTTTGGACAAAAGACGTGGCCGGGACCCTGAGATGGGGGGAAAGCCGAGAAG

GAAGAACCCTCAGGAAGGCCTGTACAATGAACTGCAGAAAGATAAGATGGCGGAGGCCT

-continued

```
ACAGTGAGATTGGGATGAAAGGCGAGCGCCGGAGGGGCAAGGGGCACGATGGCCTTTAC
CAGGGTCTCAGTACAGCCACCAAGGACACCTACGACGCCCTTCACATGCAGGCCCTGCC
CCCTCGCGGACCGCAGTGTACTAATTATGCTCTCTTGAAATTGGCTGGAGATGTTGAGA
GCAATCCCGGGCCCATGCGCATTAGCAAGCCCCACCTGCGGAGCATCAGCATCCAGTGC
TACCTGTGCCTGCTGCTGAACAGCCACTTCCTGACCGAGGCCGGCATCCACGTGTTCAT
CCTGGGCTGCTTCAGCGCCGGACTGCCCAAGACCGAGGCCAACTGGGTGAACGTGATCA
GCGACCTGAAGAAGATCGAGGACCTGATCCAGAGCATGCACATCGACGCCACCCTGTAC
ACCGAGAGCGACGTGCACCCCAGCTGCAAGGTGACCGCCATGAAGTGCTTTCTGCTGGA
ACTGCAGGTGATCAGCCTGGAAAGCGGCGACGCCAGCATCCACGACACCGTGGAGAACC
TGATCATCCTGGCCAACAACAGCCTGAGCAGCAACGGCAACGTGACCGAGAGCGGCTGC
AAAGAGTGCGAGGAACTGGAAGAGAAGAACATCAAAGAGTTTCTGCAGAGCTTCGTGCA
CATCGTGCAGATGTTCATCAACACCAGCTGA
```

A corresponding amino acid sequence for CD27TrCD3ZIL15 is as follows:

(SEQ ID NO: 49)

```
MTRVTNSPSLQAHLQALYLVQHEVWRPLAAAYQEQLDRPVVPHPYRVGDT
VWVRRHQTKNLEPRWKGPYTVLLTTPTALKVDGIAAWIHAAHVKAADPGG
GPSSRLPCSRMARPHPWWLCVLGTLVGLSATPAPKSCPERHYWAQGKLCC
QMCEPGTFLVKDCDQHRKAAQCDPCIPGVSFSPDHHTRPHCESCRHCNSG
LLVRNCTITANAECACRNGWQCRDKECTECDPLPNPSLTARSSQALSPHP
QPTHLPYVSEMLEARTAGHMQTLADFRQLPARTLSTHWPPQRSLCSSDFI
```

-continued

```
RILVIFSGMFLVFTLAGALFLHKRVKFSRSADAPAYQQGQNQLYNELNLG
RREEYDVLDKRRGRDPEMGGKPRRKNPQEGLYNELQKDKMAEAYSEIGMK
GERRRGKGHDGLYQGLSTATKDTYDALHMQALPPRGPQCTNYALLKLAGD
VESNPGPMRISKPHLRSISIQCYLCLLLNSHFLTEAGIHVFILGCFSAGL
PKTEANWVNVISDLKKIEDLIQSMHIDATLYTESDVHPSCKVTAMKCFLL
ELQVISLESGDASIHDTVENLIILANNSLSSNGNVTESGCKECEELEEKN
IKEFLQSFVHIVQMFINTS
```

GSPco27Tr3z15:

(SEQ ID NO: 27)

```
ATGACAAGAGTTACTAACAGCCCCTCTCTCCAAGCTCACTTACAGGCTCTCTACTTAGT
CCAGCACGAAGTCTGGAGACCTCTGGCGGCAGCCTACCAAGAACAACTGGACCGACCGG
TGGTACCTCACCCTTACCGAGTCGGCGACACAGTGTGGGTCCGCCGACACCAGACTAAG
AACCTAGAACCTCGCTGGAAAGGACCTTACACAGTCCTGCTGACCACCCCCACCGCCCT
CAAAGTAGACGGCATCGCAGCTTGGATACACGCCGCCCACGTGAAGGCTGCCGACCCCG
GGGGTGGACCATCCTCTAGACTGCCATGCTCGAGGATGCTTCTCCTGGTGACAAGCCTT
CTGCTCTGTGAGTTACCACACCCAGCATTCCTCCTGATCCCAGCTACACCGGCTCCGAA
GTCCTGCCCGGAGCGGCATTATTGGGCACAGGGCAAGTTGTGTTGTCAAATGTGTGAGC
CGGGAACCTTTCTCGTGAAGGATTGCGATCAGCATCGGAAGGCCGCGCAGTGCGACCCA
TGTATACCAGGGGTCTCATTTTCCCCAGATCACCATACGAGGCCGCACTGTGAGTCTTG
CAGGCATTGTAATTCCGGCTTGTTGGTCCGCAACTGTACTATTACTGCGAATGCAGAGT
GTGCTTGTAGAAACGGATGGCAGTGCAGGGACAAAGAATGTACGGAGTGTGATCCACTG
CCTAACCCCAGTCTTACAGCAAGATCTTCACAGGCCCTCAGCCCGCATCCTCAACCAAC
ACATCTTCCTTACGTGTCAGAAATGTTGGAGGCGCGAACCGCAGGCCATATGCAGACCC
TGGCGGACTTTCGGCAGCTGCCAGCACGCACACTTAGTACACACTGGCCACCACAACGC
AGCTTGTGCTCTTCCGATTTCATCCGCATACTGGTCATCTTTTCTGGAATGTTCCTTGT
GTTCACCCTGGCAGGAGCCCTGTTCCTTCACCGCGTGAAGTTCAGCAGGAGCGCAGACG
CCCCCGCGTACCAGCAGGGCCAGAACCAGCTCTATAACGAGCTCAATCTAGGACGAAGA
```

-continued

GAGGAGTACGATGTTTTGGACAAAAGACGTGGCCGGGACCCTGAGATGGGGGGAAAGCC

GAGAAGGAAGAACCCTCAGGAAGGCCTGTACAATGAACTGCAGAAAGATAAGATGGCGG

AGGCCTACAGTGAGATTGGGATGAAAGGCGAGCGCCGGAGGGGCAAGGGGCACGATGGC

CTTTACCAGGGTCTCAGTACAGCCACCAAGGACACCTACGACGCCCTTCACATGCAGGC

CCTGCCCCCTCGCGGACCGCAGTGTACTAATTATGCTCTCTTGAAATTGGCTGGAGATG

TTGAGAGCAATCCCGGGCCCATGCGCATTAGCAAGCCCCACCTGCGGAGCATCAGCATC

CAGTGCTACCTGTGCCTGCTGCTGAACAGCCACTTCCTGACCGAGGCCGGCATCCACGT

GTTCATCCTGGGCTGCTTCAGCGCCGGACTGCCCAAGACCGAGGCCAACTGGGTGAACG

TGATCAGCGACCTGAAGAAGATCGAGGACCTGATCCAGAGCATGCACATCGACGCCACC

CTGTACACCGAGAGCGACGTGCACCCCAGCTGCAAGGTGACCGCCATGAAGTGCTTTCT

GCTGGAACTGCAGGTGATCAGCCTGGAAAGCGGCGACGCCAGCATCCACGACACCGTGG

AGAACCTGATCATCCTGGCCAACAACAGCCTGAGCAGCAACGGCAACGTGACCGAGAGC

GGCTGCAAAGAGTGCGAGGAACTGGAAGAGAAGAACATCAAAGAGTTTCTGCAGAGCTT

CGTGCACATCGTGCAGATGTTCATCAACACCAGCTGA

A corresponding amino acid sequence for GSPco27Tr3z15 is as follows:

(SEQ ID NO: 50)

MTRVTNSPSLQAHLQALYLVQHEVWRPLAAAYQEQLDRPVVPHPYRVGDT

VWVRRHQTKNLEPRWKGPYTVLLTTPTALKVDGIAAWIHAAHVKAADPGG

GPSSRLPCSRMLLLVTSLLLCELPHPAFLLIPATPAPKSCPERHYWAQGK

LCCQMCEPGTFLVKDCDQHRKAAQCDPCIPGVSFSPDHHTRPHCESCRHC

NSGLLVRNCTITANAECACRNGWQCRDKECTECDPLPNPSLTARSSQALS

PHPQPTHLPYVSEMLEARTAGHMQTLADFRQLPARTLSTHWPPQRSLCSS

-continued

DFIRILVIFSGMFLVFTLAGALFLHKRVKFSRSADAPAYQQGQNQLYNEL

NLGRREEYDVLDKRRGRDPEMGGKPRRKNPQEGLYNELQKDKMAEAYSEI

GMKGERRRGKGHDGLYQGLSTATKDTYDALHMQALPPRGPQCTNYALLKL

AGDVESNPGPMRISKPHLRSISIQCYLCLLLNSHFLTEAGIHVFILGCFS

AGLPKTEANWVNVISDLKKIEDLIQSMHIDATLYTESDVHPSCKVTAMKC

FLLELQVISLESGDASIHDTVENLIILANNSLSSNGNVTESGCKECEELE

EKNIKEFLQSFVHIVQMFINTS

CD27TrCD28icd3z15:

(SEQ ID NO: 28)

ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG

GGGGTGGACCATCCTCTAGACTGCCATGCTCGAGGATGGCACGGCCACATCCCTGGTGG

CTGTGCGTTCTGGGGACCCTGGTGGGGCTCTCAGCTACTCCAGCCCCCAAGAGCTGCCC

AGAGAGGCACTACTGGGCTCAGGGAAAGCTGTGCTGCCAGATGTGTGAGCCAGGAACAT

TCCTCGTGAAGGACTGTGACCAGCATAGAAAGGCTGCTCAGTGTGATCCTTGCATACCG

GGGGTCTCCTTCTCTCCTGACCACCACACCCGGCCCCACTGTGAGAGCTGTCGGCACTG

TAACTCTGGTCTTCTCGTTCGCAACTGCACCATCACTGCCAATGCTGAGTGTGCCTGTC

GCAATGGCTGGCAGTGCAGGGACAAGGAGTGCACCGAGTGTGATCCTCTTCCAAACCCT

TCGCTGACCGCTCGGTCGTCTCAGGCCCTGAGCCCACACCCTCAGCCCACCCACTTACC

TTATGTCAGTGAGATGCTGGAGGCCAGGACAGCTGGGCACATGCAGACTCTGGCTGACT

TCAGGCAGCTGCCTGCCCGGACTCTCTCTACCCACTGGCCACCCCAAAGATCCCTGTGC

-continued

AGCTCCGATTTTATTCGCATCCTTGTGATCTTCTCTGGAATGTTCCTTGTTTTCACCCT

GGCCGGGGCCCTGTTCCTCCATAGGAGTAAGAGGAGCAGGCTCCTGCACAGTGACTACA

TGAACATGACTCCCCGCCGCCCCGGGCCCACCCGCAAGCATTACCAGCCCTATGCCCCA

CCACGCGACTTCGCAGCCTATCGCTCACGCGTGAAGTTCAGCAGGAGCGCAGACGCCCC

CGCGTACCAGCAGGGCCAGAACCAGCTCTATAACGAGCTCAATCTAGGACGAAGAGAGG

AGTACGATGTTTTGGACAAAAGACGTGGCCGGGACCCTGAGATGGGGGGAAAGCCGAGA

AGGAAGAACCCTCAGGAAGGCCTGTACAATGAACTGCAGAAAGATAAGATGGCGGAGGC

CTACAGTGAGATTGGGATGAAAGGCGAGCGCCGGAGGGGCAAGGGGCACGATGGCCTTT

ACCAGGGTCTCAGTACAGCCACCAAGGACACCTACGACGCCCTTCACATGCAGGCCCTG

CCCCCTCGCGGACCGCAGTGTACTAATTATGCTCTCTTGAAATTGGCTGGAGATGTTGA

GAGCAATCCCGGGCCCATGCGCATTAGCAAGCCCCACCTGCGGAGCATCAGCATCCAGT

GCTACCTGTGCCTGCTGCTGAACAGCCACTTCCTGACCGAGGCCGGCATCCACGTGTTC

ATCCTGGGCTGCTTCAGCGCCGGACTGCCCAAGACCGAGGCCAACTGGGTGAACGTGAT

CAGCGACCTGAAGAAGATCGAGGACCTGATCCAGAGCATGCACATCGACGCCACCCTGT

ACACCGAGAGCGACGTGCACCCCAGCTGCAAGGTGACCGCCATGAAGTGCTTTCTGCTG

GAACTGCAGGTGATCAGCCTGGAAAGCGGCGACGCCAGCATCCACGACACCGTGGAGAA

CCTGATCATCCTGGCCAACAACAGCCTGAGCAGCAACGGCAACGTGACCGAGAGCGGCT

GCAAAGAGTGCGAGGAACTGGAAGAGAAGAACATCAAAGAGTTTCTGCAGAGCTTCGTG

CACATCGTGCAGATGTTCATCAACACCAGCTGA

A corresponding amino acid sequence for CD27TrCD28icd3z15 is as follows:

(SEQ ID NO: 51)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMARPHPWWLCVLGTLVGLSATPAPKSCPERHYWA

QGKLCCQMCEPGTFLVKDCDQHRKAAQCDPCIPGVSFSPDHHTRPHCES

CRHCNSGLLVRNCTITANAECACRNGWQCRDKECTECDPLPNPSLTARS

SQALSPHPQPTHLPYVSEMLEARTAGHMQTLADFRQLPARTLSTHWPPQ

-continued

RSLCSSDFIRILVIFSGMFLVFTLAGALFLHRSKRSRLLHSDYMNMTPR

RPGPTRKHYQPYAPPRDFAAYRSRVKFSRSADAPAYQQGQNQLYNELNL

GRREEYDVLDKRRGRDPEMGGKPRRKNPQEGLYNELQKDKMAEAYSEIG

MKGERRRGKGHDGLYQGLSTATKDTYDALHMQALPPRGPQCTNYALLKL

AGDVESNPGPMRISKPHLRSISIQCYLCLLLNSHFLTEAGIHVFILGCF

SAGLPKTEANWVNVISDLKKIEDLIQSMHIDATLYTESDVHPSCKVTAM

KCFLLELQVISLESGDASIHDTVENLIILANNSLSSNGNVTESGCKECE

ELEEKNIKEFLQSFVHIVQMFINTS

GSPco27Tr28CD3z15:

(SEQ ID NO: 29)

ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG

GGGGTGGACCATCCTCTAGACTGCCATGCTCGAGGATGCTTCTCCTGGTGACAAGCCTT

CTGCTCTGTGAGTTACCACACCCAGCATTCCTCCTGATCCCAGCTACACCGGCTCCGAA

GTCCTGCCCGGAGCGGCATTATTGGGCACAGGGCAAGTTGTGTTGTCAAATGTGTGAGC

CGGGAACCTTTCTCGTGAAGGATTGCGATCAGCATCGGAAGGCCGCGCAGTGCGACCCA

TGTATACCAGGGGTCTCATTTTCCCCAGATCACCATACGAGGCCGCACTGTGAGTCTTG

-continued

```
CAGGCATTGTAATTCCGGCTTGTTGGTCCGCAACTGTACTATTACTGCGAATGCAGAGT

GTGCTTGTAGAAACGGATGGCAGTGCAGGGACAAAGAATGTACGGAGTGTGATCCACTG

CCTAACCCCAGTCTTACAGCAAGATCTTCACAGGCCCTCAGCCCGCATCCTCAACCAAC

ACATCTTCCTTACGTGTCAGAAATGTTGGAGGCGCGAACCGCAGGCCATATGCAGACCC

TGGCGGACTTTCGGCAGCTGCCAGCACGCACACTTAGTACACACTGGCCACCACAACGC

AGCTTGTGCTCTTCCGATTTCATCCGCATACTGGTCATCTTTTCTGGAATGTTCCTTGT

GTTCACCCTGGCAGGAGCCCTGTTCCTTCACAGGAGTAAGAGGAGCAGGCTCCTGCACA

GTGACTACATGAACATGACTCCCCGCCGCCCCGGGCCCACCCGCAAGCATTACCAGCCC

TATGCCCCACCACGCGACTTCGCAGCCTATCGCTCACGCGTGAAGTTCAGCAGGAGCGC

AGACGCCCCCGCGTACCAGCAGGGCCAGAACCAGCTCTATAACGAGCTCAATCTAGGAC

GAAGAGAGGAGTACGATGTTTTGGACAAAAGACGTGGCCGGGACCCTGAGATGGGGGGA

AAGCCGAGAAGGAAGAACCCTCAGGAAGGCCTGTACAATGAACTGCAGAAAGATAAGAT

GGCGGAGGCCTACAGTGAGATTGGGATGAAAGGCGAGCGCCGGAGGGGCAAGGGGCACG

ATGGCCTTTACCAGGGTCTCAGTACAGCCACCAAGGACACCTACGACGCCCTTCACATG

CAGGCCCTGCCCCCTCGCGGACCGCAGTGTACTAATTATGCTCTCTTGAAATTGGCTGG

AGATGTTGAGAGCAATCCCGGGCCCATGCGCATTAGCAAGCCCCACCTGCGGAGCATCA

GCATCCAGTGCTACCTGTGCCTGCTGCTGAACAGCCACTTCCTGACCGAGGCCGGCATC

CACGTGTTCATCCTGGGCTGCTTCAGCGCCGGACTGCCCAAGACCGAGGCCAACTGGGT

GAACGTGATCAGCGACCTGAAGAAGATCGAGGACCTGATCCAGAGCATGCACATCGACG

CCACCCTGTACACCGAGAGCGACGTGCACCCCAGCTGCAAGGTGACCGCCATGAAGTGC

TTTCTGCTGGAACTGCAGGTGATCAGCCTGGAAAGCGGCGACGCCAGCATCCACGACAC

CGTGGAGAACCTGATCATCCTGGCCAACAACAGCCTGAGCAGCAACGGCAACGTGACCG

AGAGCGGCTGCAAAGAGTGCGAGGAACTGGAAGAGAAGAACATCAAAGAGTTTCTGCAG

AGCTTCGTGCACATCGTGCAGATGTTCATCAACACCAGCTGA
```

A corresponding amino acid sequence for GSPco27Tr28CD3z15 is as follows:

```
                                                (SEQ ID NO: 52)
MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMLLLVTSLLLCELPHPAFLLIPATPAPKSCPERH

YWAQGKLCCQMCEPGTFLVKDCDQHRKAAQCDPCIPGVSFSPDHHTRPH

CESCRHCNSGLLVRNCTITANAECACRNGWQCRDKECTECDPLPNPSLT

ARSSQALSPHPQPTHLPYVSEMLEARTAGHMQTLADFRQLPARTLSTHW
```

-continued

```
PPQRSLCSSDFIRILVIFSGMFLVFTLAGALFLHRSKRSRLLHSDYMNM

TPRRPGPTRKHYQPYAPPRDFAAYRSRVKFSRSADAPAYQQGQNQLYNE

LNLGRREEYDVLDKRRGRDPEMGGKPRRKNPQEGLYNELQKDKMAEAYS

EIGMKGERRRGKGHDGLYQGLSTATKDTYDALHMQALPPRGPQCTNYAL

LKLAGDVESNPGPMRISKPHLRSISIQCYLCLLLNSHFLTEAGIHVFIL

GCFSAGLPKTEANWVNVISDLKKIEDLIQSMHIDATLYTESDVHPSCKV

TAMKCFLLELQVISLESGDASIHDTVENLIILANNSLSSNGNVTESGCK

ECEELEEKNIKEFLQSFVHIVQMFINTS
```

CD27TrCD28tmdicd3z15:

```
                                                (SEQ ID NO: 30)
ATGACAAGAGTTACTAACAGCCCCTCTCTCCAAGCTCACTTACAGGCTCTCTACTTAGT

CCAGCACGAAGTCTGGAGACCTCTGGCGGCAGCCTACCAAGAACAACTGGACCGACCGG

TGGTACCTCACCCTTACCGAGTCGGCGACACAGTGTGGGTCCGCCGACACCAGACTAAG

AACCTAGAACCTCGCTGGAAAGGACCTTACACAGTCCTGCTGACCACCCCCACCGCCCT

CAAAGTAGACGGCATCGCAGCTTGGATACACGCCGCCCACGTGAAGGCTGCCGACCCCG
```

-continued

```
GGGGTGGACCATCCTCTAGACTGCCATGCTCGAGGATGGCACGGCCACATCCCTGGTGG
CTGTGCGTTCTGGGGACCCTGGTGGGGCTCTCAGCTACTCCAGCCCCCAAGAGCTGCCC
AGAGAGGCACTACTGGGCTCAGGGAAAGCTGTGCTGCCAGATGTGTGAGCCAGGAACAT
TCCTCGTGAAGGACTGTGACCAGCATAGAAAGGCTGCTCAGTGTGATCCTTGCATACCG
GGGGTCTCCTTCTCTCCTGACCACCACACCCGGCCCCACTGTGAGAGCTGTCGGCACTG
TAACTCTGGTCTTCTCGTTCGCAACTGCACCATCACTGCCAATGCTGAGTGTGCCTGTC
GCAATGGCTGGCAGTGCAGGGACAAGGAGTGCACCGAGTGTGATCCTCTTCCAAACCCT
TCGCTGACCGCTCGGTCGTCTCAGGCCCTGAGCCCACACCCTCAGCCCACCCACTTACC
TTATGTCAGTGAGATGCTGGAGGCCAGGACAGCTGGGCACATGCAGACTCTGGCTGACT
TCAGGCAGCTGCCTGCCCGGACTCTCTCTACCCACTGGCCACCCCAAAGATCCCTGTGC
AGCTCCGATTTTATTCGCTTTTGGGTGCTGGTGGTGGTTGGTGGAGTCCTGGCTTGCTA
TAGCTTGCTAGTAACAGTGGCCTTTATTATTTTCTGGGTGAGGAGTAAGAGGAGCAGGC
TCCTGCACAGTGACTACATGAACATGACTCCCCGCCGCCCCGGGCCCACCCGCAAGCAT
TACCAGCCCTATGCCCCACCACGCGACTTCGCAGCCTATCGCTCACGCGTGAAGTTCAG
CAGGAGCGCAGACGCCCCCGCGTACCAGCAGGGCCAGAACCAGCTCTATAACGAGCTCA
ATCTAGGACGAAGAGAGGAGTACGATGTTTTGGACAAAAGACGTGGCCGGGACCCTGAG
ATGGGGGGAAAGCCGAGAAGGAAGAACCCTCAGGAAGGCCTGTACAATGAACTGCAGAA
AGATAAGATGGCGGAGGCCTACAGTGAGATTGGGATGAAAGGCGAGCGCCGGAGGGGCA
AGGGGCACGATGGCCTTTACCAGGGTCTCAGTACAGCCACCAAGGACACCTACGACGCC
CTTCACATGCAGGCCCTGCCCCCTCGCGGACCGCAGTGTACTAATTATGCTCTCTTGAA
ATTGGCTGGAGATGTTGAGAGCAATCCCGGGCCCATGCGCATTAGCAAGCCCCACCTGC
GGAGCATCAGCATCCAGTGCTACCTGTGCCTGCTGCTGAACAGCCACTTCCTGACCGAG
GCCGGCATCCACGTGTTCATCCTGGGCTGCTTCAGCGCCGGACTGCCCAAGACCGAGGC
CAACTGGGTGAACGTGATCAGCGACCTGAAGAAGATCGAGGACCTGATCCAGAGCATGC
ACATCGACGCCACCCTGTACACCGAGAGCGACGTGCACCCCAGCTGCAAGGTGACCGCC
ATGAAGTGCTTTCTGCTGGAACTGCAGGTGATCAGCCTGGAAAGCGGCGACGCCAGCAT
CCACGACACCGTGGAGAACCTGATCATCCTGGCCAACAACAGCCTGAGCAGCAACGGCA
ACGTGACCGAGAGCGGCTGCAAAGAGTGCGAGGAACTGGAAGAGAAGAACATCAAAGAG
TTTCTGCAGAGCTTCGTGCACATCGTGCAGATGTTCATCAACACCAGCTGA
```

A corresponding amino acid sequence for CD27TrCD28tmdicd3z15 is as follows:

(SEQ ID NO: 53)

```
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMARPHPWWLCVLGTLVGLSATPAPKSCPERHYWA
QGKLCCQMCEPGTFLVKDCDQHRKAAQCDPCIPGVSFSPDHHTRPHCES
CRHCNSGLLVRNCTITANAECACRNGWQCRDKECTECDPLPNPSLTARS
SQALSPHPQPTHLPYVSEMLEARTAGHMQTLADFRQLPARTLSTHWPPQ
RSLCSSDFIRFWVLVVVGGVLACYSLLVTVAFIIFWVRSKRSRLLHSDY
MNMTPRRPGPTRKHYQPYAPPRDFAAYRSRVKFSRSADAPAYQQGQNQL
```

-continued

```
YNELNLGRREEYDVLDKRRGRDPEMGGKPRRKNPQEGLYNELQKDKMAE
AYSEIGMKGERRRGKGHDGLYQGLSTATKDTYDALHMQALPPRGPQCTN
YALLKLAGDVESNPGPMRISKPHLRSISIQCYLCLLLNSHFLTEAGIHV
FILGCFSAGLPKTEANWVNVISDLKKIEDLIQSMHIDATLYTESDVHPS
CKVTAMKCFLLELQVISLESGDASIHDTVENLIILANNSLSSNGNVTES
GCKECEELEEKNIKEFLQSFVHIVQMFINTS
```

GSPco27Tr28tmdicCD3z15:

(SEQ ID NO: 31)

```
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
```

-continued

CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGCTTCTCC
TGGTGACAAGCCTTCTGCTCTGTGAGTTACCACACCCAGCATTCCTCCT
GATCCCAGCTACACCGGCTCCGAAGTCCTGCCCGGAGCGGCATTATTGG
GCACAGGGCAAGTTGTGTTGTCAAATGTGTGAGCCGGGAACCTTTCTCG
TGAAGGATTGCGATCAGCATCGGAAGGCCGCGCAGTGCGACCCATGTAT
ACCAGGGGTCTCATTTTCCCCAGATCACCATACGAGGCCGCACTGTGAG
TCTTGCAGGCATTGTAATTCCGGCTTGTTGGTCCGCAACTGTACTATTA
CTGCGAATGCAGAGTGTGCTTGTAGAAACGGATGGCAGTGCAGGGACAA
AGAATGTACGGAGTGTGATCCACTGCCTAACCCCAGTCTTACAGCAAGA
TCTTCACAGGCCCTCAGCCCGCATCCTCAACCAACACATCTTCCTTACG
TGTCAGAAATGTTGGAGGCGCGAACCGCAGGCCATATGCAGACCCTGGC
GGACTTTCGGCAGCTGCCAGCACGCACACTTAGTACACACTGGCCACCA
CAACGCAGCTTGTGCTCTTCCGATTTCATCCGCTTTTGGGTGCTGGTGG
TGGTTGGTGGAGTCCTGGCTTGCTATAGCTTGCTAGTAACAGTGGCCTT
TATTATTTTCTGGGTGAGGAGTAAGAGGAGCAGGCTCCTGCACAGTGAC
TACATGAACATGACTCCCCGCCGCCCCGGGCCCACCCGCAAGCATTACC
AGCCCTATGCCCCACCACGCGACTTCGCAGCCTATCGCTCACGCGTGAA
GTTCAGCAGGAGCGCAGACGCCCCCGCGTACCAGCAGGGCCAGAACCAG
CTCTATAACGAGCTCAATCTAGGACGAAGAGAGGAGTACGATGTTTTGG
ACAAAAGACGTGGCCGGGACCCTGAGATGGGGGGAAAGCCGAGAAGGAA
GAACCCTCAGGAAGGCCTGTACAATGAACTGCAGAAAGATAAGATGGCG
GAGGCCTACAGTGAGATTGGGATGAAAGGCGAGCGCCGGAGGGGCAAGG
GGCACGATGGCCTTTACCAGGGTCTCAGTACAGCCACCAAGGACACCTA
CGACGCCCTTCACATGCAGGCCCTGCCCCCTCGCGGACCGCAGTGTACT
AATTATGCTCTCTTGAAATTGGCTGGAGATGTTGAGAGCAATCCCGGGC
CCATGCGCATTAGCAAGCCCCACCTGCGGAGCATCAGCATCCAGTGCTA
CCTGTGCCTGCTGCTGAACAGCCACTTCCTGACCGAGGCCGGCATCCAC
GTGTTCATCCTGGGCTGCTTCAGCGCCGGACTGCCCAAGACCGAGGCCA
ACTGGGTGAACGTGATCAGCGACCTGAAGAAGATCGAGGACCTGATCCA
GAGCATGCACATCGACGCCACCCTGTACACCGAGAGCGACGTGCACCCC
AGCTGCAAGGTGACCGCCATGAAGTGCTTTCTGCTGGAACTGCAGGTGA
TCAGCCTGGAAAGCGGCGACGCCAGCATCCACGACACCGTGGAGAACCT
GATCATCCTGGCCAACAACAGCCTGAGCAGCAACGGCAACGTGACCGAG
AGCGGCTGCAAAGAGTGCGAGGAACTGGAAGAGAAGAACATCAAAGAGT
TTCTGCAGAGCTTCGTGCACATCGTGCAGATGTTCATCAACACCAGCTG
A

A corresponding amino acid sequence for GSPco27Tr28tmdicCD3z15 is as follows:

(SEQ ID NO: 54)

MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMLLLVTSLLLCELPHPAFLLIPATPAPKSCPERH
YWAQGKLCCQMCEPGTFLVKDCDQHRKAAQCDPCIPGVSFSPDHHTRPH
CESCRHCNSGLLVRNCTITANAECACRNGWQCRDKECTECDPLPNPSLT
ARSSQALSPHPQPTHLPYVSEMLEARTAGHMQTLADFRQLPARTLSTHW
PPQRSLCSSDFIRFWVLVVVGGVLACYSLLVTVAFIIFWVRSKRSRLLH
SDYMNMTPRRPGPTRKHYQPYAPPRDFAAYRSRVKFSRSADAPAYQQGQ
NQLYNELNLGRREEYDVLDKRRGRDPEMGGKPRRKNPQEGLYNELQKDK
MAEAYSEIGMKGERRRGKGHDGLYQGLSTATKDTYDALHMQALPPRGPQ
CTNYALLKLAGDVESNPGPMRISKPHLRSISIQCYLCLLLNSHFLTEAG
IHVFILGCFSAGLPKTEANWVNVISDLKKIEDLIQSMHIDATLYTESDV
HPSCKVTAMKCFLLELQVISLESGDASIHDTVENLIILANNSLSSNGNV
TESGCKECEELEEKNIKEFLQSFVHIVQMFINTS

CD27TrDAP10icd3z15:

(SEQ ID NO: 32)

ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGGCACGGC
CACATCCCTGGTGGCTGTGCGTTCTGGGGACCCTGGTGGGGCTCTCAGC
TACTCCAGCCCCCAAGAGCTGCCCAGAGAGGCACTACTGGGCTCAGGGA
AAGCTGTGCTGCCAGATGTGTGAGCCAGGAACATTCCTCGTGAAGGACT
GTGACCAGCATAGAAAGGCTGCTCAGTGTGATCCTTGCATACCGGGGGT
CTCCTTCTCTCCTGACCACCACACCCGGCCCCACTGTGAGAGCTGTCGG
CACTGTAACTCTGGTCTTCTCGTTCGCAACTGCACCATCACTGCCAATG
CTGAGTGTGCCTGTCGCAATGGCTGGCAGTGCAGGGACAAGGAGTGCAC
CGAGTGTGATCCTCTTCCAAACCCTTCGCTGACCGCTCGGTCGTCTCAG
GCCCTGAGCCCACACCCTCAGCCCACCCACTTACCTTATGTCAGTGAGA
TGCTGGAGGCCAGGACAGCTGGGCACATGCAGACTCTGGCTGACTTCAG
GCAGCTGCCTGCCCGGACTCTCTCTACCCACTGGCCACCCCAAAGATCC
CTGTGCAGCTCCGATTTTATTCGCATACTGGTCATCTTTTCTGGAATGT
TCCTTGTGTTCACCCTGGCAGGAGCCCTGTTCCTTCACCTTTGCGCACG
CCCACGCCGCAGCCCCGCCCAAGAAGATGGCAAAGTCTACATCAACATG
CCAGGCAGGGGCAAACGCGTGAAGTTCAGCAGGAGCGCAGACGCCCCCG
CGTACCAGCAGGGCCAGAACCAGCTCTATAACGAGCTCAATCTAGGACG
AAGAGAGGAGTACGATGTTTTGGACAAAAGACGTGGCCGGGACCCTGAG

-continued

ATGGGGGGAAAGCCGAGAAGGAAGAACCCTCAGGAAGGCCTGTACAATG
AACTGCAGAAAGATAAGATGGCGGAGGCCTACAGTGAGATTGGGATGAA
AGGCGAGCGCCGGAGGGGCAAGGGGCACGATGGCCTTTACCAGGGTCTC
AGTACAGCCACCAAGGACACCTACGACGCCCTTCACATGCAGGCCCTGC
CCCCTCGCGGACCGCAGTGTACTAATTATGCTCTCTTGAAATTGGCTGG
AGATGTTGAGAGCAATCCCGGGCCCATGCGCATTAGCAAGCCCCACCTG
CGGAGCATCAGCATCCAGTGCTACCTGTGCCTGCTGCTGAACAGCCACT
TCCTGACCGAGGCCGGCATCCACGTGTTCATCCTGGGCTGCTTCAGCGC
CGGACTGCCCAAGACCGAGGCCAACTGGGTGAACGTGATCAGCGACCTG
AAGAAGATCGAGGACCTGATCCAGAGCATGCACATCGACGCCACCCTGT
ACACCGAGAGCGACGTGCACCCCAGCTGCAAGGTGACCGCCATGAAGTG
CTTTCTGCTGGAACTGCAGGTGATCAGCCTGGAAAGCGGCGACGCCAGC
ATCCACGACACCGTGGAGAACCTGATCATCCTGGCCAACAACAGCCTGA
GCAGCAACGGCAACGTGACCGAGAGCGGCTGCAAAGAGTGCGAGGAACT
GGAAGAGAAGAACATCAAAGAGTTTCTGCAGAGCTTCGTGCACATCGTG
CAGATGTTCATCAACACCAGCTGA

A corresponding amino acid sequence for CD27TrDAP10icd3z15 is as follows:

(SEQ ID NO: 55)
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMARPHPWWLCVLGTLVGLSATPAPKSCPERHYWA
QGKLCCQMCEPGTFLVKDCDQHRKAAQCDPCIPGVSFSPDHHTRPHCES
CRHCNSGLLVRNCTITANAECACRNGWQCRDKECTECDPLPNPSLTARS
SQALSPHPQPTHLPYVSEMLEARTAGHMQTLADFRQLPARTLSTHWPPQ
RSLCSSDFIRILVIFSGMFLVFTLAGALFLHLCARPRRSPAQEDGKVYI
NMPGRGKRVKFSRSADAPAYQQGQNQLYNELNLGRREEYDVLDKRRGRD
PEMGGKPRRKNPQEGLYNELQKDKMAEAYSEIGMKGERRRGKGHDGLYQ
GLSTATKDTYDALHMQALPPRGPQCTNYALLKLAGDVESNPGPMRISKP
HLRSISIQCYLCLLLNSHFLTEAGIHVFILGCFSAGLPKTEANWVNVIS
DLKKIEDLIQSMHIDATLYTESDVHPSCKVTAMKCFLLELQVISLESGD
ASIHDTVENLIILANNSLSSNGNVTESGCKECEELEEKNIKEFLQSFVH
IVQMFINTS

GSPco27FLdap10icd3z15:

(SEQ ID NO: 33)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT

-continued

AGACGGCATCGCAGCTTGGATACACGCCGCCCACGTGAAGGCTGCCGAC
CCCGGGGGTGGACCATCCTCTAGACTGCCATGCTCGAGGATGCTTCTCC
TGGTGACAAGCCTTCTGCTCTGTGAGTTACCACACCCAGCATTCCTCCT
GATCCCAGCTACACCGGCTCCGAAGTCCTGCCCGGAGCGGCATTATTGG
GCACAGGGCAAGTTGTGTTGTCAAATGTGTGAGCCGGGAACCTTTCTCG
TGAAGGATTGCGATCAGCATCGGAAGGCCGCGCAGTGCGACCCATGTAT
ACCAGGGGTCTCATTTTCCCCAGATCACCATACGAGGCCGCACTGTGAG
TCTTGCAGGCATTGTAATTCCGGCTTGTTGGTCCGCAACTGTACTATTA
CTGCGAATGCAGAGTGTGCTTGTAGAAACGGATGGCAGTGCAGGGACAA
AGAATGTACGGAGTGTGATCCACTGCCTAACCCCAGTCTTACAGCAAGA
TCTTCACAGGCCCTCAGCCCGCATCCTCAACCAACACATCTTCCTTACG
TGTCAGAAATGTTGGAGGCGCGAACCGCAGGCCATATGCAGACCCTGGC
GGACTTTCGGCAGCTGCCAGCACGCACACTTAGTACACACTGGCCACCA
CAACGCAGCTTGTGCTCTTCCGATTTCATCCGCATACTGGTCATCTTTT
CTGGAATGTTCCTTGTGTTCACCCTGGCAGGAGCCCTGTTCCTTCACCT
TTGCGCACGCCCACGCCGCAGCCCCGCCCAAGAAGATGGCAAAGTCTAC
ATCAACATGCCAGGCAGGGGCAAACGCGTGAAGTTCAGCAGGAGCGCAG
ACGCCCCCGCGTACCAGCAGGGCCAGAACCAGCTCTATAACGAGCTCAA
TCTAGGACGAAGAGAGGAGTACGATGTTTTGGACAAAAGACGTGGCCGG
GACCCTGAGATGGGGGGAAAGCCGAGAAGGAAGAACCCTCAGGAAGGCC
TGTACAATGAACTGCAGAAAGATAAGATGGCGGAGGCCTACAGTGAGAT
TGGGATGAAAGGCGAGCGCCGGAGGGGCAAGGGGCACGATGGCCTTTAC
CAGGGTCTCAGTACAGCCACCAAGGACACCTACGACGCCCTTCACATGC
AGGCCCTGCCCCCTCGCGGACCGCAGTGTACTAATTATGCTCTCTTGAA
ATTGGCTGGAGATGTTGAGAGCAATCCCGGGCCCATGCGCATTAGCAAG
CCCCACCTGCGGAGCATCAGCATCCAGTGCTACCTGTGCCTGCTGCTGA
ACAGCCACTTCCTGACCGAGGCCGGCATCCACGTGTTCATCCTGGGCTG
CTTCAGCGCCGGACTGCCCAAGACCGAGGCCAACTGGGTGAACGTGATC
AGCGACCTGAAGAAGATCGAGGACCTGATCCAGAGCATGCACATCGACG
CCACCCTGTACACCGAGAGCGACGTGCACCCCAGCTGCAAGGTGACCGC
CATGAAGTGCTTTCTGCTGGAACTGCAGGTGATCAGCCTGGAAAGCGGC
GACGCCAGCATCCACGACACCGTGGAGAACCTGATCATCCTGGCCAACA
ACAGCCTGAGCAGCAACGGCAACGTGACCGAGAGCGGCTGCAAAGAGTG
CGAGGAACTGGAAGAGAAGAACATCAAAGAGTTTCTGCAGAGCTTCGTG
CACATCGTGCAGATGTTCATCAACACCAGCTGA

A corresponding amino acid sequence for GSPco27FLdap10icd3z15 is as follows:

(SEQ ID NO: 56)
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMLLLVTSLLLCELPHPAFLLIPATPAPKSCPERH

-continued

YWAQGKLCCQMCEPGTFLVKDCDQHRKAAQCDPCIPGVSFSPDHHTRPH
CESCRHCNSGLLVRNCTITANAECACRNGWQCRDKECTECDPLPNPSLT
ARSSQALSPHPQPTHLPYVSEMLEARTAGHMQTLADFRQLPARTLSTHW
PPQRSLCSSDFIRILVIFSGMFLVFTLAGALFLHLCARPRRSPAQEDGK
VYINMPGRGKRVKFSRSADAPAYQQGQNQLYNELNLGRREEYDVLDKRR
GRDPEMGGKPRRKNPQEGLYNELQKDKMAEAYSEIGMKGERRRGKGHDG
LYQGLSTATKDTYDALHMQALPPRGPQCTNYALLKLAGDVESNPGPMRI
SKPHLRSISIQCYLCLLLNSHFLTEAGIHVFILGCFSAGLPKTEANWVN
VISDLKKIEDLIQSMHIDATLYTESDVHPSCKVTAMKCFLLELQVISLE
SGDASIHDTVENLIILANNSLSSNGNVTESGCKECEELEEKNIKEFLQS
FVHIVQMFINTS

CD27TrDAP12icd3z15:

(SEQ ID NO: 34)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC
CCCGGGGGTGGACCATCCTCTAGACTGCCATGCTCGAGGATGGCACGGC
CACATCCCTGGTGGCTGTGCGTTCTGGGGACCCTGGTGGGGCTCTCAGC
TACTCCAGCCCCCAAGAGCTGCCCAGAGAGGCACTACTGGGCTCAGGGA
AAGCTGTGCTGCCAGATGTGTGAGCCAGGAACATTCCTCGTGAAGGACT
GTGACCAGCATAGAAAGGCTGCTCAGTGTGATCCTTGCATACCGGGGGT
CTCCTTCTCTCCTGACCACCACACCCGGCCCCACTGTGAGAGCTGTCGG
CACTGTAACTCTGGTCTTCTCGTTCGCAACTGCACCATCACTGCCAATG
CTGAGTGTGCCTGTCGCAATGGCTGGCAGTGCAGGGACAAGGAGTGCAC
CGAGTGTGATCCTCTTCCAAACCCTTCGCTGACCGCTCGGTCGTCTCAG
GCCCTGAGCCCACACCCTCAGCCCACCCACTTACCTTATGTCAGTGAGA
TGCTGGAGGCCAGGACAGCTGGGCACATGCAGACTCTGGCTGACTTCAG
GCAGCTGCCTGCCCGGACTCTCTCTACCCACTGGCCACCCCAAAGATCC
CTGTGCAGCTCCGATTTTATTCGCATCCTTGTGATCTTCTCTGGAATGT
TCCTTGTTTTCACCCTGGCCGGGGCCCTGTTCCTCCATTACTTCCTGGG
CCGGCTGGTCCCTCGGGGGCGAGGGGCTGCGGAGGCAGCGACCCGGAAA
CAGCGTATCACTGAGACCGAGTCGCCTTATCAGGAGCTCCAGGGTCAGA
GGTCGGATGTCTACAGCGACCTCAACACACAGAGGCCGTATTACAAAAA
ACGCGTGAAGTTCAGCAGGAGCGCAGACGCCCCCGCGTACCAGCAGGGC
CAGAACCAGCTCTATAACGAGCTCAATCTAGGACGAAGAGAGGAGTACG
ATGTTTTGGACAAAAGACGTGGCCGGGACCCTGAGATGGGGGGAAAGCC
GAGAAGGAAGAACCCTCAGGAAGGCCTGTACAATGAACTGCAGAAAGAT
AAGATGGCGGAGGCCTACAGTGAGATTGGGATGAAAGGCGAGCGCCGGA
GGGGCAAGGGGCACGATGGCCTTTACCAGGGTCTCAGTACAGCCACCAA
GGACACCTACGACGCCCTTCACATGCAGGCCCTGCCCCCTCGCGGACCG
CAGTGTACTAATTATGCTCTCTTGAAATTGGCTGGAGATGTTGAGAGCA
ATCCCGGGCCCATGCGCATTAGCAAGCCCCACCTGCGGAGCATCAGCAT
CCAGTGCTACCTGTGCCTGCTGCTGAACAGCCACTTCCTGACCGAGGCC
GGCATCCACGTGTTCATCCTGGGCTGCTTCAGCGCCGGACTGCCCAAGA
CCGAGGCCAACTGGGTGAACGTGATCAGCGACCTGAAGAAGATCGAGGA
CCTGATCCAGAGCATGCACATCGACGCCACCCTGTACACCGAGAGCGAC
GTGCACCCCAGCTGCAAGGTGACCGCCATGAAGTGCTTTCTGCTGGAAC
TGCAGGTGATCAGCCTGGAAAGCGGCGACGCCAGCATCCACGACACCGT
GGAGAACCTGATCATCCTGGCCAACAACAGCCTGAGCAGCAACGGCAAC
GTGACCGAGAGCGGCTGCAAAGAGTGCGAGGAACTGGAAGAGAAGAACA
TCAAAGAGTTTCTGCAGAGCTTCGTGCACATCGTGCAGATGTTCATCAA
CACCAGCTGA

A corresponding amino acid sequence for CD27TrDAP12icd3z15 is as follows:

(SEQ ID NO: 57)
MTRVTNSPSLQAHLQALYLVQHEVWRPLAAAYQEQLDRPVVPHPYR
VGDTVWVRRHQTKNLEPRWKGPYTVLLTTPTALKVDGIAAWIHAAHVKA
ADPGGGPSSRLPCSRMARPHPWWLCVLGTLVGLSATPAPKSCPERHYWA
QGKLCCQMCEPGTFLVKDCDQHRKAAQCDPCIPGVSFSPDHHTRPHCES
CRHCNSGLLVRNCTITANAECACRNGWQCRDKECTECDPLPNPSLTARS
SQALSPHPQPTHLPYVSEMLEARTAGHMQTLADFRQLPARTLSTHWPPQ
RSLCSSDFIRILVIFSGMFLVFTLAGALFLHYFLGRLVPRGRGAAEAAT
RKQRITETESPYQELQGQRSDVYSDLNTQRPYYKKRVKFSRSADAPAYQ
QGQNQLYNELNLGRREEYDVLDKRRGRDPEMGGKPRRKNPQEGLYNELQ
KDKMAEAYSEIGMKGERRRGKGHDGLYQGLSTATKDTYDALHMQALPPR
GPQCTNYALLKLAGDVESNPGPMRISKPHLRSISIQCYLCLLLNSHFLT
EAGIHVFILGCFSAGLPKTEANWVNVISDLKKIEDLIQSMHIDATLYTE
SDVHPSCKVTAMKCFLLELQVISLESGDASIHDTVENLIILANNSLSSN
GNVTESGCKECEELEEKNIKEFLQSFVHIVQMFINTS

GSPco27FLdap12icd3z15:

(SEQ ID NO: 35)
ATGACAAGAGTTACTAACAGCCCCTCTCTCCAAGCTCACTTACAGG
CTCTCTACTTAGTCCAGCACGAAGTCTGGAGACCTCTGGCGGCAGCCTA
CCAAGAACAACTGGACCGACCGGTGGTACCTCACCCTTACCGAGTCGGC
GACACAGTGTGGGTCCGCCGACACCAGACTAAGAACCTAGAACCTCGCT
GGAAAGGACCTTACACAGTCCTGCTGACCACCCCCACCGCCCTCAAAGT
AGACGGCATCGCAGCTTGGATACACGCCGCCCACGTGAAGGCTGCCGAC

-continued

CCCGGGGGTGGACCATCCTCTAGACTGCCATGCTCGAGGATGCTTCTCC

TGGTGACAAGCCTTCTGCTCTGTGAGTTACCACACCCAGCATTCCTCCT

GATCCCAGCTACACCGGCTCCGAAGTCCTGCCCGGAGCGGCATTATTGG

GCACAGGGCAAGTTGTGTTGTCAAATGTGTGAGCCGGGAACCTTTCTCG

TGAAGGATTGCGATCAGCATCGGAAGGCCGCGCAGTGCGACCCATGTAT

ACCAGGGGTCTCATTTTCCCCAGATCACCATACGAGGCCGCACTGTGAG

TCTTGCAGGCATTGTAATTCCGGCTTGTTGGTCCGCAACTGTACTATTA

CTGCGAATGCAGAGTGTGCTTGTAGAAACGGATGGCAGTGCAGGGACAA

AGAATGTACGGAGTGTGATCCACTGCCTAACCCCAGTCTTACAGCAAGA

TCTTCACAGGCCCTCAGCCCGCATCCTCAACCAACACATCTTCCTTACG

TGTCAGAAATGTTGGAGGCGCGAACCGCAGGCCATATGCAGACCCTGGC

GGACTTTCGGCAGCTGCCAGCACGCACACTTAGTACACACTGGCCACCA

CAACGCAGCTTGTGCTCTTCCGATTTCATCCGCATACTGGTCATCTTTT

CTGGAATGTTCCTTGTGTTCACCCTGGCAGGAGCCCTGTTCCTTCACTA

CTTCCTGGGCCGGCTGGTCCCTCGGGGGCGAGGGGCTGCGGAGGCAGCG

ACCCGGAAACAGCGTATCACTGAGACCGAGTCGCCTTATCAGGAGCTCC

AGGGTCAGAGGTCGGATGTCTACAGCGACCTCAACACACAGAGGCCGTA

TTACAAAAAACGCGTGAAGTTCAGCAGGAGCGCAGACGCCCCCGCGTAC

CAGCAGGGCCAGAACCAGCTCTATAACGAGCTCAATCTAGGACGAAGAG

AGGAGTACGATGTTTTGGACAAAAGACGTGGCCGGGACCCTGAGATGGG

GGGAAAGCCGAGAAGGAAGAACCCTCAGGAAGGCCTGTACAATGAACTG

CAGAAAGATAAGATGGCGGAGGCCTACAGTGAGATTGGGATGAAAGGCG

AGCGCCGGAGGGGCAAGGGGCACGATGGCCTTTACCAGGGTCTCAGTAC

AGCCACCAAGGACACCTACGACGCCCTTCACATGCAGGCCCTGCCCCCT

CGCGGACCGCAGTGTACTAATTATGCTCTCTTGAAATTGGCTGGAGATG

TTGAGAGCAATCCCGGGCCCATGCGCATTAGCAAGCCCCACCTGCGGAG

CATCAGCATCCAGTGCTACCTGTGCCTGCTGCTGAACAGCCACTTCCTG

ACCGAGGCCGGCATCCACGTGTTCATCCTGGGCTGCTTCAGCGCCGGAC

TGCCCAAGACCGAGGCCAACTGGGTGAACGTGATCAGCGACCTGAAGAA

GATCGAGGACCTGATCCAGAGCATGCACATCGACGCCACCCTGTACACC

GAGAGCGACGTGCACCCCAGCTGCAAGGTGACCGCCATGAAGTGCTTTC

TGCTGGAACTGCAGGTGATCAGCCTGGAAAGCGGCGACGCCAGCATCCA

CGACACCGTGGAGAACCTGATCATCCTGGCCAACAACAGCCTGAGCAGC

AACGGCAACGTGACCGAGAGCGGCTGCAAAGAGTGCGAGGAACTGGAAG

AGAAGAACATCAAAGAGTTTCTGCAGAGCTTCGTGCACATCGTGCAGAT

GTTCATCAACACCAGCTGA

A corresponding amino acid sequence for GSPco27FLdap12icd3z15 is as follows:

(SEQ ID NO: 58)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

-continued

ADPGGGPSSRLPCSRMLLLVTSLLLCELPHPAFLLIPATPAPKSCPERH

YWAQGKLCCQMCEPGTFLVKDCDQHRKAAQCDPCIPGVSFSPDHHTRPH

CESCRHCNSGLLVRNCTITANAECACRNGWQCRDKECTECDPLPNPSLT

ARSSQALSPHPQPTHLPYVSEMLEARTAGHMQTLADFRQLPARTLSTHW

PPQRSLCSSDFIRILVIFSGMFLVFTLAGALFLHYFLGRLVPRGRGAAE

AATRKQRITETESPYQELQGQRSDVYSDLNTQRPYYKKRVKFSRSADAP

AYQQGQNQLYNELNLGRREEYDVLDKRRGRDPEMGGKPRRKNPQEGLYN

ELQKDKMAEAYSEIGMKGERRRGKGHDGLYQGLSTATKDTYDALHMQAL

PPRGPQCTNYALLKLAGDVESNPGPMRISKPHLRSISIQCYLCLLLNSH

FLTEAGIHVFILGCFSAGLPKTEANWVNVISDLKKIEDLIQSMHIDATL

YTESDVHPSCKVTAMKCFLLELQVISLESGDASIHDTVENLIILANNSL

SSNGNVTESGCKECEELEEKNIKEFLQSFVHIVQMFINTS

CD27TrNKG2Dic3z15:

(SEQ ID NO: 36)

ATGACAAGAGTTACTAACAGCCCCTCTCTCCAAGCTCACTTACAGG

CTCTCTACTTAGTCCAGCACGAAGTCTGGAGACCTCTGGCGGCAGCCTA

CCAAGAACAACTGGACCGACCGGTGGTACCTCACCCTTACCGAGTCGGC

GACACAGTGTGGGTCCGCCGACACCAGACTAAGAACCTAGAACCTCGCT

GGAAAGGACCTTACACAGTCCTGCTGACCACCCCCACCGCCCTCAAAGT

AGACGGCATCGCAGCTTGGATACACGCCGCCCACGTGAAGGCTGCCGAC

CCCGGGGGTGGACCATCCTCTAGACTGCCATGCTCGAGGATGGCACGGC

CACATCCCTGGTGGCTGTGCGTTCTGGGGACCCTGGTGGGGCTCTCAGC

TACTCCAGCCCCCAAGAGCTGCCCAGAGAGGCACTACTGGGCTCAGGGA

AAGCTGTGCTGCCAGATGTGTGAGCCAGGAACATTCCTCGTGAAGGACT

GTGACCAGCATAGAAAGGCTGCTCAGTGTGATCCTTGCATACCGGGGGT

CTCCTTCTCTCCTGACCACCACACCCGGCCCCACTGTGAGAGCTGTCGG

CACTGTAACTCTGGTCTTCTCGTTCGCAACTGCACCATCACTGCCAATG

CTGAGTGTGCCTGTCGCAATGGCTGGCAGTGCAGGGACAAGGAGTGCAC

CGAGTGTGATCCTCTTCCAAACCCTTCGCTGACCGCTCGGTCGTCTCAG

GCCCTGAGCCCACACCCTCAGCCCACCCACTTACCTTATGTCAGTGAGA

TGCTGGAGGCCAGGACAGCTGGGCACATGCAGACTCTGGCTGACTTCAG

GCAGCTGCCTGCCCGGACTCTCTCTACCCACTGGCCACCCCAAAGATCC

CTGTGCAGCTCCGATTTTATTCGCATCCTTGTGATCTTCTCTGGAATGT

TCCTTGTTTTCACCCTGGCCGGGGCCCTGTTCCTCCATAGCGCGAACGA

ACGCTGCAAAAGCAAAGTGGTGCCGTGCCGCCAGAAACAGTGGCGCACC

AGCTTTGATAGCAAAAAACTGGATCTGAACTATAACCATTTTGAAAGCA

TGGAATGGAGCCATCGCAGCCGCCGCGGCCGCATTTGGGGCATGAAACG

CGTGAAGTTCAGCAGGAGCGCAGACGCCCCCGCGTACCAGCAGGGCCAG

AACCAGCTCTATAACGAGCTCAATCTAGGACGAAGAGAGGAGTACGATG

TTTTGGACAAAAGACGTGGCCGGGACCCTGAGATGGGGGGAAAGCCGAG

-continued

AAGGAAGAACCCTCAGGAAGGCCTGTACAATGAACTGCAGAAAGATAAG

ATGGCGGAGGCCTACAGTGAGATTGGGATGAAAGGCGAGCGCCGGAGGG

GCAAGGGGCACGATGGCCTTTACCAGGGTCTCAGTACAGCCACCAAGGA

CACCTACGACGCCCTTCACATGCAGGCCCTGCCCCCTCGCGGACCGCAG

TGTACTAATTATGCTCTCTTGAAATTGGCTGGAGATGTTGAGAGCAATC

CCGGGCCCATGCGCATTAGCAAGCCCCACCTGCGGAGCATCAGCATCCA

GTGCTACCTGTGCCTGCTGCTGAACAGCCACTTCCTGACCGAGGCCGGC

ATCCACGTGTTCATCCTGGGCTGCTTCAGCGCCGGACTGCCCAAGACCG

AGGCCAACTGGGTGAACGTGATCAGCGACCTGAAGAAGATCGAGGACCT

GATCCAGAGCATGCACATCGACGCCACCCTGTACACCGAGAGCGACGTG

CACCCCAGCTGCAAGGTGACCGCCATGAAGTGCTTTCTGCTGGAACTGC

AGGTGATCAGCCTGGAAAGCGGCGACGCCAGCATCCACGACACCGTGGA

GAACCTGATCATCCTGGCCAACAACAGCCTGAGCAGCAACGGCAACGTG

ACCGAGAGCGGCTGCAAAGAGTGCGAGGAACTGGAAGAGAAGAACATCA

AAGAGTTTCTGCAGAGCTTCGTGCACATCGTGCAGATGTTCATCAACAC

CAGCTGA

A corresponding amino acid sequence for CD27TrNKG2Dic3z15 is as follows:

(SEQ ID NO: 59)

MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMARPHPWWLCVLGTLVGLSATPAPKSCPERHYWA

QGKLCCQMCEPGTFLVKDCDQHRKAAQCDPCIPGVSFSPDHHTRPHCES

CRHCNSGLLVRNCTITANAECACRNGWQCRDKECTECDPLPNPSLTARS

SQALSPHPQPTHLPYVSEMLEARTAGHMQTLADFRQLPARTLSTHWPPQ

RSLCSSDFIRILVIFSGMFLVFTLAGALFLHSANERCKSKVVPCRQKQW

RTSFDSKKLDLNYNHFESMEWSHRSRRGRIWGMKRVKFSRSADAPAYQQ

GQNQLYNELNLGRREEYDVLDKRRGRDPEMGGKPRRKNPQEGLYNELQK

DKMAEAYSEIGMKGERRRGKGHDGLYQGLSTATKDTYDALHMQALPPRG

PQCTNYALLKLAGDVESNPGPMRISKPHLRSISIQCYLCLLLNSHFLTE

AGIHVFILGCFSAGLPKTEANWVNVISDLKKIEDLIQSMHIDATLYTES

DVHPSCKVTAMKCFLLELQVISLESGDASIHDTVENLIILANNSLSSNG

NVTESGCKECEELEEKNIKEFLQSFVHIVQMFINTS

GSPco27TrNKG2Dicd3z15:

(SEQ ID NO: 37)

ATGACAAGAGTTACTAACAGCCCCTCTCTCCAAGCTCACTTACAGG

CTCTCTACTTAGTCCAGCACGAAGTCTGGAGACCTCTGGCGGCAGCCTA

CCAAGAACAACTGGACCGACCGGTGGTACCTCACCCTTACCGAGTCGGC

GACACAGTGTGGGTCCGCCGACACCAGACTAAGAACCTAGAACCTCGCT

GGAAAGGACCTTACACAGTCCTGCTGACCACCCCCACCGCCCTCAAAGT

-continued

AGACGGCATCGCAGCTTGGATACACGCCGCCCACGTGAAGGCTGCCGAC

CCCGGGGGTGGACCATCCTCTAGACTGCCATGCTCGAGGATGCTTCTCC

TGGTGACAAGCCTTCTGCTCTGTGAGTTACCACACCCAGCATTCCTCCT

GATCCCAGCTACACCGGCTCCGAAGTCCTGCCCGGAGCGGCATTATTGG

GCACAGGGCAAGTTGTGTTGTCAAATGTGTGAGCCGGGAACCTTTCTCG

TGAAGGATTGCGATCAGCATCGGAAGGCCGCGCAGTGCGACCCATGTAT

ACCAGGGGTCTCATTTTCCCCAGATCACCATACGAGGCCGCACTGTGAG

TCTTGCAGGCATTGTAATTCCGGCTTGTTGGTCCGCAACTGTACTATTA

CTGCGAATGCAGAGTGTGCTTGTAGAAACGGATGGCAGTGCAGGGACAA

AGAATGTACGGAGTGTGATCCACTGCCTAACCCCAGTCTTACAGCAAGA

TCTTCACAGGCCCTCAGCCCGCATCCTCAACCAACACATCTTCCTTACG

TGTCAGAAATGTTGGAGGCGCGAACCGCAGGCCATATGCAGACCCTGGC

GGACTTTCGGCAGCTGCCAGCACGCACACTTAGTACACACTGGCCACCA

CAACGCAGCTTGTGCTCTTCCGATTTCATCCGCATACTGGTCATCTTTT

CTGGAATGTTCCTTGTGTTCACCCTGGCAGGAGCCCTGTTCCTTCACAG

CGCGAACGAACGCTGCAAAAGCAAAGTGGTGCCGTGCCGCCAGAAACAG

TGGCGCACCAGCTTTGATAGCAAAAAACTGGATCTGAACTATAACCATT

TTGAAAGCATGGAATGGAGCCATCGCAGCCGCCGCGGCCGCATTTGGGG

CATGAAACGCGTGAAGTTCAGCAGGAGCGCAGACGCCCCCGCGTACCAG

CAGGGCCAGAACCAGCTCTATAACGAGCTCAATCTAGGACGAAGAGAGG

AGTACGATGTTTTGGACAAAAGACGTGGCCGGGACCCTGAGATGGGGGG

AAAGCCGAGAAGGAAGAACCCTCAGGAAGGCCTGTACAATGAACTGCAG

AAAGATAAGATGGCGGAGGCCTACAGTGAGATTGGGATGAAAGGCGAGC

GCCGGAGGGGCAAGGGGCACGATGGCCTTTACCAGGGTCTCAGTACAGC

CACCAAGGACACCTACGACGCCCTTCACATGCAGGCCCTGCCCCCTCGC

GGACCGCAGTGTACTAATTATGCTCTCTTGAAATTGGCTGGAGATGTTG

AGAGCAATCCCGGGCCCATGCGCATTAGCAAGCCCCACCTGCGGAGCAT

CAGCATCCAGTGCTACCTGTGCCTGCTGCTGAACAGCCACTTCCTGACC

GAGGCCGGCATCCACGTGTTCATCCTGGGCTGCTTCAGCGCCGGACTGC

CCAAGACCGAGGCCAACTGGGTGAACGTGATCAGCGACCTGAAGAAGAT

CGAGGACCTGATCCAGAGCATGCACATCGACGCCACCCTGTACACCGAG

AGCGACGTGCACCCCAGCTGCAAGGTGACCGCCATGAAGTGCTTTCTGC

TGGAACTGCAGGTGATCAGCCTGGAAAGCGGCGACGCCAGCATCCACGA

CACCGTGGAGAACCTGATCATCCTGGCCAACAACAGCCTGAGCAGCAAC

GGCAACGTGACCGAGAGCGGCTGCAAAGAGTGCGAGGAACTGGAAGAGA

AGAACATCAAAGAGTTTCTGCAGAGCTTCGTGCACATCGTGCAGATGTT

CATCAACACCAGCTGA

A corresponding amino acid sequence for GSPco27TrNKG2Dicd3z15 is as follows:

```
                                    (SEQ ID NO: 60)
MTRVTNSPSLQAHLQALYLVQHEVWRPLAAAYQEQLDRPVVPHPYR

VGDTVWVRRHQTKNLEPRWKGPYTVLLTTPTALKVDGIAAWIHAAHVKA

ADPGGGPSSRLPCSRMLLLVTSLLLCELPHPAFLLIPATPAPKSCPERH

YWAQGKLCCQMCEPGTFLVKDCDQHRKAAQCDPCIPGVSFSPDHHTRPH

CESCRHCNSGLLVRNCTITANAECACRNGWQCRDKECTECDPLPNPSLT

ARSSQALSPHPQPTHLPYVSEMLEARTAGHMQTLADFRQLPARTLSTHW

PPQRSLCSSDFIRILVIFSGMFLVFTLAGALFLHSANERCKSKVVPCRQ

KQWRTSFDSKKLDLNYNHFESMEWSHRSRRGRIWGMKRVKFSRSADAPA

YQQGQNQLYNELNLGRREEYDVLDKRRGRDPEMGGKPRRKNPQEGLYNE

LQKDKMAEAYSEIGMKGERRRGKGHDGLYQGLSTATKDTYDALHMQALP

PRGPQCTNYALLKLAGDVESNPGPMRISKPHLRSISIQCYLCLLLNSHF

LTEAGIHVFILGCFSAGLPKTEANWVNVISDLKKIEDLIQSMHIDATLY

TESDVHPSCKVTAMKCFLLELQVISLESGDASIHDTVENLIILANNSLS

SNGNVTESGCKECEELEEKNIKEFLQSFVHIVQMFINTS
```

The sequence of the open reading frame encoding the chimeric receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA. Also, it may be further advantageous to use endogenous or exogenous non-coding regions to stabilize the mRNA.

It is contemplated that the chimeric construct can be introduced into immune cells of any kind as naked DNA or in a suitable vector. Methods of stably transfecting cells by electroporation using naked DNA are known in the art. See, e.g., U.S. Pat. No. 6,410,319. Naked DNA generally refers to the DNA encoding a chimeric receptor contained in a plasmid expression vector in proper orientation for expression.

Alternatively, a viral vector (e.g., a retroviral vector, adenoviral vector, adeno-associated viral vector, or lentiviral vector) can be used to introduce the chimeric construct into immune cells. Suitable vectors for use in accordance with the method of the present disclosure are non-replicating in the immune cells. A large number of vectors are known that are based on viruses, where the copy number of the virus maintained in the cell is low enough to maintain the viability of the cell, such as, for example, vectors based on HIV, SV40, EBV, HSV, or BPV. Non-viral vectors include plasmids, transposons, nanoparticles, liposome, lipids, metals, or a combination thereof.

II. Cytokines

In some embodiments, the cells expressing the anti-CD70 CAR are engineered to express one or more heterologous cytokines and/or are engineered to upregulate normal expression of one or more heterologous cytokines. The cells may or may not be transduced or transfected for one or more cytokines on the same vector as other genes.

One or more cytokines may be co-expressed from the vector as a separate polypeptide from the antigen receptor. Interleukin-15 (IL-15), for example, is tissue restricted and only under pathologic conditions is it observed at any level in the serum, or systemically. IL-15 possesses several attributes that are desirable for adoptive therapy. IL-15 is a homeostatic cytokine that induces development and cell proliferation of natural killer cells, promotes the eradication of established tumors via alleviating functional suppression of tumor-resident cells, and inhibits activation-induced cell death (AICD). In addition to IL-15, other cytokines are envisioned. These include, but are not limited to, cytokines, chemokines, and other molecules that contribute to the activation and proliferation of cells used for human application. NK cells expressing IL-15 are capable of continued supportive cytokine signaling, which is useful for their survival post-infusion.

In specific embodiments, the cells expresses one or more exogenously provided cytokines. As one example, the cytokine is IL-15, IL-12, IL-2, IL-18, IL-21, GMCSF, or a combination thereof. As another example, the cytokine is IL-21. As another example, the cytokine is IL-12. The cytokine may be exogenously provided to the NK cells because it is expressed from an expression vector within the cell. In an alternative case, an endogenous cytokine in the cell is upregulated upon manipulation of regulation of expression of the endogenous cytokine, such as genetic recombination at the promoter site(s) of the cytokine. In cases wherein the cytokine is provided on an expression construct to the cell, the cytokine may be encoded from the same vector as a suicide gene and/or as the anti-CD70 CAR. In some embodiments, the present disclosure concerns co-utilization of the CAR with IL-15. In some embodiments, the present disclosure concerns co-utilization of the CAR with IL-21. In some embodiments, the present disclosure concerns co-utilization of the CAR with IL-12.

III. Suicide Genes

In particular embodiments, a suicide gene is utilized in conjunction with the anti-CD70 cell therapy to control its use and allow for termination of the cell therapy at a desired event and/or time. The suicide gene is employed in transduced cells for the purpose of eliciting death for the transduced cells when needed. The cells of the present disclosure that have been modified to harbor a vector encompassed by the disclosure may comprise one or more suicide genes. In some embodiments, the term "suicide gene" as used herein is defined as a gene which, upon administration of a prodrug or other agent, effects transition of a gene product to a compound which kills its host cell. In other embodiments, a suicide gene encodes a gene product that is, when desired, targeted by an agent (such as an antibody) that targets the suicide gene product.

In some cases, the cell therapy may be subject to utilization of one or more suicide genes of any kind when an individual receiving the cell therapy and/or having received the cell therapy shows one or more symptoms of one or more adverse events, such as cytokine release syndrome, neurotoxicity, anaphylaxis/allergy, and/or on-target/off tumor toxicities (as examples) or is considered at risk for having the one or more symptoms, including imminently. The use of the suicide gene may be part of a planned protocol for a therapy or may be used only upon a recognized need for its use. In some cases the cell therapy is terminated by use of agent(s) that targets the suicide gene or a gene product therefrom because the therapy is no longer required.

Utilization of the suicide gene may be instigated upon onset of at least one adverse event for the individual, and that adverse event may be recognized by any means, including upon routine monitoring that may or may not be continuous from the beginning of the cell therapy. The adverse event(s) may be detected upon examination and/or testing. In cases wherein the individual has cytokine release syndrome (which may also be referred to as cytokine storm), the individual may have elevated inflammatory cytokine(s) (merely as examples: interferon-gamma, granulocyte macrophage colony-stimulating factor, IL-10, IL-6 and TNF-alpha); fever; fatigue; hypotension; hypoxia, tachycardia; nausea; capillary leak; cardiac/renal/hepatic dysfunction; or a combination thereof, for example. In cases wherein the individual has neurotoxicity, the individual may have confusion, delirium, aplasia, and/or seizures. In some cases, the individual is tested for a marker associated with onset and/or severity of cytokine release syndrome, such as C-reactive protein, IL-6, TNF-alpha, and/or ferritin Examples of suicide genes include engineered nonsecretable (including membrane bound) tumor necrosis factor (TNF)-alpha mutant polypeptides (see PCT/US19/62009, which is incorporated by reference herein in its entirety), and they may be affected by delivery of an antibody that binds the TNF-alpha mutant. Examples of suicide gene/prodrug combinations that may be used are Herpes Simplex Virus-thymidine kinase (HSV-tk) and ganciclovir, acyclovir, or FIAU; oxidoreductase and cycloheximide; cytosine deaminase and 5-fluorocytosine; thymidine kinase thymidilate kinase (Tdk::Tmk) and AZT; and deoxycytidine kinase and cytosine arabinoside. The *E. coli* purine nucleoside phosphorylase, a so-called suicide gene that converts the prodrug 6-methylpurine deoxyriboside to toxic purine 6-methylpurine, may be utilized. Other suicide genes include CD20, CD52, inducible caspase 9, purine nucleoside phosphorylase (PNP), Cytochrome p450 enzymes (CYP), Carboxypeptidases (CP), Carboxylesterase (CE), Nitroreductase (NTR), Guanine Ribosyltransferase (XGRTP), Glycosidase enzymes, Methionine-α,γ-lyase (MET), and Thymidine phosphorylase (TP), as examples.

In particular embodiments, vectors that encode the CD70-targeting CAR, or any vector in a NK cell encompassed herein, include one or more suicide genes. The suicide gene may or may not be on the same vector as a CD70-targeting CAR. In cases wherein the suicide gene is present on the same vector as the CD70-targeting CAR, the suicide gene and the CAR may be separated by an IRES or 2A element, for example.

IV. Pharmaceutical Compositions

Pharmaceutical compositions of the present disclosure comprise an effective amount of cells expressing anti-CD70 CARs dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. The preparation of an pharmaceutical composition that comprises cells expressing anti-CD70 CARs will be known to those of skill in the art in light of the present disclosure, as exemplified by Remington: The Science and Practice of Pharmacy, 21st Ed. Lippincott Williams and Wilkins, 2005, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the pharmaceutical compositions is contemplated.

The pharmaceutical compositions may comprise different types of carriers depending on whether it is to be administered in solid, liquid or aerosol form, and whether it need to be sterile for such routes of administration as injection. The presently disclosed compositions can be administered intravenously, intradermally, transdermally, intrathecally, intraarterially, intraperitoneally, intranasally, intravaginally, intrarectally, topically, intramuscularly, subcutaneously, mucosally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The cells expressing anti-CD70 CARs may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective. The formulations are easily administered in a variety of dosage forms such as formulated for parenteral administrations such as injectable solutions, or aerosols for delivery to the lungs, or formulated for alimentary administrations such as drug release capsules and the like.

Further in accordance with the present disclosure, the compositions of the present disclosure suitable for administration is provided in a pharmaceutically acceptable carrier with or without an inert diluent. The carrier should be assimilable and includes liquid, semi-solid, i.e., pastes, or solid carriers. Except insofar as any conventional media, agent, diluent or carrier is detrimental to the recipient or to the therapeutic effectiveness of a the composition contained therein, its use in administrable composition for use in practicing the methods of the present invention is appropriate. Examples of carriers or diluents include fats, oils, water, saline solutions, lipids, liposomes, resins, binders, fillers and the like, or combinations thereof. The composition may also comprise various antioxidants to retard oxidation of one or more component. Additionally, the prevention of the action of microorganisms can be brought about by preservatives such as various antibacterial and antifungal agents, including but not limited to parabens (e.g., methylparabens, propylparabens), chlorobutanol, phenol, sorbic acid, thimerosal or combinations thereof.

In accordance with the present disclosure, the composition is combined with the carrier in any convenient and practical manner, i.e., by solution, suspension, emulsification, admixture, encapsulation, absorption and the like. Such procedures are routine for those skilled in the art.

In a specific embodiment of the present disclosure, the composition is combined or mixed thoroughly with a semi-solid or solid carrier. The mixing can be carried out in any convenient manner such as grinding. Stabilizing agents can be also added in the mixing process in order to protect the composition from loss of therapeutic activity, i.e., denaturation in the stomach. Examples of stabilizers for use in an the composition include buffers, amino acids such as glycine and lysine, carbohydrates such as dextrose, mannose, galactose, fructose, lactose, sucrose, maltose, sorbitol, mannitol, etc.

In further embodiments, the present disclosure may concern the use of a pharmaceutical lipid vehicle compositions that include cells expressing anti-CD70 CARs and optionally an aqueous solvent. As used herein, the term "lipid" will be defined to include any of a broad range of substances that is characteristically insoluble in water and extractable with an organic solvent. This broad class of compounds are well known to those of skill in the art, and as the term "lipid" is used herein, it is not limited to any particular structure. Examples include compounds that contain long-chain aliphatic hydrocarbons and their derivatives. A lipid may be naturally occurring or synthetic (i.e., designed or produced by man). However, a lipid is usually a biological substance. Biological lipids are well known in the art, and include for example, neutral fats, phospholipids, phosphoglycerides, steroids, terpenes, lysolipids, glycosphingolipids, glycolipids, sulphatides, lipids with ether and ester-linked fatty acids and polymerizable lipids, and combinations thereof. Of course, compounds other than those specifically described herein that are understood by one of skill in the art as lipids are also encompassed by the compositions and methods of the present invention.

One of ordinary skill in the art would be familiar with the range of techniques that can be employed for dispersing a composition in a lipid vehicle. For example, the cells expressing anti-CD70 CARs may be dispersed in a solution containing a lipid, dissolved with a lipid, emulsified with a lipid, mixed with a lipid, combined with a lipid, covalently bonded to a lipid, contained as a suspension in a lipid, contained or complexed with a micelle or liposome, or otherwise associated with a lipid or lipid structure by any means known to those of ordinary skill in the art. The dispersion may or may not result in the formation of liposomes.

The actual dosage amount of a composition of the present disclosure administered to an animal patient can be determined by physical and physiological factors such as body weight, severity of condition, the type of disease being treated, previous or concurrent therapeutic interventions, idiopathy of the patient and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

A. Alimentary Compositions and Formulations

In particular embodiments of the present disclosure, the cells expressing anti-CD70 CARs are formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain embodiments, the active compounds may be incorporated with excipients and used in the form of ingestible tablets, buccal tables, troches, capsules, elixirs, suspensions, syrups, wafers, and the like (Mathiowitz et al., 1997; Hwang et al., 1998; U.S. Pat. Nos. 5,641,515; 5,580,579 and 5,792,451, each specifically incorporated herein by reference in its entirety). The tablets, troches, pills, capsules and the like may also contain the following: a binder, such as, for example, gum tragacanth, acacia, cornstarch, gelatin or combinations thereof; an excipient, such as, for example, dicalcium phosphate, mannitol, lactose, starch, magnesium stearate, sodium saccharine, cellulose, magnesium carbonate or combinations thereof; a disintegrating agent, such as, for example, corn starch, potato starch, alginic acid or combinations thereof; a lubricant, such as, for example, magnesium stearate; a sweetening agent, such as, for example, sucrose, lactose, saccharin or combinations thereof; a flavoring agent, such as, for example peppermint, oil of wintergreen, cherry flavoring, orange flavoring, etc. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. When the dosage form is a capsule, it may contain, in addition to materials of the above type, carriers such as a liquid carrier. Gelatin capsules, tablets, or pills may be enterically coated. Enteric coatings prevent denaturation of the composition in the stomach or upper bowel where the pH is acidic. See, e.g., U.S. Pat. No. 5,629,001. Upon reaching the small intestines, the basic pH therein dissolves the coating and permits the composition to be released and absorbed by specialized cells, e.g., epithelial enterocytes and Peyer's patch M cells. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

For oral administration the compositions of the present disclosure may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount to a composition that may include water, binders, abrasives, flavoring agents, foaming agents, and humectants. Alternatively the compositions may be fashioned into a tablet or solution form that may be placed under the tongue or otherwise dissolved in the mouth.

Additional formulations that are suitable for other modes of alimentary administration include suppositories. Suppositories are solid dosage forms of various weights and shapes, usually medicated, for insertion into the rectum. After insertion, suppositories soften, melt or dissolve in the cavity fluids. In general, for suppositories, traditional carriers may include, for example, polyalkylene glycols, triglycerides or combinations thereof. In certain embodiments, suppositories may be formed from mixtures containing, for example, the active ingredient in the range of about 0.5% to about 10%, and preferably about 1% to about 2%.

B. Parenteral Compositions and Formulations

In further embodiments, compositions may be administered via a parenteral route. As used herein, the term "parenteral" includes routes that bypass the alimentary tract. Specifically, the pharmaceutical compositions disclosed herein may be administered for example, but not limited to intravenously, intradermally, intramuscularly, intraarterially, intrathecally, subcutaneous, or intraperitoneally U.S. Pat. Nos. 6,613,308; 5,466,468; 5,543,158; 5,641,515; and 5,399,363 (each specifically incorporated herein by reference in its entirety).

Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy injectability exists. It must be stable under the conditions of manufacture and storage and must be preserved against the contaminating action of microorganisms, such as bacteria and fungi. The carrier can be a solvent or dispersion medium containing, for example, water, ethanol, polyol (i.e., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in isotonic NaCl solution and either added hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. A powdered composition is combined with a liquid carrier such as, e.g., water or a saline solution, with or without a stabilizing agent.

C. Miscellaneous Pharmaceutical Compositions and Formulations

In other particular embodiments of the disclosure, the active compound cells expressing anti-CD70 CARs may be formulated for administration via various miscellaneous routes, for example, topical (i.e., transdermal) administration, mucosal administration (intranasal, vaginal, etc.) and/or inhalation.

Pharmaceutical compositions for topical administration may include the active compound formulated for a medicated application such as an ointment, paste, cream or powder. Ointments include all oleaginous, adsorption, emulsion and water-solubly based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones and laurocapram. Possible bases for compositions for topical application include polyethylene glycol, lanolin, cold cream and petrolatum as well as any other suitable absorption, emulsion or water-soluble ointment base. Topical preparations may also include emulsifiers, gelling agents, and antimicrobial preservatives as necessary to preserve the active ingredient and provide for a homogenous mixture. Transdermal administration of the present invention may also comprise the use of a "patch". For example, the patch may supply one or more active substances at a predetermined rate and in a continuous manner over a fixed period of time.

In certain embodiments, the pharmaceutical compositions may be delivered by eye drops, intranasal sprays, inhalation, and/or other aerosol delivery vehicles. Methods for delivering compositions directly to the lungs via nasal aerosol sprays has been described e.g., in U.S. Pat. Nos. 5,756,353 and 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroethylene support matrix is described in U.S. Pat. No. 5,780,045 (specifically incorporated herein by reference in its entirety).

The term aerosol refers to a colloidal system of finely divided solid of liquid particles dispersed in a liquefied or pressurized gas propellant. The typical aerosol of the present invention for inhalation will consist of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight and the severity and response of the symptoms.

V. Combination Therapies

In certain embodiments, the compositions and methods of the present embodiments involve a cancer therapy that is additional to the compositions comprising cells expressing anti-CD70 CARs. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, hormone therapy, or a combination of the foregoing. The additional therapy may be in the form of adjuvant or neoadjuvant therapy.

In some embodiments, the additional therapy is the administration of small molecule enzymatic inhibitor(s) or anti-metastatic agent(s). In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. In some embodiments, the additional therapy is gamma irradiation. In some embodiments, the additional therapy is therapy targeting PBK/AKT/mTOR pathway, HSP90 inhibitor, tubulin inhibitor, apoptosis inhibitor, and/or chemopreventative agent(s). The additional therapy may be one or more of the chemotherapeutic agents known in the art.

An immune cell therapy (in addition to the cell therapy of the disclosure) may be administered before, during, after, or in various combinations relative to an additional cancer therapy, such as immune checkpoint therapy. The administrations may be in intervals ranging from concurrently to minutes to days to weeks. In embodiments where the immune cell therapy is provided to a patient separately from the composition(s) of the disclosure, one would generally ensure that a significant period of time did not expire between the time of each delivery, such that the two compounds would still be able to exert an advantageously combined effect on the patient. In such instances, it is contemplated that one may provide a patient with the immunotherapy therapy and the disclosed compositions within about 12 to 24 or 72 h of each other and, more particularly, within about 6-12 h of each other. In some situations it may be desirable to extend the time period for treatment significantly where several days (2, 3, 4, 5, 6, or 7) to several weeks (1, 2, 3, 4, 5, 6, 7, or 8) lapse between respective administrations.

Administration of any compound or cell therapy of the present embodiments to a patient will follow general protocols for the administration of such compounds, taking into account the toxicity, if any, of the agents. Therefore, in some embodiments there is a step of monitoring toxicity that is attributable to combination therapy.

The term "cancer," as used herein, may be used to describe a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, pancreas, prostate, skin, stomach, testis, tongue, or uterus. In some embodiments, the cancer is recurrent cancer. In some embodiments, the cancer is Stage I cancer. In some embodiments, the cancer is Stage II cancer. In some embodiments, the cancer is Stage III cancer. In some embodiments, the cancer is Stage IV cancer.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis *coli*; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/ squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

A. Chemotherapy

A wide variety of chemotherapeutic agents may be used in accordance with the present embodiments. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis.

Examples of chemotherapeutic agents include alkylating agents, such as thiotepa and cyclophosphamide; alkyl sulfonates, such as busulfan, improsulfan, and piposulfan; aziridines, such as benzodopa, carboquone, meturedopa, and uredopa; ethylenimines and methylamelamines, including altretamine, triethylenemelamine, trietylenephosphoramide, triethiylenethiophosphoramide, and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards, such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosureas, such as carmustine, chlorozotocin, fotemustine, lomustine, nimustine, and ranimnustine; antibiotics, such as the enediyne antibiotics (e.g., calicheamicin, especially calicheamicin gammalI and calicheamicin omegaI1); dynemicin, including dynemicin A; bisphosphonates, such as clodronate; an esperamicin; as well as neocarzinostatin chromophore and related chromoprotein enediyne antibiotic chromophores, aclacinomysins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins, such as mitomycin C, mycophenolic acid, nogalarnycin, olivomycins, peplomycin, potfiromycin, puromycin, quelamycin, rodorubicin, streptonigrin, streptozocin, tubercidin, ubenimex, zinostatin, and zorubicin; anti-metabolites, such as methotrexate and 5-fluorouracil (5-FU); folic acid analogues, such as denopterin, pteropterin, and trimetrexate; purine analogs, such as fludarabine, 6-mercaptopurine, thiamiprine, and thioguanine; pyrimidine analogs, such as ancitabine, azacitidine, 6-azauridine, carmofur, cytarabine, dideoxyuridine, doxifluridine, enocitabine, and floxuridine; androgens, such as calusterone, dromostanolone propionate, epitiostanol, mepitiostane, and testolactone; anti-adrenals, such as mitotane and trilostane; folic acid replenisher, such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids, such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSKpolysaccharide complex; razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; taxoids, e.g., paclitaxel and docetaxel gemcitabine; 6-thioguanine; mercaptopurine; platinum coordination complexes, such as cisplatin, oxaliplatin, and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids, such as retinoic acid; capecitabine; carboplatin, procarbazine, plicomycin, gemcitabien, navelbine, farnesyl-protein transferase inhibitors, transplatinum, and pharmaceutically acceptable salts, acids, or derivatives of any of the above.

B. Radiotherapy

Other factors that cause DNA damage and have been used extensively include what are commonly known as γ-rays, X-rays, and/or the directed delivery of radioisotopes to tumor cells. Other forms of DNA damaging factors are also contemplated, such as microwaves, proton beam irradiation (U.S. Pat. Nos. 5,760,395 and 4,870,287), and UV-irradiation. It is most likely that all of these factors affect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

C. Immunotherapy

The skilled artisan will understand that additional immunotherapies (outside of the disclosed cell therapy) may be used in combination or in conjunction with methods of the embodiments. In the context of cancer treatment, immunotherapeutics, generally, rely on the use of immune effector cells and molecules to target and destroy cancer cells. Rituximab (RITUXAN®) is such an example. The immune effector may be, for example, an antibody specific for some marker on the surface of a tumor cell. The antibody alone may serve as an effector of therapy or it may recruit other cells to actually affect cell killing. The antibody also may be conjugated to a drug or toxin (chemotherapeutic, radionuclide, ricin A chain, cholera toxin, pertussis toxin, etc.) and serve as a targeting agent. Alternatively, the effector may be a lymphocyte carrying a surface molecule that interacts, either directly or indirectly, with a tumor cell target. Various effector cells include cytotoxic T cells and NK cells other than those having knockdown or knockout of TGF-beta R2.

Antibody-drug conjugates have emerged as a breakthrough approach to the development of cancer therapeutics. Antibody-drug conjugates (ADCs) comprise monoclonal antibodies (MAbs) that are covalently linked to cell-killing drugs. This approach combines the high specificity of MAbs against their antigen targets with highly potent cytotoxic drugs, resulting in "armed" MAbs that deliver the payload (drug) to tumor cells with enriched levels of the antigen. Targeted delivery of the drug also minimizes its exposure in normal tissues, resulting in decreased toxicity and improved therapeutic index. The approval of two ADC drugs, ADCETRIS® (brentuximab vedotin) in 2011 and KADCYLA® (trastuzumab emtansine or T-DM1) in 2013 by FDA validated the approach. There are currently more than 30 ADC drug candidates in various stages of clinical trials for cancer treatment (Leal et al., 2014). As antibody engineering and linker-payload optimization are becoming more and more mature, the discovery and development of new ADCs are increasingly dependent on the identification and validation of new targets that are suitable to this approach and the generation of targeting MAbs. Two criteria for ADC targets are upregulated/high levels of expression in tumor cells and robust internalization.

In one aspect of immunotherapy, the tumor cell must bear some marker that is amenable to targeting, i.e., is not present on the majority of other cells. Many tumor markers exist and any of these may be suitable for targeting in the context of the present embodiments. Common tumor markers include CD20, carcinoembryonic antigen, tyrosinase (p97), gp68, TAG-72, HMFG, Sialyl Lewis Antigen, MucA, MucB, PLAP, laminin receptor, erb B, and p155. An alternative aspect of immunotherapy is to combine anticancer effects with immune stimulatory effects. Immune stimulating molecules also exist including: cytokines, such as IL-2, IL-4, IL-12, GM-CSF, gamma-IFN, chemokines, such as MIP-1, MCP-1, IL-8, and growth factors, such as FLT3 ligand.

Examples of immunotherapies currently under investigation or in use are immune adjuvants, e.g., *Mycobacterium bovis, Plasmodium falciparum*, dinitrochlorobenzene, and aromatic compounds (U.S. Pat. Nos. 5,801,005 and 5,739,169; Hui and Hashimoto, 1998; Christodoulides et al., 1998); cytokine therapy, e.g., interferons of any kind, IL-1, GM-CSF, and TNF (Bukowski et al., 1998; Davidson et al., 1998; Hellstrand et al., 1998); gene therapy, e.g., TNF, IL-1, IL-2, and p53 (Qin et al., 1998; Austin-Ward and Villaseca, 1998; U.S. Pat. Nos. 5,830,880 and 5,846,945); and monoclonal antibodies, e.g., anti-CD20, anti-ganglioside GM2, and anti-p185 (Hollander, 2012; Hanibuchi et al., 1998; U.S. Pat. No. 5,824,311). It is contemplated that one or more anti-cancer therapies may be employed with the antibody therapies described herein.

In some embodiments, the immunotherapy may be an immune checkpoint inhibitor. Immune checkpoints either turn up a signal (e.g., co-stimulatory molecules) or turn down a signal. Inhibitory immune checkpoints that may be targeted by immune checkpoint blockade include adenosine A2A receptor (A2AR), B7-H3 (also known as CD276), B and T lymphocyte attenuator (BTLA), cytotoxic T-lymphocyte-associated protein 4 (CTLA-4, also known as CD152), indoleamine 2,3-dioxygenase (IDO), killer-cell immunoglobulin (KIR), lymphocyte activation gene-3 (LAG3), programmed death 1 (PD-1), T-cell immunoglobulin domain and mucin domain 3 (TIM-3) and V-domain Ig suppressor of T cell activation (VISTA). In particular, the immune checkpoint inhibitors target the PD-1 axis and/or CTLA-4.

D. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

E. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

VI. Vectors

The CD70-targeting CARs may be delivered to the recipient cell, including NK cell, by any suitable vector, including by a viral vector or by a non-viral vector. Examples of viral vectors include at least retroviral, lentiviral, adenoviral, or adeno-associated viral vectors. Examples of non-viral vectors include at least plasmids, transposons, lipids, nanoparticles, liposomes, combinations thereof, and so forth.

In cases wherein the NK cell is transduced with a vector encoding the CD70-targeting CAR and also requires transduction of another gene or genes into the cell, such as a suicide gene and/or cytokine and/or an optional therapeutic gene product, the CD70-targeting CAR, optional suicide gene, optional cytokine(s) may or may not be comprised on or with the same vector. In some cases, the CD70-targeting CAR, suicide gene, and/or cytokine(s) are expressed from the same vector molecule, such as the same viral vector molecule. In such cases, the expression of the CD70-targeting CAR, suicide gene, and/or cytokine(s) may or may not be regulated by the same regulatory element(s). When the CD70-targeting CAR, suicide gene, and/or cytokines are on the same vector, they may or may not be expressed as separate polypeptides. In cases wherein they are expressed as separate polypeptides, they may be separated on the vector by a 2A element or IRES element (or both kinds may be used on the same vector once or more than once), for example.

One of skill in the art would be well-equipped to construct a vector through standard recombinant techniques (see, for example, Sambrook et al., 2001 and Ausubel et al., 1996, both incorporated herein by reference) for the expression of the antigen receptors of the present disclosure.

A. Regulatory Elements

Expression cassettes included in vectors useful in the present disclosure in particular contain (in a 5'-to-3' direction) a eukaryotic transcriptional promoter operably linked to a protein-coding sequence, splice signals including intervening sequences, and a transcriptional termination/polyadenylation sequence. The promoters and enhancers that control the transcription of protein encoding genes in eukaryotic cells may be comprised of multiple genetic elements. The cellular machinery is able to gather and integrate the regulatory information conveyed by each element, allowing different genes to evolve distinct, often complex patterns of transcriptional regulation. A promoter used in the context of the present disclosure includes constitutive, inducible, and tissue-specific promoters, for example. In cases wherein the vector is utilized for the generation of cancer therapy, a promoter may be effective under conditions of hypoxia.

B. Promoter/Enhancers

The expression constructs provided herein comprise a promoter to drive expression of the antigen receptor and other cistron gene products. A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, for example, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp-) promoter systems. In addition to producing nucleic acid sequences of promoters and enhancers synthetically, sequences may be produced using recombinant cloning and/or nucleic acid amplification technology, including PCR™, in connection with the compositions disclosed herein. Furthermore, it is contemplated that the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally, any promoter/enhancer combination (as per, for example, the Eukaryotic Promoter Data Base EPDB, through world wide web at epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Non-limiting examples of promoters include early or late viral promoters, such as, SV40 early or late promoters, cytomegalovirus (CMV) immediate early promoters, Rous Sarcoma Virus (RSV) early promoters; eukaryotic cell promoters, such as, e. g., beta actin promoter, GADPH promoter, metallothionein promoter; and concatenated response element promoters, such as cyclic AMP response element promoters (cre), serum response element promoter (sre), phorbol ester promoter (TPA) and response element promoters (tre) near a minimal TATA box. It is also possible to use human growth hormone promoter sequences (e.g., the human growth hormone minimal promoter described at GenBank®, accession no. X05244, nucleotide 283-341) or a mouse mammary tumor promoter (available from the ATCC, Cat. No. ATCC 45007). In certain embodiments, the promoter is CMV IE, dectin-1, dectin-2, human CD11c, F4/80, SM22, RSV, SV40, Ad MLP, beta-actin, MHC class I or MHC class II promoter, however any other promoter that is useful to drive expression of the therapeutic gene is applicable to the practice of the present disclosure.

In certain aspects, methods of the disclosure also concern enhancer sequences, i.e., nucleic acid sequences that increase a promoter's activity and that have the potential to act in cis, and regardless of their orientation, even over relatively long distances (up to several kilobases away from the target promoter). However, enhancer function is not necessarily restricted to such long distances as they may also function in close proximity to a given promoter.

C. Initiation Signals and Linked Expression

A specific initiation signal also may be used in the expression constructs provided in the present disclosure for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments, the use of internal ribosome entry sites (IRES) elements are used to create multigene, or polycistronic messages. IRES elements are able to bypass the ribosome scanning model of 5' methylated Cap dependent translation and begin translation at internal sites. IRES elements from two members of the picornavirus family (polio and encephalomyocarditis) have been described, as well an IRES from a mammalian message. IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

As detailed elsewhere herein, certain 2A sequence elements could be used to create linked- or co-expression of genes in the constructs provided in the present disclosure. For example, cleavage sequences could be used to co-express genes by linking open reading frames to form a single cistron. An exemplary cleavage sequence is the equine rhinitis A virus (E2A) or the F2A (Foot-and-mouth disease virus 2A) or a "2A-like" sequence (e.g., Thosea asigna virus 2A; T2A) or porcine teschovirus-1 (P2A). In specific embodiments, in a single vector the multiple 2A sequences are non-identical, although in alternative embodiments the same vector utilizes two or more of the same 2A sequences. Examples of 2A sequences are provided in US 2011/0065779 which is incorporated by reference herein in its entirety.

D. Origins of Replication

In order to propagate a vector in a host cell, it may contain one or more origins of replication sites (often termed "ori"), for example, a nucleic acid sequence corresponding to oriP of EBV as described above or a genetically engineered oriP with a similar or elevated function in programming, which is a specific nucleic acid sequence at which replication is initiated. Alternatively a replication origin of other extra-chromosomally replicating virus as described above or an autonomously replicating sequence (ARS) can be employed.

E. Selection and Screenable Markers

In some embodiments, cells such as NK cells comprising an anti-CD70 CAR-expressing construct of the present disclosure may be identified in vitro or in vivo by including a marker in the expression vector. Such markers would confer an identifiable change to the cell permitting easy identification of cells containing the expression vector. Generally, a selection marker is one that confers a property that allows for selection. A positive selection marker is one in which the presence of the marker allows for its selection, while a negative selection marker is one in which its presence prevents its selection. An example of a positive selection marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selection markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes as negative selection markers such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selection and screenable markers are well known to one of skill in the art.

VII. Cells

The present disclosure encompasses immune cells of any kind that harbor a vector that encodes a CD70-targeting CAR and that also may encode at least one cytokine and at least one suicide gene. In some cases, different vectors encode the CAR vs. encodes the suicide gene and/or cytokine. Although conventional T cells, NK cells, gamma-delta T cells, NKT and invariant NK T cells, regulatory T cells, macrophages, B cells, tumor infiltrating lymphocytes, or a mixture thereof may be employed, in particular cases the cells are NK cells. The NK cells may be derived from cord blood, peripheral blood, induced pluripotent stem cells (iPSCs), hematopoietic stem cells (HSCs), or bone marrow. The NK cells may be derived from a cell line such as, but not limited to, NK-92 cells, for example. The NK cell may be a cord blood mononuclear cell, such as a CD56+ NK cell.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell (e.g., peripheral blood stem cell) or progenitor cell obtained from an individual.

In particular embodiments, the cells of the disclosure may be specifically formulated and/or they may be cultured in a particular medium. The cells may be formulated in such a manner as to be suitable for delivery to a recipient without deleterious effects.

The medium in certain aspects can be prepared using a medium used for culturing animal cells as their basal medium, such as any of AIM V, X-VIVO-15, NeuroBasal, EGM2, TeSR, BME, BGJb, CMRL 1066, Glasgow MEM, Improved MEM Zinc Option, IMDM, Medium 199, Eagle MEM, αMEM, DMEM, Ham, RPMI-1640, and Fischer's media, as well as any combinations thereof, but the medium may not be particularly limited thereto as far as it can be used for culturing animal cells. Particularly, the medium may be xeno-free or chemically defined.

The medium can be a serum-containing or serum-free medium, or xeno-free medium. From the aspect of preventing contamination with heterogeneous animal-derived components, serum can be derived from the same animal as that of the stem cell(s). The serum-free medium refers to medium with no unprocessed or unpurified serum and accordingly, can include medium with purified blood-derived components or animal tissue-derived components (such as growth factors).

The medium may contain or may not contain any alternatives to serum. The alternatives to serum can include materials which appropriately contain albumin (such as lipid-rich albumin, bovine albumin, albumin substitutes such as recombinant albumin or a humanized albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example (incorporated herein in its entirety). Alternatively, any commercially available materials can be used for more convenience. The commercially available materials include knockout Serum Replacement (KSR), Chemically-defined Lipid concentrated (Gibco), and Glutamax (Gibco).

In certain embodiments, the medium may comprise one, two, three, four, five, six, seven, eight, nine, ten, 11, 12, 13, 14, 15, 16, 17, 18, 19, 20 or more of the following: Vitamins such as biotin; DL Alpha Tocopherol Acetate; DL Alpha-Tocopherol; Vitamin A (acetate); proteins such as BSA (bovine serum albumin) or human albumin, fatty acid free Fraction V; Catalase; Human Recombinant Insulin; Human Transferrin; Superoxide Dismutase; Other Components such as Corticosterone; D-Galactose; Ethanolamine HCl; Glutathione (reduced); L-Carnitine HCl; Linoleic Acid; Linolenic Acid; Progesterone; Putrescine 2HCl; Sodium Selenite; and/or T3 (triodo-I-thyronine). In specific embodiments, one or more of these may be explicitly excluded.

In some embodiments, the medium further comprises vitamins. In some embodiments, the medium comprises 1, 2, 3, 4, 5, 6, 7, 8, 9, 10, 11, 12, or 13 of the following (and any range derivable therein): biotin, DL alpha tocopherol acetate, DL alpha-tocopherol, vitamin A, choline chloride, calcium pantothenate, pantothenic acid, folic acid nicotinamide, pyridoxine, riboflavin, thiamine, inositol, vitamin B12, or the medium includes combinations thereof or salts thereof. In some embodiments, the medium comprises or consists essentially of biotin, DL alpha tocopherol acetate, DL alpha-tocopherol, vitamin A, choline chloride, calcium pantothenate, pantothenic acid, folic acid nicotinamide, pyridoxine, riboflavin, thiamine, inositol, and vitamin B12. In some embodiments, the vitamins include or consist essentially of biotin, DL alpha tocopherol acetate, DL alpha-tocopherol, vitamin A, or combinations or salts thereof. In some embodiments, the medium further comprises proteins. In some embodiments, the proteins comprise albumin or bovine serum albumin, a fraction of BSA, catalase, insulin, transferrin, superoxide dismutase, or combinations thereof. In some embodiments, the medium further comprises one or more of the following: corticosterone, D-Galactose, ethanolamine, glutathione, L-carnitine, linoleic acid, linolenic acid, progesterone, putrescine, sodium selenite, or triodo-I-thyronine, or combinations thereof. In some embodiments, the medium comprises one or more of the following: a B-27® supplement, xeno-free B-27® supplement, GS21™ supplement, or combinations thereof. In some embodiments, the medium comprises or further comprises amino acids, monosaccharides, inorganic ions. In some embodiments, the amino acids comprise arginine, cystine, isoleucine, leucine, lysine, methionine, glutamine, phenylalanine, threonine, tryptophan, histidine, tyrosine, or valine, or combinations thereof. In some embodiments, the inorganic ions comprise sodium, potassium, calcium, magnesium, nitrogen, or phosphorus, or combinations or salts thereof. In some embodiments, the medium further comprises one or more of the following: molybdenum, vanadium, iron, zinc, selenium, copper, or manganese, or combinations thereof. In certain embodiments, the medium comprises or consists essentially of one or more vitamins discussed herein and/or one or more proteins discussed herein, and/or one or more of the following: corticosterone, D-Galactose, ethanolamine, glutathione, L-carnitine, linoleic acid, linolenic acid, progesterone, putrescine, sodium selenite, or triodo-I-thyronine, a B-27® supplement, xeno-free B-27® supplement, GS21™ supplement, an amino acid (such as arginine, cystine, isoleucine, leucine, lysine, methionine, glutamine, phenylalanine, threonine, tryptophan, histidine, tyrosine, or valine), monosaccharide, inorganic ion (such as sodium, potassium, calcium, magnesium, nitrogen, and/or phosphorus) or salts thereof, and/or molybdenum, vanadium, iron, zinc, selenium, copper, or manganese. In specific embodiments, one or more of these may be explicitly excluded.

The medium can also contain one or more externally added fatty acids or lipids, amino acids (such as non-essential amino acids), vitamin(s), growth factors, cytokines, antioxidant substances, 2-mercaptoethanol, pyruvic acid, buffering agents, and/or inorganic salts. In specific embodiments, one or more of these may be explicitly excluded.

One or more of the medium components may be added at a concentration of at least, at most, or about 0.1, 0.5, 1, 2, 3, 4, 5, 10, 15, 20, 25, 30, 35, 40, 45, 50, 55, 60, 65, 70, 75, 80, 85, 90, 95, 100, 150, 180, 200, 250 ng/L, ng/ml, μg/ml, mg/ml, or any range derivable therein.

In specific embodiments, the cells of the disclosure are specifically formulated. They may or may not be formulated as a cell suspension. In specific cases they are formulated in a single dose form. They may be formulated for systemic or local administration. In some cases the cells are formulated for storage prior to use, and the cell formulation may comprise one or more cryopreservation agents, such as DMSO (for example, in 5% DMSO). The cell formulation may comprise albumin, including human albumin, with a specific formulation comprising 2.5% human albumin. The cells may be formulated specifically for intravenous administration; for example, they are formulated for intravenous administration over less than one hour. In particular embodiments the cells are in a formulated cell suspension that is stable at room temperature for 1, 2, 3, or 4 hours or more from time of thawing.

In some cases, the immune cells have been expanded prior to use and/or prior to manufacture. In some cases, the immune cells are NK cells that have been expanded in the presence of an effective amount of antigen-presenting cells, including universal antigen presenting cells (UAPCs), including in any suitable ratio. The cells may be cultured with the UAPCs at a ratio of 10:1 to 1:10; 9:1 to 1:9; 8:1 to 1:8; 7:1 to 1:7; 6:1 to 1:6; 5:1 to 1:5; 4:1 to 1:4; 3:1 to 1:3; 2:1 to 1:2; or 1:1, including at a ratio of 1:2, for example. In some cases, the NK cells are expanded in the presence of IL-2, such as at a concentration of 10-500, 10-400, 10-300, 10-200, 10-100, 10-50, 100-500, 100-400, 100-300, 100-200, 200-500, 200-400, 200-300, 300-500, 300-400, or 400-500 U/mL.

Following genetic modification with the vector(s), the NK cells may be immediately infused or may be stored. In certain aspects, following genetic modification, the cells may be propagated for days, weeks, or months ex vivo as a bulk population within about 1, 2, 3, 4, 5 days or more following gene transfer into cells. In a further aspect, the transfectants are cloned and a clone demonstrating presence of a single integrated or episomally maintained expression cassette or plasmid, and expression of the CD70-targeting CAR is expanded ex vivo. The clone selected for expansion demonstrates the capacity to specifically recognize and lyse CD70-expressing target cells. The recombinant immune cells may be expanded by stimulation with IL-2, or other cytokines that bind the common gamma-chain (e.g., IL-7, IL-12, IL-15, IL-21, and others). The recombinant immune cells may be expanded by stimulation with artificial antigen presenting cells. In a further aspect, the genetically modified cells may be cryopreserved.

Embodiments of the disclosure encompass cells that express one or more CD70-targeting CARs as encompassed herein. The NK cell comprises a recombinant nucleic acid that encodes one or more CD70-targeting CARs and one or more engineered nonsecretable, membrane bound TNF-alpha mutant polypeptides, in specific embodiments. In specific embodiments, in addition to expressing one or more CD70-targeting CARs, the cell also comprises a nucleic acid that encodes one or more therapeutic gene products.

The cells may be obtained from an individual directly or may be obtained from a depository or other storage facility. The cells as therapy may be autologous or allogeneic with respect to the individual to which the cells are provided as therapy.

The cells may be from an individual in need of therapy for a medical condition, and following their manipulation to express the CD70-targeting CAR, they may be provided back to the individual from which they were originally sourced. In some cases, the cells are stored for later use for the individual or another individual. In such cases, the cells may or may not be further modified prior to use.

The NK cells that harbor the CD70-targeting CAR that may be comprised in a population of cells, and that population may have a majority that are transduced with one or more CD70-targeting CARs. A cell population may comprise 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% of cells that are transduced with one or more CD70-targeting CARs.

The NK cells may be produced with the one or more CD70-targeting CARs for the intent of being modular with respect to a specific purpose. For example, cells may be generated, including for commercial distribution, expressing a CD70-targeting CARs and a user may modify them to express one or more other genes of interest (including therapeutic genes) dependent upon their intended purpose (s). For instance, a party interested in treating CD70-positive cancer may modify them to express a second CAR for the same or a different antigen. Other modifications to the cells may include modifications that tailor the cells to the needs of the individual receiving the cells, including a need specific for a particular type of cancer with which the individual is afflicted.

VIII. Gene Editing of Cells

In particular embodiments, cells comprising an anti-CD70 CAR are gene edited to modify expression of one or more endogenous genes in the cell. In specific cases, cells are modified to have reduced levels of expression of one or more endogenous genes, including inhibition of expression of one or more endogenous genes (that may be referred to as knocked out). Such cells may or may not be expanded.

In particular cases, one or more endogenous genes of the cells are modified, such as disrupted in expression where the expression is reduced in part or in full. In specific cases, one or more genes are knocked down or knocked out using processes of the disclosure. In specific cases, multiple genes are knocked down or knocked out, and this may or may not occur in the same step in their production. The genes that are edited in the cells may be of any kind, but in specific embodiments the genes are genes whose gene products inhibit activity and/or proliferation of the cells, including antigen-specific, e.g., CD70-specific, CAR NK cells, such as those derived from cord blood, as one example. In specific cases the genes that are edited in the antigen-specific, e.g., CD70-specific, CAR cells allow the antigen-specific, e.g., CD70-specific, CAR cells to work more effectively in a tumor microenvironment. In specific cases, the genes are one or more of NKG2A, SIGLEC-7, LAG3, TIM3, CISH, FOXO1, TGFBR2, TIGIT, CD96, ADORA2, NR3C1, PD1, PDL-1, PDL-2, CD47, SIRPA, SHIP1, ADAM17, RPS6, 4EBP1, CD25, CD40, IL21R, ICAM1, CD95, CD80, CD86, IL10R, CD5, and CD7. In specific embodiments, the TGFBR2 gene is knocked out or knocked down in the antigen-specific, e.g., CD70-specific, CAR cells.

In some embodiments, the gene editing is carried out using one or more DNA-binding nucleic acids, such as alteration via an RNA-guided endonuclease (RGEN). For example, the alteration can be carried out using clustered regularly interspaced short palindromic repeats (CRISPR) and CRISPR-associated (Cas) proteins; in some embodiments, CpF1 is utilized instead of Cas9. In general, “CRISPR system” refers collectively to transcripts and other elements involved in the expression of or directing the activity of CRISPR-associated (“Cas”) genes, including sequences encoding a Cas gene, a tracr (trans-activating CRISPR) sequence (e.g., tracrRNA or an active partial tracrRNA), a tracr-mate sequence (encompassing a “direct repeat” and a tracrRNA-processed partial direct repeat in the context of an endogenous CRISPR system), a guide sequence (also referred to as a “spacer” in the context of an endogenous CRISPR system), and/or other sequences and transcripts from a CRISPR locus.

The CRISPR/Cas nuclease or CRISPR/Cas nuclease system can include a non-coding RNA molecule (guide) RNA, which sequence-specifically binds to DNA, and a Cas protein (e.g., Cas9), with nuclease functionality (e.g., two nuclease domains). One or more elements of a CRISPR system can derive from a type I, type II, or type III CRISPR system, e.g., derived from a particular organism comprising an endogenous CRISPR system, such as *Streptococcus pyogenes*.

In some aspects, a Cas nuclease and gRNA (including a fusion of crRNA specific for the target sequence and fixed tracrRNA) are introduced into the cell. In general, target sites at the 5' end of the gRNA target the Cas nuclease to the target site, e.g., the gene, using complementary base pairing. The target site may be selected based on its location immediately 5' of a protospacer adjacent motif (PAM) sequence, such as typically NGG, or NAG. In this respect, the gRNA is targeted to the desired sequence by modifying the first 20, 19, 18, 17, 16, 15, 14, 14, 12, 11, or 10 nucleotides of the guide RNA to correspond to the target DNA sequence. In general, a CRISPR system is characterized by elements that promote the formation of a CRISPR complex at the site of a target sequence. Typically, “target sequence” generally refers to a sequence to which a guide sequence is designed to have complementarity, where hybridization between the target sequence and a guide sequence promotes the formation of a CRISPR complex. Full complementarity is not necessarily required, provided there is sufficient complementarity to cause hybridization and promote formation of a CRISPR complex.

The CRISPR system can induce double stranded breaks (DSBs) at the target site, followed by disruptions or alterations as discussed herein. In other embodiments, Cas9 variants, deemed “nickases,” are used to nick a single strand at the target site. Paired nickases can be used, e.g., to improve specificity, each directed by a pair of different gRNAs targeting sequences such that upon introduction of the nicks simultaneously, a 5' overhang is introduced. In other embodiments, catalytically inactive Cas9 is fused to a heterologous effector domain such as a transcriptional repressor or activator, to affect gene expression.

The target sequence may comprise any polynucleotide, such as DNA or RNA polynucleotides. The target sequence may be located in the nucleus or cytoplasm of the cell, such as within an organelle of the cell. Generally, a sequence or template that may be used for recombination into the targeted locus comprising the target sequences is referred to as an “editing template” or “editing polynucleotide” or “editing sequence”. In some aspects, an exogenous template polynucleotide may be referred to as an editing template. In some aspects, the recombination is homologous recombination.

Typically, in the context of an endogenous CRISPR system, formation of the CRISPR complex (comprising the guide sequence hybridized to the target sequence and complexed with one or more Cas proteins) results in cleavage of one or both strands in or near (e.g. within 1, 2, 3, 4, 5, 6, 7, 8, 9, 10, 20, 50, or more base pairs from) the target sequence. The tracr sequence, which may comprise or consist of all or a portion of a wild-type tracr sequence (e.g. about or more than about 20, 26, 32, 45, 48, 54, 63, 67, 85, or more nucleotides of a wild-type tracr sequence), may also form part of the CRISPR complex, such as by hybridization along at least a portion of the tracr sequence to all or a portion of a tracr mate sequence that is operably linked to the guide sequence. The tracr sequence has sufficient complementarity to a tracr mate sequence to hybridize and participate in formation of the CRISPR complex, such as at least 50%, 60%, 70%, 80%, 90%, 95% or 99% of sequence complementarity along the length of the tracr mate sequence when optimally aligned.

One or more vectors driving expression of one or more elements of the CRISPR system can be introduced into the cell such that expression of the elements of the CRISPR system direct formation of the CRISPR complex at one or more target sites. Components can also be delivered to cells as proteins and/or RNA. For example, a Cas enzyme, a guide sequence linked to a tracr-mate sequence, and a tracr sequence could each be operably linked to separate regulatory elements on separate vectors. Alternatively, two or more of the elements expressed from the same or different regulatory elements, may be combined in a single vector, with one or more additional vectors providing any components of the CRISPR system not included in the first vector. The vector may comprise one or more insertion sites, such as a restriction endonuclease recognition sequence (also referred to as a “cloning site”). In some embodiments, one or more insertion sites are located upstream and/or downstream of one or more sequence elements of one or more vectors. When multiple different guide sequences are used, a single expression construct may be used to target CRISPR activity to multiple different, corresponding target sequences within a cell.

A vector may comprise a regulatory element operably linked to an enzyme-coding sequence encoding the CRISPR enzyme, such as a Cas protein. Non-limiting examples of Cas proteins include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1 (Cas12a) homologs thereof, or modified versions thereof. These enzymes are known; for example, the amino acid sequence of *S. pyogenes* Cas9 protein may be found in the SwissProt database under accession number Q99ZW2.

The CRISPR enzyme can be Cas9 (e.g., from *S. pyogenes* or *S. pneumonia*). In some cases, Cpf1 (Cas12a) may be used as an endonuclease instead of Cas9. The CRISPR enzyme can direct cleavage of one or both strands at the location of a target sequence, such as within the target sequence and/or within the complement of the target sequence. The vector can encode a CRISPR enzyme that is mutated with respect to a corresponding wild-type enzyme such that the mutated CRISPR enzyme lacks the ability to cleave one or both strands of a target polynucleotide containing a target sequence. For example, an aspartate-to-alanine substitution (D10A) in the RuvC I catalytic domain of Cas9 from *S. pyogenes* converts Cas9 from a nuclease that cleaves both strands to a nickase (cleaves a single strand). In some embodiments, a Cas9 nickase may be used in combination with guide sequence(s), e.g., two guide sequences, which target respectively sense and antisense strands of the DNA target. This combination allows both strands to be nicked and used to induce NHEJ or HDR.

In some embodiments, an enzyme coding sequence encoding the CRISPR enzyme is codon optimized for expression in particular cells, such as eukaryotic cells. The eukaryotic cells may be those of or derived from a particular organism, such as a mammal, including but not limited to human, mouse, rat, rabbit, dog, or non-human primate. In general, codon optimization refers to a process of modifying a nucleic acid sequence for enhanced expression in the host cells of interest by replacing at least one codon of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

In general, a guide sequence is any polynucleotide sequence having sufficient complementarity with a target polynucleotide sequence to hybridize with the target sequence and direct sequence-specific binding of the CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97%, 99%, or more.

Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), Clustal W, Clustal X, BLAT, Novoalign (Novocraft Technologies, ELAND (Illumina, San Diego, Calif.), SOAP (available at soap.genomics.org.cn), and Maq (available at maq.sourceforge.net).

The CRISPR enzyme may be part of a fusion protein comprising one or more heterologous protein domains. A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-5-transferase (GST), horseradish peroxidase (HRP), chloramphenicol acetyltransferase (CAT) beta galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4A DNA binding domain fusions, and herpes simplex virus (HSV) BP16 protein fusions. Additional domains that may form part of a fusion protein comprising a CRISPR enzyme are described in US 20110059502, incorporated herein by reference.

IX. Methods of Treatment

In various embodiments CD70-targeting CAR constructs, nucleic acid sequences, vectors, host cells and so forth as contemplated herein and/or pharmaceutical compositions comprising the same are used for the prevention, treatment or amelioration of a cancerous disease, such as a tumorous disease. In particular embodiments, the pharmaceutical composition of the present disclosure may be particularly useful in preventing, ameliorating and/or treating cancer, including cancers that express CD70 and that may or may not be solid tumors, for example. The individual may utilize the treatment method of the disclosure as an initial treatment or after (or with) another treatment, such as following HSCT, for example. The immunotherapy methods may be tailored to the need of an individual with cancer based on the type and/or stage of cancer, and in at least some cases the immunotherapy may be modified during the course of treatment for the individual.

In some embodiments, the present disclosure provides methods for immunotherapy comprising administering an effective amount of the cells produced by methods of the present disclosure. In one embodiment, a medical disease or disorder is treated by transfer of cell populations produced by methods herein and that elicit an immune response. In certain embodiments of the present disclosure, cancer is treated by transfer of a cell population produced by methods of the disclosure and that elicits an immune response. Provided herein are methods for treating or delaying progression of cancer in an individual comprising administering to the individual an effective amount CD70-specific cell therapy. The present methods may be applied for the treatment of solid cancers or hematologic cancers.

Tumors for which the present treatment methods are useful include any malignant cell type, such as those found in a solid tumor or a hematological tumor. Exemplary solid tumors can include, but are not limited to, a tumor of an organ selected from the group consisting of acute myeloid leukemia, lymphoma, lung cancer, renal cancer, bladder cancer, melanoma, glioblastoma, breast cancer, head and neck cancer, mesothelioma, multiple myeloma, and pancreatic cancer.

In certain embodiments of the present disclosure, anti-CD70 CAR-expressing immune cells are delivered to an individual in need thereof, such as an individual that has cancer. The cells then enhance the individual's immune system to attack the cancer cells. In some cases, the individual is provided with one or more doses of the immune cells. In cases where the individual is provided with two or more doses of the immune cells, the duration between the administrations should be sufficient to allow time for propagation in the individual, and in specific embodiments the duration between doses is 1, 2, 3, 4, 5, 6, 7, or more days.

The NK cells for which the CD70-targeting CAR is utilized may be NK, T cells, or invariant NKT cells engineered for cell therapy for mammals, in particular embodiments. In such cases where the cells are NK cells, the NK cell therapy may be of any kind and the NK cells may be of any kind. In specific embodiments, the cells are NK cells that have been engineered to express one or more CD70-targeting CARs and are provided to an individual in a therapeutically effective amount (in a range from 103 to 1010) that ameliorates at least one symptom related to CD70-expressing cells in the individual. In specific embodiments, the cells are NK cells that are transduced with a CD70-targeting CAR. A therapeutically effective amount may be from $10^3$ to $10^{10}$, $10^3$ to $10^9$, $10^3$ to $10^8$, $10^3$ to $10^7$, $10^3$ to $10^6$, $10^3$ to $10^5$, $10^3$ to $10^4$, $10^4$ to $10^{10}$, $10^4$ to $10^9$, $10^4$ to $10^8$, $10^4$ to $10^7$, $10^4$ to $10^6$, $10^4$ to $10^5$, $10^5$ to $10^{10}$, $10^5$ to $10^9$, $10^5$ to $10^8$, $10^5$ to $10^7$, $10^5$ to $10^6$, $10^6$ to $10^{10}$, $10^6$ to $10^9$, $10^6$ to $10^8$, $10^6$ to $10^7$, $10^7$ to $10^{10}$, $10^7$ to $10^9$, $10^7$ to $10^8$, $10^8$ to $10^{10}$, $10^8$ to $10^9$, or $10^9$ to $10^{10}$ cells. Thus, in particular embodiments an individual having a CD70-positive cancer is provided once or multiple times a therapeutically effective amount of cells expressing one or more CD70-targeting CARs, including NK cells.

In particular embodiments, the present disclosure contemplates, in part, CD70 CAR-expressing cells, CD70-targeting CAR constructs, CD70-targeting CAR nucleic acid molecules and CD70-targeting CAR vectors that can administered either alone or in any combination using standard vectors and/or gene delivery systems, and in at least some aspects, together with a pharmaceutically acceptable carrier or excipient. In certain embodiments, subsequent to administration, the nucleic acid molecules or vectors may be stably integrated into the genome of the subject.

In specific embodiments, viral vectors may be used that are specific for certain cells or tissues and persist in NK cells, for example. Suitable pharmaceutical carriers and excipients are well known in the art. The compositions prepared according to the disclosure can be used for the prevention or treatment or delaying the above identified diseases.

Furthermore, the disclosure relates to a method for the prevention, treatment or amelioration of a tumorous disease comprising the step of administering to a subject in the need thereof an effective amount of cells that express a CD70-targeting CAR, a nucleic acid sequence, a vector, as contemplated herein and/or produced by a process as contemplated herein.

Possible indications for administration of the composition (s) of the exemplary CD70-targeting CAR cells are cancerous diseases, including tumorous diseases, including B cell malignancies, multiple myeloma, breast cancer, or lung cancer, for example. Exemplary indications for administration of the composition(s) of CD70-targeting CAR cells are cancerous diseases, including any malignancies that express CD70. The administration of the composition(s) of the disclosure is useful for all stages and types of cancer, including for minimal residual disease, early cancer, advanced cancer, and/or metastatic cancer and/or refractory cancer, for example.

Therapeutically effective amounts of the produced cells can be administered by a number of routes, including parenteral administration, for example, intravenous, intraperitoneal, intramuscular, intrasternal, intratumoral, intrathecal, intraventricular, through a reservoir, intraarticular injection, or infusion.

The therapeutically effective amount of the produced cells for use in adoptive cell therapy is that amount that achieves a desired effect in a subject being treated. For instance, this can be the amount of immune cells necessary to inhibit advancement, or to cause regression of cancer.

The produced cell population can be administered in treatment regimens consistent with the disease, for example a single or a few doses over one to several days to ameliorate a disease state or periodic doses over an extended time to inhibit disease progression and prevent disease recurrence. The precise dose to be employed in the formulation will also depend on the route of administration, and the seriousness of the disease or disorder, and should be decided according to the judgment of the practitioner and each patient's circumstances. The therapeutically effective amount of cells will be dependent on the subject being treated, the severity and type of the affliction, and the manner of administration. In some embodiments, doses that could be used in the treatment of human subjects range from at least $1\times10^3$, at least $1\times10^4$, $3.8\times10^4$, at least $3.8\times10^5$, at least $3.8\times10^6$, at least $3.8\times10^7$, at least $3.8\times10^8$, at least $3.8\times10^9$, or at least $3.8\times10^{10}$ T cells/$m^2$. In a certain embodiment, the dose used in the treatment of human subjects ranges from about $3.8\times10^9$ to about $3.8\times10^{10}$ T cells/$m^2$. In additional embodiments, a therapeutically effective amount of T cells can vary from about $5\times10^6$ cells per kg body weight to about $7.5\times10^8$ cells per kg body weight, such as about $2\times10^7$ cells to about $5\times10^8$ cells per kg body weight, or about $5\times10^7$ cells to about $2\times10^8$ cells per kg body weight. The exact amount of T cells is readily determined by one of skill in the art based on the age, weight, sex, and physiological condition of the subject. Effective doses can be extrapolated from dose-response curves derived from in vitro or animal model test systems.

The disclosure further encompasses co-administration protocols with other compounds, e.g. bispecific antibody constructs, targeted toxins or other compounds, which act via immune cells. The clinical regimen for co-administration of the inventive compound(s) may encompass co-administration at the same time, before or after the administration of the other component. Particular combination therapies include chemotherapy, radiation, surgery, hormone therapy, or other types of immunotherapy.

Embodiments relate to a kit comprising a CD70-targeting CAR construct as defined herein, a nucleic acid sequence as defined herein, a vector as defined herein and/or a host as defined herein. It is also contemplated that the kit of this disclosure comprises a pharmaceutical composition as described herein above, either alone or in combination with further medicaments to be administered to an individual in need of medical treatment or intervention.

X. Kits of the Disclosure

Any of the compositions described herein may be comprised in a kit. In a non-limiting example, the kit comprises anti-CD70 CAR molecules, cells encompassing same, and/or reagents to generate same, and any of these may be comprised in suitable container means in a kit of the present disclosure. Kits may comprise immune cells, including NK cells, vectors, expression construct polynucleotides for insertion into a vector (whether viral or not), CD27 sequences of any kind and as encompassed herein, and so forth. Primers for amplification of any polynucleotide may be included. In some cases, the kit comprises cryopreserved cells, including NK cells. Any reagents for transfection or transduction of the cells may be included.

The compositions of the kits may be packaged either in aqueous media or in lyophilized form. The container means of the kits will generally include at least one vial, test tube, flask, bottle, syringe or other container means, into which one or more components may be placed, and preferably, suitably aliquoted. Where there are more than one component in the kit, the kit also may generally contain a second, third or other additional container into which the additional components may be separately placed. However, various combinations of components may be comprised in a vial. The kits of the present disclosure also will typically include a means for containing the anti-CD70 CAR molecules, cells encompassing same, and/or reagents to generate same in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly envisioned. The compositions may also be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit.

However, the components of the kit may be provided as dried powder(s). When reagents and/or components are provided as a dry powder, the powder can be reconstituted by the addition of a suitable solvent. It is envisioned that the solvent may also be provided in another container means.

Irrespective of the number and/or type of containers, the kits of the disclosure may also comprise, and/or be packaged with, an instrument for assisting with the injection/administration and/or placement of the ultimate composition within the body of an animal. Such an instrument may be a syringe, pipette, forceps, and/or any such medically approved delivery vehicle. In some embodiments, reagents or apparatuses or containers are included in the kit for ex vivo use.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

CD27-Comprising Car to Target CD70-Positive Tumors

Figure 1B:
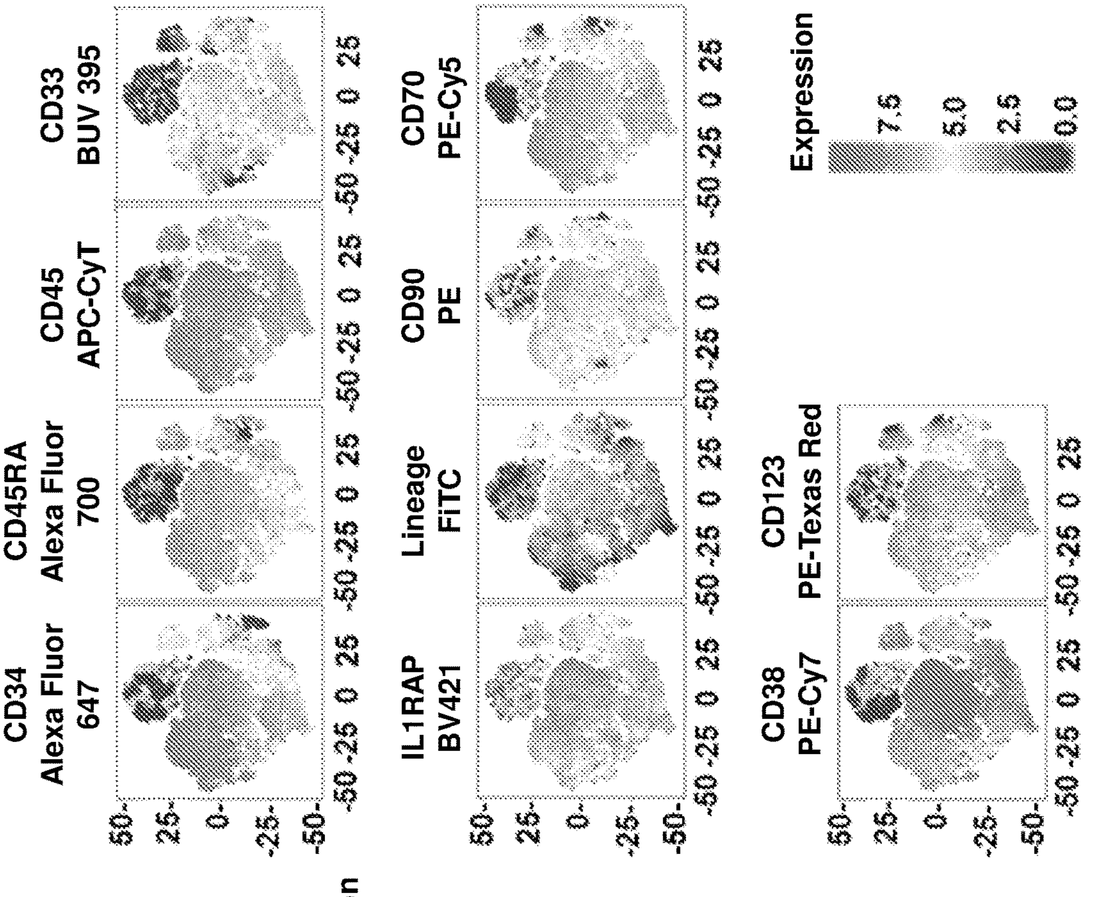
FIGS. 1A-1B show CD70 expression on AML, patient samples using Tsne plots.
Figure 1A:
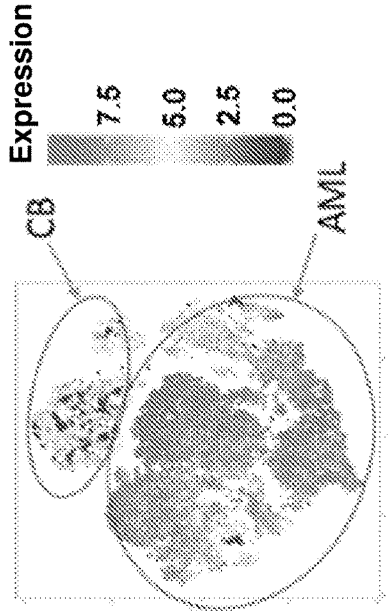

The inventors first confirmed CD70 expression on AML patient samples. A Tsne plot from mass cytometry data showed high expression of CD70 on primary AML samples (n=54) but not on healthy CB CD34+ cells (n=10) (FIG. 1A). As shown in FIG. 1, Tsne plots also showed various myeloid markers on lineage neg cells from CB (upper CB population from FIG. 1A) and AML samples (lower AML population from FIG. 1A). CD70 expression in AML samples was similar to other well-characterized myeloid markers.

FIG. 3 demonstrates that TrCD27 constructs showed higher transfection efficiency compared to flCD27 constructs. 293T cells were transfected with various CD27 constructs, as shown in figure, using GeneJuice as a transfection reagent. The transfection efficiency was determined by checking the surface expression of CD27 in 293T cells post virus collection using flow cytometry for CD27 constructs. Non transduced (NT) cells were used as control. We also included constructs containing only IL15 (i.e. IL15) and CD70scFv CAR construct containing single heavy and light chains derived from commercially available CD70 antibody sequence with IL15 (i.e. CD70-IL15). The surface expression of IgG was used to determine the transfection efficiency for the latter two constructs FIG. 4 demonstrates that TrCD27 constructs showed higher transduction efficiency compared to flCD27 constructs. The retroviral supernatant collected from transfection experiment (FIG. 3) were used to transduce cord blood derived NK (CBNK) cells and RetroNectin was used to enhance the transduction efficiency. Forty-eight hours post transduction, the transduction efficiency was measured by checking the surface expression of CD27 on CBNK cells using flow cytometry. Supernatant from non-transduced (NT) cells were used as control. For IL15 and CD70 CAR-IL15 CAR constructs, the surface expression of IgG on CBNK cells was used to determine the transduction efficiency. Because flCD27 constructs under these conditions show poor transfection and transduction efficiency, focus on trCD27 constructs was emphasized.

In FIGS. 5A-5C, CBNK cells transduced with trCD27 constructs induced cancer cell apoptosis. Annexin V-LIVE/DEAD™ Fixable Aqua staining assay was performed to investigate if CBNK cells transduced with various trCD27 constructs could induce death of CD70-expressing cancer cells. Raji and Karpas cells were used as targets since both have relatively high surface expression of CD70 (FIG. 5A, FIG. 5B, respectively). NK cells transduced with TrCD27 constructs and cancer cells were co-cultured at a 1:1 ratio for 4 hrs and Annexin V-LIVE/DEAD™ Fixable Aqua staining was performed. Various trCD70 transduced CBNK cells (such as #3, #13, #15, #17, #19 #20, etc.) exerted superior killing of both Raji (black bar) and Karpas (grey bar) cells, when compared to NT, IL15 or CD70-IL15 CAR transduced CBNK cells (FIG. 5C).

In FIG. 6, CB-NK cells transduced with trCD27 constructs showed enhanced cytotoxic activity against cancer cells. The degranulation marker CD107a is a widely accepted marker for the cytotoxic activity of NK cells. TrCD27 CAR transduced CBNK cells and cancer cells (Raji and Karpas) were co-cultured at a 1:1 ratio in the presence of CD107a antibody for 6 hrs. After incubation, CD107a expression is assessed by flow cytometry. Most of the trCD70 transduced CB-NK cells showed enhanced cytotoxic activity against Raji (middle black bar) and Karpas (right gray bar) cells when compared to NT, IL15 or CD70-IL15 CAR transduced CB-NK cells. CB-NK cells in the absence of co-culture with cancer cells shows minimal basal expression level of CD107a (left green bar).

FIGS. 7A-7B demonstrate that CB-NK cells transduced with trCD27 constructs show enhanced cytotoxic against cancer cells. To analyze the real-time cytotoxic activity of trCD27 CAR-transduced CBNK cells against cancer cells, an IncuCyte cytotoxicity assay was performed. TrCD27 CAR-transduced CB-NK cells and Raji cells (FIG. 7A) or Karpas cells (FIG. 7B) were co-cultured at 1:1 ratio, and real-time cytotoxicity of NK cells against Raji and Karpas cells was measured every hour over a 12 hour period. All of the trCD70 CAR-transduced CB-NK cells used in this assay showed enhanced cytotoxic activity against Raji (left panel) and Karpas cells (right panel) when compared to NT, IL15 or CD70-IL15 CAR transduced CB-NK cells.

FIGS. 8A-8B demonstrate that CB-NK cells transduced with trCD27 CARs have effective anti-tumor activity against CD70-positive Raji cells in vivo. NSG mice were engrafted with firefly luciferase labelled Raji cells (Raji-FFluc) which have high CD70 expression. Mice were injected with 20,000

Raji cells/mouse and 5M CBNK cells/mouse. Bioluminescence imaging of the tumor showed that CB-NK cells transduced with trCD27 CARs were able to reduce tumor burden due to CD70 high Raji cells (FIG. 8A). Additionally, survival curve showed the significant survival benefit on NSG mice with Raji, when infused with single dose of CB-NK cells transduced with various trCD27 CARs when compared to non-transduced (NT) cells and cells transduced with IL15 or CD70-IL15 CARs (FIG. 8B). The trCD27 #23 CAR construct showed the most significant survival benefit. p=0.002 (Raji+NT vs Raji+CD27 #23); p=0.0018 (Raji+ IL15 vs Raji+CD27 #23); p=0.001 (Raji+CD70-IL15 vs Raji+CD27 #23). Mantel-Cox test was used to measure p value.

FIGS. 9A-9B demonstrate that CB-NK cells transduced with trCD27 CARs have effective anti-tumor activity against CD70-positive AML cells in vivo. NSG mice were engrafted with firefly luciferase labelled THP-1 cells (THP1-FFluc), which have high CD70 expression. Mice were injected with 100,000 THP1 cells/mouse and 5M CBNK cells/mouse. Bioluminescence imaging of the tumor showed that CB-NK cells transduced with trCD27 CARs were able to reduce tumor burden due to CD70 high THP-1 cells (FIG. 9A). Additionally, survival curves showed the significant survival benefit on NSG mice with THP-1, when infused with single dose of CB-NK cells transduced with various trCD27 CARs when compared to non-transduced (NT) cells and cells transduced with IL15 or CD70-IL15 CARs (FIG. 9B). The trCD27 #15 and trCD27 #23 CAR constructs showed the most significant survival benefit. p=0.0027 (THP-1+NT vs THP-1+CD27 #15 or #23); p=0.001 (THP-1+IL15 vs THP-1+CD27 #15 or #23); p=0.001 (THP-1+CD70-IL15 vs THP-1+CD27 #15 or #23). Mantel-Cox test was used to measure p value.

Although the present disclosure and its advantages have been described in detail, it should be understood that various changes, substitutions and alterations can be made herein without departing from the spirit and scope of the design as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A polynucleotide that encodes an anti-CD70 chimeric antigen receptor (CAR) comprising a signal peptide, an anti-CD70 antigen binding domain, transmembrane domain, and at least one intracellular domain, wherein the anti-CD70 antigen binding domain does not comprise an antibody, wherein the polynucleotide comprises SEQ ID NO:30.

2. The polynucleotide of claim 1, wherein the anti-CD70 antigen binding domain is comprised in an extracellular domain of CD27 and comprises, consists of, or consists essentially of SEQ ID NO:5.

3. The polynucleotide of claim 1, wherein the transmembrane domain is from CD28.

4. The polynucleotide of claim 1, wherein the at least one intracellular domain comprises two intracellular domains, and wherein the two intracellular domains comprise CD3zeta and CD28.

5. The polynucleotide of claim 1, wherein the signal peptide is from CD27.

6. The polynucleotide of claim 1, wherein the signal peptide comprises, consists of, or consists essentially of SEQ ID NO:6; the antigen binding domain comprises, consists of, or consists essentially of SEQ ID NO:5; the transmembrane domain comprises, consists of, or consists essentially of SEQ ID NO:3; and the intracellular domain comprises SEQ ID NO:10 and SEQ ID NO:11.

7. The polynucleotide of claim 1, wherein the CAR comprises a CD27 SP, a CD27 EC, a CD28 TMD, and CD3zeta.

8. An immune cell comprising the polynucleotide of claim 1.

9. The immune cell of claim 8, wherein the immune cell is a Natural Killer (NK) cell, T cell, a gamma delta T cell, invariant NKT (iNKT) cell, B cell, macrophage, a mesenchymal stem cell (MSC), or dendritic cell.

10. The immune cell of claim 9, wherein the NK cell is derived from cord blood, peripheral blood, induced pluripotent stem cells, bone marrow, from a cell line, or a mixture thereof.

11. The immune cell of claim 9, wherein the NK cell is a CD56+ NK cell.

12. The immune cell of claim 9, wherein the NK cells express exogenously provided cytokines comprising IL-15, IL-2, IL-12, IL-18, IL-21, IL-7, or a combination thereof.

13. A method of killing CD70-positive cells in an individual, the method comprising the step of administering to the individual a therapeutically effective amount of cells harboring the polynucleotide of claim 1.

14. The method of claim 13, wherein the CD70-positive cells are T regulatory cells or CD70 expressing cancer cells.

15. The method of claim 13, wherein the cells harboring the polynucleotide are allogeneic or autologous with respect to the individual.

16. The method of claim 13, wherein the cells harboring the polynucleotide are administered to the individual once or more than once.

17. The method of claim 13, further comprising the step of providing to the individual an effective amount of an additional therapy comprising one or more antibodies, surgery, gene therapy, immunotherapy, or hormone therapy.

18. The method of claim 13, wherein the cells are administered to the individual by injection, intravenously, intraarterially, intraperitoneally, intratracheally, intratumorally, intramuscularly, endoscopically, intralesionally, intracranially, percutaneously, subcutaneously, regionally, by perfusion, in a tumor microenvironment, or a combination thereof.

19. The method of claim 13, further comprising the step of identifying CD70-positive cells in the individual.

* * * * *